(12) United States Patent
Moeller Tagmose et al.

(10) Patent No.: US 11,471,537 B2
(45) Date of Patent: Oct. 18, 2022

(54) OLIGOMER EXTENDED INSULIN-FC CONJUGATES

(71) Applicant: Novo Nordisk A/S, Bagsvaerd (DK)

(72) Inventors: Tina Moeller Tagmose, Ballerup (DK); Peter Madsen, Bagsvaerd (DK); Thomas Boerglum Kjeldsen, Virum (DK); Lone Pridal, Greve (DK); Leonardo De Maria, Partille (SE); Zhaosheng Lin, Markham (CA); Zhe Wan, Beijing (CN); Yuanyuan Zhang, Beijing (CN); Lennart Lykke, Copenhagen (DK); Martin Werner Borchsenius Muenzel, Broenshoej (DK); Janos Tibor Kodra, Koebenhavn (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/500,897

(22) PCT Filed: Apr. 4, 2018

(86) PCT No.: PCT/EP2018/058550
§ 371 (c)(1),
(2) Date: Oct. 4, 2019

(87) PCT Pub. No.: WO2018/185131
PCT Pub. Date: Oct. 11, 2018

(65) Prior Publication Data
US 2020/0261595 A1 Aug. 20, 2020

(30) Foreign Application Priority Data

Apr. 5, 2017 (EP) .................................. 17164950
Dec. 20, 2017 (EP) .................................. 17208780
Jan. 11, 2018 (EP) .................................. 18151228
Mar. 30, 2018 (CN) ........................ 201810276163.0

(51) Int. Cl.
A61K 38/28 (2006.01)
A61K 47/68 (2017.01)
A61K 47/64 (2017.01)

(52) U.S. Cl.
CPC .......... A61K 47/6811 (2017.08); A61K 38/28 (2013.01); A61K 47/64 (2017.08)

(58) Field of Classification Search
CPC .................................................... A61K 38/28
See application file for complete search history.

(56) References Cited

U.S. PATENT DOCUMENTS

| 3,914,252 | A | 10/1975 | Gordon |
| 7,404,956 | B2 | 7/2008 | Peters et al. |
| 8,492,530 | B2 | 7/2013 | Schellenberger et al. |
| 8,697,396 | B2 | 4/2014 | Dall'Acqua et al. |
| 10,537,644 | B2 * | 1/2020 | Huang ................. A61K 47/545 |
| 2003/0162949 | A1 | 8/2003 | Cox |
| 2004/0180054 | A1 | 9/2004 | Kim et al. |
| 2005/0233417 | A1 | 10/2005 | Cooper et al. |
| 2005/0287153 | A1 | 12/2005 | Dennis |
| 2006/0094083 | A1 | 5/2006 | Choi et al. |
| 2006/0094655 | A1 | 5/2006 | Guyon et al. |
| 2006/0183197 | A1 | 8/2006 | Andersen et al. |
| 2006/0276633 | A1 | 12/2006 | Jung et al. |
| 2008/0057004 | A1 | 3/2008 | Bell et al. |
| 2009/0036353 | A1 | 2/2009 | Behrens et al. |
| 2010/0069605 | A1 | 3/2010 | Hoeg-Jensen et al. |
| 2010/0239554 | A1 | 9/2010 | Schellenberger et al. |
| 2011/0054151 | A1 * | 3/2011 | Lazar ..................... C07K 16/32 530/389.2 |
| 2012/0116056 | A1 | 5/2012 | Sun et al. |
| 2013/0028918 | A1 * | 1/2013 | Song ..................... A61K 47/68 424/179.1 |
| 2014/0227264 | A1 | 8/2014 | Hamilton et al. |
| 2015/0037359 | A1 | 2/2015 | Schellenberger et al. |
| 2015/0158905 | A1 | 6/2015 | Martin |
| 2016/0000932 | A1 | 1/2016 | Gegg et al. |
| 2018/0161448 | A1 | 6/2018 | Heo et al. |
| 2018/0291076 | A1 * | 10/2018 | Kjeldsen ................... A61P 3/10 |
| 2020/0261595 | A1 | 8/2020 | Moeller Tagmose et al. |

FOREIGN PATENT DOCUMENTS

| CN | 1604965 | A | 4/2005 |
| CN | 102666586 | A | 9/2012 |
| DE | 257197 | A1 | 6/1988 |
| DE | 286509 | | 1/1991 |
| EP | 1996220 | A2 | 12/2008 |
| EP | 2164873 | A1 | 3/2010 |
| EP | 3260139 | | 12/2017 |
| JP | 2008528549 | A | 7/2008 |
| JP | 2008530178 | A | 8/2008 |
| KR | 20080095141 | A | 10/2008 |

(Continued)

OTHER PUBLICATIONS

Nomura et al. Org. Biomol. Chem. 13:8734-8739, 2015.*
Jochen G. Salfeld, "Isotype Selection in Antibody Engineering," Nature Biotechnology, 2007, vol. 25, pp. 1369-1372.
Singh et al., Novel Approaches and Strategies for Biologies, Vaccines and Cancer Therapies, 1st Edition, Jan. 5, 2015, p. 134.

(Continued)

Primary Examiner — Gyan Chandra
(74) Attorney, Agent, or Firm — Jianjie Hu

(57) ABSTRACT

This invention is in the field of protein conjugates. More specifically the invention relates to oligomer extended insulins with covalently attached Fc monomer polypeptides, for use in the treatment of a metabolic disorder or condition, and to methods of producing such oligomer extended insulin-Fc conjugates. The invention also relates to novel Fc fragments, to intermediate products, and to the use of such intermediate products in processes for the synthesis of the oligomer extended insulin-Fc conjugates of the invention. Finally the invention provides pharmaceutical compositions comprising the oligomer extended insulin-Fc conjugates of the invention, and relates to the use of such compositions for the treatment or prevention of medical conditions relating to metabolic disorders or conditions.

19 Claims, 7 Drawing Sheets

Specification includes a Sequence Listing.

(56) References Cited

FOREIGN PATENT DOCUMENTS

| | | | |
|---|---|---|---|
| WO | 91/01743 | A1 | 2/1991 |
| WO | 92/09690 | A2 | 6/1992 |
| WO | 97/11178 | A1 | 3/1997 |
| WO | 98/22577 | A1 | 5/1998 |
| WO | 0103737 | A1 | 1/2001 |
| WO | 01/45746 | A2 | 6/2001 |
| WO | 02055532 | A2 | 7/2002 |
| WO | 02/077036 | A2 | 10/2002 |
| WO | 03/070765 | | 8/2003 |
| WO | 04029207 | A2 | 4/2004 |
| WO | 2004101739 | A2 | 11/2004 |
| WO | 2005001025 | A2 | 1/2005 |
| WO | 2005047334 | A1 | 5/2005 |
| WO | 2005047335 | A1 | 5/2005 |
| WO | 2005047336 | A1 | 5/2005 |
| WO | 2005047337 | A1 | 5/2005 |
| WO | 2006048777 | A2 | 5/2006 |
| WO | 2006/081249 | A2 | 8/2006 |
| WO | 2006/087354 | | 8/2006 |
| WO | 2006107124 | A1 | 10/2006 |
| WO | 2007/073486 | A2 | 6/2007 |
| WO | 2007068906 | A2 | 6/2007 |
| WO | 2007/103515 | A2 | 9/2007 |
| WO | 2008019368 | A2 | 2/2008 |
| WO | 2008/049711 | A1 | 5/2008 |
| WO | 2008/049931 | A1 | 5/2008 |
| WO | 08052108 | A2 | 5/2008 |
| WO | 08092117 | A2 | 7/2008 |
| WO | 2008147143 | A2 | 12/2008 |
| WO | 2008147456 | A2 | 12/2008 |
| WO | 2009015345 | A1 | 1/2009 |
| WO | 2009023270 | A2 | 2/2009 |
| WO | 2009/053368 | A1 | 4/2009 |
| WO | 09155513 | A2 | 12/2009 |
| WO | 2010/001196 | A1 | 1/2010 |
| WO | 2010011096 | A2 | 1/2010 |
| WO | 2011018227 | A2 | 2/2011 |
| WO | 2011059684 | A1 | 5/2011 |
| WO | 2011122921 | A2 | 10/2011 |
| WO | 2011/144756 | A1 | 11/2011 |
| WO | 2012008779 | A2 | 1/2012 |
| WO | 2012138920 | A1 | 10/2012 |
| WO | 2013004842 | A2 | 1/2013 |
| WO | 2013170272 | A2 | 11/2013 |
| WO | 2014/195452 | A1 | 12/2014 |
| WO | 2015/038938 | A1 | 3/2015 |
| WO | 15081073 | A2 | 6/2015 |
| WO | 15132364 | A1 | 9/2015 |
| WO | 2016/042093 | A1 | 3/2016 |
| WO | 2016133372 | A2 | 8/2016 |
| WO | 2016178905 | A1 | 11/2016 |
| WO | 2016193380 | A1 | 12/2016 |
| WO | 2017031034 | A2 | 2/2017 |
| WO | 2017055582 | A1 | 4/2017 |
| WO | 2018185131 | A2 | 10/2018 |

OTHER PUBLICATIONS

Arakawa, Takeshi et al. "A Plant-Based Cholera Toxin B Subunit—Insulin Fusion Protein Protects Against the Development of Autoimmune Diabetes." Nature Biotechnology 1998 vol. 16(10) pp. 934-938.

Abbasi et al. "Dendrimers: synthesis, applications, and properties." Nanoscale Research Letters 2014 vol. 9 No. 1; 247 pp. 1-10. EP SR.
Berg et al. "Biochemistry" 2002. W.H.Freeman and Co, New York p. 925, figure 33.8. EP SR.
Berthelmann et al. "Versatile C3-symmetric scaffolds and their use for covalent stabilization of the foldon trimer" Drganic and Biomolecular Chemistry. 2014 vol. 12 No. 16 pp. 2606-2614. EP SR.
Life Technologies. "Sulfhydryl-reactive Crosslinker Chemistry." 2015. Accessed Mar. 6, 2015. https://www.lifetechnologies.com/in/en/home/life-science/protein-biology/protein-biology-learning-center/protein-biology-resource-library/pierce-protein-methods/sulfhydryl-reactive-crosslinker-chemistry.html. ISR.
Kontermann R. E. et al., Strategies for extended serum half-life of protein therapeutics, Current Opinion in Biotechnology, 2011, vol. 22, No. 6, pp. 868-876.
Huang C., Receptor-Fc fusion therapeutics, traps, and MIMETIBODY technology, Current Opinion in Biotechnology, 2009, vol. 20, No. 6, pp. 692-699.
Chantalat L. et al., The Crystal Structure of Wild-Type Growth Hormone at 2.5 A resolution, Protein and Peptide Letters, 1995, vol. 2, No. 2, pp. 333-340.
De Vos A. M. et al., Human growth hormone and extracellular domain of its receptor: crystal structure of the complex, Science, 1992, vol. 255, pp. 306-312.
Cunningham B. C. et al., Rational design of receptor-specific variants of human growth hormone, Proceedings of the National Academy of Sciences, National Academy of Sciences, US, 1991, vol. 88, No. 8, XP00020231, pp. 3407-3411.
Cunningham B. C. et al., High-Resolution Epitope Mapping of hGH-Receptor Interactions by Alanine-Scanning Mutagenesis, Science, 1989, vol. 244, No. 4908, pp. 1081-1085.
Kasimova M. R. et al., NMR Studies of the Backbone Flexibility and Structure of Human Growth Hormone: A Comparison of High and Low pH Conformations, Journal of Molecular Biology, 2002, vol. 318, pp. 679-695.
Lee C. H. et al., Expression and characterization of human growth hormone-Fc fusion proteins for transcytosis induction, Biotechnology and Applied Biochemistry, 2007, vol. 46, pp. 211-217.
Wells, "Binding in the Growth Hormone Receptor Complex," Proc. Natl. Acad. Sci. USA, 1996, vol. 93, pp. 1-6.
Yang et al., "Activation of Growth Hormone Receptors by Growth Hormone and Growth Hormone Antagonist Dimers: Insights into Receptor Triggering," Mol. Endocrinol., 2008, vol. 22, No. 4, pp. 978-988.
Pearce et al., "Growth Hormone Binding Affinity for Its Receptor Surpasses the Requirements for Cellular Activity," Biochemistry, 1999, vol. 38, pp. 81-89.
Chen et al. "Fusion protein linkers: property, design and functionality." Advanced drug delivery reviews, Oct. 2013, vol. 65, No. 10, pp. 1357-1369.
Podust et al., Extension of in vivo half-life of biologically active peptides via chemical conjugation to XTEN protein polymer, Protein Engineering, Design & Selection,Oct. 16, 2013, vol. 26, No. 11, pp. 743-753.
Jochen G. Salfeld, "Isotype Selection in Antibody Engineering," Nature Biotechnology, Dec. 2007, vol. 25, pp. 1369-1372.

* cited by examiner

OLIGOMER EXTENDED INSULIN-FC CONJUGATES

CROSS-REFERENCE TO RELATED APPLICATIONS

This application is a 35 U.S.C. § 371 National Stage application of International Application PCT/EP2018/058550 (WO 2018/185131), filed Apr. 4, 2018, which claims priority to European Patent Applications EP17164950.2, filed Apr. 5, 2017, EP17208780.1, filed Dec. 20, 2017, EP18151228.6, filed Jan. 11, 2018 and Chinese Patent Application CN201810276163.0, filed Mar. 30, 2018; the contents of which are incorporated herein by reference.

TECHNICAL FIELD

This invention is in the field of protein conjugates. More specifically the invention relates to oligomer extended insulins with covalently attached Fc monomer polypeptides, for use in the treatment of a metabolic disorder or condition, and to methods of producing such oligomer extended insulin-Fc conjugates.

The invention also relates to novel Fc fragments, to intermediate products, and to the use of such intermediate products in processes for the synthesis of the oligomer extended insulin-Fc conjugates of the invention.

Finally the invention provides pharmaceutical compositions comprising the oligomer extended insulin-Fc conjugates of the invention, and relates to the use of such compositions for the treatment or prevention of medical conditions relating to metabolic disorders or conditions.

BACKGROUND

Oligomer extended insulins are insulins created by extending the A-chain and/or the B-chain of insulins with oligomers (made up of amino acid residues).

Fc-fusion proteins (sometimes called peptibodies) are chimeric proteins typically generated by fusing (i.e. joining two or more genes that originally coded for separate proteins) a biologically active polypeptide with the fragment crystallisable region (Fc-domain) of immunoglobulin G, and fusion proteins often combine the properties of their component parts, e.g. the IgG-like property of long serum half-life by virtue of binding to the neonatal Fc receptor, FcRn.

Protein conjugates, on the other hand, are compounds having a "large", typically recombinant, effector molecule (such as e.g. IgG-Fc or albumin), covalently bound to a therapeutic polypeptide via a synthetic linker (e.g. a PEG linker). Protein conjugates are useful in multiple situations, and the identification and development of biological therapeutic compounds of increasing complexity have increased the focus on attractive methods for preparing such compounds. Difficulties with linkage of two or more proteins arise as proteins are not as stable as traditional chemical moieties, and traditional reaction chemistry may not be applied without damaging the proteins. Furthermore, linking two or more proteins is complicated by selectivity issues.

The half-lives of proteins and peptides may be extended by fusion to Fc. However, as insulin is a two chain polypeptide, that is expressed as a single chain analogue followed by enzymatic processing to obtain the two chains polypeptide, it is not ideal for protein fusions. Furthermore fusions are limited to the N- and/or C-terminal. Therefore, e.g. in order to extend the half-life of insulin by the action of Fc, a chemical conjugation is needed.

When conjugating two proteins, the properties of the linker are important. A short linker might impact the activities of the respective proteins. Bringing the two proteins too close might impact the biophysical stability of the molecule. Linker properties which can affect this could be e.g. the position of conjugation on second molecule, length of linker, flexibility of linker, polarity of linker. In some cases a flexible linker is preferred and in other cases a stiff linker is needed. Conjugating molecules/proteins to a second molecule might have a negative impact on the biophysical properties of the conjugate, which might be solved by the linker properties.

WO 2011/122921 describes an insulin conjugate having improved in vivo duration, which conjugate is prepared by covalently linking insulin with an immunoglobulin Fc region via a hydrophilic non-peptidyl (e.g. PEG) linker, having a reactive group (e.g. aldehyde functionalities as propionaldehyde) at both ends, a so called homo-bifunctional linker. The PEG linkers used are polydisperse and of 3.4 KDa to 10 KDa in size, and the use of polydisperse linkers causes challenges for the synthesis and analysis of the final product.

WO 2016/178905 describes fusion proteins comprising an insulin receptor agonist fused to a human IgG Fc region through the use of a peptide linker.

WO 2016/193380 describes novel insulins or insulins analogues that are extended with sequences of predominantly polar amino acid residues in order to improve the half-life and stability of the drug substance.

The most common way to obtain site specific conjugates between proteins and peptides, small molecules or protractor polymers, is to exploit the unique nucleophilic properties of thiols of Cys and primary amino groups of the N-terminal amino acid, and the epsilon-$NH_2$ of Lys side chains, as reactive handles. Lysine is usually abundant in proteins (Fc contains more than 30 lysine residues), restricting the use of lysine as a chemical handle. However, in the case of insulin, only one lysine is present (i.e. at position B29). Cysteine's, on the other hand, are less frequently found in proteins, and moreover usually engaged in forming disulphide bridges. Cysteine can be introduced by genetically engineering. However, in the case of insulin, this modification has proven to be difficult, in particular due to low expression yields and various folding issues.

Also challenging is to site-specifically conjugate two proteins together through their respective Cys, N-terminal amino group or Lys residues. The use of a hetero-bifunctional linker can serve this purpose. Even more challenging becomes, in turn, the task of conjugating two proteins, in which one protein is to be connected through both sulphur atoms derived from a reduced disulphide bond.

BRIEF SUMMARY OF THE INVENTION

We have developed, and are providing herein, tri-antennary linkers in which at most two termini are identical and capable to form stable covalent bonds with reduced thiol moieties of a protein, while the remaining terminus remains unaffected of thiols or any other residue within that protein. This methodology is particularly well suited for conjugating the two proteins of interest via bridging across their native disulfides (upon their reduction to free thiols).

The oligomer extended insulin-Fc conjugates of the invention display reduction of insulin receptor affinity, compared to similar non-conjugated and non extended analogues. This reduction in insulin receptor affinity contributes to the protraction of the insulin-Fc conjugate in circulation, since insulin is internalised and degraded upon receptor activation. Hence, clearance of the insulin-Fc conjugate of the invention is reduced. This reduction of insulin receptor affinity probably does not cause a loss of potency, e.g., as measured in a standard hyperinsulinaemic euglycaemic clamp assay, and the combination of a high FcRn binding and a low insulin receptor affinity is considered beneficial for obtaining long duration of action of the insulin-Fc conjugates of the invention.

Accordingly, in its first aspect, the present invention provides novel oligomer extended insulin-Fc conjugates represented by Formula I:

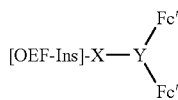

wherein, OEF, Ins, X, Y and Fc' are as defined below.

In another aspect, the present invention provides novel oligomer extended insulin-Fc conjugates represented by Formula I':

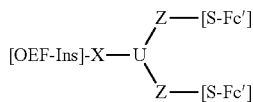

wherein, OEF, Ins, X, U, Z and S-Fc' are as defined below.

The insulin-Fc conjugates of the invention show improved pharmacokinetic and/or pharmacodynamic profiles.

In one aspect of the invention the compounds of the invention show increased pharmacodynamic potencies.

In another aspect of the invention the compounds of the invention show at least two fold increased pharmacodynamic potencies compared with currently marketed long-acting insulins.

In yet another aspect of the invention the compounds of the invention have increased solubility at physiological pH.

In another aspect of the invention the compounds of the invention have increased in vivo half-life.

In further aspects the present invention provides novel intermediate compounds, and relates to the use of such products in a process for the manufacture of the insulin-Fc conjugates of the invention.

In one aspect the invention provides novel [OEF-insulin] constructs for use as intermediates, i.e. an intermediate compound of Formula II:

[OEF-Ins]

wherein,

OEF represents a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue; and Ins represents an analogue of human insulin, which insulin analogue is a two-chain insulin molecule comprising an A- and a B-chain.

In another aspect, the invention provides novel Fc fragments for use in the manufacture of the insulin-Fc conjugate of the invention.

In a third aspect, the invention provides novel intermediates for use in the preparation of an oligomer extended insulin-Fc conjugate of the invention. The intermediate compound may be characterised by the general Formula V:

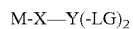

M-X—Y(-LG)$_2$ wherein

M represents a leaving group reactive towards primary amino groups;

X is as defined for Formula I below, and represents a divalent linking group; and Y is as defined for Formula I below, and represents a central trivalent linking unit, connecting the two leaving groups (LG)$_2$ to X; or X represents a covalent bond, and Y represents a central trivalent linking unit connecting the two leaving groups (LG)$_2$ to the leaving group M; and LG (that may also be designated as the Cys reactive terminus) represents the leaving group of a thiol reactive group.

In a fourth aspect the invention provides novel [OEF-Ins-X—Y(-LG)$_2$] constructs for use as intermediates in the preparation of an oligomer extended insulin-Fc conjugate of the invention. The intermediate compound according to the invention may be characterised by the general Formula VI:

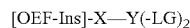

[OEF-Ins]-X—Y(-LG)$_2$ wherein,

OEF is as defined for Formula I below, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I below, and is connected to the divalent linking group X via a lysine (K) residue;

X is absent (i.e. represents a covalent bond), or X represents a divalent linking group as defined for Formula I below;

Y represents a central trivalent linking unit as defined for Formula I below; and LG represents the leaving group of a thiol reactive group, as defined above.

In a fifth aspect, the invention provides an Fc' polypeptide for use as an intermediate compound in the manufacture of an insulin-Fc conjugate of the invention.

Finally the invention provides pharmaceutical compositions comprising the insulin-Fc conjugates of the invention, and relates to the use of such conjugates for the treatment or prevention of medical conditions relating to diabetes.

DETAILED DESCRIPTION OF THE INVENTION

Protein Conjugates

Figure 1:
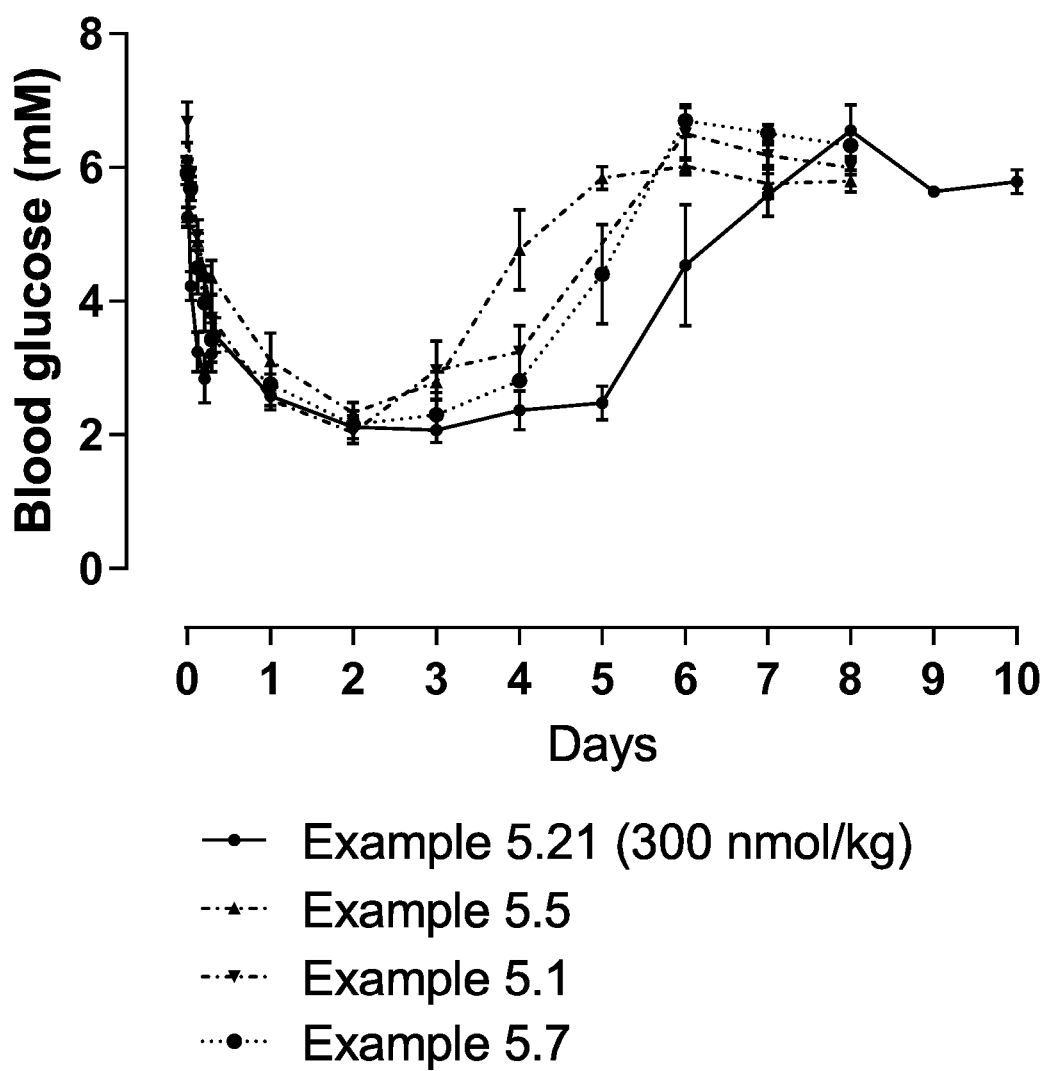
FIG. 1 shows the blood glucose lowering effect of the compounds of Examples 5.1, 5.5, 5.7, and 5.21. The compounds were administered (sc) to fed Sprague-Dawley rats in a dose of 30 nmol/kg (unless otherwise indicated).

In the context of this invention, protein conjugates represent compounds including two or more polypeptides (herein insulin or an insulin analogue, and an Fc domain or an Fc-domain analogue, respectively) that are covalently linked by chemical reactions.

Insulin Analogues

Human insulin consists of two polypeptide chains, i.e. the A-chain (a 21 amino acid peptide) and the B-chain (a 30 amino acid peptide), respectively, interconnected by two cysteine disulphide bridges. A third intra chain disulphide bridge is present in the A-chain.

Herein, the term insulin covers natural occurring insulins, e.g. human insulin, as well as analogues hereof. The numbering of the amino acid positions in insulin analogues, insulins and A- and B-chains, is done relative to human insulin.

Herein, the term insulin analogue covers a modified human insulin polypeptide which has a molecular structure which formally can be derived from the structure of a naturally occurring insulin, e.g. human insulin, by deleting and/or substituting (replacing) one or more amino acid residue occurring in the natural insulin, and/or by adding (extending) the insulin with one or more amino acid residues.

Herein terms like A1, A2, A3 etc. indicate position 1, 2 and 3, respectively, in the A-chain of insulin, when counted from the N-terminal end. Similarly, terms like B1, B2, B3 etc. indicates position 1, 2 and 3, respectively, in the B-chain of insulin, when counted from the N-terminal end. Using the established one letter codes for amino acids, terms like A21A, A21G and A21Q designate that the amino acid in the A21 position is A, G and Q, respectively. Using the established three letter codes for amino acids, the corresponding expressions are AlaA21, GlyA21 and GlnA21, respectively.

Herein terms like desB29 and desB30 indicate an insulin analogue lacking the B29 or B30 amino acid residue, respectively.

Herein the terms "A(−1)" or "B(−1)" indicate the positions of the amino acids N-terminally to A1 or B1, respectively. In this way the terms A(−2) and B(−2) indicate the positions of the first amino acids N-terminally to A(−1) and B(−1), respectively. Thus A(−3) and B(−3) indicate positions of the amino acids N-terminally to A(−2) and B(−2), respectively, and A(−4) and B(−4) indicate positions of the amino acids N-terminally to A(−3) and B(−3), respectively, and so forth.

The terms A22 and B31 indicate the positions of the amino acids C-terminally to A21 and B30, respectively. In this way the terms A23 and B32 indicate the positions of the first amino acids C-terminally to A22 and B31, respectively. Thus A24 and B33 indicate positions of the amino acids C-terminally to A23 and B32, respectively, and so forth. In this way A22G, A23G indicates that the C-terminal of the A chain has been extended with a glycine (G) residue C-terminally to position A21, followed by a glycine (G) residue located C-terminally to the glycine (G) residue at position A22 (A22G).

Nomenclature of Oligomer Extended Fusion Insulin Analogues

In the context of this invention, the oligomer extended insulin analogues [OEF-Ins] are named relative to human insulin by specification of amino acid deletions, substitutions, insertions and extensions.

In this way the compound (OEF-Ins-1) of Example 1 represents an analogue of human insulin (A14E, A21G, B25H, B29R, desB30), wherein the naturally occurring amino acid residues located in position A14 and A21 of the A-chain has been substituted for glutamic acid (E) and glycine (G) respectively, and wherein the naturally occurring amino acid residues located in position B25 and B29 have been substituted for histidine (H) and arginine (R), respectively, and position B30 has been deleted, and which analogue has been extended C-terminally from the A-chain, starting at amino acid position A22, with an extension made up of repeats of the four amino acid residues (GQEP), and in the specified order, to make up an extension consisting of a total of 76 amino acids residues (designated $(GQEP)_{19}$), followed by KP. The full extension may be designated as $(GQEP)_{19}$-KP (and the lysine is thus referred to as A98K).

This analogue may also be designated A14E, A21G, A22(GQEP)$_{19}$, A98K, A99P, B25H, B29R, desB30 human insulin, and the compound is illustrated in Chem. 1, below. A22(GQEP)$_{19}$ thus designates a (GQEP)$_{19}$ extension attached to A21, wherein the first amino acid of the extension (i.e. the amino acid attached to A21, in this example G) corresponds to the A22 position, i.e. in this example A22G.

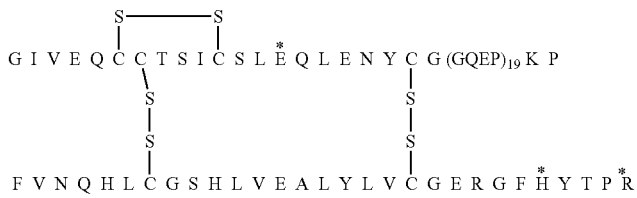

Chem. 1

In case of a N-terminal B-chain extension, e.g. the compound (OEF-Ins-4) of Example 1, represents an analogue of human insulin (A14E, B25H, B29R, desB30), wherein the naturally occurring amino acid residues located at position A14 of the A-chain has been substituted for glutamic acid (E), and wherein the naturally occurring amino acid residues located in positions B25 and B29 have been substituted for histidine (H) and arginine (R), respectively, and position B30 has been deleted, and which analogue has been extended starting N-terminally to the amino acid position B1 with an extension made up of repeats of the four amino acid residues (GQEP), in the specified order, to make up an extension consisting of a total of 76 amino acids residues (which may also be designated as $(GQEP)_{19}$) starting with KP. The full extension may designated as $KP-(GQEP)_{19}$. The lysine residue is thus referred to as B(−78K).

This analogue may also be designated A14E, B(−78K), B(−77P), B(−1)$(GQEP)_{19}$, B25H, B29R, desB30 human insulin, and the compound is illustrated in Chem. 2, below. B(−1)$(GQEP)_{19}$ thus designates a $(GQEP)_{19}$ extension attached to the N-terminus of the B-chain, wherein the last amino acid of the extension (i.e. the amino acid attached to B1, in this example P) corresponds to the B(−1) position, i.e. in this example B(−1P).

ment" or "Fc-domain" refers to the fragment crystallisable of an antibody. The Fc region is the tail of an antibody. For IgG antibodies, the Fc region contains two identical polypeptides (i.e. is a homo dimer), both comprising the second and third constant domains (CH2 and CH3) of the heavy chain. The Fc-domain may also be referred to as a dimer, as the two Fc polypeptides interact non-covalent and possibly also covalently, as hinge cysteine's may form disulphide bond(s). In the context of this invention, one Fc (monomeric) polypeptide of the Fc-domain is referred to as "Fc" or Fc' polypeptide (i.e. a monomer Fc molecule, as Fc= $(Fc')_2$). Also in the context of this invention, the protein sequences of the Fc-domain are referred to as "Fc' polypeptides", and comprise at least the CH2 and CH3 domains.

The hinge region is the protein segment between CH1 and CH2 of the constant region of the antibody.

The Fc region of human antibodies is glycosylated, and glycosylation is believed to be involved in C1q interactions, therefore C1q binding may be decreased by removing the glycosylation. Furthermore, aglycosylated Fc's have diminished or weak binding to the Fc gamma receptors I, IIa, IIb, and IIIa, respectively, which again allows for low Antibody-Dependent Cell-mediated Cytotoxicity (ADCC) and/or complement-dependent cytotoxicity (CDC).

Chem. 2

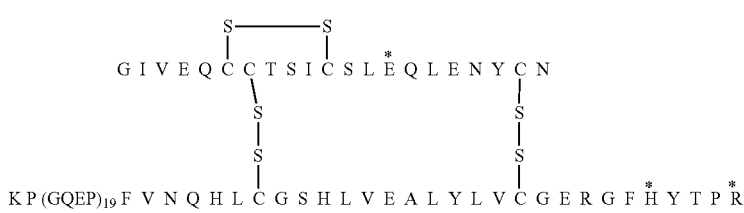

Antibodies and Fc-Domains

The Fc region is a C-terminal region of an IgG heavy chains, which is responsible for binding to Fc receptors that undertakes various functions, including recycling, which results in prolonged half-life. The Fc portion is typically derived from IgG, and conjugate moieties often include portions of the immunoglobulin sequence that include the FcRn binding site. FcRn, a salvage receptor, is responsible for recycling of immunoglobulins and returning them to circulation in blood. Mutations of the immunoglobulin Fc region are often introduced in order to modify certain properties, e.g. to obtain increased affinity for FcRn, to obtain prolonged half-life, or to reduce or increase binding to other receptors, to obtain reduced or increased immune effector functions.

The antibody isotype IgG is further grouped into subclasses (e.g. human IgG1, IgG2, IgG3 and IgG4) based on additional small differences in their amino acid heavy chain sequences.

The Fc-domain for use according to the invention may be derived from any IgG Fc, or a fragment thereof. In the context of this invention, the term "Fc region", "Fc frag- Glycosylation may be removed enzymatically. Production of Fc in *E. Coli* results in aglycosylated Fc. Techniques for the preparation of such sequence derivatives of the immunoglobulin Fc region are well known in the art, and are disclosed in e.g. WO 97/34631 and WO 96/32478.

The IgG derived Fc of the invention may be aglycosylated. The IgG derived Fc-fragment may in particular be an aglycosylated hIgG4 Fc-fragment, which naturally have weak binding to the Fc gamma receptor III.

EU Index of Kabat

The (Kabat) EU numbering scheme is a widely adopted standard for numbering the residues in an antibody in a consistent manner, developed on the basis of sequence alignment. In the context of this application the numbering of the residues in the Fc chain is done according to the EU index of Kabat (as described in Kabat et al., Sequences of Proteins of Immunological Interest, 5th Ed. Public Health Service, National Institutes of Health, Bethesda, Md. (1991)).

According to this invention, the native sequence of human IgG1-Fc starting at position 228 and ending at position 447 is designated hIgG1-Fc(228-447). As Fc consists of two identical polypeptides, only the sequence of one polypeptide is given (see SEQ ID NO:1). If proline (P) at position 228 is mutated into serine (S), the analogue is designated 228S hIgG1-Fc(228-447). In case of an N-terminal extension of the native sequence hIgG1-Fc(228-447), e.g. by alanine (A) and serine (S), this product is designated as 226A, 227S hIgG1-Fc(228-447).

Similarly, the native sequence of human IgG4-Fc starting at position 228 and ending at position 447 is designated hIgG4-Fc(228-447), and the sequence of the monomer polypeptide is given (see SEQ ID NO:3).

The Linker

In the context of this invention a linker is a chemical moiety or residue used to covalently link the proteins in question. As the linker reacts with the proteins, a linker radical is formed. The term "-linker-" is thus intended to mean the chemical unit of the insulin-Fc conjugate, which is covalently linked to an amino acid residue of each of the polypeptides of the protein conjugate.

Depending on the point of attachment, the reactivity of the linker ends may vary. The linker may have various forms, depending on the product in question. In one embodiment of the invention, the concept relates to an ordered conjugation to ensure that different proteins are attached at each end of the linker.

The terminal functional groups of the linker can bind to N-terminal, lysine, histidine or cysteine residues of the immunoglobulin Fc domain or the physiologically active polypeptide.

A reactive end is a chemical moiety that is useful for conjugation of the linker to an amino acid residue of a protein. The reactive end may be suited for linkage to the N-terminal, the C-terminal, or to internal amino acid residues. Various formats are known in the art, including chemical moieties that are amino acid residue specific, as well as moieties that are amino acid residue unspecific. Depending on the target protein in question it may be desired to use target specific amino acid residues in order to obtain a high yield and high homogeneity of the desired end product.

The reactive end (or group) may differ depending on which amino acid residue it is intended to target. Primary amino groups of an N-terminal amino acid or a lysine side chain may e.g. be targeted by an aldehyde, a ketone, or an activated carboxylic acid. These reactive ends are referred to as amino reactive ends. In one embodiment a primary amino reactive end comprises an aldehyde group (—CH(=O)), or an activated carboxylic group (active ester).

Conjugation with thiols can be obtained using various cysteine or thiol-reactive ends. The linker for use according to the invention may comprise one or more thiol or Cys reactive ends, separated by a spacer. The reactive ends of the linker may be referred to as Cys or thiol reactive ends. Additionally, the linker includes an amino reactive end. In one embodiment the thiol reactive end comprises a haloacetamide or a Michael acceptor.

Herein, the term thiol reactive groups cover, but is not limited to, haloacetamides, such as chloroacetamide, iodoacetamide and bromoacetamide groups, Michael acceptors, haloaryls, and un-symmetric disulphides, wherein the hetero-functional linker provides one of the mercapto functions in the unsymmetrical disulphide and the other functions as a leaving group. Examples of such unsymmetrical disulphides include pyridyldisulphides, (methoxy- or ethoxycarbonyl-)disulphides, and (o-nitrophenyl)disulphides.

According to this invention, the linker is used for linkage of insulin or an insulin analogue to an Fc-domain. The Fc-domain consists of two polypeptides that are usually held together by covalent and/or non-covalent bonds including inter-polypeptide disulphide-bond(s). Covalent linkage using a conventional bi-valent linker would link the protein to only one of the Fc polypeptides. However, using the trivalent linker (also referred to as tri antennary linker) according to the present invention, a protein conjugate where both of the two Fc polypeptide chains are linked to the insulin analogue is obtained.

Nomenclature of the Insulin-Fc Conjugates of the Invention

In the context of this invention, and for ease of information, the insulin-Fc conjugates of the invention are designated according to the peptide component parts (i.e. the insulin component and the immunoglobulin Fc component) constituting the conjugate of the invention, along with a specification of the (—X—Y—) linking group.

In this way the insulin-Fc conjugate of Example 5.1 (presented below as Chem. 3), which represents a conjugate linked through an A-chain C-terminal extension, may be designated as an (A14E, A21G, A22(GQEP)$_{19}$, A98K^, A99P, B25H, B29R, desB30 human insulin)/(227A, 234A, 235K hIgG4-Fc(228-447)) 4-[bis[2-[(2-acetyl)amino]ethyl]amino]-4-oxo-butanoyl conjugate, indicating that the compound is made up of an insulin component (i.e. A14E, A21G, A22(GQEP)$_{19}$, A98K A99P, B25H, B29R, desB30 human insulin) and an Fc component (i.e. 227A, 234A, 235K hIgG4-Fc(228-447)), conjugated via the trivalent linking group 4-[bis[2-[(2-acetyl)amino]ethyl]amino]-4-oxo-butanoyl (i.e. an —X—Y— linking group, wherein X represents the linker —C(O)—(CH$_2$)$_2$—C(O)—, and Y represents a compound of Formula IV, wherein L1=L2=—(CH$_2$)$_2$—), and L3=L4=-CH2-, corresponding to —C(O)—(CH$_2$)$_2$—C(O)—N(—(CH$_2$)$_2$—NH—C(O)—CH$_2$—)$_2$, and that the linker bridges the epsilon amino group of lysine A98K of the insulin component to —C(O)—, and each of the thiols of Cys229 of the Fc component polypeptides to —C(O)—CH2-.

Note that A98K^ indicates attachment point of X—Y— or X—U(Z)$_2$ to insulin. — thus indicates the position in [OEF-Ins] to which the divalent linking group X (Formula I and Formula I') is attached, or in case X is a covalent bond, — indicates the position in [OEF-Ins] to which the trivalent linking group Y (Formula I) or the trivalent linking group U (Formula I'), respectively, is attached.

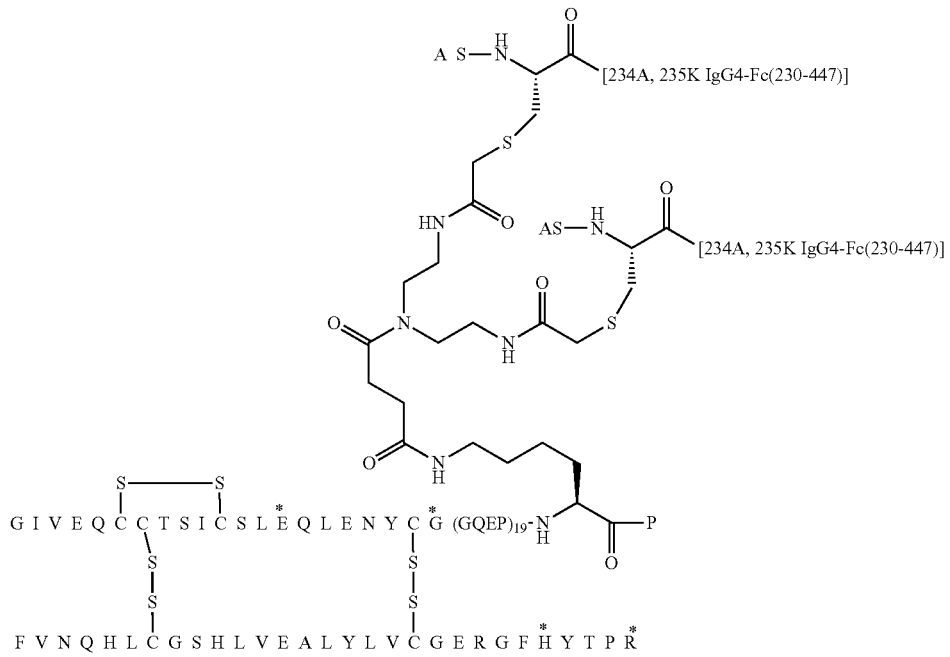

Chem. 3

In Chem. 3 the first three amino acids (i.e. A-S-C) of both Fc' polypeptide sequences are shown, and the third amino acids (i.e. Cys) are shown expanded. The mutations in the remaining part of the Fc' polypeptides (i.e. positions 230 to 447) are indicated in the brackets [e.g. 234A, 235K].

Likewise, a conjugate linked through a B-chain N-terminal extension (e.g. represented as Chem. 4, below), may be designated as an (A14E, B(-78K^), B(-77P), B(-1)(GQEP)$_{19}$, B25H, B29R, desB30 human insulin)/(227A, 234A, 235K hIgG4-Fc(228-447))4-[bis[2-[(2-acetyl)amino]ethyl]amino]-4-oxo-butanoyl conjugate (the insulin-Fc conjugate of Example 5.4), indicating that the compound is made up of an insulin component (i.e. A14E, B(-78K), B(-77P), B(-1)(GQEP)$_{19}$, B25H, B29R, desB30 human insulin) and an Fc component (i.e. 227A, 234A, 235K hIgG4-Fc(228-447)), conjugated via the linking group 4-[bis[2-[(2-acetyl)amino]ethyl]amino]-4-oxo-butanoyl (i.e. an —X—Y-linking group wherein X represents the linker —C(O)—(CH$_2$)$_2$—C(O)—, and Y represents a compound of Formula IV, wherein L3=L4=—CH$_2$—, and L1=L2=—(CH$_2$)$_2$—, corresponding to —C(O)—(CH$_2$)$_2$—C(O)—N(CH$_2$)$_2$—NH—C(O)—CH$_2$-)$_2$, and that the linker bridges B(-78K) of the insulin component and the thiols of Cys229 of the Fc component polypeptides.

Note that B(-78K⁻) indicates attachment point of X—Y— or X—U(Z)$_2$ to insulin.

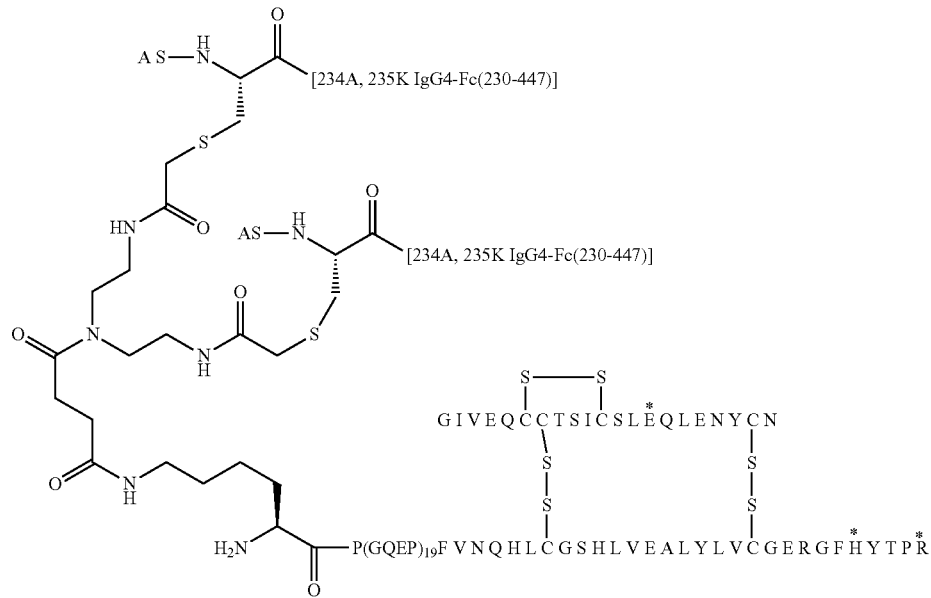

Chem. 4

In Chem. 4 the first three amino acids (i.e. A-S-C) of both Fc' polypeptide sequences are shown, and the third amino acids (i.e. Cys) are shown expanded. The mutations in the remaining part of the Fc' polypeptides (i.e. positions 230 to 447) are indicated in the brackets [e.g. 234A, 235K].

Insulin-Fc Conjugates of the Invention

In its first aspect, the present invention provides two monomer Fc polypeptides covalently joined with insulin via a linker.

More specifically, the present invention provides novel insulin-Fc conjugates represented by Formula I:

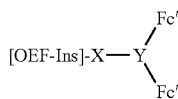

wherein,

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—Y via a lysine (K) residue; or more specifically, the [OEF-Ins] construct is connected to the trivalent linking group X—Y via the epsilon amino group of a lysine (K) residue;

X represents a covalent bond, or a divalent linking group, connecting [OEF-Ins] and Y;

Y represents a trivalent linking group, connecting the two Fc' via two sulphur atoms originating from a disulphide bridge of Fc to X; or, in case X represents a covalent bond, Y is connecting the two Fc' via two sulphur atoms to a lysine residue in the [OEF-Ins] construct (or more specifically, Y is connecting the two Fc' via two sulphur atoms to the epsilon amino group of a lysine residue in the [OEF-Ins] construct); and Fc' represents a monomer Fc polypeptide, or a fragment thereof.

In another embodiment, the present invention provides novel insulin-Fc conjugates represented by Formula I':

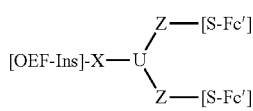

wherein

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—U(—Z)$_2$ via a lysine (K) residue; or more specifically, the [OEF-Ins] construct is connected to the trivalent linking group X—U(—Z)$_2$ via the epsilon amino group of a lysine (K) residue;

X represents a covalent bond, or a divalent linking group, connecting [OEF-Ins] and U;

U represents a central trivalent linking unit, connecting the two Z—[S-Fc'] groups to X;

or, in case X represents a covalent bond, U is connecting the two Z—[S-Fc'] groups to a lysine residue in the [OEF-Ins] construct; or more specifically, in case X represents a covalent bond, U is connecting the two Z—[S-Fc'] groups to the epsilon amino group of a lysine residue in the [OEF-Ins] construct;

Z represents a divalent linking group connecting the central linking unit (U) to a thiol moiety (S) of a monomer Fc polypeptide (Fc'), or a fragment thereof; and

[S-Fc'] represents a sulphur atom originating from a cysteine (C) residue comprised within the Fc' component; or more specifically, [S-Fc'] represents an Fc' component (i.e. a monomer Fc polypeptide, or a fragment thereof) with the S representing a sulphur atom originating from a cysteine (C) residue comprised within the Fc' component.

In a further embodiment, the present invention provides novel insulin-Fc conjugates represented by Formula I':

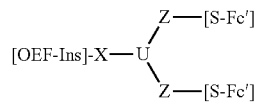

wherein

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—U(—Z)$_2$ via the epsilon amino group of a lysine (K) residue;

X represents a covalent bond, or a divalent linking group, connecting [OEF-Ins] and U;

U represents a central trivalent linking unit, connecting the two Z—[S-Fc'] groups to X;

or, in case X represents a covalent bond, U is connecting the two Z—[S-Fc'] groups to the epsilon amino group of a lysine residue in the [OEF-Ins] construct;

Z is absent or represents a divalent linking group connecting the central linking unit (U) to a thiol moiety (S) of a monomer Fc polypeptide (Fc'), or a fragment thereof; and

[S-Fc'] represents an Fc' component (i.e. a monomer Fc polypeptide, or a fragment thereof) with the S representing a sulphur atom originating from a cysteine (C) residue comprised within the Fc' component.

According to the present invention, Ins represents an analogue of human insulin containing one or more of the following substitutions: A14A or A14E, A21G or A21Q, B3E or B3Q, B16E or B16H, B25H, desB27, B29R, and/or desB30. Throughout this application, when used to describe insulin analogues, 'containing' has the same meaning as 'comprising'.

In one embodiment, Ins represents an analogue of human insulin optionally containing one or more of the following substitutions: A14A or A14E, A21G or A21Q, B3E or B3Q, B16E or B16H, B25H, desB27, B29R, and/or desB30.

In one embodiment, Ins represents an analogue of human insulin containing one or more of the following substitutions: A14A or A14E, A21G or A21Q, B3Q, B25H, B29R and/or desB30.

In yet another embodiment, Ins represents an analogue of human insulin comprising the desB30 deletion.

In a third embodiment, Ins represents an analogue of human insulin comprising the B29R substitution.

In a fourth embodiment, Ins represents an analogue of human insulin containing one or more of the following substitutions: A14E, A21G or A21Q, B3Q, B25H, B29R and/or desB30.

In a fifth embodiment, Ins represents an analogue of human insulin containing B29R, and containing one or more of the following substitutions: A14E, A21G or A21Q, B3Q, B25H and/or desB30.

In a sixth embodiment, Ins represents an analogue of human insulin containing B29R and being desB30, and containing one or more of the following substitutions: A14E, A21G or A21Q, B3Q and/or B25H.

In a seventh embodiment, Ins represents an analogue of human insulin containing A21G or A21Q, B29R and being desB30, and containing one or more of the following substitutions: A14E, B3Q and/or B25H.

In an eighth embodiment, the insulin analogue is selected from

A14A, A21G, B29R, desB30 human insulin (A-chain of SEQ ID NO:52; B-chain of SEQ ID NO:26);

A14E, A21G, B3Q, B25H, B29R, desB30 human insulin (A-chain of SEQ ID NO:47; B-chain of SEQ ID NO:23);

A14E, A21G, B3Q, B29R, desB30 human insulin (A-chain of SEQ ID NO:47; B-chain of SEQ ID NO:48);

A14E, A21G, B25H, B29R, desB30 human insulin (A-chain of SEQ ID NO:47; B-chain of SEQ ID NO:21);

A14E, A21G, B29R, desB30 human insulin (A-chain of SEQ ID NO:47; B-chain of SEQ ID NO:26);

A14E, A21Q, B25H, B29R, desB30 human insulin (A-chain of SEQ ID NO:49; B-chain of SEQ ID NO:21);

A14E, B3Q, B25H, B29R, desB30 human insulin (A-chain of SEQ ID NO:8; B-chain of SEQ ID NO:23);
A14E, B3Q, B29R, desB30 human insulin (A-chain of SEQ ID NO:8; B-chain of
SEQ ID NO:48);

A14E, B25H, B29R, desB30 human insulin (A-chain of SEQ ID NO:8; B-chain of SEQ ID NO:21);

A14E, B29R, desB30 human insulin (A-chain of SEQ ID NO:8; B-chain of SEQ ID NO:26);

A21G, B3Q, B29R, desB30 human insulin (A-chain of SEQ ID NO:76; B-chain of SEQ ID NO:48);

A21G, B29R, desB30 human insulin (A-chain of SEQ ID NO:76; B-chain of SEQ ID NO:26);

B3Q, B29R, desB30 human insulin (A-chain of SEQ ID NO:50; B-chain of SEQ ID NO:48); and B29R, desB30 human insulin (A-chain of SEQ ID NO:50; B-chain of SEQ ID NO:26).

In a ninth embodiment, the insulin analogue is selected from

A14A, A21G, B29R, desB30 human insulin (A-chain of SEQ ID NO:52; B-chain of SEQ ID NO:26);

A14E, A21G, B3Q, B25H, B29R, desB30 human insulin (A-chain of SEQ ID NO:47; B-chain of SEQ ID NO:23);

A14E, A21G, B25H, B29R, desB30 human insulin (A-chain of SEQ ID NO:47; B-chain of SEQ ID NO:21);

A14E, A21G, B29R, desB30 human insulin (A-chain of SEQ ID NO:47; B-chain of SEQ ID NO:26);

A14E, A21Q, B25H, B29R, desB30 human insulin (A-chain of SEQ ID NO:49; B-chain of SEQ ID NO:21);

A14E, B3Q, B25H, B29R, desB30 human insulin (A-chain of SEQ ID NO:8; B-chain of SEQ ID NO:23); and A14E, B25H, B29R, desB30 human insulin (A-chain of SEQ ID NO:8; B-chain of SEQ ID NO:21).

In a tenth embodiment, the insulin analogue is selected from

A14A, A21G, B29R, desB30 human insulin (A-chain of SEQ ID NO:52; B-chain of SEQ ID NO:26);

A14E, A21G, B3Q, B25H, B29R, desB30 human insulin (A-chain of SEQ ID NO:47; B-chain of SEQ ID NO:23);

A14E, A21G, B3Q, B29R, desB30 human insulin (A-chain of SEQ ID NO:47; B-chain of SEQ ID NO:48);

A14E, A21G, B25H, B29R, desB30 human insulin (A-chain of SEQ ID NO:47; B-chain of SEQ ID NO:21);

A14E, A21G, B29R, desB30 human insulin (A-chain of SEQ ID NO:47; B-chain of SEQ ID NO:26);

A14E, A21Q, B25H, B29R, desB30 human insulin (A-chain of SEQ ID NO:49; B-chain of SEQ ID NO:21);

A14E, B3Q, B25H, B29R, desB30 human insulin (A-chain of SEQ ID NO:8; B-chain of SEQ ID NO:23);

A14E, B3Q, B29R, desB30 human insulin (A-chain of SEQ ID NO:8; B-chain of SEQ ID NO:48);

A14E, B25H, B29R, desB30 human insulin (A-chain of SEQ ID NO:8; B-chain of SEQ ID NO:21);

A14E, B29R, desB30 human insulin (A-chain of SEQ ID NO:8; B-chain of SEQ ID NO:26);

A14E, A21G, B16E, B25H, B29R, desB30 human insulin (A-chain of SEQ ID NO:47; B-chain of SEQ ID NO:29);

A14E, A21G, B16H, B25H, B29R, desB30 human insulin (A-chain of SEQ ID NO:47; B-chain of SEQ ID NO:51);

A21G, B3Q, B29R, desB30 human insulin (A-chain of SEQ ID NO:76; B-chain of SEQ ID NO:48);

A21G, B29R, desB30 human insulin (A-chain of SEQ ID NO:76; B-chain of SEQ ID NO:26);

B3Q, B29R, desB30 human insulin (A-chain of SEQ ID NO:50; B-chain of SEQ ID NO:48);

B29R, desB30 human insulin (A-chain of SEQ ID NO:50; B-chain of SEQ ID NO:26);

A21G, B29R, desB30 human insulin (A-chain of SEQ ID NO:76; B-chain of SEQ ID NO:26); and A14E, A21G, B16E, B25H, B29R, desB30 human insulin (A-chain of SEQ ID NO:47; B-chain of SEQ ID NO:29).

In an eleventh embodiment, the insulin analogue is selected from

A14E, A21G, B25H, B29R, desB30 human insulin (A-chain of SEQ ID NO:47; B-chain of SEQ ID NO:21);

A14E, B3Q, B25H, B29R, desB30 human insulin (A-chain of SEQ ID NO:8; B-chain of SEQ ID NO:23);

A14E, A21G, B3Q, B25H, B29R, desB30 human insulin (A-chain of SEQ ID NO:47; B-chain of SEQ ID NO:23);

A14E, B25H, B29R, desB30 human insulin (A-chain of SEQ ID NO:8; B-chain of SEQ ID NO:21);

A14E, A21G, B29R, desB30 human insulin (A-chain of SEQ ID NO:47; B-chain of SEQ ID NO:26);

A14A, A21G, B29R, desB30 human insulin (A-chain of SEQ ID NO:52; B-chain of SEQ ID NO:26);

A21G, B29R, desB30 human insulin (A-chain of SEQ ID NO:76; B-chain of SEQ ID NO:26); and A14E, A21G, B16E, B25H, B29R, desB30 human insulin (A-chain of SEQ ID NO:47; B-chain of SEQ ID NO:29).

The OEF-Insulin Construct

According to the present invention, the entire sequence of the OEF-insulin construct contains one lysine (K) residue only.

Also according to the present invention, the construct OEF-Ins is connected to the divalent linking group X via a terminal lysine (K) residue (only in case of A-chain extensions), or via the lysine (K) residue in the terminal KP sequence (for both A-chain and B-chain extensions).

The OEF-Ins construct of the invention may be connected to the divalent linking group X according to Formula I, or according to Formula I', via a terminal lysine (K) residue, or via the lysine (K) residue in a terminal KP sequence, introduced at the C-terminus of the insulin A-chain, or of any extension of the insulin A-chain.

Alternatively, when X represents a covalent bond, the OEF-Ins construct of the invention is connected to the trivalent linking group —Y according to Formula I, or to the central trivalent linking unit U according to Formula I', via a terminal lysine (K) residue, or via the lysine (K) residue in a terminal KP sequence, introduced at the C-terminus of the insulin A-chain, or of any extension of the insulin A-chain.

In one embodiment, OEF indicates a polar recombinant extension fused C-terminally to the insulin A-chain, which extension is terminated by a lysine (K) residue, or by the KP sequence.

In another embodiment, the OEF is fused C-terminally to the insulin A-chain, which extension is terminated by a lysine (K) residue.

In a third embodiment, the OEF is fused C-terminally to the insulin A-chain, which extension is terminated by the KP sequence (added in the direction stated).

The construct OEF-Ins of the invention may also be connected to the divalent linking group X according to Formula I, or according to Formula I', via a terminal lysine (K) residue, or via the lysine (K) residue in the KP sequence, introduced at the N-terminus of the insulin B-chain, or of any extension of the insulin B-chain.

Alternatively, when X represents a covalent bond, the [OEF-Ins] construct of the invention is connected to the trivalent linking group Y according to Formula I, or to the central trivalent linking unit U according to Formula I', via a terminal lysine (K) residue, or via the lysine (K) residue in the KP sequence, introduced at the N-terminus of the insulin B-chain, or of any extension of the insulin B-chain.

In one embodiment, OEF indicates a polar recombinant extension fused N-terminally to the insulin B-chain, which extension starts with a lysine (K) residue, or with the KP sequence (in the direction stated).

In another embodiment, the OEF is fused N-terminally to the insulin B-chain, which extension starts with a lysine (K) residue.

In a third embodiment, the OEF is fused N-terminally to the insulin B-chain, which extension starts with a lysine (K) residue, followed by a proline (P) residue.

According to the present invention, OEF indicates a polar recombinant extension, which extension is made up of amino acid residues selected from the group consisting of alanine (A), aspartic acid (D), glutamic acid (E), glycine (G), proline (P), glutamine (Q), serine (S) and threonine (T), and in a combination with the lysine (K) residue (or the KP sequence), as described above.

It shall be noted that the OEF introduced according to the invention is not indented for, and does not contribute significantly to the extended half-life observed for the insulin-Fc conjugates of the invention, but in the context of the present invention, the OEF happens to provide a suitable spacing group/linker, thereby avoiding shielding of the insulin analogue, and the OEF also introduce a better (improved) solubility and/or improved glycodynamic potency.

In one embodiment, the polar recombinant extension is made up of amino acid residues selected from the group consisting of alanine (A), glutamic acid (E), glycine (G), proline (P), glutamine (Q), and serine (S), and in a combination with the lysine (K) residue (or the KP sequence), as described above.

In order to achieve its purpose, the polar recombinant OEF extensions should not be too large, and it is currently believed that the overall length of the OEF according to the invention shall be between 1 to and about 130 amino acid residues.

In one embodiment, the overall length of the OEF according to the invention shall be between 1 to and about 105 amino acid residues.

In another embodiment, the overall length of the OEF according to the invention shall be between 1 to and about 90 amino acid residues.

In a third embodiment, the overall length of the OEF according to the invention shall be between 1 to and about 80 amino acid residues.

In a fourth embodiment, the overall length of the OEF according to the invention shall be between 15 and 110 amino acid residues.

The polar recombinant OEF extension may in particular be represented by contiguous amino acid residues selected from A) a polyglycine sequence $(Gly)_x$ (Group A), wherein x represents an integer in the range of from 2 to about 102, and in a combination with K or KP as described above;

B) the group of $[A, G \text{ and } Q]_x$ (Group B), in random order or in any combination, wherein x represents an integer in the range of from 1 to about 30, and in a combination with K or KP as described above;

C) the group of $[A, P \text{ and } S]_x$ (Group C), in random order or in any combination, wherein x represents an integer in the range of from 1 to about 30, and in a combination with K or KP as described above;

D) the group of $[E, G \text{ and } Q]_x$ (Group D), in random order or in any combination, wherein x represents an integer in the range of from 1 to about 30, and in a combination with K or KP as described above;

E) the group of $[A, G, P \text{ and } Q]_x$ (Group E), in random order or in any combination, wherein x represents an integer in the range of from 1 to about 25, and in a combination with K or KP as described above;

F) the group of $[A, G, P \text{ and } S]_x$ (Group F), in random order or in any combination, wherein x represents an integer in the range of from 1 to about 25, and in a combination with K or KP as described above;

G) the group of $[E, G, P \text{ and } Q]_x$ (Group G), in random order or in any combination, wherein x represents an integer in the range of from 1 to about 25, and in a combination with K or KP as described above;

H) the group of $[E, G, P \text{ and } S]_x$ (Group H), in random order or in any combination, wherein x represents an integer in the range of from 1 to about 25, and in a combination with K or KP as described above;

I) the group of $[A, E, G, P \text{ and } Q]_x$ (Group I), in random order or in any combination, wherein x represents an integer in the range of from 1 to about 20, and in a combination with K or KP as described above; and J) the group of [A, E, G, P, S and T]$_x$ (Group J), in random order or in any combination, wherein x represents an integer in the range of from 1 to about 20, and in a combination with K or KP as described above;

and/or any combination of Groups A, B, C, D, E, F, G, H, I and 3.

In one embodiment, the polar recombinant OEF extension is represented by non-repeating sequences selected from any one of Groups B-H, i.e. sequences of random order.

In another embodiment, the polar recombinant OEF extension is represented by repeating sequences, or motifs of sequences, of amino acid residues selected from Groups B-H, i.e. sequences of certain motifs.

In a further embodiment, the polar recombinant OEF extension is represented by repeating motifs of amino acid residues selected from Groups B-H, in which sequence the terminal motif may be truncated in order to exclude an unwanted amino acid residue (and in particular proline (P)) to become located a terminal position.

The polar recombinant OEF extension for use according to the invention may in particular be represented by contiguous amino acid residues selected from Group A, i.e. a polyglycine sequence (Gly)$_x$, wherein x represents an integer in the range of from 2 to about 102, and in a combination with K or KP as described above (i.e. (Gly)$_x$-KP for A-chain extensions; and KP-(Gly)$_x$ for B-chain extensions).

In one embodiment, x represents an integer in the range of from 2 to about 90; or x represents an integer in the range of from 2 to about 75; or x represents an integer in the range of from 2 to about 50; or x represents an integer in the range of from 2 to about 35, or x represents an integer in the range of from 2 to about 30, or x represents an integer in the range of from 2 to about 25, or x represents an integer in the range of from 2 to about 20, or x represents an integer in the range of from 2 to about 18.

In another embodiment, the polar recombinant OEF extension of Group A is (Gly)$_{18}$.

The polar recombinant OEF extension for use according to the invention may also be represented by contiguous amino acid residues selected from Group B, i.e. [A, G and Q]$_x$, in random order or in any combination, wherein x represents an integer in the range of from 1 to about 30, and which sequence of Group B is further combined with K or KP as described above (i.e. [A,G,Q]$_x$-KP for A-chain extensions; and KP-[A,G,Q]$_x$ for B-chain extensions).

In one embodiment, the polar recombinant OEF extension of Group B may further be represented by one or more of the following motifs: (AGQ)$_x$, (GAQ)$_x$, (GQA)$_x$, (AQG)$_x$, (QGA)$_x$, and (QAG)$_x$; wherein x represents an integer in the range of from 1 to about 30, and in a combination with K or KP as described above.

In another embodiment, x represents an integer in the range of from 1 to about 30.

In further embodiments, x represents an integer in the range of from 1 to about 25; or x represents an integer in the range of from 1 to about 20; or x represents an integer in the range of from 1 to about 15; or x represents an integer in the range of from 1 to about 10.

The polar recombinant OEF extension for use according to the invention may also be represented by contiguous amino acid residues selected from Group C, i.e. [A, P and S]$_x$, in random order or in any combination, wherein x represents an integer in the range of from 1 to about 30, and which sequence of Group C is further combined with K or KP as described above (i.e. [A,P,S]$_x$-KP for A-chain extensions; and KP-[A,P,S]$_x$ for B-chain extensions).

In one embodiment, the polar recombinant OEF extension of Group C may further be represented by one or more of the following motifs: (APS)$_x$, (PAS)$_x$, (PSA)$_x$, (ASP)$_x$, (SPA)$_x$, (SAP)$_x$; wherein x represents an integer in the range of from 1 to about 30, and in a combination with K or KP as described above.

In case the OEF extension of Group C is represented by the motifs (PAS)$_x$, (PSA)$_x$, or (SAP)X, the extension is not terminated by a proline (P) residue, i.e. the terminal motif may be truncated (exemplified by e.g. SA), resulting in a C-terminal motif of two amino acid residues, followed by KP (exemplified by e.g. SA-KP).

In another embodiment, x represents an integer in the range of from 1 to about 30.

In further embodiments, x represents an integer in the range of from 1 to about 25; or x represents an integer in the range of from 1 to about 20; or x represents an integer in the range of from 1 to about 15; or x represents an integer in the range of from 1 to about 10.

The polar recombinant OEF extension for use according to the invention may also be represented by contiguous amino acid residues selected from Group D, i.e. [E, G and Q]$_x$, in random order or in any combination, wherein x represents an integer in the range of from 1 to about 30, and which sequence of Group D is further combined with K or KP as described above (i.e. [E,G,Q]$_x$-KP for A-chain extensions; and KP-[E,G,Q]$_x$ for B-chain extensions).

In one embodiment, the polar recombinant OEF extension of Group D may further be represented by one or more of the following motifs: (EGQ)$_x$, (GEQ)$_x$, (GQE)$_x$, (EQG)$_x$, (QGE)$_x$, and (QEG)$_x$; wherein x represents an integer in the range of from 1 to about 30, and in a combination with K or KP as described above.

In another embodiment, x represents an integer in the range of from 1 to about 30.

In further embodiments, x represents an integer in the range of from 1 to about 25; or x represents an integer in the range of from 1 to about 20; or x represents an integer in the range of from 1 to about 15; or x represents an integer in the range of from 1 to about 10.

The polar recombinant OEF extension for use according to the invention may also be represented by contiguous amino acid residues selected from Group E, i.e. the group of [A, G, P and Q]$_x$, in random order or in any combination, wherein x represents an integer in the range of from 1 to about 25, and which sequence of Group E is further combined with K or KP as described above (i.e. [A,G,P,Q]$_x$-KP for A-chain extensions; and KP-[A,G,P,Q]$_x$ for B-chain extensions).

In one embodiment, the polar recombinant OEF extension of Group E may further be represented by one or more of the following motifs: (AGPQ)$_x$, (GAPQ)$_x$, (GPAQ)$_x$, (GPQA)$_x$, (APGQ)$_x$, (PAGQ)$_x$, (PGAQ)$_x$, (PGQA)$_x$, (AQGP)$_x$, (QAGP)$_x$, (QGAP)$_x$, (QGPA)$_x$, (APQG)$_x$, (PAQG)$_x$, (PQGA)$_x$, (PQAG)$_x$, (AGQP)$_x$, (GAQP)$_x$, (GQPA)$_x$, (GQAP)$_x$; wherein x represents an integer in the range of from 1 to about 25, and in a combination with K or KP as described above.

In case the OEF extension of Group E is represented by the motifs (PAGQ)$_x$, (PGAQ)$_x$, (PGQA)$_x$, (PAQG)$_x$, (PQGA)$_x$, (PQAG)$_x$, (AQGP)$_x$, (QAGP)$_x$, (QGAP)$_x$, (AGQP)$_x$, (GAQP)$_x$, or (GQAP)$_x$, the extension is not always terminated by a proline (P) residue, i.e. the terminal motif may be truncated (exemplified by e.g. AQG, QAG, QGA, AGQ, GAQ, and GQA), resulting in a C-terminal motif of three amino acid residues, followed by KP (exemplified by e.g. GQA-KP).

In another embodiment, the polar recombinant OEF extension of Group E is selected from $(GQAP)_x$, $(GQPA)_x$, $(GPQA)_x$, $(GPAQ)_x$, $(GAQP)_x$ and $(GAPQ)_x$; wherein x represents an integer in the range of from 1 to about 25, and in a combination with K or KP as described above.

In a third embodiment, the polar recombinant OEF extension of Group E is an A-chain extension represented by $(GQAP)_x$-KP; $(GQAP)_x$-GQA-KP; $(GQPA)_x$-KP; $(GPQA)_x$-KP; $(GPAQ)_x$-KP; $(GAQP)_x$-KP; $(GAQP)_x$-GAQ-KP; $(GAPQ)_x$-KP; $(GQAP)_x$-GQA-KP; or a B-chain extension represented by KP-$(GQAP)_x$; KP-$(GQPA)_x$; KP-$(GPQA)_x$; KP-$(GPAQ)_x$; KP-$(GAQP)_x$; KP-$(GAPQ)_x$;

wherein x represents an integer in the range of from 1 to about 25.

In further embodiments, x represents an integer in the range of from 1 to about 25; or x represents an integer in the range of from 1 to about 20; or x represents an integer in the range of from 1 to about 15; or x represents an integer in the range of from 1 to about 10.

In an even further embodiment, x represents 19.

The polar recombinant OEF extension for use according to the invention may also be represented by contiguous amino acid residues selected from Group F, i.e. the group of [A, G, P and S]$_x$, in random order or in any combination, wherein x represents an integer in the range of from 1 to about 25, and which sequence of Group F is further combined with K or KP as described above (i.e. [A,G,P,S]$_x$-KP for A-chain extensions; and KP-[A,G,P,S]$_x$ for B-chain extensions).

In one embodiment, the polar recombinant OEF extension of Group F may further be represented by one or more of the following motifs: $(AGPS)_x$, $(GAPS)_x$, $(GPAS)_x$, $(GPSA)_x$, $(APGS)_x$, $(PAGS)_x$, $(PGAS)_x$, $(PGSA)_x$, $(ASGP)_x$, $(SAGP)_x$, $(SGAP)_x$, $(SGPA)_x$, $(APSG)_x$, $(PASG)_x$, $(PSGA)_x$, $(PSAG)_x$, $(AGSP)_x$, $(GASP)_x$, $(GSPA)_x$, $(GSAP)_x$; wherein x represents an integer in the range of from 1 to about 25, and in a combination with K or KP as described above.

In case the OEF extension of Group F is represented by the motifs $(PAGS)_x$, $(PGAS)_x$, $(PGSA)_x$, $(PASG)_x$, $(PSGA)_x$, $(PSAG)_x$, $(ASGP)_x$, $(SAGP)_x$, $(SGAP)_x$, $(SGPA)_x$, $(AGSP)_x$, $(GASP)_x$, $(GSPA)_x$, $(GSAP)_x$, the extension is not terminated by a proline (P) residue, i.e. the terminal motif may be truncated (exemplified by e.g. ASG, SAG, SGA, AGS, GAS, and GSA), resulting in a C-terminal motif of three amino acid residues, followed by KP (exemplified by e.g. SAG-KP).

In further embodiments, x represents an integer in the range of from 1 to about 25; or x represents an integer in the range of from 1 to about 20; or x represents an integer in the range of from 1 to about 15; or x represents an integer in the range of from 1 to about 10.

The polar recombinant OEF extension for use according to the invention may also be represented by contiguous amino acid residues selected from Group G, i.e. the group of [E, G, P and Q]$_x$, in random order or in any combination, wherein x represents an integer in the range of from 1 to about 25, and which sequence of Group G is further combined with K or KP as described above (i.e. [E,G,P,Q]$_x$-KP for A-chain extensions; and KP-[E,G,P,Q]$_x$ for B-chain extensions).

In one embodiment, the polar recombinant OEF extension of Group G may further be represented by one or more of the following motifs: $(EGPQ)_x$, $(GEPQ)_x$, $(GPEQ)_x$, $(GPQE)_x$, $(EPGQ)_x$, $(PEGQ)_x$, $(PGEQ)_x$, $(PGQE)_x$, $(EQGP)_x$, $(QEGP)_x$, $(QGEP)_x$, $(QGPE)_x$, $(EPQG)_x$, $(PEQG)_x$, $(PQGE)_x$, $(PQEG)_x$, $(EGQP)_x$, $(GEQP)_x$, $(GQPE)_x$, $(GQEP)_x$; wherein x represents an integer in the range of from 1 to about 25, and in a combination with K or KP as described above.

In case the OEF extension of Group G is represented by the motifs $(PEGQ)_x$, $(PGEQ)_x$, $(PGQE)_x$, $(PEQG)_x$, $(PQGE)_x$, $(PQEG)_x$, $(EQGP)_x$, $(QEGP)_x$, $(QGEP)_x$, $(EGQP)_x$, $(GEQP)_x$, or $(GQEP)_x$, the extension is not always terminated by a proline (P) residue, i.e. the terminal motif may be truncated (exemplified by e.g. EQG, QEG, QGE, EGQ, GEQ, and GQE), resulting in a C-terminal motif of three amino acid residues, followed by KP (exemplified by e.g. GQE-KP).

In another embodiment, the polar recombinant OEF extension of Group G is selected from $(GQEP)_x$, $(GQPE)_x$, $(GPQE)_x$, $(GPEQ)_x$, $(GEQP)_x$, $(GEPQ)_x$; wherein x represents an integer in the range of from 1 to about 25, and in a combination with K or KP as described above.

In a third embodiment, the polar recombinant OEF extension of Group G is an A-chain extension represented by $(GQEP)_x$-KP, $(GQEP)_x$-GQE-KP, $(GQPE)_x$-KP, $(GPQE)_x$-KP, $(GPEQ)_x$-KP, $(GEQP)_x$-KP, $(GEQP)_x$-GEQ-KP, $(GEPQ)_x$-KP, or $(GQEP)_x$-GQE-KP; or a B-chain extension represented by KP-$(GQEP)_x$, KP-$(GQPE)_x$, KP-$(GPQE)_x$, KP-$(GPEQ)_x$, KP-$(GEQP)_x$ and KP-$(GEPQ)_x$;

wherein x represents an integer in the range of from 1 to about 25.

In further embodiments, x represents an integer in the range of from 1 to about 20, or x represents an integer in the range of from 1 to about 15.

In an even further embodiment, the polar recombinant OEF extension of Group G is an A-chain extension represented by $(GQEP)_3$-GQE-KP, $(GQEP)_6$-KP, $(GQEP)_{12}$-KP, or $(GQEP)_{19}$-KP;

or a B-chain extension represented by KP-$(GQEP)_4$, KP-$(GQEP)_6$ or KP-$(GQEP)_{19}$.

The polar recombinant OEF extension for use according to the invention may also be represented by contiguous amino acid residues selected from Group H, i.e. the group of [E, G, P and S]$_x$, in random order or in any combination, wherein x represents an integer in the range of from 1 to about 25, and which sequence of Group H is further combined with K or KP as described above (i.e. [E,G,P,S]$_x$-KP for A-chain extensions; and KP-[E,G,P,S]$_x$ for B-chain extensions).

In one embodiment, the polar recombinant OEF extension of Group H may further be represented by one or more of the following motifs: $(EGPS)_x$, $(GEPS)_x$, $(GPES)_x$, $(GPSE)_x$, $(EPGS)_x$, $(PEGS)_x$, $(PGES)_x$, $(PGSE)_x$, $(ESGP)_x$, $(SEGP)_x$, $(SGEP)_x$, $(SGPE)_x$, $(EPSG)_x$, $(PESG)_x$, $(PSGE)_x$, $(PSEG)_x$, $(EGSP)_x$, $(GESP)_x$, $(GSPE)_x$, and $(GSEP)_x$; wherein x represents an integer in the range of from 1 to about 25, and in a combination with K or KP as described above.

In case the OEF extension of Group H is represented by the motifs $(PEGS)_x$, $(PGES)_x$, $(PGSE)_x$, $(PESG)_x$, $(PSGE)_x$, $(PSEG)_x$, $(ESGP)_x$, $(SEGP)_x$, $(SGEP)_x$, $(EGSP)_x$, $(GESP)_x$, or $(GSEP)_x$, the extension is not terminated by a proline (P) residue, i.e. the terminal motif may be truncated (exemplified by e.g. ESG, SEG, SGE, EGS, GES, and GSE), resulting in a C-terminal motif of three amino acid residues, followed by KP (exemplified by e.g. SEG-KP).

In further embodiments, x represents an integer in the range of from 1 to about 20, or x represents an integer in the range of from 1 to about 15.

The polar recombinant OEF extension for use according to the invention may also be represented by contiguous amino acid residues selected from Group I, i.e. the group of [A, E, G, P and Q]$_x$, in random order or in any combination, wherein x represents an integer in the range of from 1 to about 20, and which sequence of Group I is further combined with K or KP as described above (i.e. [A,E,G,P,Q]$_x$-KP for A-chain extensions; and KP-[A,E,G,P,Q]$_x$ for B-chain extensions).

In one embodiment, the polar recombinant OEF extension of Group I may further be represented by one or more of the following motifs: (AEGPQ)$_x$, (EAGPQ)$_x$, (EGAPQ)$_x$, (EGPAQ)$_x$, (EGPQA)$_x$, (AGEPQ)$_x$, (GAEPQ)$_x$, (GEAPQ)$_x$, (GEPAQ)$_x$, (GEPQA)$_x$, $_x$, (AEPGQ)$_x$, (EAPGQ)$_x$, (EPAGQ)$_x$, (EPGAQ)$_x$, (EPGQA)$_x$, (AEGQP)$_x$, (EAGQP)$_x$, (EGAQP)$_x$, (EGQAP)$_x$, (EGQPA)$_x$, (GAPEQ)$_x$, (GAPQE)$_x$, (GPEAQ)$_x$, (GPAEQ)$_x$, (GPAQE)$_x$, (GPEQA)$_x$, (GPQEA)$_x$, (GPQAE)$_x$, (PQAEG)$_x$, (QPAEG)$_x$, (QAPEG)$_x$, (QAEPG)$_x$, (QAEGP)$_x$, (EPQAG)$_x$, (PEQAG)$_x$, (PQEAG)$_x$, (PQAGE)$_x$, (APQEG)$_x$, (PAQEG)$_x$, (PQEAG)$_x$, (PQEGA)$_x$, (AGQEP)$_x$, (GAQEP)$_x$, (GQAEP)$_x$, (GQEAP)$_x$, (GQEPA)$_x$; wherein x represents an integer in the range of from 1 to about 20, and in a combination with K or KP as described above.

In case the OEF extension of Group I is represented by the motifs (PQAEG),
(PEQAG), (PQEAG), (PQAGE), (PAQEG), (PQEAG), (PQEGA), (AEGQP)$_x$, (EAGQP)$_x$, (EGAQP)$_x$, (EGQAP)$_x$, (QAEGP)$_x$, (AGQEP)$_x$, (GAQEP)$_x$, (GQAEP)$_x$, or (GQEAP)$_x$, the extension is not terminated by a proline (P) residue, i.e. the terminal motif may be truncated (exemplified by e.g. AEGQ, EAGQ, EGAQ, EGQA, QAEG, AGQE, GAQE, GQAE, and GQEA), resulting in a C-terminal motif of four amino acid residues, followed by KP (exemplified by e.g. EGAQ-KP).

In another embodiment, the polar recombinant OEF extension of Group I is selected from (GQAPGQEP)$_x$, (GQAPGQEP)$_x$-GQA-KP, (GQAPGQEP)$_x$-GQE-KP, (GQAPGQAPGQEP)$_x$, (GQAPGQAPGQEP)$_x$-GQA-KP, (GQAPGQAPGQEP)$_x$-GQE-KP, (GQAPGQAPGQAPGQEP)$_x$, and (GQAPGQAPGQAPGQEP)$_x$-GQA-KP, (GQAPGQAPGQAPGQEP)$_x$-GQE-KP; wherein x represents an integer in the range of from 1 to about 20.

In further embodiments, x represents an integer in the range of from 1 to about 20, or x represents an integer in the range of from 1 to about 15.

In a third embodiment, the polar recombinant OEF extension of Group I is
an A-chain extension represented by (GQAPGQEP)$_6$-KP, (GQAPGQAPGQEP)$_6$-KP, (GQAPGQAPGQEP)$_6$-GQA-KP; or (GQAPGQAPGQAPGQEP)$_6$-GQAP-KP;
a B-chain extension represented by KP-(GQAPGQEP)$_6$ or KP-(GQAPGQAPGQEP)$_6$; or
an A-chain extension represented by (GQAPGQAPGQAPGQEP)$_6$GQAP-KP or (GQAPGQAPGQAPGQEP)$_6$-GQA-KP.

The polar recombinant OEF extension for use according to the invention may also be represented by contiguous amino acid residues selected from Group J, i.e. the group of [A, E, G, P, S and T]$_x$, in random order or in any combination, wherein x represents an integer in the range of from 1 to about 20, and which sequence of Group 3 is further combined with K or KP as described above (i.e. [A,E,G,P,S,T]$_x$-KP for A-chain extensions; and KP-[A,E,G,P,S,T]$_x$ for B-chain extensions).

In one embodiment, the polar recombinant OEF extension of Group 3 may further be represented by one or more of the following motifs: (AEGPST)$_x$, (EAGPST)$_x$, (EGAPST)$_x$, (EGPAST)$_x$, (EGPSAT)$_x$, (EGPSTA)$_x$, (AGEPST)$_x$, (AGPEST)$_x$, (AGPSET)$_x$, (AGPSTE)$_x$, (GEAPST)$_x$, (GAEPST)$_x$, (GAPEST)$_x$, (GAPSET)$_x$, (GAPSTE)$_x$, (GEPAST)$_x$, (GPEAST)$_x$, (GPAEST)$_x$, (GPASET)$_x$, (GPASTE)$_x$, (GEPSAT)$_x$, (GPESAT)$_x$, (GPSEAT)$_x$, (GPSAET)$_x$, (GPSATE)$_x$, (GEPSTA)$_x$, (GPESTA)$_x$, (GPSETA)$_x$, (GPSTEA)$_x$, (GPSTAE)$_x$, (PSTAEG)$_x$, (PTSAEG)$_x$, (PTASEG)$_x$, (PTAESG)$_x$, (PTAEGS)$_x$, (SPTAEG)$_x$, (STPAEG)$_x$, (STAPEG)$_x$, (STAEPG)$_x$, (STAEGP)$_x$, (TAEGPS)$_x$, (TEAGPS)$_x$, (TEGAPS)$_x$, (TEGPAS)$_x$, (TEGPSA)$_x$, (ATEGPS)$_x$, (AETGPS)$_x$, (AEGTPS)$_x$, (AEGPTS)$_x$, (TEAPGS)$_x$, (TAEPGS)$_x$, (ETAPGS)$_x$, (EATPGS)$_x$, (EAPTGS)$_x$, (EAPGTS)$_x$, (EAPGST)$_x$, (TEPAGS)$_x$, (ETPAGS)$_x$, (EPTAGS)$_x$, (EPATGS)$_x$, (EPAGTS)$_x$, (EPAGST)$_x$, (TEPGAS)$_x$, (ETPGAS)$_x$, (EPTGAS)$_x$, (EPGTAS)$_x$, (EPGATS)$_x$, (EPGAST)$_x$, (TEPGSA)$_x$, (ETPGSA)$_x$, (EPTGSA)$_x$, (EPGTSA)$_x$, (EPGSTA)$_x$, (EPGSAT)$_x$, (TEASGP)$_x$, (ETASGP)$_x$, (EATSGP)$_x$, (EASTGP)$_x$, (EASGTP)$_x$, (EASGPT)$_x$, (TESAGP)$_x$, (ETSAGP)$_x$, (ESTAGP)$_x$, (ESATGP)$_x$, (ESAGTP)$_x$, (ESAGPT)$_x$, (TESGAP)$_x$, (ETSGAP)$_x$, (ESTGAP)$_x$, (ESGTAP)$_x$, (ESGATP)$_x$, (ESGAPT)$_x$, (TESGPA)$_x$, (ETSGPA)$_x$, (ESTGPA)$_x$, (ESGTPA)$_x$, (ESGPTA)$_x$, (ESGPAT)$_x$, (TEAPSG)$_x$, (ETAPSG)$_x$, (EATPSG)$_x$, (EAPTSG)$_x$, (EAPSTG)$_x$, (EAPSGT)$_x$, (TEPASG)$_x$, (ETPASG)$_x$, (EPTASG)$_x$, (EPATSG)$_x$, (EPASTG)$_x$, (EPASGT)$_x$, (TEPSGA)$_x$, (ETPSGA)$_x$, (EPTSGA)$_x$, (EPSTGA)$_x$, (EPSGTA)$_x$, (EPSGAT)$_x$, (TEPSAG)$_x$, (ETPSAG)$_x$, (EPTSAG)$_x$, (EPSTAG)$_x$, (EPSATG)$_x$, (EPSAGT)$_x$, (TEAGSP)$_x$, (ETAGSP)$_x$, (EATGSP)$_x$, (EAGTSP)$_x$, (EAGSTP)$_x$, (EAGSPT)$_x$, (TEGASP)$_x$, (ETGASP)$_x$, (EGTASP)$_x$, (EGATSP)$_x$, (EGASTP)$_x$, (EGASPT)$_x$, (TEGSPA)$_x$, (ETGSPA)$_x$, (EGTSPA)$_x$, (EGSTPA)$_x$, (EGSPTA)$_x$, (EGSPAT)$_x$, (TEGSAP)$_x$, (ETGSAP)$_x$, (EGTSAP)$_x$, (EGSTAP)$_x$, (EGSATP)$_x$, (EGSAPT)$_x$, (PAEGST)$_x$, (PEAGST)$_x$, (PEGAST)$_x$, (PEGSAT)$_x$, (PEGSTA)$_x$, (SAEGPT)$_x$, (SEAGPT)$_x$, (SEGAPT)$_x$, (SEGPAT)$_x$, (SEGPTA)$_x$; wherein x represents an integer in the range of from 1 to about 20, and in a combination with K or KP as described above.

In case the OEF extension of Group 3 is represented by the motif (PSTAEG)$_x$, (PTSAEG)$_x$, (PTASEG)$_x$, (PTAESG)$_x$, (PTAEGS)$_x$, (STAEGP)$_x$, (TEASGP)$_x$, (ETASGP)$_x$, (EATSGP)$_x$, (EASTGP)$_x$, (EASGTP)$_x$, (TESAGP)$_x$, (ETSAGP)$_x$, (ESTAGP)$_x$, (ESATGP)$_x$, (ESAGTP)$_x$, (TESGAP)$_x$, (ETSGAP)$_x$, (ESTGAP)$_x$, (ESGTAP)$_x$, (ESGATP)$_x$, (TEAGSP)$_x$, (ETAGSP)$_x$, (EATGSP)$_x$, (EAGTSP)$_x$, (EAGSTP)$_x$, (TEGASP)$_x$, (ETGASP)$_x$, (EGTASP)$_x$, (EGATSP)$_x$, (EGASTP)$_x$, (EGASPT)$_x$, (TEGSAP)$_x$, (ETGSAP)$_x$, (EGTSAP)$_x$, (EGSTAP)$_x$, (EGSATP)X, the extension is not terminated by a proline (P) residue, i.e. the terminal motif may be truncated (exemplified by e.g. STAEG, TEASG, ETASG, EATSG, EASTG, EASGT, TESAG, ETSAG, ESTAG, ESATG, ESAGT, TESGA, ETSGA, ESTGA, ESGTA, ESGAT, TEAGS, ETAGS, EATGS, EAGTS, EAGST, TEGAS, ETGAS, EGTAS, EGATS, EGAST, EGASP, TEGSA, ETGSA, EGTSA, EGSTA, EGSAT), resulting in a C-terminal motif of five amino acid residues, followed by KP (exemplified by e.g. STAEG-KP).

In further embodiments, x represents an integer in the range of from 1 to about 20, or x represents an integer in the range of from 1 to about 15.

The polar recombinant OEF extension for use according to the invention may also be represented by any combination of Groups A, B, C, D, E, F, G and H, but, as noted above, the polar recombinant OEF extensions should not be too large, and it is currently believed that the overall length of the OEF according to the invention shall be between 1 to and about 150 amino acid residues.

In one embodiment, the polar recombinant OEF extension for use according to the invention may be represented by combinations of Groups C and E.

In another embodiment, the polar recombinant OEF extension for use according to the invention represented by a combination of Groups C and E is ((GQAP)(GQEP))$_x$, ((GQAP)(GQAP)(GQEP))$_x$, or ((GQAP)(GQAP)(GQAP) (GQEP))$_x$; and which combined sequence is further combined with K or KP as described above (i.e. ((GQAP) (GQEP))$_x$-KP, ((GQAP)(GQAP)(GQEP))$_x$-KP or ((GQAP) (GQAP)(GQAP)(GQEP))$_x$-KP for A-chain extensions; and KP-((GQAP)(GQEP))$_x$, KP-((GQAP)(GQAP)(GQEP))$_x$ or KP-((GQAP)(GQAP)(GQAP)(GQEP))$_x$ for B-chain extensions); wherein x represents an integer in the range of from 1 to 7.

In a third embodiment, the polar recombinant OEF extension represented by a combination of Groups C and E is an A-chain extension represented by ((GQAP)(GQEP))$_6$-KP, or ((GQAP)(GQAP)(GQEP))$_6$-(GQAP)-KP, or a B-chain extension represented by KP-((GQAP) (GQEP))$_6$, or KP-((GQAP)(GQAP)(GQEP))$_6$-(GQAP).

In a further embodiment, the polar recombinant OEF extension for use according to the invention is represented by repeating motifs selected from (GAPQ), (GEPQ), (GQAP), (GQEP), (PQAG) and (PQEG), or a mixture of these motifs, in combination with a lysine (K) residue, or with a KP sequence, as described above.

In even further embodiments, OEF indicates a polar recombinant extension fused C-terminally of the insulin A-chain (i.e. insulin A-chain extensions), which extension is selected from the following motifs and extensions:

[G,E,S,T,A,P]$_n$-KP (i.e. G,E,S,T,A,P in random order), and [G,E,Q,A,P]$_n$-KP (i.e. G,E,Q,A,P in random order);

wherein n represent an integer in the range of from 1 to about 20; and (GAPQ)$_x$-KP, (GAQP)$_x$-KP, (GEPQ)$_x$-KP, (GEQP)$_x$-KP, (GPAQ)$_x$-KP, (GPEQ)$_x$-KP, (GPQA)$_x$-KP, (GPQE)$_x$-KP, (GQAP)$_x$-KP, (GQEP)$_x$-KP, (GQPA)$_x$-KP, and (GQPE)$_x$-KP;

wherein x represents an integer in the range of from 1 to about 25; and (GQAPGQEP)$_y$-KP;

wherein y represents an integer in the range of from 1 to about 15; and (GQAPGQAPGQEP)$_z$-KP;

wherein z represents an integer in the range of from 1 to about 10; and (GQAPGQAPGQAPGQEP)$_V$-KP;

wherein v represents an integer in the range of from 1 to about 8.

In even further embodiments, OEF indicates a polar recombinant extension fused N-terminally of the insulin B-chain (i.e. insulin B-chain extensions), which extension is selected from the following motifs and extensions:

KP-[G,E,S,T,A,P]$_n$ (i.e. G,E,S,T,A,P in random order), and KP-[G,E,Q,A,P]$_n$ (i.e. G,E,Q,A,P in random order);

wherein n represent an integer in the range of from 1 to about 20; and KP-(GAPQ)$_x$, KP-(GAQP)$_x$, KP-(GEPQ)$_x$, KP-(GEQP)$_x$, KP-(GPAQ)$_x$, KP-(GPEQ)$_x$, KP-(GPQA)$_x$, KP-(GPQE)$_x$, KP-(GQAP)$_x$, KP-(GQEP)$_x$, KP-(GQPA)$_x$, and KP-(GQPE)$_x$;

wherein x represents an integer in the range of from 1 to about 25; and

KP-(GQAPGQEP)$_y$;

wherein y represents an integer in the range of from 1 to 15; and

KP-(GQAPGQAPGQEP)$_z$;

wherein z represents an integer in the range of from 1 to 10; and

KP-(GQAPGQAPGQAPGQEP)$_V$;

wherein v represents an integer in the range of from 1 to 8.

In a further embodiment, the polar recombinant OEF extension of the A-chain and the amino acid in position 21 of the A-chain for use according to the invention is:

A21Q, A22(G)$_{18}$, A40K*, (SEQ ID NO:53);

A21G, A22(GQAP)$_{18}$, A94G, A95Q, A96A, A97K*, A98P (SEQ ID NO:54);

A21G, A22(GQAP)$_{19}$, A98K*, A99P (SEQ ID NO:55);

A21G, A22(GQAPGQEP)$_6$, A70K*, A71P (SEQ ID NO:56);

A21G, A22(GQAPGQAPGQEP)$_6$-GQAP, A98K*, A99P (SEQ ID NO:57);

A21G, A22(GQAPGQAPGQAPGQEP)$_6$-GQAP, A122K*, A123P (SEQ ID NO:58);

A21G, A22(GQAP)$_{24}$, A118G, A119Q, A120A, A121K*, A122P (SEQ ID NO:59);

A21G, A22(GQEP)$_3$, A34G, A35Q, A36E, A37K*, A38P (SEQ ID NO:60);

A21G, A22(GQEP)$_6$, A46K*, A47P (SEQ ID NO:61);

A21G, A22(GQEP)$_{12}$, A70K*, A71P (SEQ ID NO:62); or

A21G, A22(GQEP)$_{19}$, A98K*, A99P (SEQ ID NO:63);

wherein * indicates the point of the Fc' conjugation.

In a further embodiment, the polar recombinant OEF extension of the B-chain for use according to the invention is:

B(−78K*), B(−77P), (GQAPGQAPGQEP)$_6$-GQAP (SEQ ID NO:64);

B(−78K*), B(−77P), B(−1)(GQEP)$_{19}$ (SEQ ID NO:65);

B(−78K*), B(−77P), B(−1)(GQAP)$_{19}$ (SEQ ID NO:66);

B(−26K*), B(−25P), B(−1)(GQAP)$_6$ (SEQ ID NO:67);

wherein * indicates the point of the Fc' conjugation.

The Linking Group

The insulin-Fc conjugates of the invention may be characterised as being composed of two monomer Fc polypeptides (Fc') covalently joined with the OEF-Ins construct via a linker.

A particular feature of the present invention is the manner in which two monomer Fc components are joined to the oligomer extended insulin analogue. The linker employed for obtaining such a construct may be regarded as a "tri-arm" linker, as defined by X and Y according to Formula I, or by X, U and Z according to Formula I', wherein X represents a covalent bond, or a divalent linking group, connecting [OEF-Ins] and Y;

Y represents a trivalent linking group according to Formula I, connecting the two Fc' via two sulphur atoms to X; or, in case X represents a covalent bond, Y is connecting the two Fc' via two sulphur atoms to a lysine residue in the [OEF-Ins] construct; or more specifically, Y is connecting the two Fc' via two sulphur atoms to the epsilon amino group of a lysine residue in the [OEF-Ins] construct; and Fc' represents a monomer Fc polypeptide, or a fragment thereof; or U represents a central trivalent linking unit according to Formula I', connecting the two Z—[S-Fc'] groups to X; or, in case X represents a covalent bond, U is connecting the two Z—[S-Fc'] groups to a lysine residue in the [OEF-Ins] construct; or more specifically, in case X represents a covalent bond, U is connecting the two Z—[S-Fc'] groups to the epsilon amino group of a lysine residue in the [OEF-Ins] construct; and Z according to Formula I' represents a divalent linking group connecting the central linking unit (U) to a thiol moiety (S) of a monomer Fc polypeptide (Fc'), or a fragment thereof.

In a particular embodiment, Y according to Formula I represents a trivalent linking group connecting X to the two thiol moieties (S) of the two monomer Fc polypeptides (Fc'), which trivalent linking group comprises a Sp2 hybridised carbon atom (—($\underline{C}$=O)—) and a methylene group, as presented by Formula III —$\underline{CO}$—CH$_2$—

In another particular embodiment, according to Formula I', Z represents a divalent linking group connecting the central unit (U) to a thiol moiety (S) of a monomer Fc polypeptide (Fc'), or a fragment thereof, which divalent linking group comprises an Sp2 hybridised carbon atoms (—($\underline{C}$=O)—) and a methylene group, as presented by Formula III'

—$\underline{CO}$—CH$_2$— wherein Fc' represents a monomer Fc polypeptide, or a fragment thereof, and S represents a sulphur atom originating from a cysteine (C) residue comprised within the Fc' component.

In one embodiment, the sulphur atom originates from a cysteine (C) residue located in the hinge region of the Fc, which cysteine residue is capable of forming a disulphide bridge (as illustrated by Chem. 5, below).

In another embodiment, the insulin-Fc conjugate of the invention is a compound of Formula I or Formula I', wherein X is absent (i.e. represents a covalent bond), or X represents a divalent linker of the structure —C(O)—(CH$_2$)$_l$—C(O)—; wherein l represents an integer in the range of from 1 to 20.

In further embodiments, l represents an integer in the range of from 1 to 15; or l represents an integer in the range of from 1 to 10; or l represents an integer in the range of from 1 to 6; or l represents an integer in the range of from 1 to 5; or l represents an integer in the range of from 1 to 4.

In further embodiments, l represents an integer in the range of from 2 to 15; or l represents an integer in the range of from 2 to 10; or l represents an integer in the range of from 2 to 6; or l represents an integer in the range of from 2 to 5; or l represents an integer in the range of from 2 to 4.

In further embodiments, l represents 2, or l represents 3, or l represents 4, or l represents 5, or l represents 6.

In a further embodiment, X represents the linker —CO—CH$_2$—CH$_2$—CO—.

In a further embodiment, X represents the linker —CO—CH$_2$—CH$_2$—CH$_2$—CH$_2$—CO—.

In further embodiments, X represents a divalent linker of the structure —C(O)—(CH$_2$)$_o$—NH—C(O)—; wherein o represents an integer in the range of from 1 to 20.

In further embodiments, o represents an integer in the range of from 1 to 15; or o represents an integer in the range of from 1 to 10; or o represents an integer in the range of from 1 to 5; or l represents an integer in the range of from 1 to 3.

In a further embodiment, X represents the linker —CO—CH$_2$—CH$_2$—CH$_2$—NH—CO—.

In an even further embodiment, X represents a covalent bond.

The insulin-Fc conjugate of the invention may be a compound of Formula I, wherein Y represents a trivalent linking group, connecting the two Fc' via two sulphur atoms to X; or, in case X represents a covalent bond, Y is connecting the two Fc' via two sulphur atoms to a lysine residue in the [OEF-Ins] construct, or more specifically, Y is connecting the two Fc' via two sulphur atoms to the epsilon amino group of a lysine residue in the [OEF-Ins] construct.

In another embodiment the insulin-Fc conjugate of the invention is a compound of Formula I', wherein U represents a central trivalent linking unit, connecting the two Z—[S-Fc'] groups to X; or, in case X represents a covalent bond, U is connecting the two Z—[S-Fc'] groups to a lysine residue in the [OEF-Ins] construct; or more specifically, in case X represents a covalent bond, U is connecting the two Z—[S-Fc'] groups to the epsilon amino group of a lysine residue in the [OEF-Ins] construct.

In one embodiment, the central linking unit (U) according to Formula I' represents a nitrogen atom (N).

In one embodiment, the insulin-Fc conjugate of the invention is a compound of Formula I, wherein the central trivalent linking unit (Y) is represented by Formula IV

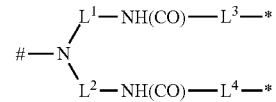

wherein,

N is a nitrogen atom (N);

* indicates the point of attachment to a sulphur atom originating from a reduced disulphide bridge of Fc (i.e. the [Fc'] moiety according to Formula I);

N is a nitrogen atom (N);

# indicates the point of attachment to X; and

L$^1$ and L$^2$, independently of each other, represent —(CH$_2$)$_{m1}$—; wherein m1 represents an integer in the range of from 1 to 6; and L$^3$ and L$^4$, independently of each other, represent —(CH2)$_{n1}$—;

wherein n1 represents an integer in the range of from 1 to 6.

In one embodiment, each of L$^1$ and L$^2$ represent —(CH$_2$)$_2$—, or —(CH$_2$)$_3$—; and each of L$^3$ and L$^4$ represents —(CH$_2$)—.

In another embodiment, the insulin-Fc conjugate of the invention is a compound of Formula I', wherein the central trivalent linking unit (U) and divalent linking group (Z) are represented by Formula IV'

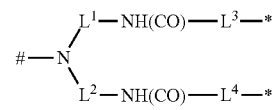

wherein,

N is a nitrogen atom (N) and represents the central linking unit (U) according to Formula I';

L$_1$-NH(CO)-L$_3$ and L$_2$-NH(CO)-L$_4$, respectively, represents the divalent linking group (Z) according to Formula I';

\* indicates the point of attachment to a sulphur atom originating from a disulphide bridge of Fc (i.e. the [S-Fc'] moiety according to Formula I');

\# indicates the point of attachment to X; and $L^1$ and $L^2$, independently of each other, represent —$(CH_2)_{m1}$—; wherein m1 represents an integer in the range of from 1 to 6; and $L^3$ and $L^4$, independently of each other, represent —$(CH_2)_{n1}$—;

wherein n1 represents an integer in the range of from 1 to 6.

In another embodiment, the central linking unit (U) according to Formula I', represents a benzene ring.

In a further embodiment, the central linking unit (U) represents a 3,5-disubstituted benzoate or benzoyl moiety.

In an even further embodiment, the central linking unit (U) represents a 3,5-disubstituted benzoate moiety as illustrated by Formula VII:

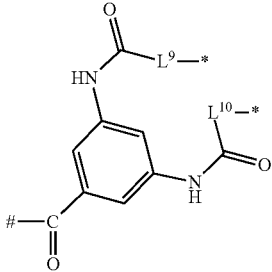

wherein

\* indicates the point of attachment to a sulphur atom originating from a disulphide bridge of Fc (i.e. the [S-Fc'] moiety according to Formula I');

\# indicates the point of attachment to X, or, in case X is absent (i.e. represents a covalent bond), to the a primary amino group in a lysine residue in the [OEF-Ins] construct; and $L^9$ and $L^{10}$, independently of each other, represents —$(CH_2)_{n3}$—; wherein n3 represents an integer in the range of from 1 to 6 (and Z according to Formula I' is absent).

In one embodiment, each of $L^9$ and $L^{10}$ represents —$(CH_2)$—.

In an even further embodiment, the central linking unit (U) represents a 3,5-disubstituted benzene ring and —U(—$Z)_2$ according to Formula I' is illustrated by Formula VII':

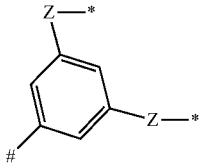

wherein

\* indicates the point of attachment to a sulphur atom originating from a disulphide bridge of Fc (i.e. the [S-Fc'] moiety according to Formula I');

\# indicates the point of attachment to X; and

Z is independently NH(C=O)-$L^9$ or NH(C=O)-$L^{10}$, $L^9$ and $L^{10}$, independently of each other, represents —$(CH_2)_{n3}$—; wherein n3 represents an integer in the range of from 1 to 6.

In a third embodiment, the central linking unit (U) according to Formula I' is represented by a methyl group attached to a carbonyl (C=O) group, and U(—$Z)_2$ of Formula I' becomes —(C=O)—CH(—$Z)_2$.

In a further embodiment, X is absent (i.e. represents a covalent bond), and U(—$Z)_2$ according to Formula I' is represented by Formula VIII:

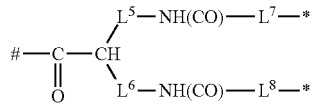

wherein,

\* indicates the point of attachment to a sulphur atom originating from a disulphide bridge of Fc (i.e. the [S-Fc'] moiety according to Formula I');

\# indicates the point of attachment to X, or in case X is absent (i.e. represents a covalent bond), to a primary amino group in a lysine residue in the [OEF-Ins] construct; and $L^5$ and $L^6$, independently of each other, represents —$(CH_2)_{m2}$—; wherein m2 represents an integer in the range of from 0 to 6; and $L^7$ and $L^8$, independently of each other, represents —$(CH_2)_{n2}$—; wherein n2 represents an integer in the range of from 1 to 6.

In one embodiment, $L^5$ represents a covalent bond (i.e. m2=0) and $L^6$ represents —$(CH_2)_4$ (i.e. m2 represents 4); and each of $L^7$ and $L^8$ represents —$(CH_2)$—.

In another embodiment, the linking group X—U(—$Z)_2$ according to Formula I', represents —C(O)—$(CH_2)_2$—C(O)—N[—$(CH_2)_2$—NH—C(O)—$CH_2$-$]_2$-; —C(O)—(($CH_2)_3$—NH—C(O)—N[($CH_2)_2$—NH—C(O)—$CH_2$-$]_2$-; —C(O)—CH(NH—C(O)—$CH_2$—)—$(CH_2)_4$—NH—C(O)—$CH_2$)—; or —C(O)—$C_6H_3$(NH(CO)—$CH_2$-$)_2$.

In a third embodiment, the central linking unit (U) is represented by a methyl group and the Y(—$Z)_2$ moiety of Formula I', and X is as defined above.

In a further embodiment, U(—$Z)_2$ is represented by Formula VIII'

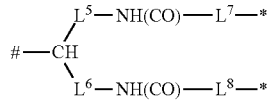

wherein,

\* indicates the point of attachment to a sulphur atom originating from a disulphide bridge of Fc (i.e. the [S-Fc'] moiety according to Formula I');

\# indicates the point of attachment to X; and $L^5$ and $L^6$, independently of each other, represents —$(CH_2)_{m2}$—; wherein m2 represents an integer in the range of from 0 to 6; and $L^7$ and $L^8$, independently of each other, represents —$(CH_2)_{n2}$—; wherein n2 represents an integer in the range of from 1 to 6.

In one embodiment, $L^5$ represents a covalent bond (i.e. m2=0) and $L^6$ represents —$(CH_2)_4$ (i.e. m2 represents 4); and each of $L^7$ and $L^8$ represents —$(CH_2)$—.

In another embodiment, the linking group X—U(—$Z)_2$ represents —C(O)—$(CH_2)_2$—C(O)—N[—$(CH_2)_2$—NH—C(O)—$CH_2$-$]_2$-; —C(O)—(($CH_2)_3$—NH—C(O)—

N[(CH$_2$)$_2$—NH—C(O)—CH$_2$-]$_2$-;  —C(O)—CH(NH—C(O)—CH$_2$—)—(CH$_2$)$_4$—NH—C(O)—CH$_2$)—; or —C(O)—C$_6$H$_3$(NH(CO)—CH$_2$-)$_2$.

The Antibody Fc Component (Fc')

As described above, the insulin-Fc conjugates of the invention may be described as two monomer Fc polypeptides covalently joined with insulin via the linker described above.

According to the present invention, the Fc component is modified (i.e. cleaved) so that the hinge region of the Fc polypeptide comprises only one (native) cysteine (C) residue. This cysteine of the first Fc monomer is capable of forming a disulphide bond with the similar cysteine residue, located on the second monomer of the original (homo dimer) Fc polypeptide, e.g. as illustrated in Chem. 5, below.

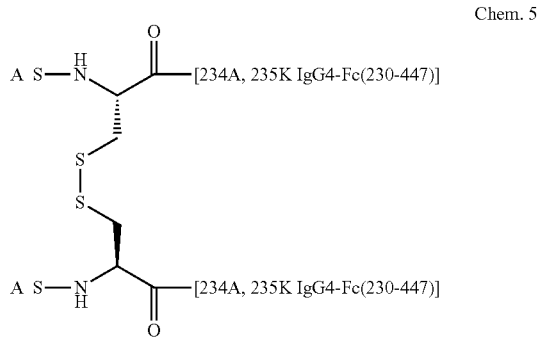

Chem. 5

The linkages to the Fc' polypeptides of the invention takes place via sulphur atoms (—S—) derived from a cysteine residue in the Fc polypeptides, as described above.

The hinge region of the Fc polypeptide may include only native amino acid residues. In one embodiment, the Fc polypeptide does not include a methionine at the N-terminal. In another embodiment, the hinge sequence of the Fc hinges is derived from the IgG1 hinge sequence PKSCDKTHTCPPCP (SEQ ID NO:4). In a third embodiment, the hinge sequence is selected from the group consisting of: PKSCDKTHTCPPCP (SEQ ID NO:4), AGPCP (SEQ ID NO:68), ASPC (SEQ ID NO:69), PPCP (SEQ ID NO:70), PCP and CP.

The constant region of IgG1 may be modified at native residue P228 (marked above in bold and underlined, numbered according to the EU index) by substitution into a serine residue (P228S).

The hinge sequence of the Fc hinges may also be derived from the IgG4 hinge sequence SKYGPPCPSCP (SEQ ID NO:6). In one embodiment, the hinge sequence is selected from the group consisting of: SKYGPPCPSCP, AGSCP (SEQ ID NO:73), AGPCP (SEQ ID NO:68), PSCP (SEQ ID NO:74), SCP and CP.

The constant region may be modified to stabilize the molecule. In an IgG4 hinge region, native residue S228 (marked above in bold and underlined, numbered according to the EU index) may be substituted by a proline residue (S228P). In one embodiment, the Fc polypeptide includes a proline residue in position S228, or in a position corresponding to P228 in an IgG1 derived hinge sequence.

The Fc polypeptides each may have an N-terminal extension of the native sequence, which extension comprises one or more amino acids selected from the group of A, G and S. In one embodiment of the invention, this extension does not start with a serine (S) residue. In another embodiment, the hinge sequence of IgG1 is ASPCP (SEQ ID NO:71), AGPCP (SEQ ID NO:68) or ASCP (SEQ ID NO:72). In a further embodiment, the hinge sequence of IgG4 is ASCP (SEQ ID NO:72), AGSCP (SEQ ID NO:73), AGPCP (SEQ ID NO:68) or GASCP (SEQ ID NO:75).

The Fc polypeptides each may have C-terminal deletions of the native sequence. Herein the terms like des 447 indicate that the Fc analogue is lacking the (native)C-terminal amino acid residue at position 447.

The Fc polypeptides of the Fc-domain may thus be covalently linked by di-sulphide bridges or, alternatively, be non-covalently linked.

Also the Fc region may be engineered to include modifications within the Fc region, typically to alter one or more of its functional properties, such as e.g. serum half-life, complement fixation, Fc-receptor binding, protein stability and/or antigen-dependent cellular cytotoxicity, or lack thereof. Furthermore, the Fc-domain may be chemically modified (e.g. one or more chemical moieties can be attached to the Fc part) to alter its glycosylation, to also alter one or more functional properties of the antibody.

An IgG1 derived Fc-domain for use according to the invention may comprise one or more of the following amino acid substitutions, that will result in decreased affinity to certain Fc receptors: L234A, L235E or 235A or 235K, and G237A, and/or in reduced C1q-mediated complement fixation: A330S and P331S, respectively.

An IgG2 derived Fc-domain for use according to the invention may comprise one or more, and perhaps all of the following amino acid substitutions, that will result in decreased affinity to certain Fc receptors: V234A, A235K, and P237A, and/or in reduced C1q-mediated complement fixation: A330S and P331S, respectively.

An IgG4 derived Fc-domain for use according to the invention may comprise one or more, and perhaps all of the following amino acid substitutions, that will result in decreased affinity to certain Fc receptors: P227A, F234A, and L235A or L235K.

In order to improve binding affinity to FcRn, substitutions in the Fc may be included to obtain amino acid substitutions such as M428L and/or N434S in an Fc-domain of the IgG1 or IgG4 isotype. In another embodiment of the invention, improved FcRn binding affinity may be obtained by including the amino acid substitutions such as M252Y and/or S254T and/or T256E in an Fc domain of IgG1 or IgG4.

In order to improve chemical stability of the Fc-domain, asparagines, prone to deamidation, may be substituted by glutamine, aspartic acid or glutamic acid. Examples of such asparagines in both IgG1 and IgG4 are N297, N315 and N384. In one embodiment, the Fc's of the inventions include the N315Q and the N384Q substitutions. In another embodiment, the Fc's of the inventions include the N297Q or N297E mutations.

In order to improve physical stability of the Fc-domain, position 235 of Fc derived from IgG1 or IgG4 may be substituted by arginine or lysine. In one embodiment, the Fc's of the inventions comprise the L235K or L235R. In another embodiment, the Fc's of the inventions comprise the L235K mutation.

Furthermore, the C-terminal lysine of IgG's is cleaved in vivo in the human blood, and endogenous IgG isolated from human blood contains very low levels of C-terminal lysine. Therefore the C-terminal lysine at position 447 may be deleted, e.g. the Fc analogue may include des447.

In one embodiment, Fc represents an IgG derived Fc, or a fragment thereof, and the Fc' polypeptide of the invention represents a monomer of such IgG derived Fc, or Fc fragment.

In another embodiment, Fc represents an IgG1 or an IgG4 derived Fc, or a fragment thereof, and the Fc' polypeptide of the invention represents a monomer of such IgG derived Fc, or Fc fragment.

In a third embodiment, Fc represents an IgG1 or an IgG4 derived Fc, or fragment thereof, with a short hinge containing only one disulphide bridge, and the Fc' polypeptide of the invention represents a monomer of such IgG derived Fc fragment.

In a fourth embodiment, the Fc' monomer molecule, or fragment thereof, is connected to Y via a cysteine residue deriving from a reduced disulphide bridge in the hinge region of the Fc at position 229 (229C).

In a fifth embodiment, Fc' represents a fragment of a human IgG1 derived Fc sequence, starting at position 228 and ending at position 447, and Fc' represents a monomer of such IgG derived Fc fragment (i.e. hIgG1-Fc(228-447); SEQ ID NO:1).

The hIgG1-Fc(228-447) polypeptide for use according to the invention may contain one or more extensions and/or substitutions and/or deletions selected from the group of 226A, 227A or 227G or 227S, 228S, 234A, 235K, 235E, 235A, 237A, 330S, 331S, 297Q, 297E, N315Q, N384Q, and des447.

In one embodiment, Fc' represents
226A, 227S hIgG1-Fc(228-447) (Fc7);
226A, 227S, 234A, 235E, 237A, 330S, 331S hIgG1-Fc(228-447) (Fc13);
226A, 227S, 234A, 235K, 237A, 315Q, 330S, 331S, 384Q hIgG1-Fc(228-447) (Fc12);
226A, 227S, 234A, 235K, 237A, 330S, 331S hIgG1-Fc(228-447) (Fc11);
226A, 227S, 235K, 237A, 330S, 331S hIgG1-Fc(228-447) (Fc10); or
227A, 228S, 235K, 315Q, 384Q hIgG1-Fc(228-447) (Fc4).

In a further embodiment, Fc' represents a fragment of a human IgG4 derived Fc sequence, starting at position 228 and ending at position 447, and Fc' represents a monomer of such IgG derived Fc fragment (i.e. hIgG4-Fc(228-447); SEQ ID NO:3).

In one embodiment, Fc' represents a fragment of a hIgG4 derived Fc sequence, starting at position 228 and ending at position 447, which sequence may contain one or more extensions and/or substitutions selected from the group of 226A or 226G, 227A or 227G, 228P, 234A, 235A, 235K, N297Q, N297E, 315Q, 384Q and des447.

In one embodiment, Fc' represents a fragment of a hIgG4 derived Fc sequence, starting at position 228 and ending at position 447, which sequence may contain one or more extensions and/or substitutions selected from the group of 226A or 226G, 227A or 227G, 228P, 234A, 235A, 235K, N297Q, N297E, 315Q, 384Q and des447.

In another embodiment, Fc' represents
226G, 227A hIgG4-Fc(228-447) (Fc3);
227A hIgG4-Fc(228-447) (Fc1);
227A, 234A, 235A hIgG4-Fc(228-447) (Fc6);
227A, 234A, 235K hIgG4-Fc(228-447) (Fc9);
227A, 234A, 235K, 297E, 315Q, 384Q, des447 hIgG4-Fc(228-447) (Fc15);
227A, 234A, 235K, 297E, des447 hIgG4-Fc(228-447) (Fc16);
227A, 234A, 235K, 297Q hIgG4-Fc(228-447) (Fc14);
227A, 235K hIgG4-Fc(228-447) (Fc8);
227A, 235K, 315Q, 384Q hIgG4-Fc(228-447) (Fc5); or
227A, 315Q, 384Q hIgG4-Fc(228-447) (Fc2).

In a third embodiment, Fc' represents
226A, 227G, 228P, 234A, 235K, des447 hIgG4-Fc(228-447) (Fc17);
226A, 227G, 234A, 235K, des447 hIgG4-Fc(228-447);
226G, 227A hIgG4-Fc(228-447) (Fc3);
227A hIgG4-Fc(228-447) (Fc1);
227A, 234A, 235A hIgG4-Fc(228-447) (Fc6);
227A, 234A, 235K hIgG4-Fc(228-447) (Fc9);
227A, 234A, 235K, 297E, 315Q, 384Q, des447 hIgG4-Fc(228-447) (Fc15);
227A, 234A, 235K, 297E, des447 hIgG4-Fc(228-447) (Fc16);
227A, 234A, 235K, 297Q hIgG4-Fc(228-447) (Fc14);
227A, 235K hIgG4-Fc(228-447) (Fc8);
227A, 235K, 315Q, 384Q hIgG4-Fc(228-447) (Fc5); or
227A, 315Q, 384Q hIgG4-Fc(228-447) (Fc2).

In a fourth embodiment, Fc' represents
227A, 234A, 235A hIgG4-Fc(228-447) (Fc6); or
227A, 234A, 235K, 297E, 315Q, 384Q, des447 hIgG4-Fc(228-447) (Fc15).

In a fifth embodiment, Fc' represents
227A, 234A, 235K hIgG4-Fc(228-447) (Fc9);
226A, 227G, 228P, 234A, 235K, des447 hIgG4-Fc(228-447) (Fc17); or 227A, 234A, 235K, 297E, 315Q, 384Q, des447 hIgG4-Fc(228-447) (Fc15).

Insulin-Fc Conjugates of the Invention

In further embodiments, the insulin-Fc conjugate of the invention is selected from:

(A14E, A21G, A22(GQEP)19, A98K^, A99P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)19, A98K— A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(−78K—) B(−77P), B(−1)(GQAPGQAPGQEP)6-GQAP, B3Q, B25H, B29R, desB30 human insulin/(227A, 234A, 235K hIgG4-Fc(228-447))4-[bis[2-[(2-iodoacetyl)amino]ethyl]amino]-4-oxo-butanoyl conjugate;

A14E, B(−76K^), B(−75P), B(−1)(GQEP)19, B25H, B29R, desB30 human insulin/(227A, 234A, 235K hIgG4-Fc(227-447))4-[bis[2-[(2-acetyl)amino]ethyl]amino]-4-oxo-butanoyl conjugate;

A14E, A21G, A22(GQAPGQAPGQEP)6-GQAP, A98K^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)19, A98K— A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)6, A46K^, A47P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)12, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQEP)6, A70K^, A71P, B25H, B29R, desB30 human insulin/(227A, 234A, 235K hIgG4-Fc(227-447))4-[bis[2-[(2-acetyl)amino]ethyl]amino]-4-oxo-butanoyl conjugate;

A14E, A21G, A22(GQEP)3, A34G, A35Q, A36E, A37K^, A38P, B25H, B29R, desB30 human insulin/(227A, 234A, 235K hIgG4-Fc(227-447))4-[bis[2-[(2-acetyl)amino]ethyl]amino]-4-oxo-butanoyl conjugate;

A14E, B(-76K^), B(-75P), B(-1)(GQEP)19, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQEP)19, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)6-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQEP)6, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)19, A98K A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)19, A98K^, A99P, B25H, B29R, desB30 human insulin)/(227A, 234A, 235K, 297E, 315Q, 384Q, des447 hIgG4-Fc(227-447))4-[bis[2-[(2-acetyl)amino]ethyl]amino]-4-oxo-hexanoyl conjugate;

A14E, A21G, A22(GQEP)12, A70K^, A71P, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, B(-76K^), B(-75P), B(-1)(GQAP)19, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQEP)6-GQAP, A98K^, A99P, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQAPGQEP)6-GQAP, A122K^, A123P, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(G)17, A40K^, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAP)24, A118G, A119Q, A120A, A121K^, A122P, B25H, B29R, desB30 human insulin/(227A, 234A, 235K, 297E, 315Q, 384Q, des447 hIgG4-Fc(227-447))3,5-bis[(2-acetyl)amino]benzoyl conjugate;

(A14E, A21G, A22(GQAP)24, A118G, A119Q, A120A, A121K^, A122P, B25H, B29R, desB30 human insulin)/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQEP)6-GQAP, A98K^, A99P, B3Q, B25H, B29R, desB30 human insulin/(227A, 234A, 235K, 297E, 315Q, 384Q, des447 hIgG4-Fc(227-447))4-[bis[2-[(2-acetyl)amino]ethyl]carbamoylamino]-butanoyl conjugate; and (A14E, A21G, A22(GQAP)18, A94G, A95Q, A96A, A97K^, A98P, B29R, desB30 human insulin)/(227A, 234A, 235K, 297E, 315Q, 384Q, des447 hIgG4-Fc(227-447))4-[bis[2-[(2-acetyl)amino]ethyl]amino]-4-oxo-butanoyl conjugate.

In further embodiments, the insulin-Fc conjugate of the invention is selected from:

(A14E, A21G, A22(GQEP)$_{19}$, A98K^, A99P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

(A14E, A21G, A22(GQEP)$_{19}$, A98K^, A99P, B3Q, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, B(-78K—) B(-77P), B(-1)(GQAPGQAPGQEP)$_6$-GQAP, B3Q, B25H, B29R, desB30 human insulin)/(227A, 234A, 235K hIgG4-Fc(228-447))4-[bis[2-[(2-iodoacetyl)amino]ethyl]amino]-4-oxo-butanoyl conjugate;

(A14E, B(-76K^), B(-75P), B(-1)(GQEP)$_{19}$, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

(A14E, A21G, A22(GQAPGQAPGQEP)$_6$-GQAP, A98K^, A99P, B3Q, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

(A14E, A21G, A22(GQEP)$_{19}$, A98K— A99P, B3Q, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

(A14E, A21G, A22(GQEP)$_6$, A46K^, A47P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

(A14E, A21G, A22(GQEP)$_{12}$, A70K^, A71P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

A14E, A21G, A22(GQAPGQEP)$_6$, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_3$, A34G, A35Q, A36E, A37K^, A38P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, B(-76K^), B(-75P), B(-1)(GQEP)$_{19}$, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQEP)$_{19}$, A98K^, A99P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQEP)$_6$, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)$_{19}$, A98K A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)₁₉, A98Kˆ, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-6-oxo-hexanoyl conjugate;

A14E, A21G, A22(GQEP)₁₂, A70Kˆ, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(−76Kˆ), B(−75P), B(−1)(GQAP)₁₉, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98Kˆ, A99P, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQAPGQEP)₆-GQAP, A122Kˆ, A123P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(G)₁₈, A40Kˆ, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAP)₂₄, A118G, A119Q, A120A, A121Kˆ, A122P, B25H, B29R, desB30 human insulin/(227A, 234A, 235K, 297E, 315Q, 384Q, des447 hIgG4-Fc(228-447))3,5-bis[(2-acetyl)amino]benzoyl conjugate;

(A14E, A21G, A22(GQAP)₂₄, A118G, A119Q, A120A, A121Kˆ, A122P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98Kˆ, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]carbamoylamino]-butanoyl conjugate;

(A14A, A21G, A22(GQAP)₁₈, A94G, A95Q, A96A, A97Kˆ, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14A, A21G, A22(GQAP)₁₈, A94G, A95Q, A96A, A97Kˆ, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A1(N(alpha)acetyl), A14E, A21G, A22(GQAP)₁₉, A98Kˆ, A99P, B1(N(alpha)acetyl), B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A21G, A22(GQAP)₁₈, A94G, A95Q, A96A, A97Kˆ, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)₂₄, A118G, A119Q, A120A, A121Kˆ, A122P, B29R, desB30 human insulin)/(227A, 234A, 235K, 297E, 315Q, 384Q, des447 hIgG4-Fc(228-447))₃,₅-bis[(2-acetyl)amino]benzoyl conjugate;

(A21G, A22(GQAP)₁₈, A94G, A95Q, A96A, A97Kˆ, A98P, B16E, B25H, B29R, desB30 human insulin)/(227A, 234A, 235K, 297E, 315Q, 384Q, des447 hIgG4-Fc(228-447))₃,₅-bis[(2-acetyl)amino]benzoyl conjugate;

(A14E, A21G, A22(GQAP)₁₈, A94G, A95Q, A96A, A97Kˆ, A98P, B16E, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQEP)₆, A46K, A47P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate; and (A14E, A21G, A22(GQEP)₁₉, 98Kˆ, A99P, B25H, B29R, desB30 human insulin)/(226A, 227G, 228P, 234A, 235K, des447 IgG4-Fc(228-447))3,5-bis[(2-acetyl)amino]benzoyl conjugate.

Intermediate Products

[OEF-Ins] Constructs

In further aspects, the invention provides intermediate compounds for use in the manufacture of the insulin-Fc conjugate of the invention.

The [OEF-Ins] construct may be obtained by methods known in the art, e.g. as described in WO 2016/193380.

In one embodiment, the intermediate compound for use according to the invention is a construct of Formula II

[OEF-Ins]

wherein,

OEF represents a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue; and Ins represents an analogue of human insulin, which insulin analogue is a two-chain insulin molecule comprising an A- and a B-chain.

In further embodiments, the intermediate compound for Formula II for use according to the invention is selected from the following examples.

Insulin Analogues with A-Chain Extensions

A14E, A21G, A22(GQEP)₁₉, A98K, A99P, B25H, B29R, desB30 human insulin (OEF-Ins-1);

A14E, A21G, A22(GQAPGQAPGQEP)₆, A94G, A95Q, A96A, A97P, A98K, A99P, B3Q, B25H, B29R, desB30 human insulin (OEF-Ins-3);

A14E, A21G, A22(GQEP)₁₉, A98K, A99P, B3Q, B25H, B29R, desB30 human insulin (OEF-Ins-5);

A14E, A21G, A22(GQEP)₁₂, A70K, A71P, B25H, B29R, desB30 human insulin (OEF-Ins-6);

A14E, A21G, A22(GQEP)₆, A46K, A47P, B25H, B29R, desB30 human insulin (OEF-Ins-7);

A14E, A21G, A22(GQEP)₃-GQE-KP, A38K, A39P, B25H, B29R, desB30 human insulin;

A14E, A21G, A22(GQAPGQEP)₆, A70K, A71P, B25H, B29R, desB30 human insulin (OEF-Ins-9);

A14E, A21G, A22(GQAP)₁₉, A98K, A99P, B25H, B29R, desB30 human insulin (OEF-Ins-13);

A14E, A21G, A22(GQAPGQAPGQEP)₆, A94G, A95Q, A96A, A97P, A98K, A99P, B25H, B29R, desB30 human insulin (OEF-Ins-14);

A14E, A21G, A22(GQAPGQAPGQAPGQEP)₆, A118G, A119Q, A120A, A121P, A122K, A123P, B25H, B29R, desB30 human insulin;

A14A, A21G, A22(GQAP)₁₈-GQAKP, B29R, desB30 (OEF-Ins-16);

A14E, A21G, A22(GQAP)₁₈-GQAKP, B29R, desB30 (OEF-Ins-17);

A14E, A21G, A22(GQAP)₁₈-GQAKP, B25H, B29R, desB30 (OEF-Ins-18);

A14E, A21G, A22(G)$_{17}$, A40K, B25H, B29R, desB30 human insulin; and

A14E, A21G, A22(GQAP)$_{24}$-GQAKP, B25H, B29R, desB30 human insulin (OEF-Ins-20).

Insulin Analogues with A-Chain Extensions

A14E, A21G, A22(GQEP)$_{19}$, A98K, A99P, B25H, B29R, desB30 human insulin (OEF-Ins-1);

A14E, A21G, A22(GQAPGQAPGQEP)$_6$, A94G, A95Q, A96A, A97P, A98K, A99P, B3Q, B25H, B29R, desB30 human insulin (OEF-Ins-3);

A14E, A21G, A22(GQEP)$_{19}$, A98K, A99P, B3Q, B25H, B29R, desB30 human insulin (OEF-Ins-5);

A14E, A21G, A22(GQEP)$_{12}$, A70K, A71P, B25H, B29R, desB30 human insulin (OEF-Ins-6);

A14E, A21G, A22(GQEP)$_6$, A46K, A47P, B25H, B29R, desB30 human insulin (OEF-Ins-7);

A14E, A21G, A22(GQEP)$_3$-GQE-KP, A38K, A39P, B25H, B29R, desB30 human insulin;

A14E, A21G, A22(GQAPGQEP)$_6$, A70K, A71P, B25H, B29R, desB30 human insulin (OEF-Ins-9);

A14E, A21G, A22(GQAP)$_{19}$, A98K, A99P, B25H, B29R, desB30 human insulin (OEF-Ins-13);

A14E, A21G, A22(GQAPGQAPGQEP)$_6$, A94G, A95Q, A96A, A97P, A98K, A99P, B25H, B29R, desB30 human insulin (OEF-Ins-14);

A14E, A21G, A22(GQAPGQAPGQAPGQEP)$_6$, A118G, A119Q, A120A, A121P, A122K, A123P, B25H, B29R, desB30 human insulin;

A14A, A21G, A22(GQAP)$_{18}$-GQAKP, B29R, desB30 human insulin (OEF-Ins-16);

A14E, A21G, A22(GQAP)$_{18}$-GQAKP, B29R, desB30 human insulin (OEF-Ins-17);

A14E, A21G, A22(GQAP)$_{18}$-GQAKP, B25H, B29R, desB30 human insulin (OEF-Ins-18);

A14E, A21Q, A22(G)$_{18}$, A40K, B25H, B29R, desB30 human insulin (OEF-Ins-19);

A14E, A21G, A22(GQAP)$_{24}$-GQAKP, B25H, B29R, desB30 human insulin (OEF-Ins-20);

A14E, A21G, A22(GQAP)$_{24}$, A118G, A119Q, A120A, A121K, A122P, B29R, desB30 human insulin (OEF-Ins-21);

A21G, A22(GQAP)$_{18}$, A94G, A95Q, A96A, A97K, A98P, B29R, desB30 human insulin (OEF-Ins-22);

A21G, A22(GQAP)$_{18}$, A94G, A95Q, A96A, A97K, A98P, B16E, B25H, B29R, desB30 human insulin (OEF-Ins-23).

Insulin Analogues with B-Chain Extensions

A14E, B(-78K), B(-77P), B(-1)(GQAPGQAPGQEP)$_6$-GQAP, B3Q, B25H, B29R, desB30 human insulin (OEF-Ins-2);

A14E, B(-78K), B(-77P), B(-1)(GQEP)$_{19}$, B25H, B29R, desB30 human insulin (OEF-Ins-4);

A14E, B(-26K), B(-25P), B(-1)(GQEP)$_6$, B25H, B29R, desB30 human insulin (OEF-Ins-10);

A14E, B(-18K), B(-17P), B(-1)(GQEP)$_4$, B25H, B29R, desB30 human insulin; and

A14E, B(-78K), B(-77P), B(-1)(GQAP)$_{19}$, B25H, B29R, desB30 human insulin (OEF-Ins-12).

Fc Fragments

The insulin-Fc conjugates of the present invention involve the use of two monomer Fc polypeptides covalently joined with insulin via a linker.

In a further aspect, the invention provides an Fc' polypeptide for use as an intermediate compound in the manufacture of an insulin-Fc conjugate of the invention.

In one embodiment, the Fc' polypeptide for use according to the invention is a hIgG1-Fc(228-447) polypeptide that contains one or more extensions and/or substitutions and/or deletions selected from the group of 226A, 227A or 227S, 228S, 234A, 235A or 235E or 235K, 237A or 297Q, 297E, N315Q, 330S, 331S, N384Q, and des447.

In another embodiment, the Fc' polypeptide for use according to the invention is a hIgG1-Fc(228-447) polypeptide that contains one or more extensions and/or substitutions and/or deletions selected from the group of 226A, 227A or 227G or 227S, 228S, 234A, 235A or 235E or 235K, 237A or 297Q, 297E, N315Q, 330S, 331S, N384Q, and des447.

In another embodiment, Fc' represents
226A, 227S hIgG1-Fc(228-447) (Fc7);
226A, 227S, 234A, 235E, 237A, 330S, 331S hIgG1-Fc(228-447) (Fc13);
226A, 227S, 234A, 235K, 237A, 315Q, 330S, 331S, 384Q hIgG1-Fc(228-447) (Fc12);
226A, 227S, 234A, 235K, 237A, 330S, 331S hIgG1-Fc(228-447) (Fc11);
226A, 227S, 235K, 237A, 330S, 331S hIgG1-Fc(228-447) (Fc10); or
227A, 228S, 235K, 315Q, 384Q hIgG1-Fc(228-447) (Fc4).

In a further embodiment, the Fc' polypeptide for use according to the invention is a fragment of a hIgG2 derived Fc sequence, starting at position 228 and ending at position 446, which sequence contains one or more extensions and/or substitutions selected from the group of 227A, L234A, 235K, and 377A.

In a further embodiment, the Fc' polypeptide for use according to the invention is a fragment of a hIgG4 derived Fc sequence, starting at position 228 and ending at position 447, which sequence contains one or more extensions and/or substitutions selected from the group of 226G, 227A, 234A, 235A or 235K, N297E or N297Q, 315Q, 384Q and des447.

In a further embodiment, the Fc' polypeptide for use according to the invention is a fragment of a hIgG4 derived Fc sequence, starting at position 228 and ending at position 447, which sequence contains one or more extensions and/or substitutions selected from the group of 226A or 226G, 227A or 227G, 228P, 234A, 235A or 235K, N297E or N297Q, 315Q, 384Q and des447.

In one embodiment, Fc' represents
226G, 227A hIgG4-Fc(228-447) (Fc3);
227A hIgG4-Fc(228-447) (Fc1);
227A, 234A, 235A hIgG4-Fc(228-447) (Fc6);
227A, 234A, 235K hIgG4-Fc(228-447) (Fc9);
227A, 234A, 235K, 297E, 315Q, 384Q, des447 hIgG4-Fc(228-447) (Fc15);
227A, 234A, 235K, 297E, des447 hIgG4-Fc(228-447) (Fc16);
227A, 234A, 235K, 297Q hIgG4-Fc(228-447) (Fc14);
227A, 235K hIgG4-Fc(228-447) (Fc8);
227A, 235K, 315Q, 384Q hIgG4-Fc(228-447) (Fc5); or
227A, 315Q, 384Q hIgG4-Fc(228-447) (Fc2).

In another embodiment, Fc' represents
226A, 227G, 228P, 234A, 235K, des447 hIgG4-Fc(228-447) (Fc17);
226A, 227G, 234A, 235K, des447 hIgG4-Fc(228-447);
226G, 227A hIgG4-Fc(228-447) (Fc3);
227A hIgG4-Fc(228-447) (Fc1);
227A, 234A, 235A hIgG4-Fc(228-447) (Fc6);
227A, 234A, 235K hIgG4-Fc(228-447) (Fc9);
227A, 234A, 235K, 297E, 315Q, 384Q, des447 hIgG4-Fc(228-447) (Fc15);
227A, 234A, 235K, 297E, des447 hIgG4-Fc(228-447) (Fc16);
227A, 234A, 235K, 297Q hIgG4-Fc(228-447) (Fc14);
227A, 235K hIgG4-Fc(228-447) (Fc8);

227A, 235K, 315Q, 384Q hIgG4-Fc(228-447) (Fc5); or
227A, 315Q, 384Q hIgG4-Fc(228-447) (Fc2).

Linking Groups

In another aspect the present invention provides an intermediate compound for use in the manufacture of the insulin-Fc conjugate of the invention.

More specifically tri-antennary linkers are provided, in which the first terminus is capable of forming a stable covalent bond with the epsilon amino group of a lysine residue of the insulin component (Ins) of Formula I, and which terminus remains unaffected by thiols, or by any other residue within the protein.

The second and third termini of the linker are identical, and capable of forming stable covalent bonds with thiol moieties (i.e. —SH) of the Fc' component of Formula I (called the "Cys-reactive termin-us/-i"). After the first conjugation event has taken place (i.e. conjugation of the first terminus to lysine), the Cys-reactive termin-us/i can react directly (using e.g. bromo or iodo acetamides, Michael acceptors, etc., or can be amenable of a chemical transformation, such that it will make them reactive towards thiol(s) of a second protein (changing e.g. chloroacetamide to iodoacetamide), thereby giving the desired insulin-Fc conjugate of Formula I in a sequential, two-step fashion.

The particular design of the linker of the invention, containing two reactive ends that each comprises an Sp2 hybridised carbon C atom, a $CH_2$ group and a halogen (Hlg) atom (represented as (C=O)—$CH_2$-Hlg), is particularly well suited for conjugating inter-chain disulphides of Fc fragments, as these can be easily and selectively reduced to free thiols without interfering with other intra-chain disulphides.

The intermediate product of the invention represents a tri-antennary linker which allows for an efficient protein-protein conjugation by means of hetero-functional linkers. By use of different leaving groups, the linkage of reactants can be controlled, and the intermediate is particularly useful in a method of synthesis in order to covalently link two or more proteins in an ordered fashion, ensuring that different proteins can be attached at each end of the linker.

In one embodiment, the intermediate compound for use according to the invention may be characterised by the general Formula V:

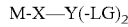

wherein

M (that may also be designated as the Lys reactive terminus) represents a leaving group reactive towards primary amino groups;

X is absent (i.e. represents a covalent bond), or X represents a divalent linking group as defined for Formula I above;

Y represents a central trivalent linking unit as defined for Formula I above; and LG (that may also be designated as the Cys reactive terminus) represents the leaving group of a thiol reactive group.

In another embodiment, the intermediate compound for use according to the invention may be characterised by the general Formula V':

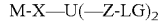

wherein

M (that may also be designated as the Lys reactive terminus) represents a leaving group reactive towards primary amino groups;

X is absent (i.e. represents a covalent bond), or X represents a divalent linking group as defined for Formula I' above;

U represents a central trivalent linking unit as defined for Formula I' above;

Z represents a divalent linking group connecting the central linking unit (U) to the leaving group (LG); and LG (that may also be designated as the Cys reactive terminus) represents the leaving group of a thiol reactive group.

In the context of this invention, M represents a leaving group reactive towards primary amino groups such as of commonly used active esters. Such leaving groups include active esters conventionally used in peptide synthesis, including but not limited to, N-hydroxysuccinimide (NHS) esters, sulfo-NHS ester, pentafluorophenol (PFP) ester, p-nitrophenol (PNP) ester, hydroxybenzotriazole (HOBt) ester and ethyl (hydroxyimino)cyanoacetate ester (Oxyma).

In one embodiment, the "Lys reactive terminus" (M) is represented by a succinimide ester (OSu ester) activated carboxylic acid moiety, and the "Cys reactive termini" $(LG)_2$ are represented by 2×iodo-, 2×bromo- or 2×chloroacetamides. After reaction of N-eps of the Lys positioned in the terminal part of the extension of insulin (i.e. the first protein) with the OSu ester, and appropriate purification, the resulting conjugate is reacted with the thiols of the Fc-fragments (i.e. the second and third protein) formed upon reduction of the inter chain disulphide, directly, or in the case of chloroacetamide, after exposure to high concentration of iodide ions, to bring about the so-called "Finkelstein reaction", which reaction results in a chloro to iodo exchange, thus generating a 2×iodoacetamide moiety. The final result is the formation of a covalent, site-specific conjugate between the two proteins of interest, i.e. an insulin-Fc conjugate of Formula I.

In another embodiment, the intermediate product is a compound of Formula V, wherein M represents a leaving group reactive towards Lys.

In a third embodiment, M represents a leaving group of commonly used active esters of HOSu (N-succinimidyloxy or 2,5-dioxopyrrolidin-1-yl-oxy), HOAt, HOBt, benzotriazole and the like.

In one embodiment, the intermediate product is a compound of Formula V, wherein the thiol reactive group (LG) represents a halogen atom selected from chloro, bromo or iodo; pyridyldisulphide; methoxy- or ethoxycarbonyldisulphide; or o-nitro-phenyldisulphide.

In another embodiment, LG represents a thiol reactive group a halogen atom selected from chloro, bromo and iodo.

In a third embodiment, the intermediate product is a compound of Formula V of the invention is 2,5-dioxopyrrolidin-1-yl)-4-[bis[2-[(2-iodoacetyl)amino]ethyl]amino]-4-oxo-butanoate (illustrated as Chem. 6, see Example 3.1):

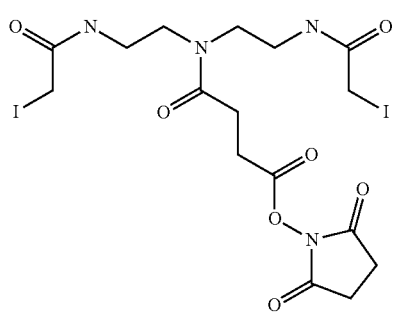

In a fourth embodiment, the intermediate product is a compound of Formula V of the invention is (2,5-dioxopyrrolidin-1-yl)-6-[bis[2-[(2-iodoacetyl)amino]ethyl] amino]-6-oxo-hexanoate (illustrated as Chem. 7, see Example 3.2):

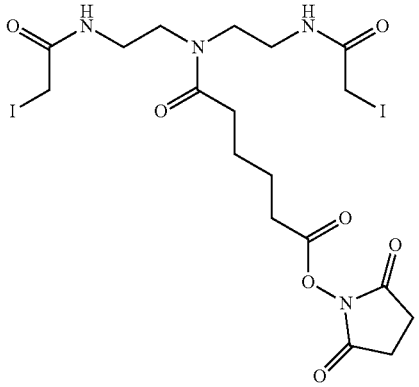 [SMILES: O=C(CI)NCCN(CCNC(=O)CI)C(=O)CCCCC(=O)ON1C(=O)CCC1=O]

In a fifth embodiment, the intermediate product is a compound of Formula V' of the invention is (2,5-dioxopyrrolidin-1-yl)-(2S)-2,6-bis[(2-iodoacetyl)amino]-hexanoate (illustrated as Chem. 8, see Example 3.3):

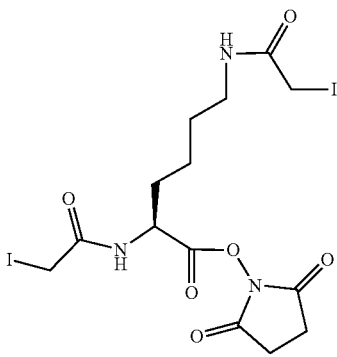 [SMILES: O=C(CI)NCCCC[C@H](NC(=O)CI)C(=O)ON1C(=O)CCC1=O]

In a fifth embodiment, the intermediate product is a compound of Formula V of the invention is 4-[Bis[2-[(2-iodoacetyl)amino]ethyl]carbamoylamino]butanoic acid (illustrated as Chem. 9, see Example 3.4):

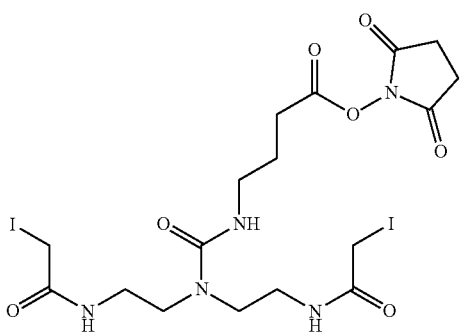 [SMILES: O=C(CI)NCCN(CCNC(=O)CI)C(=O)NCCCC(=O)ON1C(=O)CCC1=O]

In a sixth embodiment, the intermediate product is a compound of Formula V' of the invention is (2,5-dioxopyrrolidin-1-yl)-3,5-bis[(2-bromoacetyl)amino]benzoate (illustrated as Chem. 10, see Example 3.5):

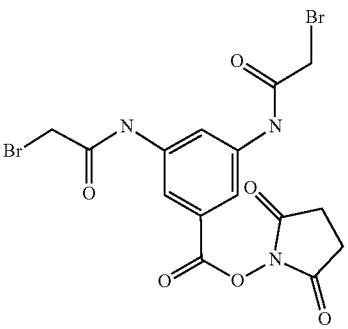

In another embodiment, the intermediate compound according to the invention is a compound characterised by the general Formula VI:

[OEF-Ins]-X—Y(-LG)$_2$ wherein,

OEF is as defined for Formula I above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I above, and is connected to the divalent linking group X via a lysine (K) residue; or more specifically, which [OEF-Ins] construct is as defined for Formula I above, and is connected to the divalent linking group X via the epsilon amino group of a lysine (K) residue;

X represents a divalent linking group as defined for Formula I above;

Y represents a central trivalent linking unit as defined for Formula I above;

or X represents a covalent bond, and Y represents a central trivalent linking unit connecting the two leaving groups (LG)$_2$ to [OEF-Ins]; and LG represents the leaving group of a thiol reactive group.

In another embodiment, the intermediate compound according to the invention is a compound characterised by the general Formula VI':

[OEF-Ins]-X—U(—Z-LG)$_2$ wherein,

OEF is as defined for Formula I' above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I' above, and is connected to the divalent linking group X via a lysine (K) residue; or more specifically, which [OEF-Ins] construct is as defined for Formula I' above, and is connected to the divalent linking group X via the epsilon amino group of a lysine (K) residue;

X represents a divalent linking group as defined for Formula I' above; and U represents a central trivalent linking unit as defined for Formula I' above, connecting the two divalent linking groups (Z) to X; or X represents a covalent bond; and U represents a central trivalent linking unit as defined for Formula I' above, connecting the two divalent linking groups (Z) to the [OEF-Ins] construct; and LG represents the leaving group of a thiol reactive group.

In one embodiment, the intermediate product is a compound of Formula VI of the invention is selected from the group of A14E, A21G, A22(GQEP)19, A98K(N(eps)4-[bis[(2-acetyl)amino]ethyl] amino]-4-oxo-butanoyl), A99P, B25H, B29R, desB30 human insulin (cf. Example 4.1);

A14E, B(−78K(N(eps)4-[bis[(2-acetyl)amino]ethyl]amino]-4-oxo-butanoyl)), B(−77P), (GQAPGQAPGQEP)6-GQAP, B3Q, B25H, B29R, desB30 human insulin (cf. Example 4.2);

A14E, B(−78K(4-[bis[2-[(2-acetyl)amino]ethyl]amino]-4-oxo-butanoyl)), B(−77P), B(−1)(GQEP)19, B25H, B29R, desB30 human insulin (cf. Example 4.3);

A14E, A21G, A22(GQAPGQAPGQEP)6-GQAP, A98K(N(eps)4-[bis[(2-acetyl)amino]ethyl]amino]-4-oxo-butanoyl), A99P, B3Q, B25H, B29R, desB30 human insulin (cf. Example 4.4);

A14E, A21G, A22(GQEP)19, A98K(N(eps)4-[bis[(2-acetyl)amino]ethyl]amino]-4-oxo-butanoyl), A99P, B3Q, B25H, B29R, desB30 human insulin (cf. Example 4.5);

A14E, A21G, A22(GQEP)6, A46K(N(eps)4-[bis[(2-acetyl)amino]ethyl]amino]-4-oxo-butanoyl), A47P, B25H, B29R, desB30 human insulin (cf. Example 4.6);

A14E, A21G, A22(GQEP)12, A70K(N(eps)4-[bis[(2-acetyl)amino]ethyl]amino]-4-oxo-butanoyl), A71P, B25H, B29R, desB30 human insulin (cf. Example 4.7);

A14E, A21G, A22(GQAPGQEP)6, A70K(N(eps)4-[bis[(2-acetyl)amino]ethyl]amino]-4-oxo-butanoyl), A71P, B25H, B29R, desB30 human insulin (cf. Example 4.8);

A14E, A21G, A22(GQEP)3, A34G, A35Q, A36E, A37K(N(eps)4-[bis[(2-acetyl)amino]ethyl]amino]-4-oxo-butanoyl), A38P, B25H, B29R, desB30 human insulin (cf. Example 4.9);

A14E, A21G, A22(GQAP)19, A98K(N(eps)4-[bis[(2-acetyl)amino]ethyl]amino]-4-oxo-butanoyl), A99P, B25H, B29R, desB30 human insulin (cf. Example 4.10);

A14E, A21G, A22(GQAP)19, A98K(N(eps)4-[bis[(2-acetyl)amino]ethyl]amino]-4-oxo-hexanoyl), A99P, B25H, B29R, desB30 human insulin (cf. Example 4.11);

A14E, B(−78K(N(eps)4-[bis[(2-acetyl)amino]ethyl]amino]-4-oxo-hexanoyl)), B(−77P), B(−1)(GQAP)19, B25H, B29R, desB30 human insulin (cf. Example 4.12);

A14E, A21G, A22(GQAPGQAPGQEP)6-GQAP, A98K(N(eps)4-[bis[(2-acetyl)amino]ethyl]amino]-4-oxo-butanoyl), A99P, B29R, desB30 human insulin (cf. Example 4.13);

A14E, A21G, A22(GQAPGQAPGQAPGQEP)6-GQAP, A122K(N(eps)4-[bis[(2-acetyl)amino]ethyl]amino]-4-oxo-butanoyl), A123P, B25H, B29R, desB30 human insulin (cf. Example 4.14);

A14E, A21Q, A22(G)17, A40K(N(eps)4-[bis[(2-acetyl)amino]ethyl]amino]-4-oxo-butanoyl), B25H, B29R, desB30 human insulin (cf. Example 4.15);

A14E, A21G, A22(GQAP)24, A118GA, 119Q, A120A, A121K(N(eps)-3,5-bis[(2-bromoacetyl)amino]benzoyl), A122P, B25H, B29R, desB30 human insulin (cf. Example 4.16);

A14E, A21G, A22(GQAP)24, A118GA, 119Q, A120A, A121K(N(eps)-4-[bis[(2-acetyl)amino]ethyl]amino]-4-oxo-butanoyl), A122P, B25H, B29R, desB30 human insulin (cf. Example 4.17);

A14E, A21G, A22(GQAPGQAPGQEP)6-GQAP, A98K(N(eps)4-[bis[2-[(2-iodoacetyl)amino]ethyl]carbamoylamino]butanoyl, A99P, B3Q, B25H, B29R, desB30 human insulin (cf. Example 4.18); and A14E, A21G, A22(GQAP)18, A94Q, A95Q, A96A, A97K(N(eps)4-[bis[(2-acetyl)amino]ethyl]amino]-4-oxo-hexanoyl), A98P, B29R, desB30 human insulin (cf. Example 4.19).

In another embodiment, the intermediate product is a compound of Formula VI of the invention is selected from the group of A14E, A21G, A22(GQEP)19, A98K(N(eps)4-[bis[(2-acetyl)amino]ethyl] amino]-4-oxo-butanoyl), A99P, B25H, B29R, desB30 human insulin (cf. Example 4.1);

A14E, B(−78K(N(eps)4-[bis[(2-acetyl)amino]ethyl]amino]-4-oxo-butanoyl)), B(−77P), (GQAPGQAPGQEP)6-GQAP, B3Q, B25H, B29R, desB30 human insulin (cf. Example 4.2);

A14E, B(−78K(4-[bis[2-[(2-acetyl)amino]ethyl]amino]-4-oxo-butanoyl)), B(−77P), B(−1)(GQEP)19, B25H, B29R, desB30 human insulin (cf. Example 4.3);

A14E, A21G, A22(GQAPGQAPGQEP)6-GQAP, A98K(N(eps)4-[bis[(2-acetyl)amino]ethyl]amino]-4-oxo-butanoyl), A99P, B3Q, B25H, B29R, desB30 human insulin (cf. Example 4.4);

A14E, A21G, A22(GQEP)19, A98K(N(eps)4-[bis[(2-acetyl)amino]ethyl]amino]-4-oxo-butanoyl), A99P, B3Q, B25H, B29R, desB30 human insulin (cf. Example 4.5);

A14E, A21G, A22(GQEP)6, A46K(N(eps)4-[bis[(2-acetyl)amino]ethyl]amino]-4-oxo-butanoyl), A47P, B25H, B29R, desB30 human insulin (cf. Example 4.6);

A14E, A21G, A22(GQEP)12, A70K(N(eps)4-[bis[(2-acetyl)amino]ethyl]amino]-4-oxo-butanoyl), A71P, B25H, B29R, desB30 human insulin (cf. Example 4.7);

A14E, A21G, A22(GQAPGQEP)6, A70K(N(eps)4-[bis[(2-acetyl)amino]ethyl]amino]-4-oxo-butanoyl), A71P, B25H, B29R, desB30 human insulin (cf. Example 4.8);

A14E, A21G, A22(GQEP)3, A34G, A35Q, A36E, A37K(N(eps)4-[bis[(2-acetyl)amino]ethyl]amino]-4-oxo-butanoyl), A38P, B25H, B29R, desB30 human insulin (cf. Example 4.9);

A14E, A21G, A22(GQAP)19, A98K(N(eps)4-[bis[(2-acetyl)amino]ethyl]amino]-4-oxo-butanoyl), A99P, B25H, B29R, desB30 human insulin (cf. Example 4.10);

A14E, A21G, A22(GQAP)19, A98K(N(eps)4-[bis[(2-acetyl)amino]ethyl]amino]-4-oxo-hexanoyl), A99P, B25H, B29R, desB30 human insulin (cf. Example 4.11);

A14E, B(−78K(N(eps)4-[bis[(2-acetyl)amino]ethyl]amino]-4-oxo-hexanoyl)), B(−77P), B(−1)(GQAP)19, B25H, B29R, desB30 human insulin (cf. Example 4.12);

A14E, A21G, A22(GQAPGQAPGQEP)6-GQAP, A98K(N(eps)4-[bis[(2-acetyl)amino]ethyl]amino]-4-oxo-butanoyl), A99P, B29R, desB30 human insulin (cf. Example 4.13);

A14E, A21G, A22(GQAPGQAPGQEP)6-GQAP, A122K(N(eps)4-[bis[(2-acetyl)amino]ethyl]amino]-4-oxo-butanoyl), A123P, B25H, B29R, desB30 human insulin (cf. Example 4.14);

A14E, A21Q, A22(G)$_{18}$, A40K(N(eps)4-[bis[(2-acetyl)amino]ethyl]amino]-4-oxo-butanoyl), B25H, B29R, desB30 human insulin (cf. Example 4.15);

A14E, A21G, A22(GQAP)24, A118G, A119Q, A120A, A121K(N(eps)-3,5-bis[(2-bromoacetyl)amino]benzoyl), A122P, B25H, B29R, desB30 human insulin (cf. Example 4.16);

A14E, A21G, A22(GQAP)24, A118G, A119Q, A120A, A121K(N(eps)-4-[bis[(2-acetyl)amino]ethyl]amino]-4-oxo-butanoyl), A122P, B25H, B29R, desB30 human insulin (cf. Example 4.17);

A14E, A21G, A22(GQAPGQAPGQEP)6-GQAP, A98K (N(eps)4-[bis[2-[(2-iodoacetyl)amino]ethyl]carbamoy-lamino]butanoyl), A99P, B3Q, B25H, B29R, desB30 human insulin (cf. Example 4.18); and A14A, A21G, A22(GQAP)18, A94G, A95Q, A96A, A97K(N(eps)4-[bis[(2-acetyl)amino]ethyl]amino]-4-oxo-hexanoyl), A98P, B29R, desB30 human insulin (cf. Example 4.19);

A14E, A21G, A22(GQAP)18, A94G, A95Q, A96A, A97K(N(eps)4-[bis[(2-acetyl)amino]ethyl]amino]-4-oxo-butanoyl), A98P, B29R, desB30 human insulin (cf. Example 4.20);

A1(N(alpha)acetyl), A14E, A21G, A22(GQAP)19, A98K (N(eps)4-[bis[(2-acetyl)amino]ethyl]amino]-4-oxo-bu-tanoyl), A99P, B1(N(alpha)acetyl),B25H, B29R, desB30 human insulin (cf. Example 4.21);

A21G, A22(GQAP)18, A94G, A95Q, A96A, A97K(N (eps)4-[bis[(2-acetyl)amino]ethyl]amino]-4-oxo-butanoyl), A98P, B29R, desB30 human insulin (cf. Example 4.22);

A14E, A21G, A22(GQAP)24, A118G, A119Q, A120A, A121K(N(eps)-3,5-bis[(2-bromoacetyl)amino]benzoyl), A122P, B29R, desB30 human insulin (cf. Example 4.23);

A14E, A21G, A22(GQAP)18, A94G, A95Q, A96A, A97K(N(eps)-3,5-bis[(2-bromoacetyl)amino]benzoyl), A98P, B16E, B29R, desB30 human insulin (cf. Example 4.24);

A14E, A21G, A22(GQAP)18, A94G, A95Q, A96A, A97K(N(eps)4-[bis[(2-acetyl)amino]ethyl]amino]-4-oxo-butanoyl), A98P, B61E, B25H, B29R, desB30 human insulin (cf. Example 4.25);

A14E, A21G, A22(GQEP)19, A98K(N(eps)-3,5-bis[(2-bromoacetyl)amino]benzoyl), A99P, B25H, B29R, desB30 human insulin (cf. Example 4.26).

In yet another embodiment, the intermediate product is a compound of Formula VI' of the invention selected from the group of A14E, A21G, A22(GQEP)$_{19}$, A98K(N(eps)4-[bis[2-[(2-iodoacetyl)amino]ethyl] amino]-4-oxo-butanoyl), A99P, B25H, B29R, desB30 human insulin (cf. Example 4.1);

A14E, B(-78K(N(eps)4-[bis[2-[(2-iodoacetyl)amino] ethyl]amino]-4-oxo-butanoyl)), B(-77P), (B-1) (GQAPGQAPGQEP)$_6$-GQAP, B3Q, B25H, B29R, desB30 human insulin (cf. Example 4.2);

A14E, B(-78K(N(eps)4-[bis[2-[(2-iodoacetyl)amino] ethyl]amino]-4-oxo-butanoyl)), B(-77P), B(-1)(GQEP)$_{19}$, B25H, B29R, desB30 human insulin (cf. Example 4.3);

A14E, A21G, A22(GQAPGQAPGQEP)$_6$-GQAP, A98K (N(eps)4-[bis[2-[(2-iodoacetyl)amino]ethyl]amino]-4-oxo-butanoyl), A99P, B3Q, B25H, B29R, desB30 human insulin (cf. Example 4.4);

A14E, A21G, A22(GQEP)$_{19}$, A98K(N(eps)4-[bis[2-[(2-iodoacetyl)amino]ethyl]amino]-4-oxo-butanoyl), A99P, B3Q, B25H, B29R, desB30 human insulin (cf. Example 4.5);

A14E, A21G, A22(GQEP)$_6$, A46K(N(eps)4-[bis[2-[(2-iodoacetyl)amino]ethyl]amino]-4-oxo-butanoyl), A47P, B25H, B29R, desB30 human insulin (cf. Example 4.6);

A14E, A21G, A22(GQEP)$_{12}$, A70K(N(eps)4-[bis[2-[(2-iodoacetyl)amino]ethyl]amino]-4-oxo-butanoyl), A71P, B25H, B29R, desB30 human insulin (cf. Example 4.7);

A14E, A21G, A22(GQAPGQEP)$_6$, A70K(N(eps)4-[bis [2-[(2-iodoacetyl)amino]ethyl]amino]-4-oxo-butanoyl), A71P, B25H, B29R, desB30 human insulin (cf. Example 4.8);

A14E, A21G, A22(GQEP)$_3$, A34G, A35Q, A36E, A37K (N(eps)4-[bis[2-[(2-iodoacetyl)amino]ethyl]amino]-4-oxo-butanoyl), A38P, B25H, B29R, desB30 human insulin (cf. Example 4.9);

A14E, A21G, A22(GQAP)$_{19}$, A98K(N(eps)4-[bis[2-[(2-iodoacetyl)amino]ethyl]amino]-4-oxo-butanoyl), A99P, B25H, B29R, desB30 human insulin (cf. Example 4.10);

A14E, A21G, A22(GQAP)$_{19}$, A98K(N(eps)$_6$-[bis[2-[(2-iodoacetyl)amino]ethyl]amino]-6-oxo-hexanoyl), A99P, B25H, B29R, desB30 human insulin (cf. Example 4.11);

A14E, B(-78K(N(eps)4-[bis[2-[(2-iodoacetyl)amino] ethyl]amino]-4-oxo-butanoyl)), B(-77P), B(-1)(GQAP)$_{19}$, B25H, B29R, desB30 human insulin (cf. Example 4.12);

A14E, A21G, A22(GQAPGQAPGQEP)$_6$-GQAP, A98K (N(eps)4-[bis[2-[(2-iodoacetyl)amino]ethyl]amino]-4-oxo-butanoyl), A99P, B25H, B29R, desB30 human insulin (cf. Example 4.13);

A14E, A21G, A22(GQAPGQAPGQAPGQEP)$_6$-GQAP, A122K(N(eps)4-[bis[2-[(2-iodoacetyl)amino]ethyl]amino]-4-oxo-butanoyl), A123P, B25H, B29R, desB30 human insulin (cf. Example 4.14);

A14E, A21Q, A22(G)$_{18}$, A40K(N(eps)4-[bis[2-[(2-iodoacetyl)amino]ethyl]amino]-4-oxo-butanoyl), B25H, B29R, desB30 human insulin (cf. Example 4.15);

A14E, A21G, A22(GQAP)$_{24}$, A118G, A119Q, A120A, A121K(N(eps)-3,5-bis[(2-bromoacetyl)amino]benzoyl), A122P, B25H, B29R, desB30 human insulin (cf. Example 4.16);

A14E, A21G, A22(GQAP)$_{24}$, A118G, A119Q, A120A, A121K(N(eps)4-[bis[2-[(2-iodoacetyl)amino]ethyl]amino]-4-oxo-butanoyl), A122P, B25H, B29R, desB30 human insulin (cf. Example 4.17);

A14E, A21G, A22(GQAPGQAPGQEP)$_6$-GQAP, A98K (N(eps)4-[bis[2-[(2-iodoacetyl)amino]ethyl]carbamoy-lamino]butanoyl), A99P, B3Q, B25H, B29R, desB30 human insulin (cf. Example 4.18);

A14A, A21G, A22(GQAP)$_{18}$, A94G, A95Q, A96A, A97K (N(eps)4-[bis[2-[(2-iodoacetyl)amino]ethyl]amino]-4-oxo-butanoyl), A98P, B29R, desB30 human insulin (cf. Example 4.19);

A14E, A21G, A22(GQAP)$_{18}$, A94G, A95Q, A96A, A97K (N(eps)4-[bis[2-[(2-iodoacetyl)amino]ethyl]amino]-4-oxo-butanoyl), A98P, B29R, desB30 human insulin (cf. Example 4.20);

A1(N(alpha)acetyl), A14E, A21G, A22(GQAP)$_{19}$, A98K (N(eps)4-[bis[2-[(2-iodoacetyl)amino]ethyl]amino]-4-oxo-butanoyl), A99P, B1(N(alpha)acetyl),B25H, B29R, desB30 human insulin (cf. Example 4.21);

A21G, A22(GQAP)$_{18}$, A94G, A95Q, A96A, A97K(N (eps)4-[bis[2-[(2-iodoacetyl)amino]ethyl]amino]-4-oxo-bu-tanoyl), A98P, B29R, desB30 human insulin (cf. Example 4.22);

A14E, A21G, A22(GQAP)$_{24}$, A118G, A119Q, A120A, A121K(N(eps)-3,5-bis[(2-bromoacetyl)amino]benzoyl), A122P, B29R, desB30 human insulin (cf. Example 4.23);

A14E, A21G, A22(GQAP)$_{18}$, A94G, A95Q, A96A, A97K (N(eps)-3,5-bis[(2-bromoacetyl)amino]benzoyl), A98P, B16E, B25H, B29R, desB30 human insulin (cf. Example 4.24);

A14E, A21G, A22(GQAP)$_{18}$, A94G, A95Q, A96A, A97K (N(eps)4-[bis[2-[(2-iodoacetyl)amino]ethyl]amino]-4-oxo-butanoyl), A98P, B16E, B25H, B29R, desB30 human insulin (cf. Example 4.25); and A14E, A21G, A22(GQEP)$_{19}$, A98K(N(eps)-3,5-bis[(2-bromoacetyl)amino]benzoyl), A99P, B25H, B29R, desB30 human insulin (cf. Example 4.26).

Methods for the Preparation of Intermediate Products

Depending on the insulin analogue in question and the individual linker to be used, various methods for synthesis may be applied. The linkers for use according to the invention may be produced by standard technologies, e.g. as described in the working examples below.

The proteins to be conjugated and the linker may be prepared and purified separately.

In one aspect, the invention may be regarded drawn to the coupling of two proteins, and a sequential reaction is accomplished by use of a linker with different reactive ends.

In another embodiment, one end of the linker is a primary amino group reactive group, and the other end has two thiol reactive groups.

In a third embodiment, a primary amino group of insulin is reacted with the linker, followed by reaction with an Fc with two free cysteines.

In a further embodiment, Fc is connected through both sulphur atoms derived from a reduced disulphide bond.

Methods for the Preparation of Insulin-Fc Conjugates

In a further aspect, the invention provides a method for preparing the insulin-Fc conjugates of the invention.

The method of the invention comprises the (consecutive) steps of
A) Preparation of the intermediate compound M-X—Y(-LG)$_2$ of Formula V; or the intermediate compound M-X—U(—Z-LG)$_2$ of Formula V';
B) Coupling the [OEF-Ins] construct to the intermediate compound M-X—Y(-LG)$_2$ of Formula V, or to the intermediate compound M-X—U(—Z-LG)$_2$ of Formula V', to obtain the intermediate compound [OEF-Ins]-X—Y(-LG)$_2$ of Formula VI, or to obtain intermediate compound [OEF-Ins]-X—U(—Z-LG)$_2$ of Formula VI';
C) Reduction of the inter-chain disulphide bond of Fc to obtain two Fc's, each holding a free cysteine; and
D) Coupling the two Fc's to the [OEF-Ins]-X—Y(-LG)$_2$ of Formula VI, or to the [OEF-Ins]-X—U(—Z-LG)$_2$ of Formula VI', to obtain the insulin-Fc conjugate of Formula I, or of Formula I'.

Generally the individual components, i.e. the insulin component, the OEF-Ins component, the Fc component, and the linker, are produced separately and coupled together under suitable reaction conditions.

The insulin components for incorporation into the insulin-Fc conjugate according to the invention may be obtained by conventional methods for the preparation of insulin, insulin analogues and insulin derivatives, e.g. as outlined in WO 2008/034881, or in WO 2016/193380.

Fc domains may be obtained from full length antibodies isolated from humans and other animals, or may be produced recombinantly and obtained from transformed mammalian cells or microorganisms. Multiple technologies to obtain Fc-domains are known in the art.

An Fc-domain can be produced from a full length antibody by digestion with a proteolytic enzyme such as papain or pepsin. Affinity chromatography and DEAE anion-exchange chromatography can be used to separate the resulting Fab and F(ab')$_2$ from the Fc-domain. Based on SEC-HPLC analysis, the purity of the Fc-fragment can be determined.

When recombinant methods are used, the desired polypeptide can be expressed and the Fc domain subsequently purified. In one embodiment the Fc domain is a human-derived Fc-domain, such as a human IgG Fc-domain obtained from transformed microorganisms or mammalian cells.

In addition, the Fc-fragment of the present invention may be in the form of having native sugar chains, increased sugar chains compared to a native form or decreased sugar chains compared to the native form, or may be in an aglycosylated form. The increase, decrease or removal of sugar chains of the Fc-fragment may be achieved by methods known in the art, such as a chemical method or an enzymatic method. Otherwise the asparagine at position 297, which is the natural glycosylation site can be mutated by molecular engineering to e.g. alanine. In the case where the recombinant DNA technology method is using the microorganism *E. coli*, the Fc produced will be aglycosylated.

The method described herein is suitable for preparing protein conjugates when at least one of the proteins to be conjugated includes a free cysteine. A free cysteine is a cysteine residue available for conjugation via a thiol reactive linking. A free Cys is usually a cysteine residue that does not engage in intra protein di-sulphide bonds. Frequently the free cysteine need to be liberated prior to the conjugation reaction, as proteins with a free Cys may form mixed disulphide with other sulphur molecules, usually small organic molecules present in the cell extract when the protein is produced and purified.

Free cysteine's may also be generated by reducing an existing disulphide bond, which will make available two free cysteine's, using reducing agents including trialkylphosphines such as TCEP, BSPP or the like, or with thiols such as DTT, mercapto ethanol and the like.

In one embodiment, two equivalent cysteine's may be generated by reduction of an Fc-domain comprising a disulphide bond adjoining the two monomer polypeptides (Fc') of the Fc-domain.

In a further embodiment, the Fc-domain comprises a single inter chain disulphide bond in the hinge region of the Fc-domain, e.g. in the 229 position of an IgG1-Fc' or an IgG4-Fc' fragment. Such a fragment may be linked with the two arms of the trivalent linker (as illustrated by * in Formula IV) using methods described herein. The resulting protein conjugation (or conjugate intermediate) will have a bi-functional (often, but not necessarily, symmetrical) linkage with the Fc-domain (Fc'), and a third arm conjugated with the insulin component [OEF-Ins].

As described herein, the linker is covalently bound to the insulin analogue via the epsilon amino group of a lysine. Lysines are usually abundant in proteins and therefore not suitable for selective conjugation. However, the insulin analogue for use according to the invention only holds one lysine residue.

In one embodiment, a lysine residue located at the C-terminus sequence Lys-Pro (KP) end of an A-chain extension is used as conjugation site.

In another embodiment, an N-terminal lysine residue located at the B-chain N-terminal extension is used as conjugation site.

Pharmaceutical Compositions

The present invention relates to insulin-Fc conjugates useful as medicaments, and in particular for use in the treatment, prevention or alleviation of a metabolic disease or disorder or condition.

Pharmaceutical compositions comprising the insulin-Fc conjugate of the invention or a pharmaceutically acceptable salt, amide, or ester thereof, and a pharmaceutically acceptable excipient may be prepared according to methods known in the art.

Therefore, in another aspect, the invention provides novel pharmaceutical compositions comprising a therapeutically effective amount of an insulin-Fc conjugate of the present invention, optionally together with one or more adjuvants, excipients, carriers and/or diluents.

The term "excipient" broadly refers to any component other than the active therapeutic ingredient(s). The excipient may be an inert substance, an inactive substance, and/or a not medicinally active substance.

Injectable compositions may be prepared by using conventional techniques, which typically includes dissolving and mixing the ingredients as appropriate to give the desired end product, addition of isotonic agents, preservatives and/or buffers as required, and adjusting the pH value of the solution, e.g. using an acid, for example, hydrochloric acid, or a base, for example, aqueous sodium hydroxide, as needed. Finally, the volume of the solution may be adjusted with water to give the desired concentration of the ingredients.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

A solution or suspension may be made by dissolving an insulin-Fc conjugate of the invention in an aqueous medium.

In one embodiment, the insulin-Fc conjugate is present in a concentration in the range of from about 600 to about 4200 nmole/ml. In another embodiment, the insulin-Fc conjugate is present in a concentration in the range of from about 600 to about 3600 nmole/ml. In a third embodiment, the insulin-Fc conjugate is present in a concentration in the range of from about 600 to about 3000 nmole/ml.

In another embodiment, the insulin-Fc conjugate is present in a concentration in the range of from about 100 to about 4200 nmole/ml. In another embodiment, the insulin-Fc conjugate is present in a concentration in the range of from about 100 to about 600 nmole/ml. In a third embodiment, the insulin-Fc conjugate is present in a concentration in the range of from about 200 to about 600 nmole/ml.

In further embodiments, the pharmaceutical composition of the invention is used for administration to a subject in need hereof at intervals less frequent than once-daily (i.e. at intervals longer than 24 hours), during a period of time of at least 3 months, at least 6 months, or of at least 1 year.

In one embodiment, the pharmaceutical composition of the invention is used for administration to the subject with a frequency in the range of from every $2^{nd}$ day to every $11^{th}$ day, on average.

In another embodiment, the pharmaceutical composition of the invention is used for administration to the subject with a frequency in the range of from every $3^{rd}$ day to every $10^{th}$ day, on average.

In a third embodiment, the pharmaceutical composition of the invention is used for administration to the subject with a frequency in the range of from every $4^{th}$ day to every $9^{th}$ day, on average.

In a fourth embodiment, the pharmaceutical composition of the invention is used for administration to the subject with a frequency in the range of from every $5^{th}$ day to every $8^{th}$ day, on average.

In a fifth embodiment, the pharmaceutical composition of the invention is used for administration to the subject with a frequency in the range of from every $6^{th}$ day to every $7^{th}$ day, on average.

In a sixth embodiment, the pharmaceutical composition of the invention is used for administration to the subject once a week, i.e. on every $7^{th}$ day, on average, during a period of time of at least 3 months, at least 6 months, or of at least 1 year.

Methods of Therapy

The present invention relates to drugs for therapeutic use. More specifically the invention relates to the use of the insulin-Fc conjugate of the invention for the treatment or prevention of a metabolic disease or disorder or condition of a living animal body, including a human, which method comprises the step of administering to such a living animal body in need thereof, a therapeutically effective amount of an insulin-Fc conjugate according to the present invention.

In one embodiment, the invention provides a method for the treatment or alleviation of medical conditions relating to diabetes.

In another embodiment, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises the step of administering to a subject in need thereof a therapeutically effective amount of the insulin-Fc conjugate of the invention.

In a third embodiment, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin-Fc conjugate of the invention.

In a fourth embodiment, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In a fifth embodiment, the invention provides a method for the treatment or alleviation of a disease or disorder or condition of a living animal body, including a human, which disease, disorder or condition may be selected from a disease, disorder or condition relating to diabetes, and in particular Type 1 diabetes, or Type 2 diabetes.

PARTICULAR EMBODIMENTS

The invention is further described by the following non-limiting embodiments of the invention:

1. An oligomer extended insulin-Fc conjugate represented by Formula I:

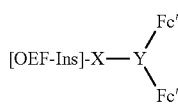

wherein,

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—Y via a lysine (K) residue;

X represents a covalent bond, or a divalent linking group, connecting [OEF-Ins] and Y;

Y represents a trivalent linking group, connecting the two Fc' via two sulphur atoms originating from a disulphide bridge of Fc to X; or, in case X represents a covalent bond, Y is connecting the two Fc' via two sulphur atoms to a lysine residue in the [OEF-Ins] construct; and Fc' represents a monomer Fc polypeptide, or a fragment thereof.

2. An oligomer extended insulin-Fc conjugate represented by Formula I':

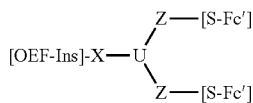

wherein

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—U(—Z)$_2$ via a lysine (K) residue;

X represents a covalent bond, or a divalent linking group, connecting [OEF-Ins] and U;

U represents a central trivalent linking unit, connecting the two Z—[S-Fc'] groups to X; or, in case X represents a covalent bond, U is connecting the two Z—[S-Fc'] groups to a lysine residue in the [OEF-Ins] construct;

Z represents a divalent linking group connecting the central linking unit (U) to a thiol moiety (S) of a monomer Fc polypeptide (Fc'), or a fragment thereof; and

[S-Fc'] represents a sulphur atom originating from a cysteine (C) residue comprised within the Fc' component.

3. The oligomer extended insulin-Fc conjugate of embodiment 1 or of embodiment 2, wherein Ins represents an analogue of human insulin containing one or more of the following substitutions: A14E, A21G or A21Q, B3E or B3Q, B16E or B16H, B25H, desB27 or desB29, B29R, and/or desB30.

4. The oligomer extended insulin-Fc conjugate of embodiment 1 or of embodiment 2, wherein the polar recombinant OEF extension is represented by contiguous amino acid residues selected from A) a polyglycine sequence (Gly)$_x$ (Group A), wherein x represents an integer in the range of from 2 to about 102, and in a combination with K or KP as described above;

B) the group of [A, G and Q]$_x$ (Group B), in random order or in any combination, wherein x represents an integer in the range of from 1 to about 30, and in a combination with K or KP as described above;

C) the group of [A, P and S]$_x$ (Group C), in random order or in any combination, wherein x represents an integer in the range of from 1 to about 30, and in a combination with K or KP as described above;

D) the group of [E, G and Q]$_x$ (Group D), in random order or in any combination, wherein x represents an integer in the range of from 1 to about 30, and in a combination with K or KP as described above;

E) the group of [A, G, P and Q]$_x$ (Group E), in random order or in any combination, wherein x represents an integer in the range of from 1 to about 25, and in a combination with K or KP as described above;

F) the group of [A, G, P and S]$_x$ (Group F), in random order or in any combination, wherein x represents an integer in the range of from 1 to about 25, and in a combination with K or KP as described above;

G) the group of [E, G, P and Q]$_x$ (Group G), in random order or in any combination, wherein x represents an integer in the range of from 1 to about 25, and in a combination with K or KP as described above;

H) the group of [E, G, P and S]$_x$ (Group H), in random order or in any combination, wherein x represents an integer in the range of from 1 to about 25, and in a combination with K or KP as described above;

I) the group of [A, E, G, P and Q]$_x$ (Group I), in random order or in any combination, wherein x represents an integer in the range of from 1 to about 20, and in a combination with K or KP as described above; and J) the group of [A, E, G, P, S and T]$_x$ (Group J), in random order or in any combination, wherein x represents an integer in the range of from 1 to about 20, and in a combination with K or KP as described above;

and/or any combination of Groups A, B, C, D, E, F, G, H, I and 3.

5. The oligomer extended insulin-Fc conjugate of embodiment 1 or of embodiment 2, wherein X represents a divalent linker of the structure

wherein I represents an integer in the range of from 1 to 20.

6. The oligomer extended insulin-Fc conjugate of embodiment 1, wherein the trivalent linking group (Y), or the oligomer extended insulin-Fc conjugate of embodiment 2, wherein the linking group U(—Z)$_2$, are represented by Formula IV

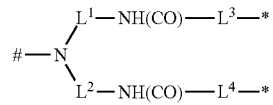

wherein,

N represents the central linking unit (U) according to Formula I';

L$_1$-NH(CO)-L$_3$ and L$_2$-NH(CO)-L$_4$, respectively, represents the divalent linking group (Z) according to Formula I';

\* indicates the point of attachment to a sulphur atom originating from a disulphide bridge of Fc (i.e. the [S-Fc'] moiety according to Formula I');

\# indicates the point of attachment to X; and

L$^1$ and L$^2$, independently of each other, represents —(CH$_2$)$_{m1}$—; wherein m1 represents an integer in the range of from 1 to 6; and L$^3$ and L$^4$, independently of each other, represents —(CH$_2$)$_{n1}$—;

wherein n1 represents an integer in the range of from 1 to 6.

7. The oligomer extended insulin-Fc conjugate of embodiment 1 or of embodiment 2, wherein Fc' represents a monomer of an IgG1 Fc polypeptide, of an IgG2 Fc polypeptide, of an IgG4 Fc polypeptide, or a fragment thereof.

8. The oligomer extended insulin-Fc conjugate of embodiment 7, wherein Fc' represents an hIgG1-Fc(228-447) polypeptide comprising one or more extensions and/or substitutions and/or deletions selected from the group of 226A, 227A or 227S, 228S, 234A, 235A or 235E or 235K, 237A or 297Q, 297E, N315Q, 330S, 331S, N384Q, and des447

9. The oligomer extended insulin-Fc conjugate of embodiment 7, wherein Fc' represents an hIgG4-Fc(228-447) polypeptide comprising one or more extensions and/or substitutions and/or deletions selected from the group of 226G, 227A, 234A, 235A or 235K, N297E or N297Q, 315Q, 384Q and des447.

10. The oligomer extended insulin-Fc conjugate represented by Formula I' of embodiment 2, wherein the central linking unit (U) represents a 3,5-disubstituted benzoate moiety as illustrated by Formula VII:

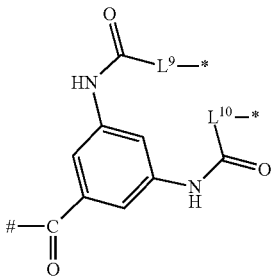

wherein

\* indicates the point of attachment to a sulphur atom originating from a disulphide bridge of Fc (i.e. the [S-Fc'] moiety according to Formula I');

\# indicates the point of attachment to X, or, in case X is absent (i.e. represents a covalent bond), to the a primary amino group in a lysine residue in the [OEF-Ins] construct; and L$^9$ and L$^{10}$, independently of each other, represents —(CH$_2$)$_{n3}$—; wherein n3 represents an integer in the range of from 1 to 6.

11. The oligomer extended insulin-Fc conjugate represented by Formula I' of embodiment 2, wherein X is absent (i.e. represents a covalent bond), and U(—Z)$_2$ according to Formula I' is represented by Formula VIII:

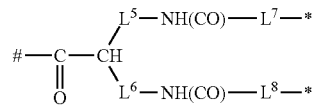

wherein,

\* indicates the point of attachment to a sulphur atom originating from a disulphide bridge of Fc (i.e. the [S-Fc'] moiety according to Formula I);

\# indicates the point of attachment to X, or in case X is absent (i.e. represents a covalent bond), to a primary amino group in a lysine residue in the [OEF-Ins] construct;

L$^5$ and L$^6$, independently of each other, represents —(CH$_2$)$_{m2}$—; wherein m2 represents an integer in the range of from 0 to 6; and L$^7$ and L$^8$, independently of each other, represents —(CH$_2$)$_{n2}$—; wherein n2 represents an integer in the range of from 1 to 6.

12. The oligomer extended insulin-Fc conjugate of embodiment 1 or embodiment 2, which is (A14E, A21G, A22(GQEP)$_{19}$, A98Kˆ, A99P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_{19}$, A98K⎯A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(−78K⎯) B(−77P), B(−1)(GQAPGQAPG QEP)$_6$-GQAP, B3Q, B25H, B29R, desB30 human insulin/(227A, 234A, 235K hIgG4-Fc(228-447))4-[bis[2-[(2-iodo-acetyl)amino]ethyl]amino]-4-oxo-butanoyl conjugate;

A14E, B(−76Kˆ), B(−75P), B(−1)(GQEP)$_{19}$, B25H, B29R, desB30 human insulin/(227A, 234A, 235K hIgG4-Fc(227-447))4-[bis[2-[(2-acetyl)amino]ethyl]amino]-4-oxo-butanoyl conjugate;

A14E, A21G, A22(GQAPGQAPGQEP)$_6$-GQAP, A98Kˆ, A99P, B3Q, B25H, B29R, desB30 human insulin/(227A, 234A, 235K hIgG4-Fc(228-447))4-[bis[2-[(2-acetyl)amino] ethyl]amino]-4-oxo-butanoyl conjugate;

A14E, A21G, A22(GQEP)$_{19}$, A98K⎯A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_6$, A46Kˆ, A47P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_{12}$, A70Kˆ, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQEP)$_6$, A70Kˆ, A71P, B25H, B29R, desB30 human insulin/(227A, 234A, 235K hIgG4-Fc(227-447))4-[bis[2-[(2-acetyl)amino]ethyl]amino]-4-oxo-butanoyl conjugate;

A14E, A21G, A22(GQEP)$_3$, A34G, A35Q, A36E, A37Kˆ, A38P, B25H, B29R, desB30 human insulin/(227A, 234A, 235K hIgG4-Fc(227-447))4-[bis[2-[(2-acetyl)amino]ethyl] amino]-4-oxo-butanoyl conjugate;

A14E, B(−76Kˆ), B(−75P), B(−1)(GQEP)$_{19}$, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQEP)$_{19}$, A98K^, A99P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQEP)$_6$, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)$_{19}$, A98K A99P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAP)$_{19}$, A98K^, A99P, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-hexanoyl conjugate;

A14E, A21G, A22(GQEP)$_{12}$, A70K^, A71P, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, B(−76K^), B(−75P), B(−1)(GQAP)$_{19}$, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQAPGQEP)$_6$-GQAP, A122K^, A123P, B25H, B29R, desB30 human insulin/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(G)$_{17}$, A40K^, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAP)$_{24}$, A118G, A119Q, A120A, A121K^, A122P, B25H, B29R, desB30 human insulin/(227A, 234A, 235K, 297E, 315Q, 384Q, des447 hIgG4-Fc(227-447))$_{3,5}$-bis[(2-acetyl)amino]benzoyl conjugate;

(A14E, A21G, A22(GQAP)$_{24}$, A118G, A119Q, A120A, A121K^, A122P, B25H, B29R, desB30 human insulin)/(227A, 234A, 235K, 297E, 315Q, 384Q, des447 hIgG4-Fc(227-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K, 297E, 315Q, 384Q, des447 hIgG4-Fc(227-447))4-[bis[2-[(2-acetyl)amino]ethyl]carbamoylamino]-butanoyl conjugate; and (A14E, A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(227-447))4-[bis[2-[(2-acetyl)amino]ethyl]amino]-4-oxo-butanoyl conjugate.

13. An intermediate compound of Formula II

[OEF-Ins]

wherein,

OEF represents a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue; and Ins represents an analogue of human insulin, which insulin analogue is a two-chain insulin molecule comprising an A- and a B-chain.

14. An intermediate compound characterised by being a monomer Fc polypeptide (F'), or a fragment thereof, characterised by being (i) a hIgG1-Fc(228-447) polypeptide that contains one or more extensions and/or substitutions and/or deletions selected from the group of 226A, 227A or 227S, 228S, 234A, 235A or 235E or 235K, 237A or 297Q, 297E, N315Q, 330S, 331S, N384Q, and des447; or (ii) a hIgG2 derived Fc sequence, starting at position 228 and ending at position 446, which sequence contains one or more extensions and/or substitutions selected from the group of 227A, L234A, 235K, and 377A; or (iii) a fragment of a hIgG4 derived Fc sequence, starting at position 228 and ending at position 447, which sequence contains one or more extensions and/or substitutions selected from the group of 226G, 227A, 234A, 235A or 235K, N297E or N297Q, 315Q, 384Q and des447.

15. An intermediate compound characterised by the general Formula V

M-X—Y(-LG)$_2$ wherein

M (that may also be designated as the Lys reactive terminus) represents a leaving group reactive towards primary amino groups;

X is absent (i.e. represents a covalent bond), or X represents a divalent linking group as defined for Formula I above;

Y represents a central trivalent linking unit as defined for Formula I above; and LG (that may also be designated as the Cys reactive terminus) represents the leaving group of a thiol reactive group.

16. An intermediate compound characterised by the general Formula V':

M-X—U(—Z-LG)$_2$ wherein

M (that may also be designated as the Lys reactive terminus) represents a leaving group reactive towards primary amino groups;

X is absent (i.e. represents a covalent bond), or X represents a divalent linking group as defined for Formula I' above;

U represents a central trivalent linking unit as defined for Formula I' above;

Z represents a divalent linking group connecting the central linking unit (U) to the leaving group (LG); and LG (that may also be designated as the Cys reactive terminus) represents the leaving group of a thiol reactive group.

17. An intermediate compound characterised by the general Formula VI

[OEF-Ins]-X—Y(-LG)$_2$ wherein,

OEF is as defined for Formula I above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I above, and is connected to the divalent linking group X via a lysine (K) residue;

X represents a divalent linking group as defined for Formula I above; and Y represents a central trivalent linking unit as defined for Formula I above; or X represents a covalent bond; and Y represents a central trivalent linking unit connecting the two leaving groups (LG)$_2$ to [OEF-Ins]; and LG represents the leaving group of a thiol reactive group.

18. An intermediate compound characterised by the general Formula VI':

[OEF-Ins]-X—U(—Z-LG)$_2$ wherein,

OEF is as defined for Formula I' above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I' above, and is connected to the divalent linking group X via a lysine (K) residue;

X represents a divalent linking group as defined for Formula I' above; and U represents a central trivalent linking unit as defined for Formula I' above, connecting the two divalent linking groups (Z) to X; or X represents a covalent bond; and U represents a central trivalent linking unit as defined for Formula I' above, connecting the two divalent linking groups (Z) to the [OEF-Ins] construct; and LG represents the leaving group of a thiol reactive group.

19. A pharmaceutical composition comprising the insulin-Fc conjugate according to any one of embodiments 1-12, and one or more pharmaceutically acceptable carriers or diluents.

20. A method of treatment, prevention or alleviation of a metabolic disease or disorder or condition of a living animal body, including a human, which method comprises the step of administering to such a living animal body in need thereof, a therapeutically effective amount of an insulin-Fc conjugate according to any one of embodiments 1-12.

The invention is even further described by the following non-limiting embodiments of the invention:

1. An oligomer extended insulin-Fc conjugate represented by Formula I:

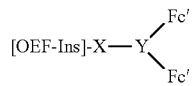

wherein,

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—Y via the epsilon amino group of a lysine (K) residue;

X represents a covalent bond, or a divalent linking group, connecting [OEF-Ins] and Y;

Y represents a trivalent linking group, connecting the two Fc' via two sulphur atoms originating from a disulphide bridge of Fc to X; or, in case X represents a covalent bond, Y is connecting the two Fc' via two sulphur atoms to the epsilon amino group of a lysine residue in the [OEF-Ins] construct; and Fc' represents a monomer Fc polypeptide, or a fragment thereof.

2. An oligomer extended insulin-Fc conjugate represented by Formula I':

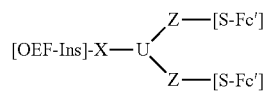

wherein

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—U(—Z)$_2$ via the epsilon amino group of a lysine (K) residue;

X represents a covalent bond, or a divalent linking group, connecting [OEF-Ins] and U;

U represents a central trivalent linking unit, connecting the two Z—[S-Fc'] groups to X; or, in case X represents a covalent bond, U is connecting the two Z—[S-Fc'] groups to the epsilon amino group of a lysine residue in the [OEF-Ins] construct;

Z represents a divalent linking group connecting the central linking unit (U) to a thiol moiety (S) of a monomer Fc polypeptide (Fc'), or a fragment thereof; and

[S-Fc'] represents a sulphur atom originating from a cysteine (C) residue comprised within the Fc' component.

3. The oligomer extended insulin-Fc conjugate of embodiment 1 or of embodiment 2, wherein X represents a divalent linker of the structure

—C(O)—(CH$_2$)$_I$—C(O)— wherein I represents an integer in the range of from 1 to 20.

4. The oligomer extended insulin-Fc conjugate of embodiment 1, wherein the trivalent linking group (Y) is represented by Formula IV

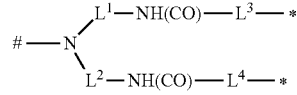

wherein,

\* indicates the point of attachment to a sulphur atom originating from a reduced disulphide bridge of Fc (i.e. the [Fc'] moiety according to Formula I);

\# indicates the point of attachment to X; and $L^1$ and $L^2$, independently of each other, represent —$(CH_2)_{m1}$—; wherein m1 represents an integer in the range of from 1 to 6; and $L^3$ and $L^4$, independently of each other, represent —$(CH_2)_{n1}$—;

wherein n1 represents an integer in the range of from 1 to 6.

5. The oligomer extended insulin-Fc conjugate of embodiment 1 or of embodiment 2, wherein Fc' represents a monomer of an IgG1 Fc polypeptide, of an IgG2 Fc polypeptide, of an IgG4 Fc polypeptide, or a fragment thereof.

6. The oligomer extended insulin-Fc conjugate represented by Formula I' of embodiment 2, wherein X represents a covalent bond and wherein the central linking unit (U) represents a 3,5-disubstituted benzoyl moiety as illustrated by Formula VII:

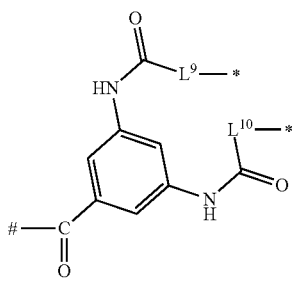

wherein

\* indicates the point of attachment to a sulphur atom originating from a disulphide bridge of Fc (i.e. the [S-Fc'] moiety according to Formula I');

\# indicates the point of attachment to the epsilon amino group in a lysine residue in the [OEF-Ins] construct; and $L^9$ and $L^{10}$, independently of each other, represents —$(CH_2)_{n3}$—; wherein n3 represents an integer in the range of from 1 to 6.

7. The oligomer extended insulin-Fc conjugate represented by Formula I' of embodiment 2, wherein X is absent (i.e. represents a covalent bond), and U(—Z)$_2$ according to Formula I' is represented by Formula VIII:

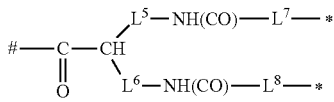

wherein,

\* indicates the point of attachment to a sulphur atom originating from a disulphide bridge of Fc (i.e. the [S-Fc'] moiety according to Formula I);

\# indicates the point of attachment to X, or in case X is absent (i.e. represents a covalent bond), to the epsilon amino group in a lysine residue in the [OEF-Ins] construct;

$L^5$ and $L^6$, independently of each other, represents —$(CH_2)_{m2}$—; wherein m2 represents an integer in the range of from 0 to 6; and $L^7$ and $L^8$, independently of each other, represents —$(CH_2)_{n2}$—; wherein n2 represents an integer in the range of from 1 to 6.

8. An intermediate compound of Formula II

[OEF-Ins]

wherein,

OEF represents a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue; and Ins represents an analogue of human insulin, which insulin analogue is a two-chain insulin molecule comprising an A- and a B-chain.

9. An intermediate compound characterised by being a monomer Fc polypeptide (Fc'), or a fragment thereof, characterised by being (i) a hIgG1-Fc(228-447) polypeptide that contains one or more extensions and/or substitutions and/or deletions selected from the group of 226A, 227A or 227S, 228S, 234A, 235A or 235E or 235K, 237A or 297Q, 297E, N315Q, 330S, 331S, N384Q, and des447; or (ii) a hIgG2 derived Fc sequence, starting at position 228 and ending at position 446, which sequence contains one or more extensions and/or substitutions selected from the group of P227A, VL234A, 2A35K, and P337A; or (iii) a fragment of a hIgG4 derived Fc sequence, starting at position 228 and ending at position 447, which sequence contains one or more extensions and/or substitutions selected from the group of 226G, 227A, 228P, 234A, 235A or 235K, N297E or N297Q, 315Q, 384Q and des447.

10. An intermediate compound characterised by the general Formula V

M-X—Y(-LG)$_2$ wherein

M (that may also be designated as the Lys reactive terminus) represents a leaving group reactive towards primary amino groups;

X is absent (i.e. represents a covalent bond), or X represents a divalent linking group as defined for Formula I above;

Y represents a central trivalent linking unit as defined for Formula I above; and LG (that may also be designated as the Cys reactive terminus) represents the leaving group of a thiol reactive group.

11. An intermediate compound characterised by the general Formula V':

M-X—U(—Z-LG)$_2$ wherein

M (that may also be designated as the Lys reactive terminus) represents a leaving group reactive towards primary amino groups;

X is absent (i.e. represents a covalent bond), or X represents a divalent linking group as defined for Formula I' above;

U represents a central trivalent linking unit as defined for Formula I' above;

Z represents a divalent linking group connecting the central linking unit (U) to the leaving group (LG); and LG (that may also be designated as the Cys reactive terminus) represents the leaving group of a thiol reactive group.

12. An intermediate compound characterised by the general Formula VI

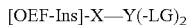

wherein,

OEF is as defined for Formula I above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I above, and is connected to the divalent linking group X via a lysine (K) residue;

X represents a divalent linking group as defined for Formula I above; and Y represents a central trivalent linking unit as defined for Formula I above; or X represents a covalent bond; and Y represents a central trivalent linking unit connecting the two leaving groups (LG)₂ to [OEF-Ins]; and LG represents the leaving group of a thiol reactive group.

13. An intermediate compound characterised by the general Formula VI':

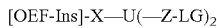

wherein,

OEF is as defined for Formula I' above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I' above, and is connected to the divalent linking group X via a lysine (K) residue;

X represents a divalent linking group as defined for Formula I' above; and U represents a central trivalent linking unit as defined for Formula I' above, connecting the two divalent linking groups (Z) to X; or X represents a covalent bond; and U represents a central trivalent linking unit as defined for Formula I' above, connecting the two divalent linking groups (Z) to the [OEF-Ins] construct; and LG represents the leaving group of a thiol reactive group.

14. A pharmaceutical composition comprising the insulin-Fc conjugate according to any one of embodiments 1-12, and one or more pharmaceutically acceptable carriers or diluents.

15. A method of treatment, prevention or alleviation of a metabolic disease or disorder or condition of a living animal body, including a human, which method comprises the step of administering to such a living animal body in need thereof, a therapeutically effective amount of an insulin-Fc conjugate according to any one of embodiments 1-12.

The invention is even further described by the following non-limiting embodiments of the invention:

1. An oligomer extended insulin-Fc conjugate represented by Formula I':

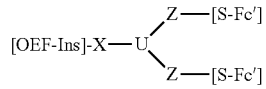

wherein

Ins represents an analogue of human insulin, which insulin analogue is a two-chain insulin molecule comprising an A- and a B-chain;

OEF indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

the [OEF-Ins] construct is connected to the trivalent linking group X—U(—Z)₂ via the epsilon amino group of a lysine (K) residue;

X represents a covalent bond, or a divalent linking group, connecting [OEF-Ins] and U;

U represents a central trivalent linking unit, connecting the two Z—[S-Fc'] groups to X; or, in case X represents a covalent bond, U is connecting the two Z—[S-Fc'] groups to the epsilon amino group of a lysine residue in the [OEF-Ins] construct;

Z is absent or represents a divalent linking group connecting the central linking unit (U) to a thiol moiety (S) of a monomer Fc polypeptide (Fc'), or a fragment thereof; or, in case Z is absent, U is connected directly to [S-Fc']; and

[S-Fc'] represents an Fc' component (i.e. a monomer Fc polypeptide, or a fragment thereof) with the S representing a sulphur atom originating from a cysteine (C) residue comprised within the Fc' component.

2. The oligomer extended insulin-Fc conjugate of embodiment 1, wherein X represents a covalent bond;

a divalent linker of the structure —C(O)—(CH₂)ᵢ—C(O)—, wherein I represents an integer in the range of from 1 to 20; or a divalent linker of the structure —C(O)—(CH₂)ₒ—NH—C(O)—, wherein o represents an integer in the range of from 1 to 20.

3. The oligomer extended insulin-Fc conjugate of any one of embodiments 1-2, wherein X represents a divalent linker of the structure —C(O)—(CH₂)ᵢ—C(O)—, wherein I represents an integer in the range of from 1 to 20; or a divalent linker of the structure —C(O)—(CH₂)ₒ—NH—C(O)—, wherein o represents an integer in the range of from 1 to 20.

4. The oligomer extended insulin-Fc conjugate according to any one of embodiments 1-3, wherein I represents an integer in the range of from 2 to 4, and o is 3.

5. The oligomer extended insulin-Fc conjugate according to any one of embodiments 1-4, wherein X represents the linker —CO—CH₂—CH₂—CO—.

6. The oligomer extended insulin-Fc conjugate according to any one of embodiments 1-4, wherein X represents the linker —CO—CH₂—CH₂—CH₂—CH₂—CO—.

7. The oligomer extended insulin-Fc conjugate according to any one of embodiments 1-4, wherein X represents the linker —CO—CH₂—CH₂—CH₂—NH—CO—.

8. The oligomer extended insulin-Fc conjugate according to any one of embodiments 1-7, wherein the central trivalent linking unit (U) and divalent linking group (Z) are represented by Formula IV'

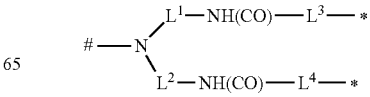

wherein,

N is a nitrogen atom (N) and represents the central linking unit (U) according to Formula I';

$L_1$-NH(CO)-$L_3$ and $L_2$-NH(CO)-$L_4$, respectively, represents the divalent linking group (Z) according to Formula I';

* indicates the point of attachment to a sulphur atom originating from a disulphide bridge of Fc (i.e. the [S-Fc'] moiety according to Formula I');

# indicates the point of attachment to X; and $L^1$ and $L^2$, independently of each other, represent —$(CH_2)_{m1}$—; wherein m1 represents an integer in the range of from 1 to 6; and $L^3$ and $L^4$, independently of each other, represent —$(CH_2)_{n1}$—;

wherein n1 represents an integer in the range of from 1 to 6.

9. The oligomer extended insulin-Fc conjugate according to embodiment 8, wherein $L^1$ and $L^2$, independently of each other, represent —$(CH_2)_{m1}$—; wherein m1 is 2; and $L^3$ and $L^4$, independently of each other, represent —$(CH_2)_{n1}$—; wherein n1 is 1.

10. The oligomer extended insulin-Fc conjugate according to any one of embodiments 1-9, wherein X represents a covalent bond and wherein U—(—Z)$_2$ represents a 3,5-disubstituted benzoyl moiety as illustrated by Formula VII:

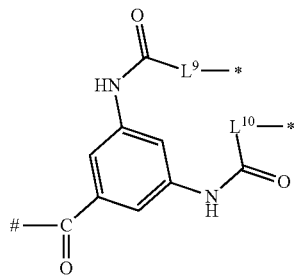

wherein

* indicates the point of attachment to a sulphur atom originating from a disulphide bridge of Fc (i.e. the [S-Fc'] moiety according to Formula I');

# indicates the point of attachment to the epsilon amino group in a lysine residue in the [OEF-Ins] construct; and $L^9$ and $L^{10}$, independently of each other, represents —$(CH_2)_{n3}$—; wherein n3 represents an integer in the range of from 1 to 6.

11. The oligomer extended insulin-Fc conjugate according to embodiment 10, wherein n3 represents an integer in the range of from 1 to 3.

12. The oligomer extended insulin-Fc conjugate according to embodiment 11, wherein n3 is 1.

13. The oligomer extended insulin-Fc conjugate of any one of embodiments 1-12, wherein Ins represents an analogue of human insulin containing one or more of the following substitutions: A14E, A21G or A21Q, B3E or B3Q, B16E or B16H, B25H, desB27 or desB29, B29R, and/or desB30.

14. The oligomer extended insulin-Fc conjugate of any one of embodiments 1-12, wherein Ins represents an analogue of human insulin containing one or more of the following substitutions: A14A or A14E, A21G or A21Q, B3Q, B16E or B16H, B25H, B29R, and desB30.

15. The oligomer extended insulin-Fc conjugate of any one of embodiments 1-12, wherein Ins represents an analogue of human insulin containing one or more of the following substitutions: A14E, A21G or A21Q, B3Q, B16E or B16H, B25H, B29R, and desB30.

16. The oligomer extended insulin-Fc conjugate of any one of embodiments 1-12, wherein Ins represents an analogue of human insulin containing one or more of the following substitutions: A14E, A21G or A21Q, B3Q, B16E, B25H, B29R, and desB30.

17. The oligomer extended insulin-Fc conjugate of any one of embodiments 1-12, wherein Ins represents an analogue of human insulin containing one or more of the following substitutions: A14E, A21G, B3Q, B25H, B29R, and desB30.

18. The oligomer extended insulin-Fc conjugate of any one of embodiments 1-12, wherein Ins represents an analogue of human insulin containing one or more of the following substitutions: A14A or A14E, A21G or A21Q, B3Q, B16E, B25H, B29R, and desB30.

19. The oligomer extended insulin-Fc conjugate of any one of embodiments 1-12, wherein Ins represents an analogue of human insulin containing the following substitutions: A14A or A14E, A21G or A21Q, B29R, and desB30; and which analogue optionally has one or more of the following substitutions: B3Q, B16E or B16H, and B25H.

20. The oligomer extended insulin-Fc conjugate of any one of embodiments 1-12, wherein Ins represents an analogue of human insulin containing the following substitutions: A14E, A21G or A21Q, B29R, and desB30; and which analogue optionally has one or more of the following substitutions: B3Q, B16E or B16H, and B25H.

21. The oligomer extended insulin-Fc conjugate of any one of embodiments 1-12, wherein Ins represents an analogue of human insulin containing the following substitutions: A14E, A21G or A21Q, B29R, and desB30; and which analogue optionally has one or more of the following substitutions: B3Q, B16E, and B25H.

22. The oligomer extended insulin-Fc conjugate of any one of embodiments 1-21, wherein OEF represents a polar recombinant OEF extension fused to the insulin A-chain C-terminus, or fused to the insulin B-chain N-terminus, which extension includes one or more of the following amino acid residues: Ala (A), Glu (E), Gly (G), Pro (P), and Gln (Q), in a combination with a lysine (K) residue, to render an [OEF-Ins] construct with a total number of amino acid residues of the OEF in the range of 15 to 110.

23. The oligomer extended insulin-Fc conjugate of any one of embodiments 1-22, wherein OEF represents a polar recombinant OEF extension, which extension is an A-chain extension represented by $(G)_x$-K, $(GQEP)_x$-KP, $(GQEP)_3$-GQE-KP, $(GQAP)_x$-KP; $(GQAP)_x$-GQA-KP; $(GQAPGQEP)_6$-KP; $(GQAPGQAPGQEP)_6$-GQAP-KP; or $(GQAPGQAPGQAPGQEP)_6$-GQAP-KP; or a B-chain extension represented by KP-$(GQAP)_x$, KP-$(GQEP)_x$, or KP-$(GQAPGQAPGQEP)_6$-GQAP;

wherein each x independently represents an integer in the range of from 3 to 24.

24. The oligomer extended insulin-Fc conjugate of embodiment 23, wherein each x independently represents an integer in the range of from 6 to 24.

25. The oligomer extended insulin-Fc conjugate of embodiment 24, wherein each x independently represents an integer in the range of from 18 to 24.

26. The oligomer extended insulin-Fc conjugate of any one of embodiments 1-25, wherein Fc' represents a monomer of an IgG1 Fc polypeptide, of an IgG2 Fc polypeptide, of an IgG4 Fc polypeptide, or a fragment thereof.

27. The oligomer extended insulin-Fc conjugate of embodiment 26, wherein Fc' represents an hIgG1-Fc(228-

447) polypeptide comprising one or more substitutions and/or deletions selected from the group of 228S, 234A, 235A or 235E or 235K, 237A or 297Q, 297E, N315Q, 330S, 331S, N384Q, and des447; and/or an extension consisting of one or two amino acid residues selected from the group of 226A, 227A or 227S.

28. The oligomer extended insulin-Fc conjugate of embodiment 26, wherein Fc' represents an hIgG1-Fc(228-447) polypeptide comprising one or more substitutions and/or deletions selected from the group of 228S, 234A, 235K, 237A, 315Q, 330S, 331S, and 384Q; and/or an extension consisting of one or two amino acid residues selected from the group of 226A, 227A or 227S.

29. The oligomer extended insulin-Fc conjugate of embodiment 26, wherein Fc' represents a monomer of an IgG4 Fc polypeptide, or a fragment thereof.

30. The oligomer extended insulin-Fc conjugate of embodiment 29, wherein Fc' represents an hIgG4-Fc(228-447) polypeptide comprising one or more substitutions and/or deletions selected from the group of 234A, 235A or 235K, N297E or N297Q, 315Q, 384Q and des447; and/or an extension consisting of one or two amino acid residues selected from the group of 226G and 227A.

31. The oligomer extended insulin-Fc conjugate of embodiment 29, wherein Fc' represents an hIgG4-Fc(228-447) polypeptide comprising one or more substitutions and/or deletions selected from the group of 228P, 234A, 235A or 235K, N297E or 297Q, 315Q, 384Q and des447; and/or an extension consisting of one or two amino acid residues selected from the group of 226A or 226G, 227A or 227G.

32. The oligomer extended insulin-Fc conjugate of embodiment 29, wherein Fc' represents an hIgG4-Fc(228-447) polypeptide comprising one or more substitutions and/or deletions selected from the group of 228P, 234A, 235K, N297E, 315Q, 384Q and des447; and/or an extension consisting of one or two amino acid residues selected from the group of 226A, 227A or 227G.

33. The oligomer extended insulin-Fc conjugate of embodiment 1, which is (A14E, A21G, A22(GQEP)$_{19}$, A98K^, A99P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_{19}$, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(−78K^), B(−77P), B(−1)(GQAPGQAPGQEP)$_6$-GQAP, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, B(−78K^), B(−77P), B(−1)(GQEP)$_{19}$, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_{19}$, A98K^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_6$, A46K^, A47P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_{12}$, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQEP)$_6$, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)$_3$, A34G, A35Q, A36E, A37K^, A38P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, B(−78K^), B(−77P), B(−1)(GQEP)$_{19}$, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQEP)$_{19}$, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQEP)$_6$, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)$_{19}$, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)$_{19}$, A98K^, A99P, B25H, B29R, desB30 human insulin)/(227A, 234A, 235K, 297E, 315Q, 384Q, des447 hIgG4-Fc(228-447))$_6$-[bis[2-[(2-acetyl)amino]ethyl]amino]-6-oxo-hexanoyl conjugate;

A14E, A21G, A22(GQEP)$_{12}$, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(−78K^), B(−77P), B(−1)(GQAP)$_{19}$, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQAPGQEP)$_6$-GQAP, A122K^, A123P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21Q, A22(G)$_{18}$, A40K^, B25H, B29R, desB30 human insulin/(227A, 234A, 235K hIgG4-Fc(228-447))4-[bis[2-[(2-acetyl)amino]ethyl]amino]-4-oxo-butanoyl conjugate;

(A14E, A21G, A22(GQAP)$_{24}$, A118G, A119Q, A120A, A121K^, A122P, B25H, B29R, desB30 human insulin)/(227A, 234A, 235K, 297E, 315Q, 384Q, des447 hIgG4-Fc(228-447))$_{3,5}$-bis[(2-acetyl)amino]benzoyl conjugate;

(A14E, A21G, A22(GQAP)$_{24}$, A118G, A119Q, A120A, A121K^, A122P, B25H, B29R, desB30 human insulin)/ (227A, 234A, 235K, 297E, 315Q, 384Q, des447 hIgG4-Fc (228-447))4-[bis[2-[(2-acetyl)amino]ethyl]amino]-4-oxo-butanoyl conjugate;

A14E, A21G, A22(GQAPGQAPGQEP)$_6$-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]carbamoylamino]butanoyl conjugate;

(A14A, A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A1(N(alpha)acetyl), A14E, A21G, A22(GQAP)$_{19}$, A98K^, A99P, B1(N(alpha)acetyl), B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)$_{24}$, A118G, A119Q, A120A, A121K^, A122P, B29R, desB30 human insulin)/(227A, 234A, 235K, 297E, 315Q, 384Q, des447 hIgG4-Fc(228-447))$_{3,5}$-bis[(2-acetyl)amino]benzoyl conjugate;

A14E, A21G, A22(GQAP)$_{18}$, A94G, A95Q, A96A, A97K^, A98P, B16E, B25H, B29R, desB30 human insulin)/ (227A, 234A, 235K, 297E, 315Q, 384Q, des447 hIgG4-Fc (228-447))$_{3,5}$-bis[(2-acetyl)amino]benzoyl conjugate;

(A14E, A21G, A22(GQAP)$_{18}$, A94G, A95Q, A96A, A97K^, A98P, B16E, B25H, B29R, desB30 human insulin)/ (227A, 234A, 235K, 297E, 315Q, 384Q, des447 hIgG4-Fc (228-447))4-[bis[2-[(2-acetyl)amino]ethyl]amino]-4-oxo-butanoyl conjugate;

A14E, A21G, A22(GQEP)$_6$, A46K^, A47P, B25H, B29R, desB30 human insulin/(227A, 234A, 235K, 297E, 315Q, 384Q, des447 hIgG4-Fc(228-447))4-[bis[2-[(2-acetyl) amino]ethyl]amino]-4-oxo-butanoyl conjugate; or (A14E, A21G, A22(GQEP)$_{19}$, 98K^, A99P, B25H, B29R, desB30 human insulin)/(226A, 227G, 228P, 234A, 235K, des447 hIgG4-Fc(228-447))$_{3,5}$-bis[(2-acetyl)amino]benzoyl conjugate.

34. An intermediate compound of Formula II

[OEF-Ins]

wherein,

OEF represents a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue; and Ins represents an analogue of human insulin, which insulin analogue is a two-chain insulin molecule comprising an A- and a B-chain.

35. An intermediate compound characterised by being a monomer Fc polypeptide (Fc'), or a fragment thereof, characterised by being (i) a hIgG1-Fc(228-447) polypeptide that contains one or more substitutions and/or deletions selected from the group of, 228S, 234A, 235K, 237A, 315Q, 330S, 331S, and 384Q; and/or an extension consisting of one or two amino acid residues selected from the group of 226A, 227A or 227S; or (ii) a fragment of a hIgG4 derived Fc sequence, starting at position 228 and ending at position 447, which sequence contains one or more substitutions selected from the group of 228P, 234A, 235A or 235K, N297E or 297Q, 315Q, 384Q and des447; and/or an extension consisting of one or two amino acid residues selected from the group of 226A or 226G, 227A or 227G.

36. An intermediate compound characterised by the general Formula V':

M-X—U(—Z-LG)$_2$ wherein

M (that may also be designated as the Lys reactive terminus) represents a leaving group reactive towards primary amino groups;

X is absent (i.e. represents a covalent bond), or X represents a divalent linking group as defined for Formula I' above;

U represents a central trivalent linking unit as defined for Formula I' above;

Z represents a divalent linking group connecting the central linking unit (U) to the leaving group (LG); and LG (that may also be designated as the Cys reactive terminus) represents the leaving group of a thiol reactive group.

37. An intermediate compound characterised by the general Formula VI':

[OEF-Ins]-X—U(—Z-LG)$_2$ wherein,

OEF is as defined for Formula I' above, and indicates a polar recombinant extension fused to the insulin A-chain C-terminus, or fused to the insulin B-chain N-terminus, which extension includes one or more of the following amino acid residues: Ala (A), Asp (D), Glu (E), Gly (G), Pro (P), Gln (Q), Ser (S), and Thr (T), in a combination with a lysine (K) residue, to render an [OEF-Ins] construct;

which [OEF-Ins] construct is as defined for Formula I' above, and is connected to the divalent linking group X via a lysine (K) residue;

X represents a divalent linking group as defined for Formula I' above; and U represents a central trivalent linking unit as defined for Formula I' above, connecting the two divalent linking groups (Z) to X; or X represents a covalent bond; and U represents a central trivalent linking unit as defined for Formula I' above, connecting the two divalent linking groups (Z) to the [OEF-Ins] construct; and LG represents the leaving group of a thiol reactive group.

38. A pharmaceutical composition comprising the insulin-Fc conjugate according to any one of embodiments 1-33, and one or more pharmaceutically acceptable carriers or diluents.

39. An oligomer extended insulin-Fc conjugate according to any of embodiments 1-33 for use as a medicament.

40. An oligomer extended insulin-Fc conjugate according to any of embodiments 1-33 for use in the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers.

41. A method of treatment, prevention or alleviation of a metabolic disease or disorder or condition of a living animal body, including a human, which method comprises the step of administering to such a living animal body in need thereof, a therapeutically effective amount of an insulin-Fc conjugate according to any one of embodiments 1-33.

SEQUENCE INFORMATION

Fc polypeptide sequences for IgG1-Fc(228-447) and IgG4-Fc(228-447) (corresponding to AA228-447 of full length heavy chain according to EU numbering) are provided in the sequence listing and are replicated here for convenience.

```
IgG1-Fc (228-447)
                                        (SEQ ID NO: 1)
PC PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSREEMT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

Amino acid residues marked in bold and underlined correspond to L234, L235, G237, A330 and P331, respectively.

Amino acid residues marked in Italics and underlined mark deamidation sites (i.e. N297, N314 and N315).

According to the present invention, the C-terminal lysine (K447) residue may be deleted.

```
IgG2-Fc (220-446)
                                        (SEQ ID NO: 2)
RKCCVECPPC PAPPVAGPSV FLFPPKPKDT LMISRTPEVT

CVVVDVSHED PEVQFNWYVD GVEVHNAKTK PREEQFNSTF

RVVSVLTVVH QDWLNGKEYK CKVSNKGLPA PIEKTISKTK

GQPREPQVYT LPPSREEMTK NQVSLTCLVK GFYPSDISVE

WESNGQPENN YKTTPPMLDS DGSFFLYSKL TVDKSRWQQG

NVFSCSVMHE ALHNHYTQKS LSLSPGK
```

Amino acid residues marked in bold and underlined correspond to L234 and L235

Amino acid residues marked in Italics and underlined mark deamidation sites (i.e. N297, N314 and N315).

According to the present invention, the C-terminal lysine (K446) residue may be deleted.

```
IgG4-Fc (228-447)
                                        (SEQ ID NO: 3)
SC PAPEFLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY
```

```
-continued
TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

Amino acid residues marked in bold and underlined correspond to L234, L235 and G237, respectively.

Amino acid residues marked in Italics and underlined mark deamidation sites (i.e. N297, N314 and N315).

According to the present invention, the C-terminal lysine (K378) residue may be deleted.

```
IgG1 hinge
                                        (SEQ ID NO: 4)
PKSCDKTHTC PPCP
```

This sequence corresponds to AA217-230 of human IgG1 full length heavy chain according to EU numbering.

The amino acid residue marked in bold and underlined corresponds to the native P228 residue.

```
IgG2 hinge
                                        (SEQ ID NO: 5)
RKCCVECPPC P
```

This sequence corresponds to AA220-230 of human IgG2 full length heavy chain according to EU numbering.

```
IgG4 hinge
                                        (SEQ ID NO: 6)
ESKYGPPCPS CP
```

This sequence corresponds to AA218-229 of human IgG4 full length heavy chain according to EU numbering.

Residue S, marked in bold and underlined, corresponds to S228 of full length IgG4 heavy chain according to EU numbering.

EXAMPLES

The invention is further illustrated with reference to the following examples, which are not intended to be in any way limiting to the scope of the invention as claimed.

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention.

Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, i.e. by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials.

All temperatures are set forth in degrees Celsius and unless otherwise indicated, all parts and percentages are by weight when referring to yields and all parts are by volume when referring to solvents and eluents.

List of Abbreviations

Acetic acid Da: Deuterated acetic acid
BSPP: Bis(p-sulfonatophenyl)phenylphosphine dihydrate dipotassium salt
CTB: Carboxypeptidase B
CV: Colum volume
DCM: Dichloromethane
DTT: Dithiothreitol
EDAC: (3-dimethylaminopropyl) ethyl carbodiimide
EDTA: Ethylenediaminetetraacetic acid
DIC: Diisopropylcarbodiimide
DIPEA: Diisopropylethylamin
EtOH: Ethanol
Fmoc: 9H-Fluoren-9-ylmethoxycarbonyl
GABA: Gamma-aminobutyric acid
HATU: 2-(7-Aza-1H-benzotriazole-1-yl)-1,1,3,3-tetramethyluronium hexafluorophosphate
HBTU: 2-(1H-Benzotriazol-1-yl)-1,1,3,3-tetramethyluronium hexafluorophosphate
HOAT: 1-Hydroxy-7-azabenzotriazole
HOBT: Hydroxybenzotriazole
HPLC: High Performance Liquid Chromatography
ivDde: 4,4-Dimethyl-2,6-dioxocyclohex-1-ylidene)-3-methylbutyl
LCMS: Liquid Chromatography Mass Spectroscopy
MeCN: Acetonitrile
MQ: MiliQ water
OtBu: tert-Butyl ester
Rt: Retention time
RT: Room temperature
RP: Revers phase
TATU: O-(7-Azabenzotriazol-1-yl)-N,N,N',N'-tetramethyluronium tetrafluoroborate
TBTU: 2-(1H-Benzotriazol-1-yl)-1,1,3,3-tetramethyluronium hexafluorophosphate
TCEP: tris(2-Carboxyethyl)phosphine
TCTU: O-(6-Chloro-benzotriazol-1-yl)-N,N,N',N'-tetramethyluronium tetrafluoroborate
TFA: Trifluoroacetic acid
THF: Tetrahydrofuran
Tris: tris(Hydroxymethyl)aminomethane or 2-amino-2-hydroxymethylpropane-1,3-diol
UPLC: Ultra Performance Liquid Chromatography Materials and Methods
General Methods of Detection and Characterisation
LCMS Method 1
System: Waters Acquity UPLC
Column: Waters Acquity BEH C4 column, 1.7 μm, 150× 1.0 mm
Column temperature: 60° C.
Auto sampler temperature: 8° C.
Detection: Synapt G2 instrument & UV215 nm
Eluents: Solvent A: 0.05% (v/v) TFA in MQ water; Solvent B: 0.05% (v/v) TFA in MeCN
Flow: 0.12 mL/min
Gradient: 0-24 min 28-35% B
Results: Average mass (MaxEnt1)
LCMS Method 2
System: Agilent 1290 infinity series UPLC Column: Aeris WIDEPORE 3.6μ XB—C18 2.1×50 mm Detector: Agilent Technologies LC/MSD TOF 6230 (G6230A);
Detector setup: Ionisation method: Agilent Jet Stream source Scanning range: m/z min. 100, m/z max. 3200 linear reflector mode positive mode;
Conditions: Linear gradient: 5% to 95% B Gradient run-time: 10 minutes: 0-8 min 5-95% B, 8-9 min 95% B, 9-9.5 min 95-5% B 9.5-10 min 5% B Flow rate: 0.40 ml/min fixed Column temperature: 40° C.;
Eluents: Solvent A: 99.90% $H_2O$, 0.02% TFA Solvent B: 99.90% $CH_3CN$, 0.02% TFA Solvent C: NA;
Results specification and validation: Mass found is either m/z ((m+z)/z) of the compound for compounds with m<4000 or mass (average) as the result of a deconvolution using Masshunter Workstation Software Version B.05.00 Build 5.0.519.13 SP1 (Agilent);
Calculated Mass is the average molecular weight of the desired compound;
Calculated m/z is the molecular weight (m+z)/z of the desired compound.
LCMS Method 3
System: Agilent 1290 infinity series UPLC Column: Phenomenex Aeris widepore 3.6μ C4 50×2.1 mm;
Detector: Agilent Technologies LC/MSD TOF 6230 (G6230A);
Detector setup: Ionisation method: Agilent Jet Stream source Scanning range: m/z min. 100, m/z max. 3200 linear reflector mode positive mode;
Conditions: Step gradient: 5% to 90% B Gradient run-time: 10 minutes: 0-1 min 5-20% B, 1-7 min 20-90% B, 7-8 min 90% B 8-8.5 min 90-5% B 8.5-10 min 5% B Flow rate: 0.40 ml/min fixed Column temperature: 40° C.;
Eluents Solvent A: 99.90% $H_2O$, 0.02% TFA Solvent B: 99.90% $CH_3CN$, 0.02% TFA Solvent C: NA;
Results specification and validation: Mass found is either m/z ((m+z)/z) of the compound for compounds with m<4000 or mass (average) as the result of a deconvolution using Masshunter Workstation Software Version B.05.00 Build 5.0.519.13 SP1 (Agilent);
Calculated Mass is the average molecular weight of the desired compound Calculated m/z is the molecular weight (m+z)/z of the desired compound.
LCMS Method 4
System: Waters Acquity UPLC SQD 2000 Column: Acquity UPLC BEH 1.7μ C18 100 Å 2.1×50 mm;
Detector: UV: PDA, SQD 2000;
Detector setup: Ionisation method: ES+ Scanning range: 500-2000 Cone Voltage: 60 V Scantime 0.5;
Conditions: Linear gradient: 10% to 90% B Gradient run-time: 3 min Total run-time: 4 min Flow rate: 0.3 ml/min; Column temperature: 40° C. PDA: 210-400 nm;
Eluents: Solvent A: 99.90% $H_2O$, 0.1% TFA Solvent B: 99.90% $CH_3CN$, 0.1% TFA Solvent C: NA;
Results specification and validation: Mass found is the mass found of the compound M/z found is the molecular ion found ((M+z)/z) of the compound;
Calculated Mass is the molecular weight of the desired compound;
Calculated M/z is the molecular weight (M+z)/z of the desired compound.
LCMS Method 5
System: Waters Acquity UPLC SQD 2000 Column: Acquity UPLC BEH 1.7μ C18 100 Å 2.1×50 mm;
Detector: UV: PDA, SQD 2000;
Detector setup: Ionisation method: ES+ Scanning range: 100-1500 Cone Voltage: 25 V Scantime 0.5;
Conditions: Linear gradient: 10% to 90% B Gradient run-time: 9 min
Total run-time: 10 min Flow rate: 0.3 ml/min;

Column temperature: 40° C. PDA: 210-400 nm;

Eluents: Solvent A: 99.90% $H_2O$, 0.1% TFA Solvent B: 99.90% $CH_3CN$, 0.1% TFA Solvent C: NA;

Results specification and validation: Mass found is the mass found of the compound M/z found is the molecular ion found ((M+z)/z) of the compound;

Calculated Mass is the molecular weight of the desired compound Calculated M/z is the molecular weight (M+z)/z of the desired compound;

Purity: Total ion current (TIC) AUC of analyte peak, in percent of total AUC excl. solvent peak, as reported by system software;

Identity: Mass of each analyte mass peak expressed as m/z from highest to lowest. Scanning range is the range scanned in the method used. Detection method is e.g. linear reflector.

LCMS Method 6

System: Waters Acquity UPLC H-Class SQD2 2000

Column: Acquity UPLC BEH 1.7μ C18 100 Å 2.1×50 mm. Part no: 186002350

Detector: UV: PDA, SQD 2000

Detector setup: Ionisation method: ES+ Scanning range: 500-2000 Cone Voltage: 60 V Scantime: 0.5

Conditions: Linear gradient: 10% to 80% B Gradient run-time: 2.50 min Total run-time: 4 min Flow rate: 0.3 ml/min (0-2.51 min) and 0.8 ml/min (2.51-4.00 min)

Column temperature: 40° C. PDA: 210-400 nm

Eluents: Solvent A: 99.90% $H_2O$, 0.1% TFA Solvent B: 99.90% $CH_3CN$, 0.1% TFA Solvent C: NA]

Results specification and validation: Mass found of the compound is M/z, which is the molecular ion found ((M+z)/z) of the compound.

Calculated Mass is the molecular weight of the desired compound Calculated M/z is the molecular weight (M+z)/z of the desired compound Purity: Total ion current (TIC) AUC of analyte peak, in percent of total AUC excl solvent peak, as reported by system software.

Identity: Mass of each analyte mass peak expressed as m/z from highest to lowest.

Scanning range is the range scanned in the method used. Detection method is e.g. linear reflector.

LCMS Method 7

System: Agilent 1290 infinity series UPLC

Column: Eclipse C18+2.1×50 mm 1.8u.

Detector: Agilent Technologies LC/MSD TOF 6230 (G6230A).

Ionisation method: Agilent Jet Stream source Scanning range: m/z min. 100, m/z max. 3200 linear reflector mode positive mode.

Linear gradient: 5% to 95% B

Gradient run-time: 6 minutes 0-4.5 min 5-95% B, 4.5-5 95% B, 5-5.5 95-5% B, 5.5-6 5% B Flow rate: 0.40 ml/min fixed Column temperature: 40° C.

Solvent A: 99.90% $H_2O$, 0.02% TFA Solvent B: 99.90% $CH_3CN$, 0.02% TFA

Mass found is either m/z ((m+z)/z) of the compound for compounds with m<4000 or mass (average) as the result of a deconvolution using Masshunter Workstation Software Version B.05.00 Build 5.0.519.13 SP1 (Agilent).

Calculated Mass is the average molecular weight of the desired compound.

Calculated m/z is the molecular weight (m+z)/z of the desired compound.

LCMS Method 8

System: Waters Acquity UPLC SQD 2000

Column: Acquity UPLC BEH 1.7μ C18 100 Å 2.1×50 mm

Detector: UV: PDA, SQD 2000

Detector setup: Ionisation method: ES+ Scanning range: 100-1500 Cone Voltage: 25 V Scantime 0.5

Conditions: Linear gradient: 0% to 50% B Gradient run-time: 2.5 min

Total run-time: 4 min

Flow rate: 0.3 ml/min

Column temperature: 40° C.

PDA: 210-400 nm

Eluents: Solvent A: 99.90% $H_2O$, 0.1% TFA Solvent B: 99.90% $CH_3CN$, 0.1% TFA Solvent C: NA Results specification and validation: Mass found is the mass found of the compound M/z found is the molecular ion found ((M+z)/z) of the compound Calculated Mass is the molecular weight of the desired compound Calculated M/z is the molecular weight (M+z)/z of the desired compound.

Purity: Total ion current (TIC) AUC of analyte peak, in percent of total AUC excl solvent peak, as reported by system software. Identity: Mass of each analyte mass peak expressed as m/z from highest to lowest. Scanning range is the range scanned in the method used. Detection method is e.g linear reflector LCMS Method 9

LC-system: Waters Acquity UPLC H Class

Column: Waters Acquity BEH, C-18, 1.7 μm, 2.1 mm×50 mm

Detector: Waters Xevo G2-XS QTof

Detector setup: Ionisation method: ES Scanning range: 50-4000 amu Operating mode: MS resolution mode positive/ne: positive mode Voltage: Capillary 3.00 kV; Sample cone 80 V, Source 60 V Temperature: Source 150° C., Desolvation 500° C., Scantime 0.500 s Interscandelay: 0.014 s Conditions: Linear gradient: 5% to 95% B Gradient run-time: 4.0 minutes Total run-time: 7.0 minutes Flow rate: 0.4 ml/min Column temperature: 40° C.

Eluents: Solvent A: 99.90% MQ-water, 0.1% formic acid Solvent B: 99.90% acetonitrile, 0.1% formic acid Solvent C: 99.99% MQ water 0.01% TFA Gradient: A 90-0%; B 5-95%, C 5%

Results specification and validation: Mass found is the mass found of the compound M/z found is the molecular ion found ((M+z)/z) of the compound Calculated Mass is the molecular weight of the desired compound Calculated M/z is the molecular weight (M+z)/z of the desired compound Purity: Total ion current (TIC) AUC of analyte peak, in percent of total AUC excl solvent peak, as reported by system software.

Identity: Mass of each analyte mass peak expressed as m/z from highest to lowest. Scanning range is the range scanned in the method used. Detection method is e.g linear reflector LCMS Method 10

LC-system: Waters Acquity UPLC H

Class Column: Waters Acquity BEH, C-18, 1.7 μm, 2.1 mm×50 mm,

Detector: Waters Xevo G2-XS QTof

Detector setup: Ionisation method: ES Scanning range: 50-4000 amu Operating mode: MS resolution mode positive/ne: positive mode Voltage: Capillary 3.00 kV, Sample cone 80 V, Source 60 V, Temperature: Source 150° C., Desolvation 500° C., Scan time 0.500 s, Inter scan delay: 0.014 s Conditions: Linear gradient: 5% to 95% B Gradient run-time: 4.0 minutes, Total run-time: 7.0 minutes, Flow rate: 0.4 ml/min Column temperature: 40° C.

Eluents: Solvent A: 99.90% MQ-water, 0.1% formic acid Solvent B: 99.90% acetonitrile, 0.1% formic acid Solvent C: 99.99% MQ water 0.01% TFA Gradient: A 90-70% 1 min, 70-30% 6 min, 30-0% 0.5 min, 0% 0.5 min, B 5-25% 1 min, 25-65% 6 min, 65-95% 0.5 min, 95% 0.5 min, C 5%

Results specification and validation: Mass found is the mass found of the compound M/z found is the molecular ion found ((M+z)/z) of the compound Calculated Mass is the molecular weight of the desired compound Calculated M/z is the molecular weight (M+z)/z of the desired compound Purity: Total ion current (TIC) AUC of analyte peak, in percent of total AUC excl solvent peak, as reported by system software.

Identity: Mass of each analyte mass peak expressed as m/z from highest to lowest. Scanning range is the range scanned in the method used. Detection method is e.g. linear reflector.

Example 1: Preparation of the [OEF-Ins] Compounds of the Invention

The oligomer extended fusion insulin compounds for use according to the invention may be produced by various techniques known in the art, e.g. as described in WO 2016/193380 A1.

Insulin-coding DNA is fused with DNA coding for the recombinant extensions. The DNA is cloned in yeast and the insulin is expressed and harvested. The extended insulin is expressed as single-chain precursor which is cleaved to two-chain extended insulin using ALP enzyme (or trypsin and optionally CPB etc).

Capture of the Precursor on SP Sepharose:

The SP column (approx. 200 mL) was regenerated with 0.5M NaOH and equilibrated with 0.1M citric acid pH 3.5. The capture run (cation exchange) was conducted at 20° C.

The yeast supernatant was diluted with water 1:1 and loaded with a flow of 10-20 mL/min.

A wash with 0.1 M citric acid pH 3.5 and a wash with 60% EtOH was performed. The analogue was eluted with 0.2 M Na-Acetate pH 5.5/40% EtOH.

The SP-pool (appr. 600 ml) was diluted twice with water and 50 mM Glycine was added. pH was adjusted to 9.3, and 3-5 mg Trypsin per g insulin was added. Reaction was followed on the UPLC.

After 3 hours, citric acid was added, pH adjusted to 3.5 and purified on a 50 mm 15μ Gemini column Column: 10 μm Gemini C18 50×250 mm 200A, 477 ml
Buffers:
A: 10 ml formic acid/5 L 10% w/w acetonitrile
B: 70% w/w acetonitrile
The gradient was 10-50% B-buffer.
Gradient time/total cv 120 min
Flow 80 ml/min

TABLE 1

| | | [OEF-Ins] compounds | | | |
|---|---|---|---|---|---|
| Compound | Insulin analogue | Extension - A-chain (Extension from C-terminus) | Extension - B-chain (Extension from N-terminus) | [Calc. mass (Da)] Mean Value | LCMS Method 3 [Found mass (Da)] Mean Value |
| OEF-Ins-1 (A-chain of SEQ ID NO: 7 and B-chain of SEQ ID NO: 21) | A14E, A21G, B25H, B29R, desB30 | $(GQEP)_{19}$-KP | | 13675.0 | 13676.0 |
| OEF-Ins-2 (A-chain of SEQ ID NO: 8 and B-chain of SEQ ID NO: 24) | A14E, B3Q, B25H, B29R, desB30 | | KP-$(GQAPGQAPGQEP)_6$-GQAP | 12992.0 | 12993.0 |
| OEF-Ins-3 (A-chain of SEQ ID NO: 9 and B-chain of SEQ ID NO: 23) | A14E, A21G, B3Q, B25H, B29R, desB30 | $(GQAPGQAPGQEP)_6$-GQAP-KP. | | 12935.0 | 12936.0 |
| OEF-Ins-4 (A-chain of SEQ ID NO: 8 and B-chain of SEQ ID NO: 22) | A14E, B25H, B29R, desB30 | | KP$(GQEP)_{19}$ | 13732.0 | 13733.0 |
| OEF-Ins-5 (A-chain of SEQ ID NO: 7 and B-chain of SEQ ID NO: 23) | A14E, A21G, B3Q, B25H, B29R, desB30 | $(GQEP)_{19}$-KP | | 13689.0 | 13690.0 |
| OEF-Ins-6 (A-chain of SEQ ID NO: 11 and B-chain of SEQ ID NO: 21) | A14E, A21G, B25H, B29R, desB30 | $(GQEP)_{12}$-KP | | 10795.0 | 10796.0 |
| OEF-Ins-7 (A-chain of SEQ ID NO: 10 and B-chain of SEQ ID NO: 21) | A14E, A21G, B25H, B29R, desB30 | $(GQEP)_6$-KP | | 8327.0 | 8328.0 |
| OEF-Ins-8 (A-chain of SEQ ID NO: 13 and B-chain of SEQ ID NO: 21) | A14E, A21G, B25H, B29R, desB30 | $(GQEP)_3$-GQE-KP | | 7407.1 | 7407.9 |
| OEF-Ins-9 (A-chain of SEQ ID NO: 12 and B-chain of SEQ ID NO: 21) | A14E, A21G, B25H, B29R, desB30 | $(GQAPGQEP)_6$-KP | | 10447.4 | |

TABLE 1-continued

| | | [OEF-Ins] compounds | | | |
|---|---|---|---|---|---|
| Compound | Insulin analogue | Extension - A-chain (Extension from C-terminus) | Extension - B-chain (Extension from N-terminus) | [Calc. mass (Da)] Mean Value | LCMS Method 3 [Found mass (Da)] Mean Value |
| OEF-Ins-10 (A-chain of SEQ ID NO: 8 and B-chain of SEQ ID NO: 27) | A14E, B25H, B29R, desB30 | | KP(GQEP)$_6$ | 8384.1 | 8384.6 |
| OEF-Ins-11 (A-chain of SEQ ID NO: 8 and B-chain of SEQ ID NO: 28) | A14E, B25H, B29R, desB30 | | KP(GQEP)$_4$ | 7561.3 | 7562.1 |
| OEF-Ins-12 (A-chain of SEQ ID NO: 8 and B-chain of SEQ ID NO: 25) | A14E, B25H, B29R, desB30 | | KP(GQAP)$_{19}$ | 12629.9 | 12630.4 |
| OEF-Ins-13 (A-chain of SEQ ID NO: 14 and B-chain of SEQ ID NO: 21) | A14E, A21G, B25H, B29R, desB30 | (GQAP)$_{19}$-KP | | 12572.8 | 12573.3 |
| OEF-Ins-14 (A-chain of SEQ ID NO: 9 and B-chain of SEQ ID NO: 26) | A14E, A21G, B29R, desB30 | (GQAPGQAPGQEP)6-GQAP-KP | | 12931.0 | 12931.6 |
| OEF-Ins-15 (A-chain of SEQ ID NO: 15 and B-chain of SEQ ID NO: 21) | A14E, A21G, B25H, B29R, desB30 | (GQAPGQAPGQAPGQEP)6-GQAP-KP | | 15041.3 | 15041.5 |
| OEF-Ins-16 (A-chain of SEQ ID NO: 17 and B-chain of SEQ ID NO: 26) | A14A, A21G, B29R, desB30 | (GQAP)18-GQA-KP | | 12427.7 | 12428.4 |
| OEF-Ins-17 (A-chain of SEQ ID NO: 18 and B-chain of SEQ ID NO: 26) | A14E, A21G, B29R, desB30 | (GQAP)18-GQA-KP | | 12485.7 | 12486.1 |
| OEF-Ins-18 (A-chain of SEQ ID NO: 18 and B-chain of SEQ ID NO: 21) | A14E, A21G, B25H, B29R, desB30 | (GQAP)18-GQA-KP | | 12475.7 | 12476.1 |
| OEF-Ins-19 (A-chain of SEQ ID NO: 19 and B-chain of SEQ ID NO: 21) | A14E, A21Q, B25H, B29R, desB30 | (G)18-K | | 6859.5 | 6853.2* |
| OEF-Ins-20 (A-chain of SEQ ID NO: 16 and B-chain of SEQ ID NO: 21) | A14E, A21G, B25H, B29R, desB30 | (GQAP)24-GQA-KP | | 14596.0 | 14596.4 |
| OEF-Ins-21 (A-chain of SEQ ID NO: 16 and B-chain of SEQ ID NO: 26) | A14E, A21G, B29R, desB30 | (GQAP)24-GQA-KP | | 14606.0 | 14606.3 |
| OEF-Ins-22 (A-chain of SEQ ID NO: 20 and B-chain of SEQ ID NO: 26) | A21G, B29R, desB30 | (GQAP)18-GQA-KP | | 12519.8 | 12520.2** |
| OEF-Ins-23 (A-chain of SEQ ID NO: 18 and B-chain of SEQ ID NO: 29) | A14E, A21G, B16E, B25H, B29R, desB30 | (GQAP)18-GQA-KP | | 12441.7 | 12442.0 |

*MALDI data;
**MS method 7

Example 2: General Preparation of Fc

A DNA sequence encoding MA-IgG4 Fc amino acid sequence (226M, 227 Å IgG4-Fc(228-447)) was first constructed using p3700-A-IgG4-Fc(228-447) sequence:

```
(A SCPAPEFLGG PSVFLFPPKP KDTLMISRTP EVTCVVVDVS

QEDPEVQFNW YVDGVEVHNA KTKPREEQFN STYRVVSVLT

VLHQDWLNGK EYKCKVSNKG LPSSIEKTIS KAKGQPREPQ

VYTLPPSQEE MTKNQVSLTC LVKGFYPSDI AVEWESNGQP

ENNYKTTPPV LDSDGSFFLY SRLTVDKSRW QEGNVFSCSV

MHEALHNHYT QKSLSLSLGK)
```

A 227A, IgG4-Fc(228-447) (Fc1) was then produced at high level from *E. coli* as inclusion bodies.

The inclusion bodies were washed two times using distilled water, and solubilized in 6M Urea, 10 mM DTT, 50 mM Tris pH 9.0 at 10 mg/m. After being fully dissolved, the solution was acidified to pH 4.5 to remove impurities. The Fc molecules were refolded through a solution-solid phase procedure as described in more details below: The solubilized inclusion bodies were fast diluted to the refolding solution (3M urea, 0.25 arginine, 1 mM cysteine, 50 mM Tris pH 9.0) to a final concentration at 1 mg/mL for 24 hours. The Fc proteins were correctly refolded after solid-phase capturing using hydrophobic interaction resins (Phenyl Fast-Flow).

The refolded Fc molecules were further purified using Capto Mix-Mode Chromatography, and the purified Fc molecules were finally solubilized in 100 mM Tris pH 8.0.

TABLE 2

Fc analogues. The Fc analogues were prepared as described above. Intact mass determined by LCMS (using LCMS Method 1) are given for the compounds.

| Compound No. | Fc sequence mutations | Calculated average mass | Found average mass LCMS Method 1 |
|---|---|---|---|
| Fc1 (SEQ ID NO: 31) | 227A hIgG4-Fc(228-447) | 49741.48 | 49741.59 |
| Fc2 (SEQ ID NO: 33) | 227A, 315Q, 384Q hIgG4-Fc(228-447) | 49797.60 | 49797.69 |
| Fc3 (SEQ ID NO: 34) | 226G, 227A hIgG4-Fc(228-447) | 49856.58 | 49858.75 |
| Fc4 (SEQ ID NO: 35) | 227A, 228S, 235K, 315Q, 384Q hIgG1-Fc(228-447) | 49727.76 | 49726.87 |
| Fc5 (SEQ ID NO: 36) | 227A, 235K, 315Q, 384Q hIgG4-Fc(228-447) | 49827.62 | 49826.69 |
| Fc6 (SEQ ID NO: 37) | 227A, 234A, 235A hIgG4-Fc(228-447) | 49505.14 | 49505.8 |
| Fc7 (SEQ ID NO: 38) | 226A, 227S hIgG1-Fc(228-447) | 49835.86 | 49835.26 |
| Fc8 (SEQ ID NO: 39) | 227A, 235K hIgG4-Fc(228-447) | 49771.50 | 49772.2 |
| Fc9 (SEQ ID NO: 30) | 227A, 234A, 235K hIgG4-Fc(228-447) | 49619.32 | 49619.96 |
| Fc10 (SEQ ID NO: 40) | 226A, 227S, 235K, 237A, 330S, 331S hIgG1-Fc(228-447) | 49905.86 | 49905.77 |
| Fc11 (SEQ ID NO: 41) | 226A, 227S, 234A, 235K, 237A, 330S, 331S hIgG1-Fc(228-447) | 49821.70 | 49821.54 |
| Fc12 (SEQ ID NO: 42) | 226A, 227S, 234A, 235K,237A,315Q, 330S, 331S, 384Q hIgG1-Fc(228-447) | 49877.82 | 49877.38 |
| Fc13 (SEQ ID NO: 43) | 226A, 227S, 234A, 235E, 237A, 330S, 331S hIgG1-Fc(228-447) | 49823.58 | 49822.66 |
| Fc14 (SEQ ID NO: 44) | 227A, 234A, 235K, 297Q hIgG4-Fc(228-447) | 49647.4 | 49647.1 |
| Fc15 (SEQ ID NO: 32) | 227A, 234A, 235K, 297E, 315Q, 384Q, des447 hIgG4-Fc(228-447) | 49449.11 | 49449.4 |
| Fc16 (SEQ ID NO: 45) | 227A, 234A, 235K, 297E, des447 hIgG4-Fc(228-447) | 49393.0 | 49393.4 |
| Fc17 (SEQ ID NO: 46) | 226A, 227G, 228P, 234A, 235K, des447 hIgG4-Fc(228-447) | 49497.2 | 49498.5 |

Example 3: Preparation of Linkers for Derivatisation of Insulin Analogues

Example 3.1

Synthesis of (2,5-dioxopyrrolidin-1-yl)-4-[bis[2-[(2-iodoacetyl)amino]ethyl]amino]-4-oxo-butanoate (Chem. 6)

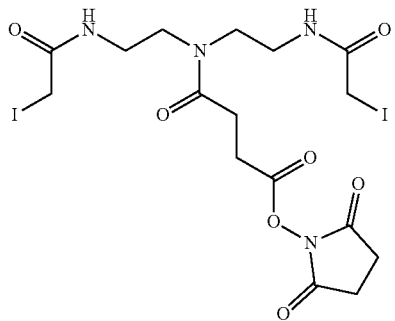 [SMILES: O=C(CI)NCCN(CCNC(=O)CI)C(=O)CCC(=O)ON1C(=O)CCC1=O]

Step 1: 4-[Bis[2-(tert-butoxycarbonylamino)ethyl]amino]-4-oxo-butanoic acid tert-Butyl N-[2-[2-(tert-butoxycarbonylamino)ethylamino]ethyl]carbamate (3.0 g) was dissolved in DCM (50 ml). Succinic anhydride (1.08 g) was added followed by molecular sieves, 3 Å (2.0 g). The mixture was stirred at RT. After 1.5 h more molecular sieves, 3 Å (2.0 g) was added. After stirring for 20 h the reaction mixture was filtered and concentrated in vacuo to give an oil. This oil was dissolved in ethyl acetate (100 ml) and washed with 5% citric acid and dried with anhydrous $MgSO_4$. After filtration, the filtrate was concentrated in vacuo to give the product as clear foam.

LCMS Method 5: Calc. m/1: 404.5; Found m/1: 404.3; rt 3.67 min.

Step 2: 4-[Bis(2-aminoethyl)amino]-4-oxo-butanoic acid

4-[Bis[2-(tert-butoxycarbonylamino)ethyl]amino]-4-oxo-butanoic acid (4.0 g) was dissolved in dichloromethane (50 ml). TFA (10 ml) was added. The mixture was stirred at RT for 2 hours. The deprotected product as TFA salt precipitates as oil. The mixture was concentrated in vacuo to give a clear oil. It was easily dissolved in acetonitrile, concentrated again to an oil followed by co-concentration with toluene twice. The residue was left in vacuo overnight. Crystallisation in ether was followed by drying in vacuo. White crystals were formed.

Step 3: 4-[Bis[2-[(2-iodoacetyl)amino]ethyl]amino]-4-oxo-butanoic acid

4-[Bis(2-aminoethyl)amino]-4-oxo-butanoic (600 mg) was dissolved in 0.2M $Na_2CO_3$ (30 ml) and Acetonitrile (20 ml). Iodoacetic acid hydroxy-succinimide ester (905 mg) as powder was added in portions. pH was kept at 9-9.5 during the addition. The reaction mixture was stirred at RT for 30 min. The reaction was acidified with citric acid (no precipitation), concentrated to half volume to remove acetonitrile and extracted with ethyl acetate (3×100 ml). The combined yellow ethyl acetate layers were dried ($MgSO_4$) and concentrated in vacuo to give a yellow oil, which was purified by RP-chromatography.

Column: 30×250 mm (Gemini-NX 5um_C18_110A AXIA_30×250 mm) CV=177 ml
A Buffer: Milli-Q water+0.1% TFA
B Buffer: 80% acetonitril in Milli-Q water+0.1% TFA
Flow: 25 ml/min
Gradient: 0-70% B—45 min
The product fractions were pooled and freeze dried.
LCMS Method 5: Calc. m/1: 540.1; Found m/1: 540.0; rt 1.42 min.

Step 4: (2,5-Dioxopyrrolidin-1-yl)-4-[bis[2-[(2-iodoacetyl)amino]ethyl]amino]-4-oxo-butanoate 4-[Bis[2-[(2-iodoacetyl)amino]ethyl]amino]-4-oxo-butanoic acid (1.50 g) was dissolved in dry THF (100 ml). N-hydroxysuccinimide (351 mg) and DIC (0.861 ml) was added. The mixture was stirred at RT overnight. The mixture was concentrated in vacuo. The residue was dissolved in 50 ml acetonitrile, cooled on ice and the precipitate was filtered off. The filtrate was concentrated in vacuo The residue was stirred in diethylether, the formed solid was filtered off, washed with ether and dried in vacuum, to give the product as a light yellow solid. Yield 1.75 g (96%).
LCMS Method 5: Calc. m/1: 636.2; Found m/1: 637.0; rt 2.1.2 min.

Example 3.2

Synthesis of (2,5-dioxopyrrolidin-1-yl)-6-[bis[2-[(2-iodoacetyl)amino]ethyl]amino]-6-oxo-hexanoate (Chem. 7)

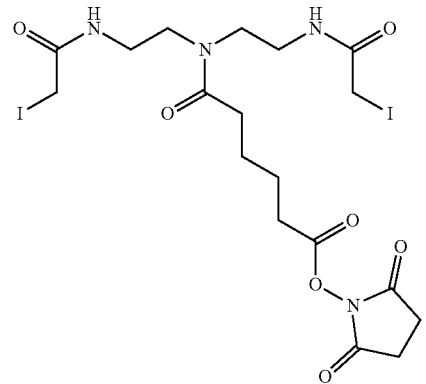 [SMILES: O=C(CI)NCCN(CCNC(=O)CI)C(=O)CCCCC(=O)ON1C(=O)CCC1=O]

Step 1: Methyl 6-[bis[2-(tert-butoxycarbonylamino)ethyl]amino]-6-oxo-hexanoate

Mono-methyl adipate (1.50 g) was dissolved in DCM. HOAT (1.274 g), EDCA (1.795 g) and DIPEA (1.632 ml) was added. After stirring at RT for 1 h, tert-Butyl N-[2-[2-(tert-butoxycarbonylamino)ethylamino]ethyl]carbamate (2.90 g) was added. The mixture was stirred at RT overnight. The mixture was diluted with DCM (100 ml) and washed with 2×50 ml water, 50 ml 0.1M $Na_2CO_3$ and 50 ml 5% citric acid. Dried over $MgSO_4$.

Concentrated in vacuo to give a colourless clear oil. Yield 3.99 g (96%).
LCMS Method 5: Calc. m/1: 446.6; Found m/1: 446.5 rt 4.77 min.

Step 2: 6-[Bis[2-[(2-methylpropan-2-yl)oxycarbonylamino]ethyl]amino]-6-oxohexanoic acid Methyl 6-[bis[2-(tert-butoxycarbonylamino)ethyl]amino]-6-oxo-hexanoate (4.15 g) was dissolved in acetonitrile (50 ml). 5M NaOH (10 ml) was added. The mixture was stirred vigorously at RT overnight. 10% Citric acid was added to pH 5.0, the acetonitrile was evaporated off in vacuo, the residual water phase was diluted with 50 ml water (pH 4.5) and was extracted with ethyl acetate (200 ml). The organic layer was dried over MgSO$_4$ and concentrated in vacuo to give the product. Yield 4.0 g (quantitative).

LCMS Method 5: Calc. m/1: 432.5; Found m/1: 432.5 rt 3.94 min.

Step 3: 6-[Bis(2-aminoethyl)amino]-6-oxo-hexanoic acid

6-[Bis[2-[(2-methylpropan-2-yl)oxycarbonylamino] ethyl]amino]-6-oxohexanoic acid 4.0 g) was dissolved in dichloromethane (50 ml) and TFA (15 ml) was added. The mixture was stirred at RT for 2 h. The deprotected product as TFA salt, separated as an oil. The mixture was concentrated in vacuo to give a clear oil, which was dissolved in acetonitrile, concentrated again to an oil, stripped twice with toluene. The residue was stirred in ether. The ether was decanted off and the residue was dried in vacuo. overnight to give a stiff oil. Yield 4.2 g (quantitative).

Step 4: 6-[Bis[2-[(2-iodoacetyl)amino]ethyl]amino]-6-oxohexanoic acid

6-[Bis(2-aminoethyl)amino]-6-oxo-hexanoic acid (1.00 g) was dissolved in 0.2M Na$_2$CO$_3$ (30 ml) and acetonitrile (20 ml) and pH was adjusted to 9.3 with 1N NaOH. Iodoacetic acid OSu ester (1.537 g) as powder was added in portions. pH was kept at 9-9.5 during the addition and after. The clear solution was stirred at RT for 30 min. The reaction was acidified with 10% citric acid to pH 4 followed by concentration to half volume (to remove acetonitril), then diluted to 100 ml with water before purification by RP chromatography:

Column: 30×250 mm (Gemini-NX 5um_C18_110A AXIA_30×250 mm) CV=177 ml
A Buffer: 0% acetonitril in Milli-Q water+0.1% TFA
B Buffer: 80% acetonitril in Milli-Q water+0.1% TFA
Flow: 25 ml/min
Gradient: 0-50% B—60 min The product pool was concentrated in vacuo, stripped 3 times with acetonitrile and dried in exicator in vacuo, to give the pure product as hard oily residue. Yield 1.2 g (95%).

LCMS Method 5: Calc. m/1: 568.2; Found m/1: 568.2 rt 1.80 min.

Step 5: (2,5-Dioxopyrrolidin-1-yl)-6-[bis[2-[(2-iodoacetyl)amino]ethyl]amino]-6-oxo-hexanoate (Chem. 7)

6-[Bis[2-[(2-iodoacetyl)amino]ethyl]amino]-6-oxo-hexanoic acid (975 mg) was dissolved in dry THF (75 ml). N-hydroxysuccinimide (220 mg) and DIC (532 µL) were added. The mixture was stirred at RT for 24 h. The precipitate was removed by filtration. The filtrate was concentrated in vacuo. The residue was dissolved in acetonitrile (50 ml) and cooled on ice. The precipitate was filtered off. The filtrate was concentrated in vacuo. The residue was stirred in ether. The formed solid was filtered off, washed with ether and dried in vacuum, to give the product as a light yellow solid. Yield 1.03 g (90%).

LCMS Method 5: Calc. m/1: 665.2; Found m/1: 665.2 rt 2.51 min.

Example 3.3

Synthesis of (2,5-dioxopyrrolidin-1-yl)-(2S)-2,6-bis[(2-iodoacetyl)amino]-hexanoate (Chem. 8)

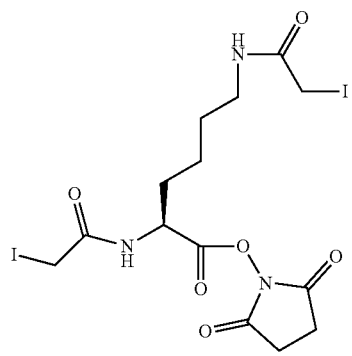 [SMILES: O=C(CI)NCCCC[C@H](NC(=O)CI)C(=O)ON1C(=O)CCC1=O]

Step 1: (2S)-2,6-Bis[(2-Chloroacetyl)amino] hexanoic acid

To a solution of L-lysine monohydrochloride monohydrate (53.2 g, 291 mmol) in water (200 mL) was added a solution of sodium hydroxide (69.8 g, 1.75 mol) in water (200 mL) and the mixture was cooled down to 0° C. A solution of chloroacetyl chloride (69.5 mL, 874 mmol) in diethyl ether (200 mL) was added drop-wise over 45 minutes. The reaction mixture was stirred at 0° C. for 2 hours, then overnight at room temperature. Aqueous layer was separated, washed with diethyl ether (2×300 mL) and dichloromethane (3×300 mL), then was acidified with concentrated hydrochloric acid to pH 2 and extracted with dichloromethane (3×400 mL). Dichloromethane extracts were combined, dried over anhydrous sodium sulphate. After filtration the solvent was removed under reduced pressure. Aqueous phase was freeze-dried. The product 2 was detected in the both phases. The title compound (2) was purified by RP HPLC (4 round; Column Deltapak C18, 50×500 mm, acetonitrile/water 2:98 to 20:80 during 180 min, 20:80 to 40:60 during 30 min+0.05% TFA). The freeze-drying gave (2S)-2,6-Bis[(2-chloroacetyl)amino] hexanoic acid (2) as a colourless oil.

Yield: 26.0 g (30%).

1H NMR spectrum (300 MHz, Acetic acid D$_a$, dH): 4.66 (dd, 3=8.4 and 5.0 Hz, 1H); 4.22 (s, 2H); 4.17 (s, 2H); 3.33 (t, 3=7.0 Hz, 2H); 2.02-1.76 (m, 2H); 1.68-1.53 (m, 2H); 1.52-1.37 (m, 2H).

LC-MS Rt (Kinetex C18, 4.6×50 mm, acetonitrile/water 5:95 to 100:0+0.1% FA): 2.76 min.

LC-MS m/1: 299.3.

Step 2: (2S)-2,6-Bis[(2-iodoacetyl)amino]hexanoic acid

Mixture of the above compound (26.0 g, 86.9 mmol) and sodium iodide (65.2 g, 435 mmol) in dry acetonitrile (1000 mL) was stirred at room temperature overnight. After filtration the solvent was removed in vacuo. The residue was dissolved in 2% aqueous acetonitrile and sodium thiosulphate was added until the solution became colourless. The mixture was purified by RP HPLC (3 round; Column Deltapak C18, 50×500 mm, acetonitrile/water 2:98 to 20:80 during 60 min, then 20:80 to 40:60 during 30 min+0.05% TFA). The freeze-drying gave the title compound as a hygroscopic white solid.

Yield: 10.3 g (25%).

1H NMR spectrum (300 MHz, Acetic acid Da, 80 C, dH): 4.66 (dd, 3=8.3 and 5.1 Hz, 1H); 3.90 (dd, 3=12.4 and 10.6 Hz, 2H); 3.83 (s, 2H); 3.32 (t, 3=6.8 Hz, 2H); 2.04-1.94 (m, 1H); 1.91-1.77 (m, 1H); 1.70-1.47 (m, 4H).

LC-MS Rt (Kinetex C18, 4.6×50 mm, acetonitrile/water 5:95 to 100:0+0.1% FA): 2.94 min.

LC-MS m/1: 483.3.

Step 3: (2,5-Dioxopyrrolidin-1-yl)-(2S)-2,6-big(2-iodoacetyl)amino]hexanoate (Chem. 8)

To a solution of (2S)-2,6-bis[(2-iodoacetyl)amino] hexanoic acid (500 mg) in dry THF (10 ml) was added N-hydroxysuccinimide (150 mg) and DIC (0,201 ml). The mixture was stirred at RT for 24 h followed by concentrated in vacuo. The residue was dissolved in acetonitril (100 ml), cooled on ice and filtered. The acetonitrile phase was concentrated in vacuo. The residue was stirred in ether, the formed solid was filtered off, washed with ether and dried in vacuum, to give the product as a light yellow solid.

LCMS Method 4: Calc. m/1: 580.1; Found m/1: 580.1 rt 1.75 min.

Example 3.4

Synthesis of (2,5-dioxopyrrolidin-1-yl) 4-[bis[2-[(2-iodoacetyl)amino]ethyl]carbamoylamino]butanoate (Chem. 9)

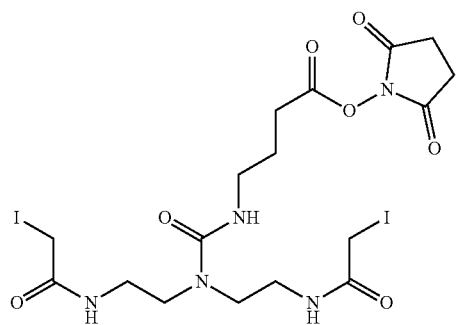 [SMILES: O=C(CI)NCCN(CCNC(=O)CI)C(=O)NCCCC(=O)ON1C(=O)CCC1=O]

Step 1: 4-[Bis[2-[(2-iodoacetyl)amino]ethyl]carbamoylamino]butanoic acid

2-Chlorotrityl resin 100-200 mesh 1.5 mmol/g (1, 9.22 g, 13.8 mmol) was left to swell in dry dichloromethane (50 mL) for 1 hour. A solution of Fmoc-GABA-OH (3.00 g, 9.22 mmol) and N,N-diisopropylethylamine (6.40 mL, 36.9 mmol) in a mixture of dry N,N-dimethylformamide (30 mL) and dry dichloromethane (20 mL) was added to resin and the mixture was shaken overnight. Resin was washed with N,N-dimethylformamide (3×50 mL), 2-propanol (3×50 mL) and dichloromethane (3×50 mL). Fmoc group was removed by treatment with 20% piperidine in N,N-dimethylformamide (1×5 min, 1×30 min, 2×50 mL). Resin was washed with N,N-dimethylformamide (3×50 mL), 2-propanol (3×50 mL) and dichloromethane (3×50 mL).

A solution of 4-nitrophenyl chloroformate (9.27 g, 46.1 mmol) and N,N-diisopropylethylamine (9.64 mL, 55.3 mmol) in a dry tetrahydrofuran/dichloromethane mixture (1:1, 50 mL) was added to resin and the mixture was shaken for 110 minutes. Resin was filtered and washed with dichloromethane (3×50 mL), N,N-dimethylformamide (3×50 mL) and dichloromethane (3×50 mL). A solution of 2-(1-((2-((2-((1-(4,4-dimethyl-2,6-dioxocyclohexylidene)-3-methylbutyl)amino)ethyl)amino) ethyl)amino)butylidene)-5,5-dimethylcyclohexane-1,3-dione (2, 14.3 g, 27.7 mmol) and N,N-diisopropylethylamine (4.80 mL, 27.7 mmol) in N,N-dimethylformamide (50 mL) was added to resin and the mixture was shaken for 90 minutes. Resin was filtered and washed with N,N-dimethylformamide (3×50 mL), 2-propanol (3×50 mL) and dichloromethane (3×50 mL).

IvDde groups were removed by treatment with 2% hydrazine monohydrate in N,N-dimethylformamide (4×4 min, 3×40 mL). Resin was washed with N,N-dimethylformamide (3×50 mL), dichloromethane (3×50 mL) and N,N-dimethylformamide (3×50 mL). A solution of iodoacetic anhydride (9.80 g, 27.7 mmol) and 2,4,6-collidine (1.20 mL, 9.22 mmol) in N,N-dimethylformamide (40 mL) was added to resin and the mixture was shaken for 20 minutes. Resin was filtered and washed with N,N-dimethylformamide (4×50 mL) and dichloromethane (10×50 mL). Resin was treated with 2% solution of trifluoroacetic acid in dichloromethane (2×1.5 hours, 2×40 mL), then washed with dichloromethane (3×50 mL). Solutions were combined and evaporated to dryness. The residue was purified by RP HPLC (Column Deltapak C18, 50×500 mm, acetonitrile/water+0.05% TFA, 2:98 to 20:80 during 60 min, 20:80 to 50:50 during 60 min+0.05% TFA). The freeze-drying gave the title compound as a white solid.

Yield: 560 mg (11%).

1H NMR spectrum (300 MHz, Acetic acid Da, dH): 3.82 (s, 4H); 3.45 (t, 3=6.3 Hz, 8H); 3.30 (t, 3=6.9 Hz, 2H); 2.43 (t, 3=7.4 Hz, 2H); 1.92-1.81 (m, 2H).

LC-MS Rt (Kinetex C18, 4.6×50 mm, acetonitrile/water 5:95 to 100:0+0.1% FA): 2.89 min.

LC-MS m/1: 569.5.

Step 2: (2,5-dioxopyrrolidin-1-yl) 4-[bis[2-[(2-iodoacetyl)amino]ethyl]carbamoylamino]butanoate 4-[Bis[2-[(2-iodoacetyl)amino]ethyl]carbamoylamino]butanoic acid (Chem. 9)

4-[Bis[2-[(2-iodoacetyl)amino]ethyl]carbamoylamino] butanoic acid (250 mg) was dissolved in dry THF (20 ml). N-hydroxysuccinimide (62 mg) and DIC (0.15 ml) were added. The mixture was stirred at RT for 24h. The precipitate was filtered off and the filtrate was concentrated in vacuo. The residue was dissolved in acetonitrile (50 ml), cooled on ice. The precipitate was filtered off (dicyclohexylurinstof) and the filtrate was concentrated in vacuo.

The residue was stirred in ether, the formed solid was filtered off, washed with ether and dried in vacuum, to give the product as a light yellow solid. Yield 295 mg.

LCMS Method 8: Calc. m/1: 666.2; Found m/1: 666.1 rt 2.61 min.

Example 3.5

Synthesis of (2,5-dioxopyrrolidin-1-yl)-3,5-bis[(2-bromoacetyl)amino]benzoate (Chem. 10)

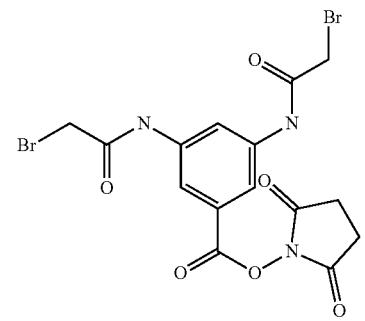 [SMILES: O=C(CBr)Nc1cc(NC(=O)CBr)cc(C(=O)ON2C(=O)CCC2=O)c1]

3,5-diaminobenzoic acid (0.5 g) was dissolved in 5 ml anhydrous DMF. The reaction was cooled on ice while bromoacetic acid anhydride (1.8 g) dissolved in DMF (1.8 mL) was added drop-wise at +5° C. in the reaction. The ice bath was removed and the reaction was stirred for 4h at RT. To the reaction was added 50 ml ice cold water, a grey precipitate was formed. The mixture was stored in the fridge overnight.

The precipitate was filtered off and washed with water. The precipitate was dissolved in 2-methy-tetrahydrofuran (20 mL), dried over $Na_2SO_4$, filtered, and concentrated in vacuo. To the residue was added N-hydroxysuccinimide (416 mg) and DIC (1.0 mL). After stirring at RT for 3h, the mixture was concentrated in vacuo. Acetonitrile (20 mL) was added, and urea was filtered off. The filtrate was reduced to ~5 mL in vacuo. Precipitation from diethylether. The precipitate was washed and centrifuged twice. The isolated compound was dried under a stream of nitrogen in vacuum.

LCMS Method 9: m/1: calculated 492.1; found 491.9.

Example 4: Preparation of Insulin Derivatives

The preparation of a representative insulin derivative is given in Example 4.1. The insulin derivatives of Examples 4.2-4.26 are prepared by the method provided in Example 4.1, unless otherwise stated.

Example 4.1

Synthesis of A14E, A21G, A22(GQEP)$_{19}$, A98K(N(eps)4-[bis[2-[(2-iodoacetyl)amino]ethyl] amino]-4-oxo-butanoyl), A99P, B25H, B29R, desB30 Human Insulin A solution of A14E, A21G, A22(GQEP)$_{19}$, A98K, A99P, B25H, B29R, desB30 human insulin (OEF-Ins-1) (1300 mg) in water (10 ml) and acetonitrile (2 ml) was adjusted to pH 10 with 1N NaOH. $CaCl_2$), $2H_2O$ (20 mol excess, 28 mg) was added. pH was readjusted to 11.3. (2,5-dioxopyrrolidin-1-yl)-4-[bis[2-[(2-iodoacetyl)amino]ethyl]amino]-4-oxo-butanoate (Chem. 6) of Example 3.1, dissolved in THF/MeCN 1:1 (3 ml), was added drop-wise under vigorous stirring. pH dropped to 10.6. The mixture was stirred for 45 min and was diluted with water to 80 ml, pH was adjusted with 1N HCl to 2.5. Purification by RP-chromatography.

Column: Phenomenex, Gemini-NX, AXIA, 5μ, C18, 110 Å, 30×250 mm

Buffers: A: 0.1% TFA in water: 0.1% TFA in acetonitrile

Gradient: 20-40% B over 60 min

The product pool was lyophilized to give the title compound in 61% yield.

LCMS Method 6: Calc. m/4: 1290.6; Found m/4: 1291.9; rt 1.37 min.

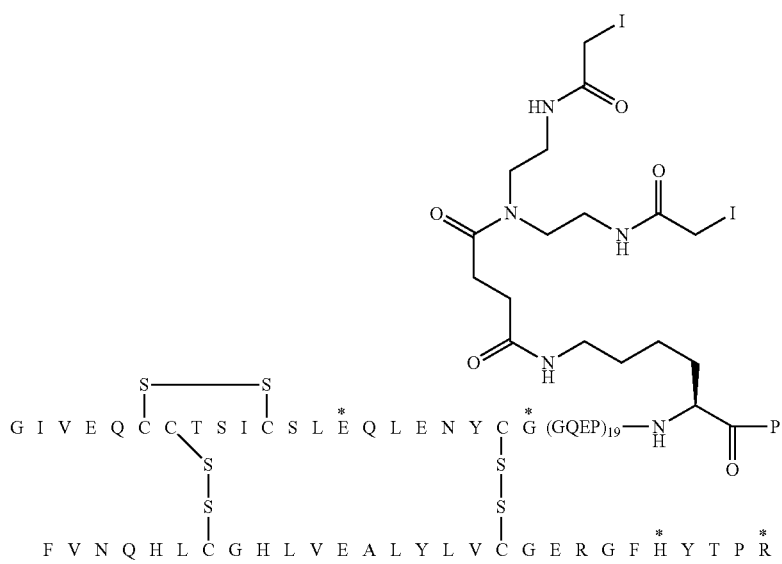

Example 4.2

Synthesis of A14E, B(-78K(N(eps)4-[bis[2-[(2-iodoacetyl)amino]ethyl]amino]-4-oxo-butanoyl)), B(-77P), (B-1)(GQAPGQAPGQEP)₆-GQAP, B30, B25H, B29R, desB30 Human Insulin

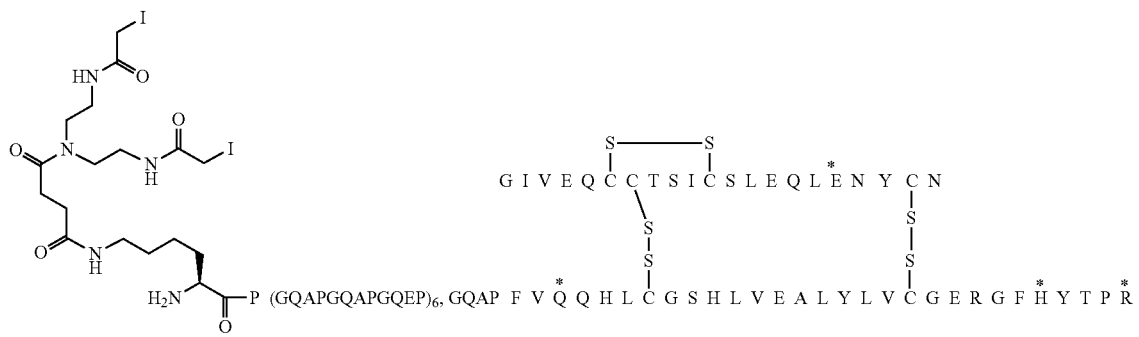

The title compound was prepared from A14E, B(-78K), B(-77P), (B-1)(GQAPGQAPGQEP)₆-GQAP, B3Q, B25H, B29R, desB30 human insulin (OEF-Ins-2), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 4: Calc. m/11 1229.0; Found m/11: 1231.9; rt 1.6 min.

Example 4.3

Synthesis of A14E, B(-78K(N(eps)4-[bis[2-[(2-iodoacetyl)amino]ethyl]amino]-4-oxo-butanoyl)), B(-77P), B(-1)(GQEP)₁₉, B25H, B29R, desB30 Human Insulin

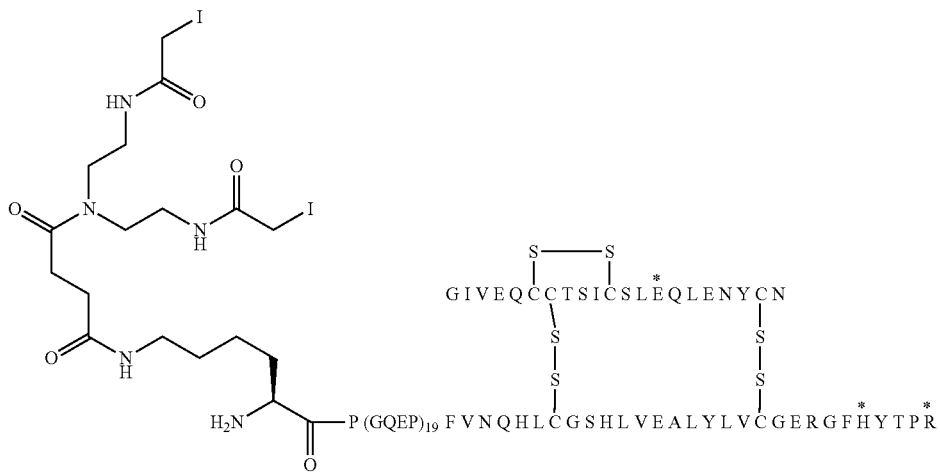

The title compound was prepared from of A14E, B(-78K), B(-77P), B(-1)(GQEP)₁₉, B25H, B29R, desB30 human insulin (OEF-Ins-4), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 3: Calc. mass 14253.0; Found mass 14254.0.

Example 4.4

Synthesis of A14E, A21G, A22 (GQAPGQAPGQEP)$_6$-GQAP, A98K(N(eps)4-[bis [2-[(2-iodoacetyl)amino]ethyl]amino]-4-oxo-butanoyl), A99P, B30, B25H, B29R, desB30 Human Insulin

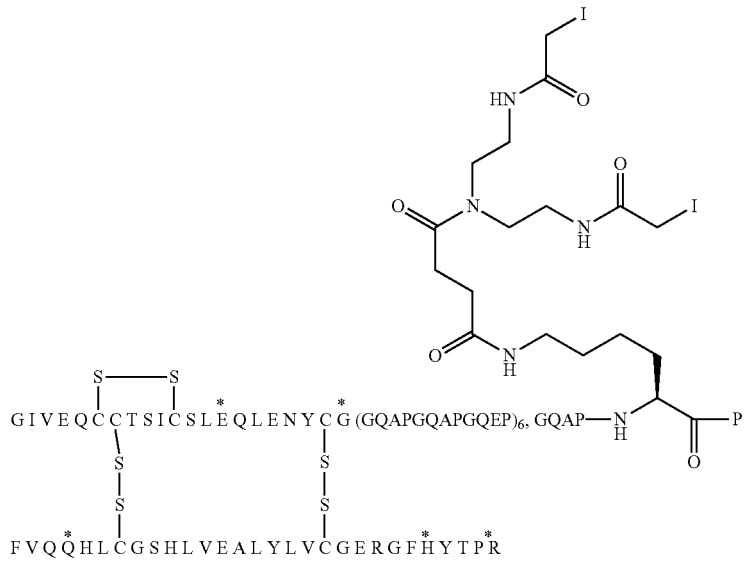

The title compound was prepared from of A14E, A21G, A22(GQAPGQAPGQEP)$_6$-GQAP, A98K, A99P, B3Q, B25H, B29R, desB30 human insulin (OEF-Ins-3), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 4: Calc. m/9 1496.2; Found m/9: 1496.2; rt 1.56 min.

Example 4.5

Synthesis of A14E, A21G, A22(GQEP)$_{19}$, A98K(N (eps)4-[bis[2-[(2-iodoacetyl)amino]ethyl]amino]-4-oxo-butanoyl), A99P, B30, B25H, B29R, desB30 Human Insulin The title compound was prepared from of A14E, A21G, A22(GQEP)$_{19}$, A98K, A99P, B3Q, B25H, B29R, desB30 human insulin (OEF-Ins-5), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 6: Calc. m/10 1421.1; Found m/10: 1422.1; rt 1.35 min.

Example 4.6

Synthesis of A14E, A21G, A22(GQEP)$_6$, A46K(N (eps)4-[bis[2-[(2-iodoacetyl)amino]ethyl]amino]-4-oxo-butanoyl), A47P, B25H, B29R, desB30 Human Insulin

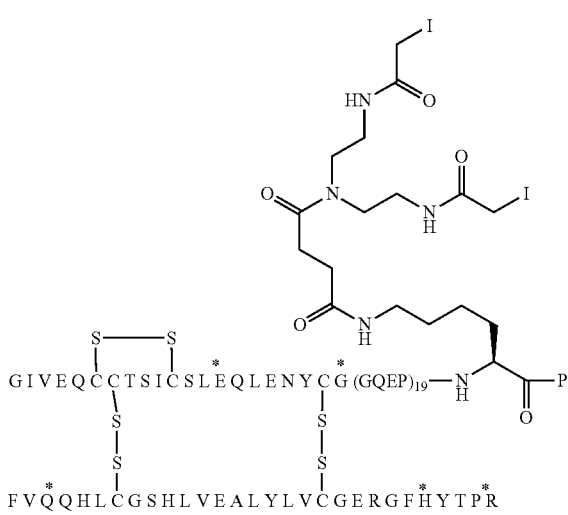

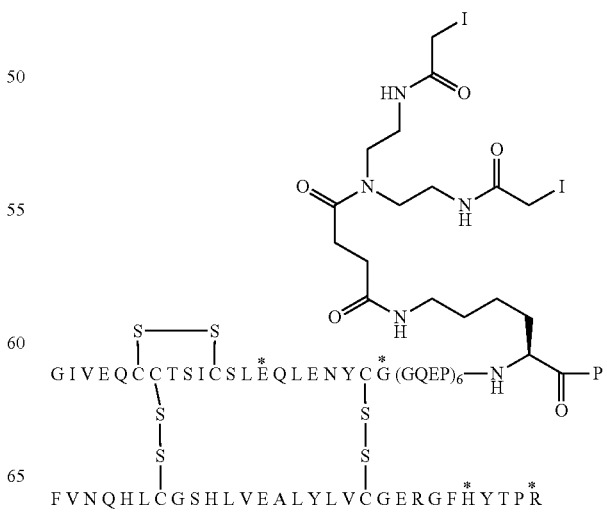

The title compound was prepared from of A14E, A21G, A22(GQEP)₆, A46K, A47P, B25H, B29R, desB30 human insulin (OEF-Ins-7), and (2,5-dioxopyrrolidin-1-yl)-4-[bis [2-[(2-iodoacetyl)amino]ethyl]amino]-4-oxo-butanoate (Chem. 6) of Example 3.1, following the general linker to insulin conjugation procedure described in Example 4.1.

LCMS Method 5: Calc. m/5 1770.6; Found m/5: 1770.6; rt 1.37 min.

Example 4.7

Synthesis of A14E, A21G, A22(GQEP)₁₂, A70K(N (eps)4-[bis[2-[(2-iodoacetyl)amino]ethyl]amino]-4-oxo-butanoyl), A71P, B25H, B29R, desB30 Human Insulin

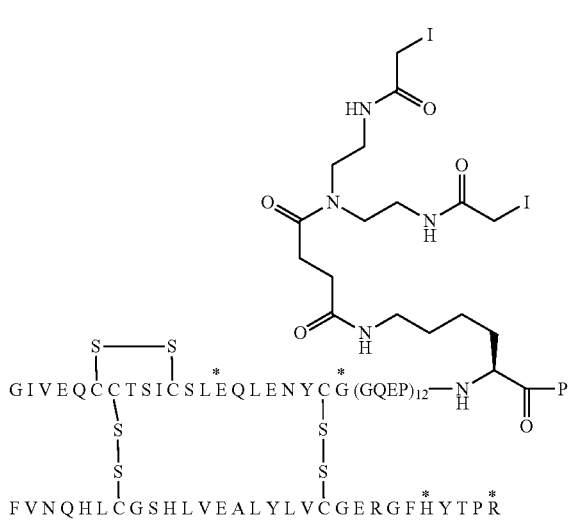

The title compound was prepared from of A14E, A21G, A22(GQEP)₁₂, A70K, A71P, B25H, B29R, desB30 human insulin (OEF-Ins-6), and (2,5-dioxopyrrolidin-1-yl)-4-[bis [2-[(2-iodoacetyl)amino]ethyl]amino]-4-oxo-butanoate (Chem. 6) of Example 3.1, following the general linker to insulin conjugation procedure described in Example 4.1.

LCMS Method 4: Calc. m/6 1887.1; Found m/6: 1887.2; rt 1.6 min.

Example 4.8

Synthesis of A14E, A21G, A22(GQAPGQEP)₆, A70K(N(eps)4-[bis[2-[(2-iodoacetyl)amino]ethyl] amino]-4-oxo-butanoyl), A71P, B25H, B29R, desB30 Human Insulin

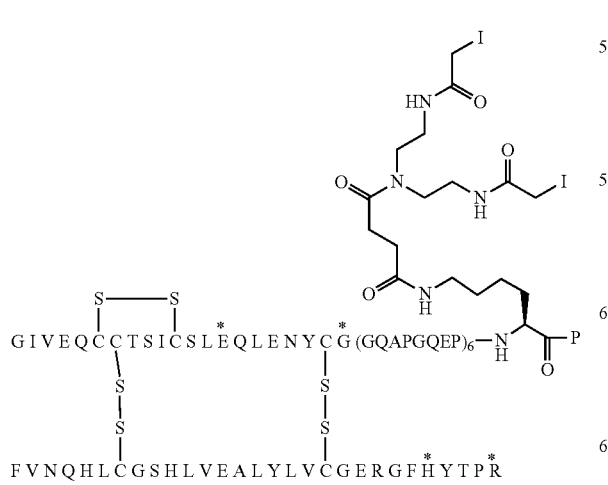

The title compound was prepared from of A14E, A21G, A22(GQAPGQEP)₆, A70K, A71P, B25H, B29R, desB30 human insulin (OEF-Ins-9), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 3: Calc. mass: 10968; Found mass: 10969.

Example 4.9

Synthesis of A14E, A21G, A22(GQEP)₃, A34G, A35Q, A36E, A37K(N(eps)4-[bis[2-[(2-iodoacetyl) amino]ethyl]amino]-4-oxo-butanoyl), A38P, B25H, B29R, desB30 Human Insulin

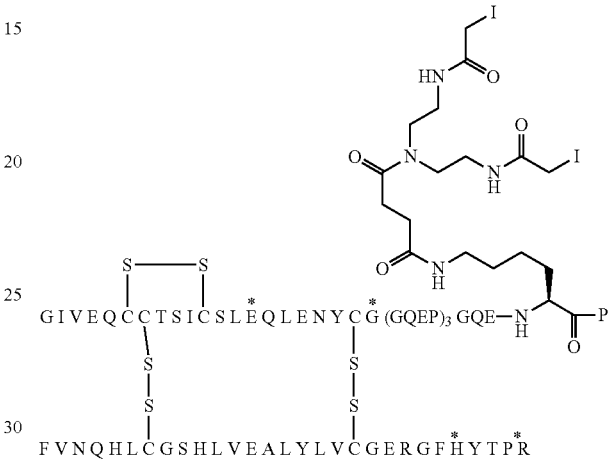

The title compound was prepared from of A14E, A21G, A22(GQEP)₃, A34G, A35Q, A36E, A37K, A38P, B25H, B29R, desB30 human insulin (OEF-Ins-8), and (2,5-dioxopyrrolidin-1-yl)-4-[bis[2-[(2-iodoacetyl)amino]ethyl] amino]-4-oxo-butanoate (Chem. 6) of Example 3.1, following the general linker to insulin conjugation procedure described in Example 4.1.

LCMS Method 3: Calc. mass: 7928; Found mass: 7928.

Example 4.10

Synthesis of A14E, A21G, A22(GQAP)₁₉, A98K(N (eps)4-[bis[2-[(2-iodoacetyl)amino]ethyl]amino]-4-oxo-butanoyl), A99P, B25H, B29R, desB30 Human Insulin

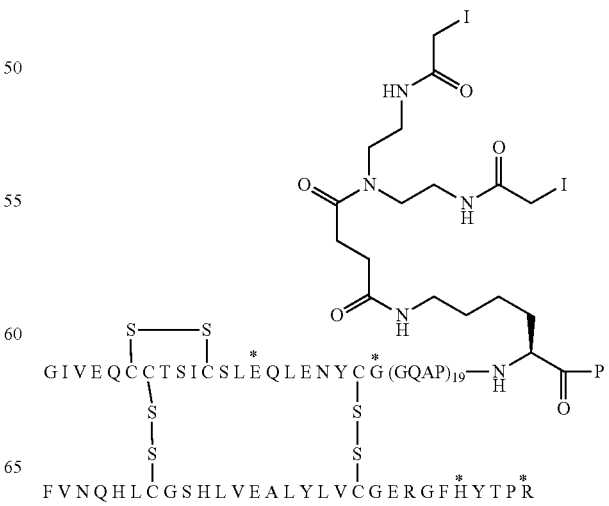

The title compound was prepared from of A14E, A21G, A22(GQAP)$_{19}$, A98K, A99P, B25H, B29R, desB30 human insulin (OEF-Ins-13), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 3: Calc. mass 13093.0; Found mass: 13097.8.

Example 4.11

Synthesis of A14E, A21G, A22(GQAP)$_{19}$, A98K(N(eps)$_6$-[bis[2-[(2-iodoacetyl)amino]ethyl]amino]-6-oxo-hexanoyl), A99P, B25H, B29R, desB30 Human Insulin

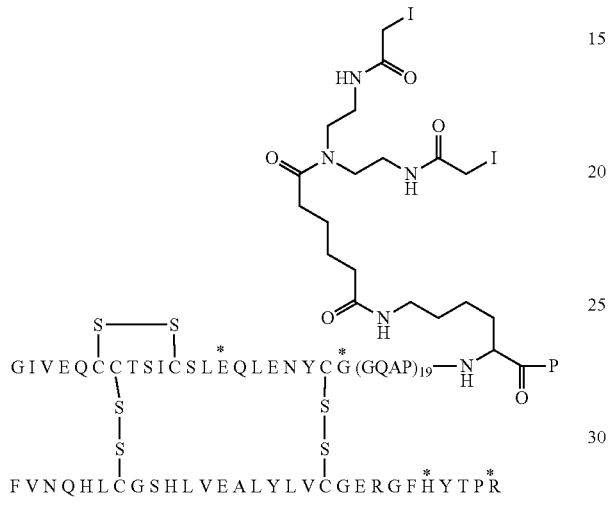

The title compound was prepared from of A14E, A21G, A22(GQAP)$_{19}$, A98K, A99P, B3Q, B25H, B29R, desB30 human insulin (OEF-Ins-13), and (2,5-dioxopyrrolidin-1-yl)-6-[bis[2-[(2-iodoacetyl)amino]ethyl]amino]-6-oxo-hexanoate (Chem. 7) of Example 3.2, following the general linker to insulin conjugation procedure described in Example 4.1.

LCMS Method 3: Calc. mass 13122.0; Found mass: 13123.

Example 4.12

Synthesis of A14E, B(-78K(N(eps)4-[bis[2-[(2-iodoacetyl)amino]ethyl]amino]-4-oxo-butanoyl)), B(-77P), B(-1)(GQAP)$_{19}$, B25H, B29R, desB30 Human Insulin

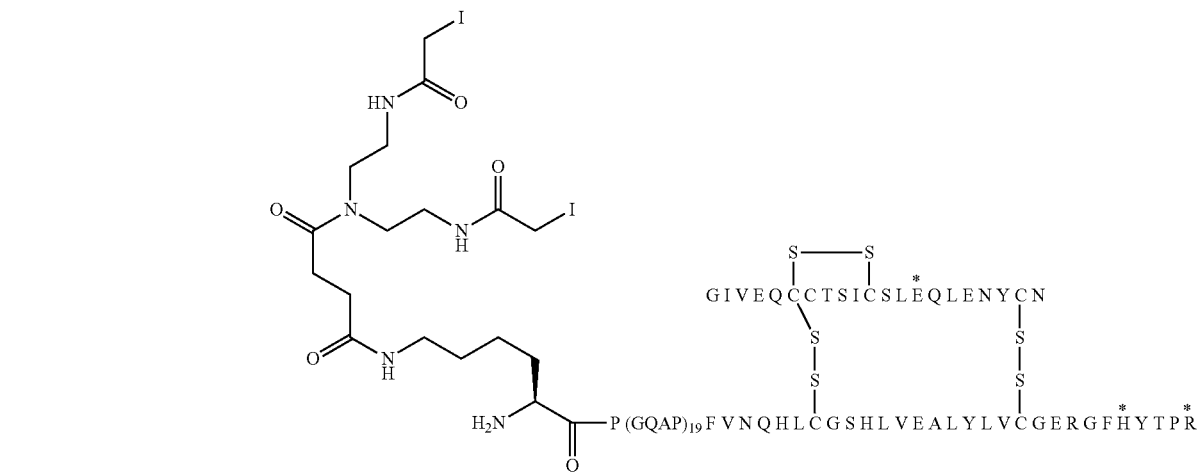

The title compound was prepared from of A14E, B(-78K), B(-77P), B(-1)(GQAP)$_{19}$, B25H, B29R, desB30 human insulin (OEF-Ins-12), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 3: Calc. mass 13151.0; Found mass 13151.3.

Example 4.13

Synthesis of A14E, A21G, A22 (GQAPGQAPGQEP)$_6$-GQAP, A98K(N(eps)4-[bis [2-[(2-iodoacetyl)amino]ethyl]amino]-4-oxo-butanoyl), A99P, B29R, desB30 Human Insulin

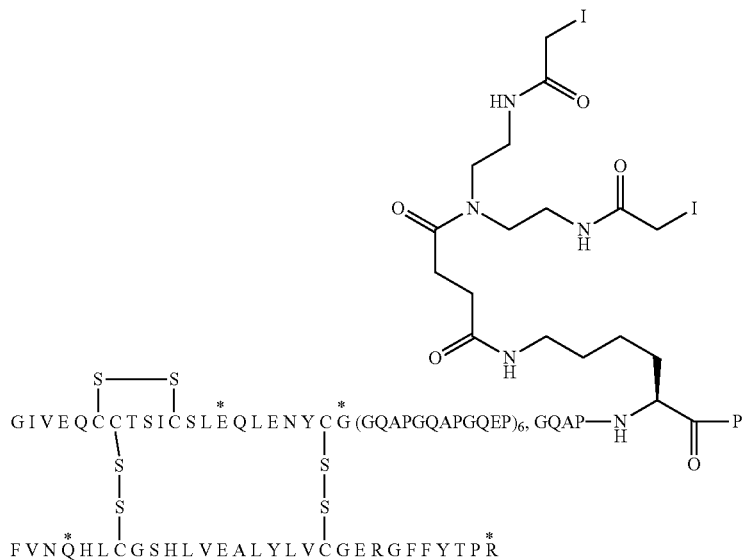

The title compound was prepared from of A14E, A21G, A22(GQAPGQAPGQEP)$_6$-GQAP, A98K, A99P, B29R, desB30 human insulin (OEF-Ins-14), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 7: Calc. 13452.7; Found 13452.

Example 4.14

Synthesis of A14E, A21G, A22 (GQAPGQAPGQAPGQEP)$_6$-GQAP, A122K(N(eps) 4-[bis[2-[(2-iodoacetyl)amino]ethyl]amino]-4-oxo-butanoyl), A123P, B25H, B29R, desB30 Human Insulin

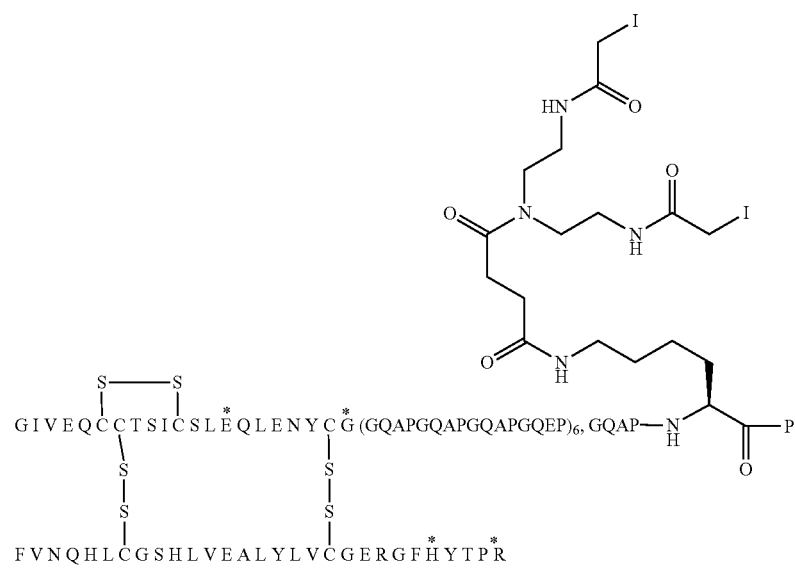

The title compound was prepared from of A14E, A21G, A22(GQAPGQAPGQAPGQEP)$_6$-GQAP, A122K, A123P, B25H, B29R, desB30 human insulin (OEF-Ins-15), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 3: Calc. 15562.4; Found 15562.5.

Example 4.15

Synthesis of A14E, A21Q, A22(G)$_{18}$, A40K(N(eps) 4-[bis[2-[(2-iodoacetyl)amino]ethyl]amino]-4-oxo-butanoyl), B25H, B29R, desB30 Human Insulin

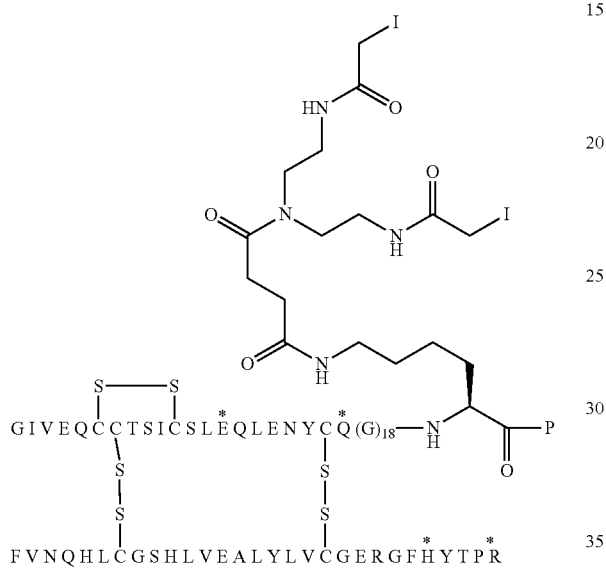

The title compound was prepared from A14E, A21Q, A22(G)$_{18}$, A40K, B25H, B29R, desB30 human insulin (OEF-Ins-19), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 4: Calc. m/4: 1845.1; Found m/4: 1845.8; rt 1.66 min.

Example 4.16

Synthesis of A14E, A21G, A22(GQAP)$_{24}$, A118G, A119Q, A120A, A121K(N(eps)-3,5-bis[(2-bromo-acetyl)amino]benzoyl), A122P, B25H, B29R, desB30 Human Insulin

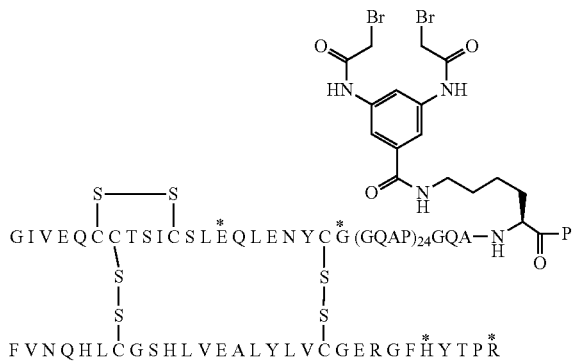

The title compound was prepared from of A14E, A21G, A22(GQAP)$_{24}$, A118G, A119Q, A120A, A121K, A122P, B25H, B29R, desB30 human insulin (OEF-Ins-20), and (2,5-dioxopyrrolidin-1-yl)-3,5-bis[(2-bromoacetyl)amino]benzoate (Chem. 10) of Example 3.5, following the general linker to insulin conjugation procedure described in Example 4.1.

LCMS Method 9: Calc. mass 14972; Found mass: 14973.

Example 4.17

Synthesis of A14E, A21G, A22(GQAP)$_{24}$, A118G, A119Q, A120A, A121K(N(eps)4-[bis[2-[(2-iodo-acetyl)amino]ethyl]amino]-4-oxo-butanoyl), A122P, B25H, B29R, desB30 Human Insulin

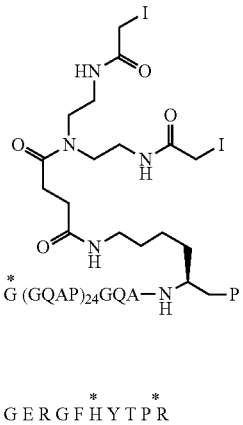

The title compound was prepared from of A14E, A21G, A22(GQAP)$_{24}$, A118G, A119Q, A120A, A121K, A122P, B25H, B29R, desB30 human insulin (OEF-Ins-20), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 9: Calc. m/8: 1891; Found m/8 1891.

Example 4.18

Synthesis of A14E, A21G, A22(GQAPGQAPGQEP)$_6$-GQAP, A98K(N(eps)4-[bis[2-[(2-iodoacetyl)amino]ethyl]carbamoylamino]butanoyl), A99P, B3Q, B25H, B29R, desB30 Human Insulin

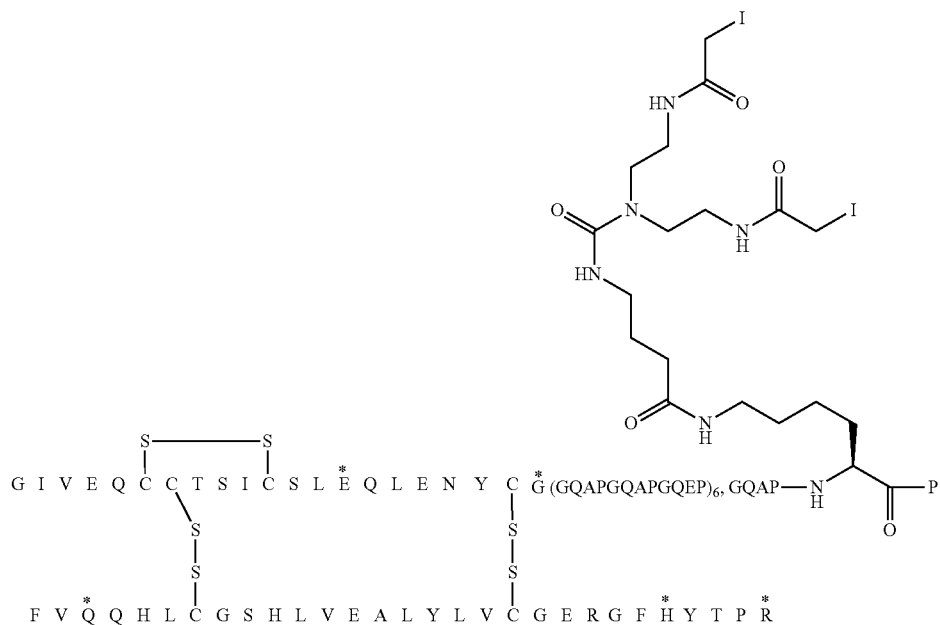

The title compound was prepared from of A14E, A21G, A22(GQAPGQAPGQEP)$_6$-GQAP, A98K, A99P, B3Q, B25H, B29R, desB30 human insulin (OEF-Ins-3), and (2,5-dioxopyrrolidin-1-yl) 4-[bis[2-[(2-iodoacetyl)amino]ethyl]carbamoylamino]butanoate (Chem. 9) of Example 3.4, following the general linker to insulin conjugation procedure described in Example 4.1.

LCMS Method 7: Calc. mass 13485.2 Found mass 13485.7.

Example 4.19

Synthesis of A14A, A21G, A22(GQAP)₁₈, A94G, A95Q, A96A, A97K(N(eps)4-[bis[2-[(2-iodoacetyl)amino]ethyl]amino]-4-oxo-butanoyl), A98P, B29R, desB30 Human Insulin

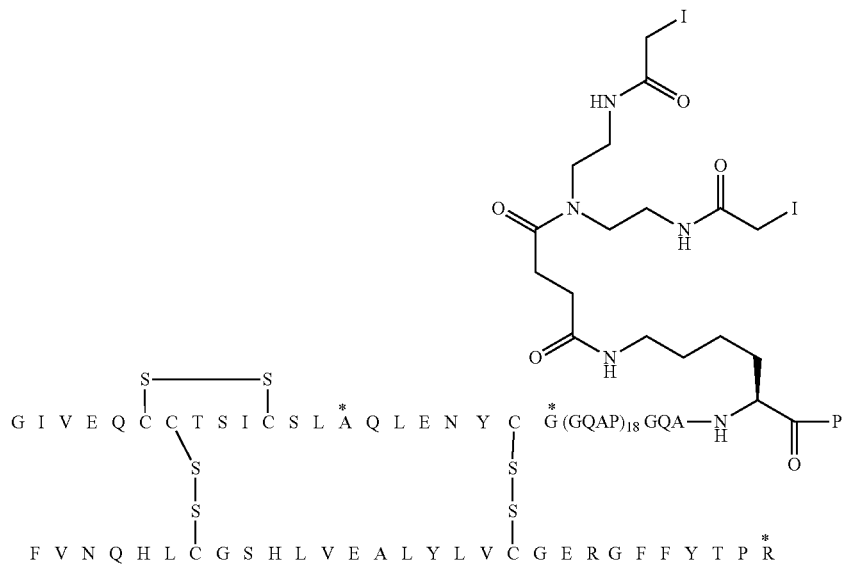

The title compound was prepared from of A14A, A21G, A22(GQAP)₁₈, A94G, A95Q, A96A, A97K, A98P, B29R, desB30 human insulin (OEF-Ins-16), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 7: Calc. mass 12848.8; Found mass: 12949.3.

Example 4.20

Synthesis of A14E, A21G, A22(GQAP)₁₈, A94G, A95Q, A96A, A97K(N(eps)4-[bis[2-[(2-iodoacetyl)amino]ethyl]amino]-4-oxo-butanoyl), A98P, B29R, desB30 Human Insulin

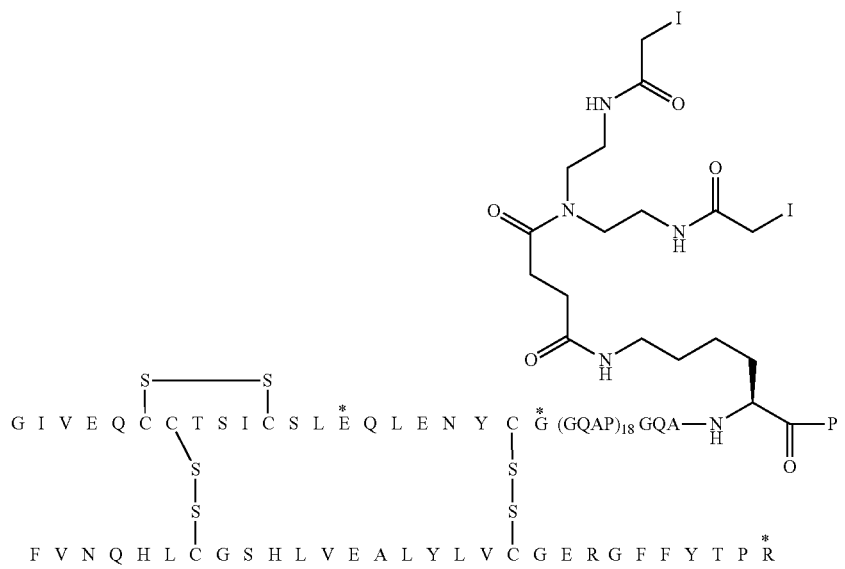

The title compound was prepared from of A14E, A21G, A22(GQAP)$_{18}$, A94G, A95Q, A96A, A97K, A98P, B29R, desB30 human insulin (OEF-Ins-17), and (2,5-dioxopyrrolidin-1-yl)-4-[bis[2-[(2-iodoacetyl)amino]ethyl]amino]-4-oxo-butanoate (Chem. 6) of Example 3.1 following the general linker to insulin conjugation procedure described in Example 4.1.

LCMS Method 10: Calc. m/8 1626.9; Found m/8: 1627; rt 2.18 min.

Example 4.21

Synthesis of A1(N(alpha)acetyl), A14E, A21G, A22 (GQAP)$_{19}$, A98K(N(eps)4-[bis[2-[(2-iodoacetyl) amino]ethyl]amino]-4-oxo-butanoyl), A99P, B1(N (alpha)acetyl),B25H, B29R, desB30 Human Insulin

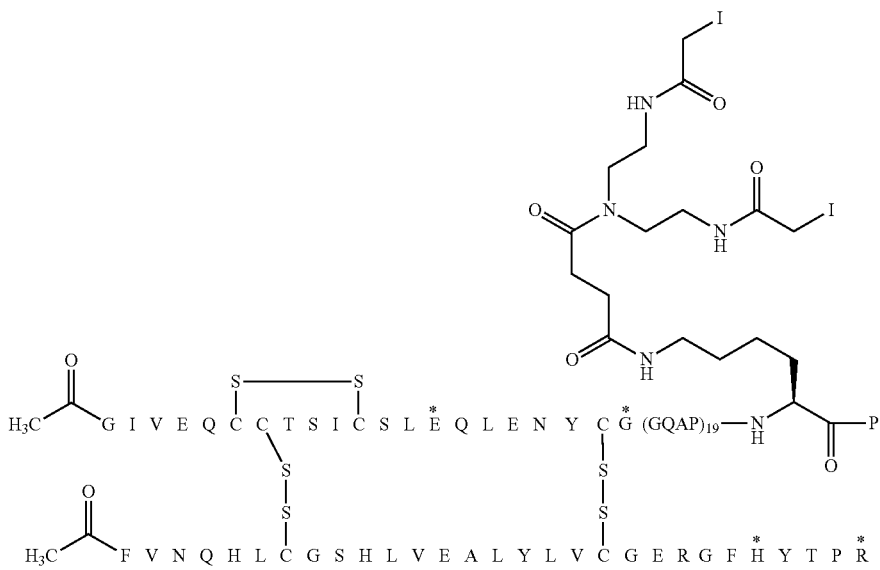

The title compound was prepared from a crude reaction mixture of A14E, A21G, A22(GQAP)$_{19}$, A98K(N(eps)4-[bis [2-[(2-iodoacetyl)amino]ethyl]amino]-4-oxo-butanoyl), A99P, B25H, B29R, desB30 human insulin prepared as described in Example 4.10 by adding acetic acid anhydride (2 equivalents) and stirring 30 min before purification as described in Example 4.1.

LCMS Method 7: Calc. mass 13178.0; Found mass: 13178.3.

Example 4.22

Synthesis of A21G, A22(GQAP)$_{18}$, A94G, A95Q, A96A, A97K(N(eps)4-[bis[2-[(2-iodoacetyl)amino]ethyl]amino]-4-oxo-butanoyl), A98P, B29R, desB30 Human Insulin

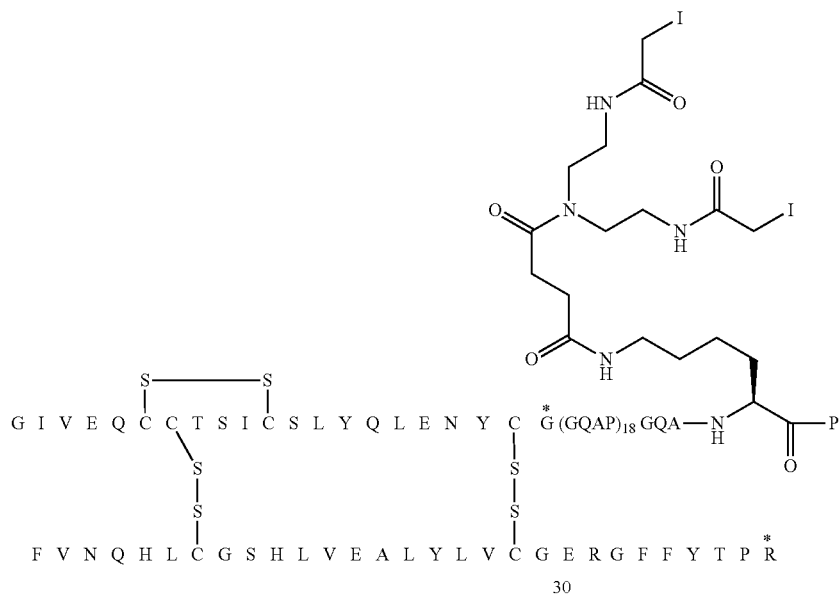

The title compound was prepared from of A21G, A22(GQAP)$_{18}$, A94G, A95Q, A96A, A97K, A98P, B29R, desB30 human insulin (OEF-Ins-22), and (2,5-dioxopyrrolidin-1-yl)-4-[bis[2-[(2-iodoacetyl)amino]ethyl]amino]-4-oxo-butanoate (Chem. 6) of Example 3.1, following the general linker to insulin conjugation procedure described in Example 4.1.

LCMS Method 7: Calc. mass: 13040.9; Found mass: 13041.5.

Example 4.23

Synthesis of A14E, A21G, A22(GQAP)$_{24}$, A118G, A119Q, A120A, A121K(N(eps)-3,5-bis[(2-bromoacetyl)amino]benzoyl), A122P, B29R, desB30 Human Insulin

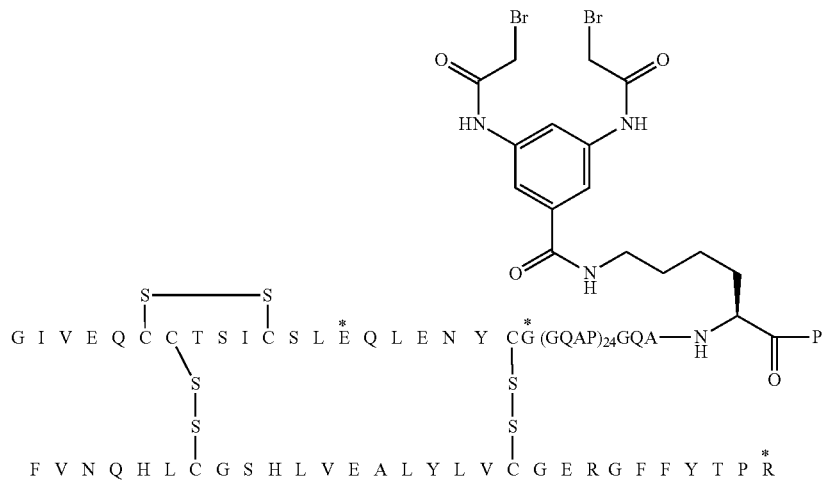

The title compound was prepared from of A14E, A21G, A22(GQAP)$_{24}$, A118G, A119Q, A120A, A121K, A122P, B29R, desB30 human insulin (OEF-Ins-21), and (2,5-dioxopyrrolidin-1-yl)-3,5-bis[(2-bromoacetyl)amino]benzoate (Chem. 10) of Example 3.5, following the general linker to insulin conjugation procedure described in Example 4.1.

LCMS Method 7: Calc. mass 14982.0; Found mass: 14982.4.

Example 4.24

Synthesis of A14E, A21G, A22(GQAP)$_{18}$, A94G, A95Q, A96A, A97K(N(eps)-3,5-bis[(2-bromoacetyl)amino]benzoyl), A98P, B16E, B25H, B29R, desB30 Human Insulin

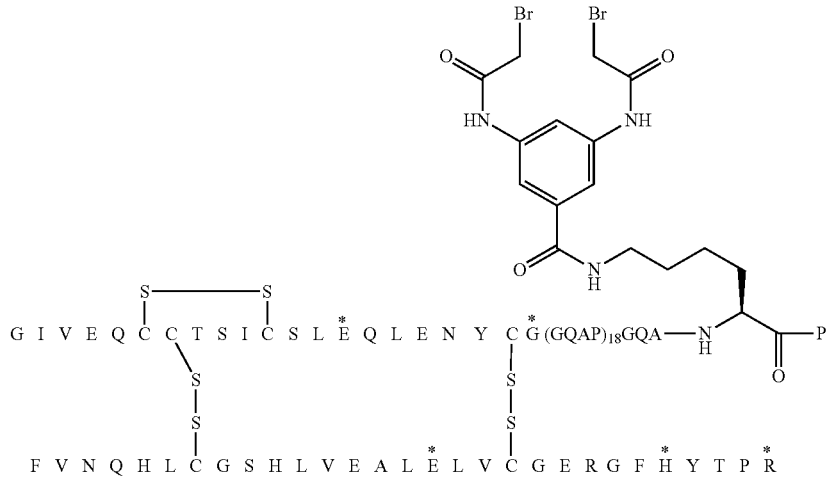

The title compound was prepared from of A14E, A21G, A22(GQAP)$_{18}$, A94G, A95Q, A96A, A97K, A98P, B16E, B25H, B29R, desB30 human insulin (OEF-Ins-23), and (2,5-dioxopyrrolidin-1-yl)-3,5-bis[(2-bromoacetyl)amino] benzoate (Chem. 10) of Example 3.5, following the general linker to insulin conjugation procedure described in Example 4.1.

LCMS Method 7: Calc. mass 12817.7; Found mass: 142828.2.

Example 4.25

Synthesis of A14E, A21G, A22(GQAP)$_{18}$, A94G, A95Q, A96A, A97K(N(eps)4-[bis[2-[(2-iodoacetyl)amino]ethyl]amino]-4-oxo-butanoyl), A98P, B16E, B25H, B29R, desB30 Human Insulin

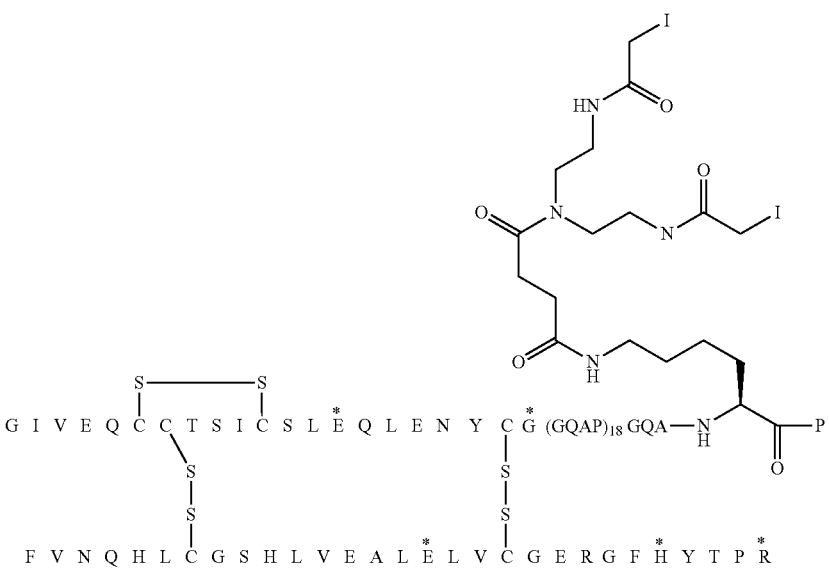

The title compound was prepared from of A14E, A21G, A22(GQAP)$_{18}$, A94G, A95Q, A96A, A97K, A98P, B16E, B25H, B29R, desB30 human insulin (OEF-Ins-23), and (2,5-dioxopyrrolidin-1-yl)-4-[bis[2-[(2-iodoacetyl)amino]ethyl]amino]-4-oxo-butanoate (Chem. 6) of Example 3.1 following the general linker to insulin conjugation procedure described in Example 4.1.

LCMS Method 7: Calc. mass: 12962.7; Found mass: 12963.1.

Example 4.26

Synthesis of A14E, A21G, A22(GQEP)$_{19}$, A98K(N (eps)-3,5-bis[(2-bromoacetyl)amino]benzoyl), A99P, B25H, B29R, desB30 Human Insulin

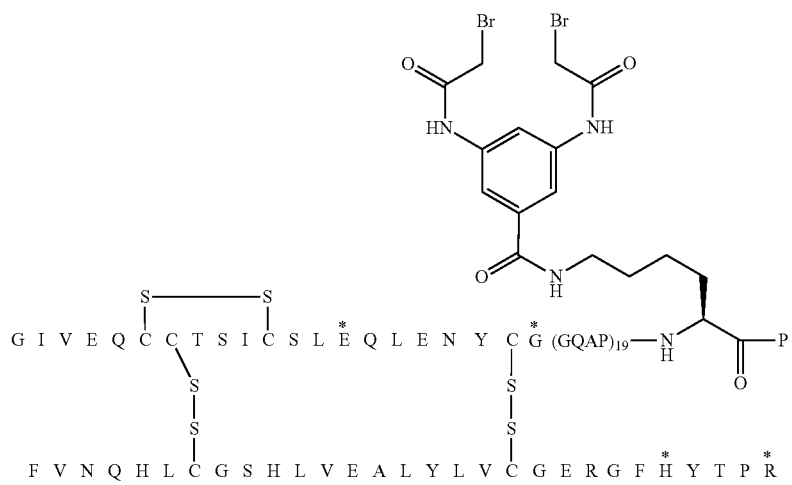

The title compound was prepared from of A14E, A21G, A22(GQEP)$_{19}$, A98K, A99P, B25H, B29R, desB30 human insulin (OEF-Ins-1), and (2,5-dioxopyrrolidin-1-yl)-3,5-bis[(2-bromoacetyl)amino]benzoate (Chem. 10) of Example 3.5, following the general linker to insulin conjugation procedure described in Example 4.1.

LCMS Method 7: Calc. mass 14051.4; Found mass: 14052.0.

Example 5

Preparation of Insulin-Fc Conjugates

The preparation of a representative insulin-Fc conjugate is given in Example 5.1 and 5.2. The insulin conjugates of Examples 5.3-5.33 are prepared by the method provided in Example 5.1 or 5.2, unless otherwise stated.

Example 5.1

General Insulin Fc Conjugation Procedure 1

Preparation of the (A14E, A21G, A22(GQEP)$_{19}$, A98K^, A99P, B25H, B29R, desB30 human insulin)/(227A, 234A, 235K hIgG4-Fc(228-447))4-[bis [2-[(2-acetyl)amino]ethyl]amino]-4-oxo-butanoyl Conjugate

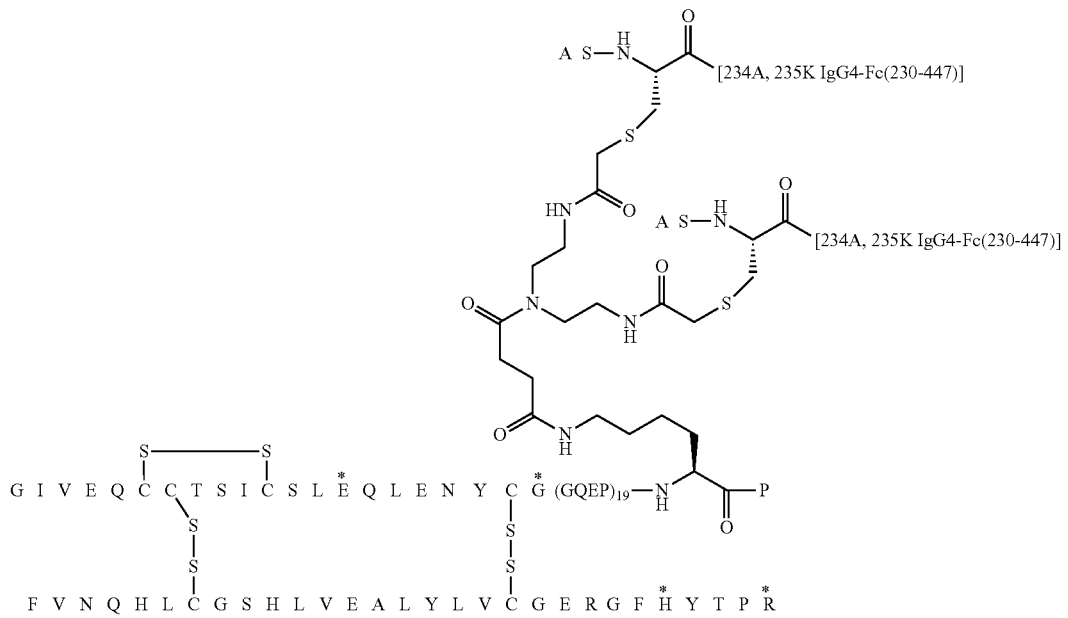

To 227A, 234A, 235K hIgG4-Fc(228-447)) (Fc9) (1600 mg) 10 mg/ml in 20 mM

Tris, 25 mM NaCl, pH7.5 (160 ml) was added 10 mM EDTA (700 mg). pH was adjusted with 1N HCl to 7.6. BSPP (137 mg), dissolved in water was added and stirred gently at RT for 20 hours.

The mixture was buffer exchanged to 20 mM Tris, 10 mM EDTA pH 7.5 using a 412 ml G-25 fine sephadex desalting column.

To the elution pool (200 ml half Fc approximately 8 mg/ml) at pH 7.6 was added A14E, A21G, A22(GQEP)$_{19}$, A98K(N(eps)4-[bis[2-[(2-iodoacetyl)amino]ethyl] amino]-4-oxo-butanoyl), A99P, B25H, B29R, desB30 human insulin prepared as described in Example 4.1 (549 mg) dissolved in water (13 ml) and acetonitril (2 ml) drop-wise at RT. pH was adjusted to 7.5 with 1N NaOH and 2 ml and stirred at RT overnight.

The reaction was diluted 1+5 with A-buffer, pH adjusted to 8.5 with 1N NaOH, conductivity 1.33 mS/cm and was purified by anion exchange.

Column: 140 ml Poros 50HQ
A buffer: 20 mM Tris at pH 9.0 (0.27 mS/cm)
B buffer: 20 mM Tris, 500 mM NaCl at pH 9.0 (48.1 mS/cm)
Flow: 6.5 CV/h
Gradient, step: 0-40% B over 3 CV, 40-60% B over 15 CV, 60-100% B over 3 CV, 100% B over 3 CV.
Fractionation: 25 mL/fraction
Load: 6.5 CV/h The compound pool was concentrated and desalted into MilliQ H$_2$O by TFF:
System: Millipore Labscale
Membrane: Millipore Pellicon XL
Cut-off: 10 kDa
Feed pressure: 1.4 bar
Retentate pressure: 0.6 bar
TOV: 5
The product was then lyophilized.

Overall yield: 35%

LCMS Method 1: Calc. mass: 63562.0; Found mass: 63562.0.

Example 5.2

General Insulin Fc Conjugation (Procedure 2)

Preparation of the A14E, A21G, A22(GQEP)$_{19}$, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

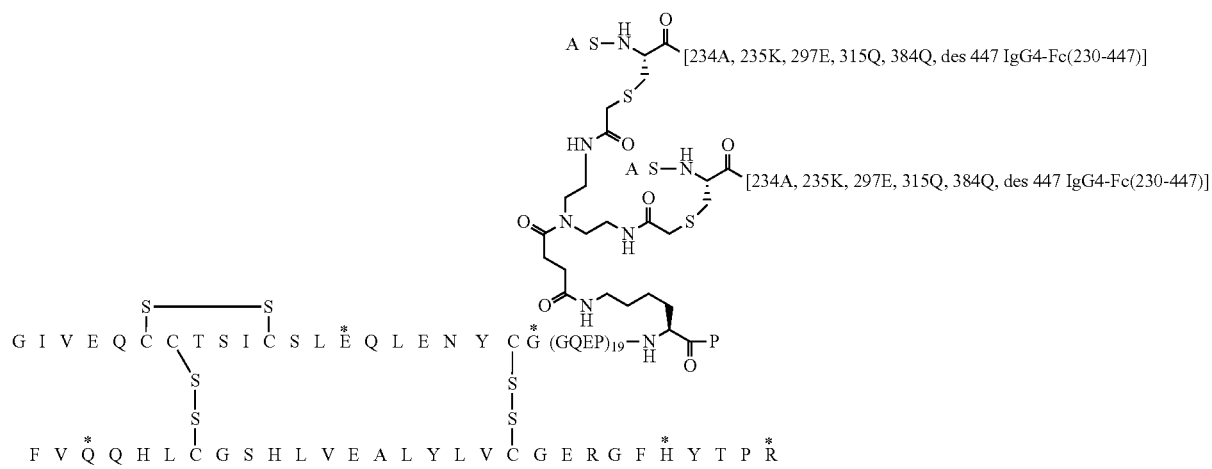

To a solution of 227A, 234A, 235K, 297E, 315Q, 384Q, des447 hIgG4-Fc(228-447) (Fc15) (0.03312 mmol, 1638 mg, 156.8 ml) in 20 mM Tris, 30 mm NaCl, pH 7.6 was diluted with 40 mM NH$_4$HCO$_3$, 10 mM EDTA disodium salt pH 8.5 (156 ml). A 8.83 mg/ml TCEP-solution in 40 mM NH$_4$HCO$_3$, 10 mM EDTA disodium salt pH 8.5 (1.0 eq, Mw 286.62 g/mol, 9.49 mg, 1.07 ml). The resulting mixture was stirred gently at RT, under N2-flow for 2 h. A14E, A21G, A22(GQEP)$_{19}$, A98K(N(eps)4-[bis[2-[(2-iodoacetyl)amino]ethyl]amino]-4-oxo-butanoyl), A99P, B3Q, B25H, B29R, desB30 human insulin (470 mg) prepared as described in Example 4.5 dissolved in 40 mM NH$_4$HCO$_3$, 10 mM EDTA disodium salt pH 8.5, 20% MeCN (10.65 ml) was slowly added. The mixture was left over night at RT. The reaction was diluted with water (500 ml), pH adjusted to 8.8 with 1N NaOH, conductivity 1.95 mS/cm and was purified by anion exchange.

Column: 40 ml Poros 50HQ

A buffer: 20 mM TRIS at pH 9.0 (1.5 mS/cm)

B buffer: 20 mM TRIS, 500 mM NaCl at pH 9.0 (44 mS/cm)

Flow: 35 ml/min

Gradient, step: 0-25% B over 1CV, 25% B 1 CV, 25-60% B over 6 CV

Fractionation: Manual at 280 nm, starting at 25% B-buffer 1CV

Load: 35 ml/min

The compound pool was lyophilized followed by buffer exchange to water.

Column: Desalting column, 400 ml Sephadex G-25 fine

The product pool was lyophilized. Yield 1.0 g (47%)

LCMS Method 3: Calc. mass: 63405.8; Found mass: 63406.5.

Example 5.3

Preparation of the A14E, B(-78K^), B(-77P), B(-1)(GQAPGQAPGQEP)₆-GQAP, B3Q, B25H, B29R, desB30 human insulin/(227A, 234A, 235K hIgG4-Fc(228-447))4-[bis[2-[(2-acetyl)amino]ethyl]amino]-4-oxo-butanoyl Conjugate

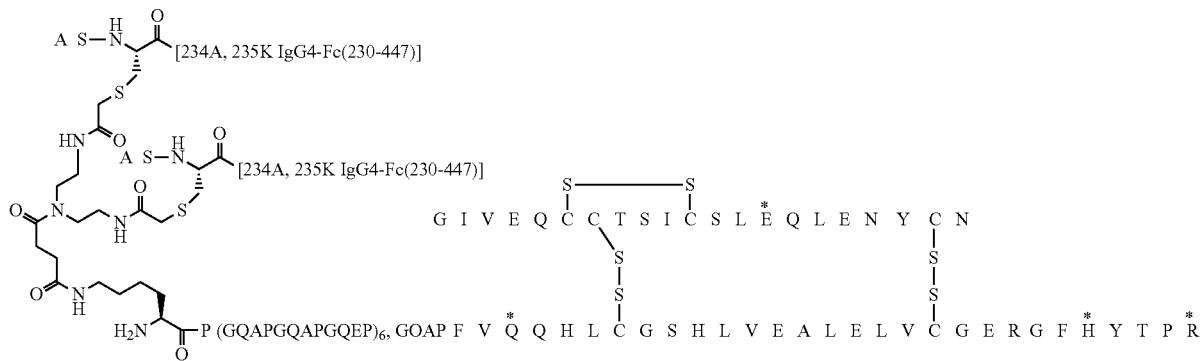

The title compound was synthesised from A14E, B(-78K (N(eps)4-[bis[2-[(2-iodoacetyl)amino]ethyl]amino]-4-oxo-butanoyl)), B(-77P), B(-1)(GQAPGQAPGQEP)₆-GQAP, B3Q, B25H, B29R, desB30 human insulin prepared as described in Example 4.2, and 227A, 234A, 235K hIgG4-Fc(228-447) (Fc9) prepared as described in Example 2, following the general insulin Fc conjugation Procedure 1 described in Example 5.1

LCMS Method 1: Calc. mass: 62878.7; Found mass: 62879.3.

Example 5.4

Preparation of the A14E, B(-78K^), B(-77P), B(-1)(GQEP)₁₉, B25H, B29R, desB30 human insulin/(227A, 234A, 235K hIgG4-Fc(228-447))4-[bis [2-[(2-acetyl)amino]ethyl]amino]-4-oxo-butanoyl Conjugate

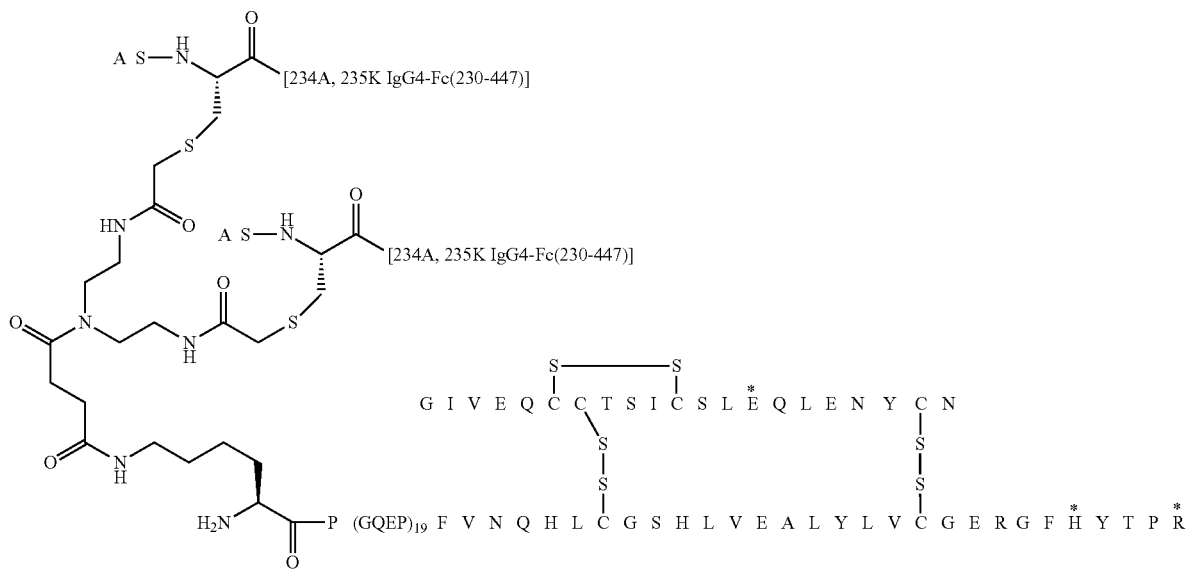

The title compound was synthesised from A14E, B(-78K (N(eps)4-[bis[2-[(2-iodoacetyl)amino]ethyl]amino]-4-oxo-butanoyl)), B(-77P), B(-1)(GQEP)$_{19}$, B25H, B29R, desB30 human insulin prepared as described in Example 4.3, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 63619.1; Found mass: 63618.3.

Example 5.5

Preparation of the A14E, A21G, A22 (GQAPGQAPGQEP)$_6$-GQAP, A98K^, A99P, B3Q, B25H, B29R, desB30 human insulin/(227A, 234A, 235K hIgG4-Fc(228-447))4-[bis[2-[(2-acetyl)amino] ethyl]amino]-4-oxo-butanoyl Conjugate

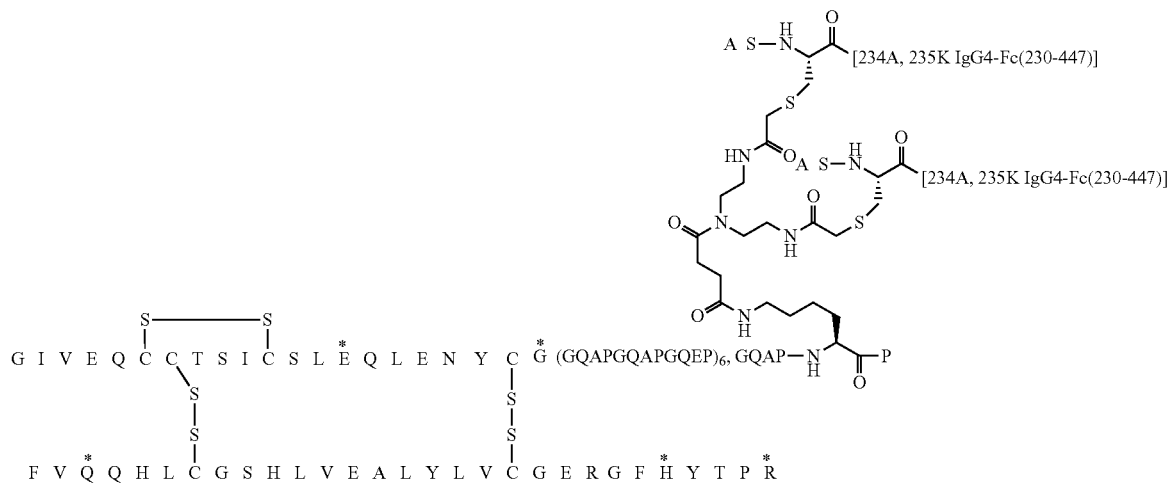

The title compound was synthesised from of A14E, A21G, A22(GQAPGQAPGQEP)$_6$-GQAP, A98K(N(eps)4-[bis[2-[(2-iodoacetyl)amino]ethyl]amino]-4-oxo-butanoyl), A99P, B3Q, B25H, B29R, desB30 human insulin prepared as described in Example 4.4, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 62821.6; Found mass: 62822.1.

Example 5.6

Preparation of the A14E, A21G, A22(GQEP)₁₉, A98K^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl Conjugate

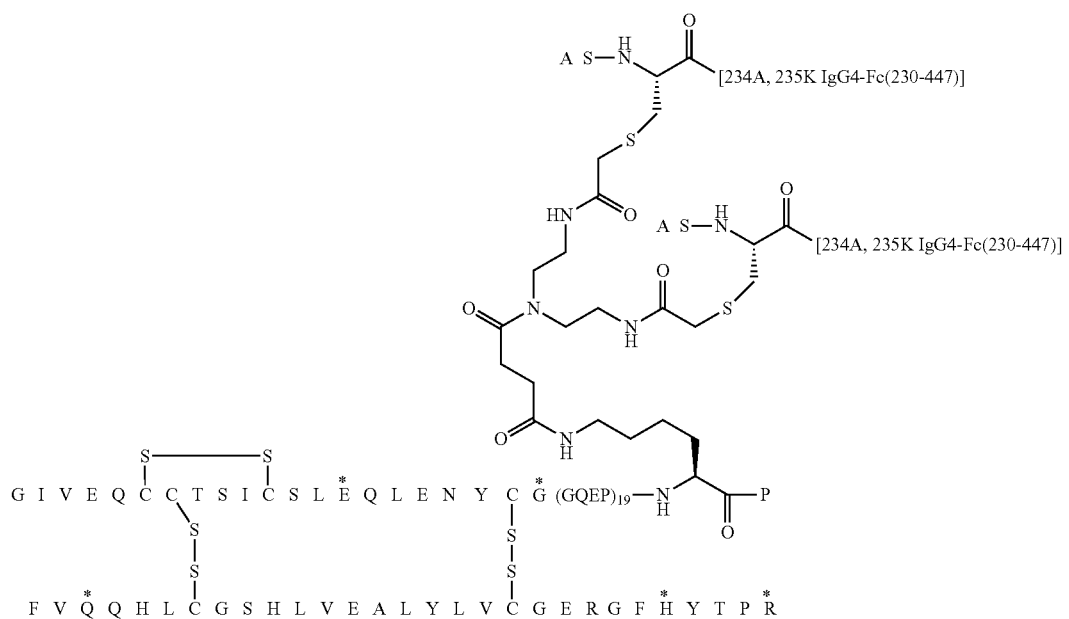

The title compound was synthesised from A14E, A21G, A22(GQEP)₁₉, A98K(N(eps)4-[bis[2-[(2-iodoacetyl)amino]ethyl]amino]-4-oxo-butanoyl), A99P, B3Q, B25H, B29R, desB30 human insulin prepared as described in Example 4.5, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 63576.0; Found mass: 63575.8.

Example 5.7

Preparation of the A14E, A21G, A22(GQEP)₆, A46K^, A47P, B25H, B29R, desB30 human insulin/ (227A, 234A, 235K hIgG4-Fc(228-447))4-[bis[2-[(2-acetyl)amino]ethyl]amino]-4-oxo-butanoyl Conjugate

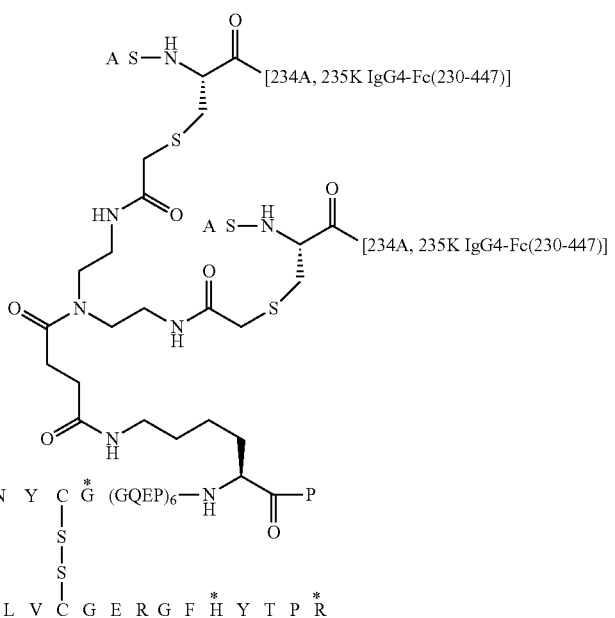

The title compound was synthesised from A14E, A21G, A22(GQEP)₆, A46K(N(eps)4-[bis[2-[(2-iodoacetyl)amino]ethyl]amino]-4-oxo-butanoyl), A47P, B25H, B29R, desB30 human insulin prepared as described in Example 4.6, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 58213.7; Found mass: 58213.2.

Example 5.8

Preparation of the A14E, A21G, A22(GQEP)₁₂, A70K^, A71P, B25H, B29R, desB30 human insulin/ (227A, 234A, 235K hIgG4-Fc(228-447))4-[bis[2-[(2-acetyl)amino]ethyl]amino]-4-oxo-butanoyl Conjugate

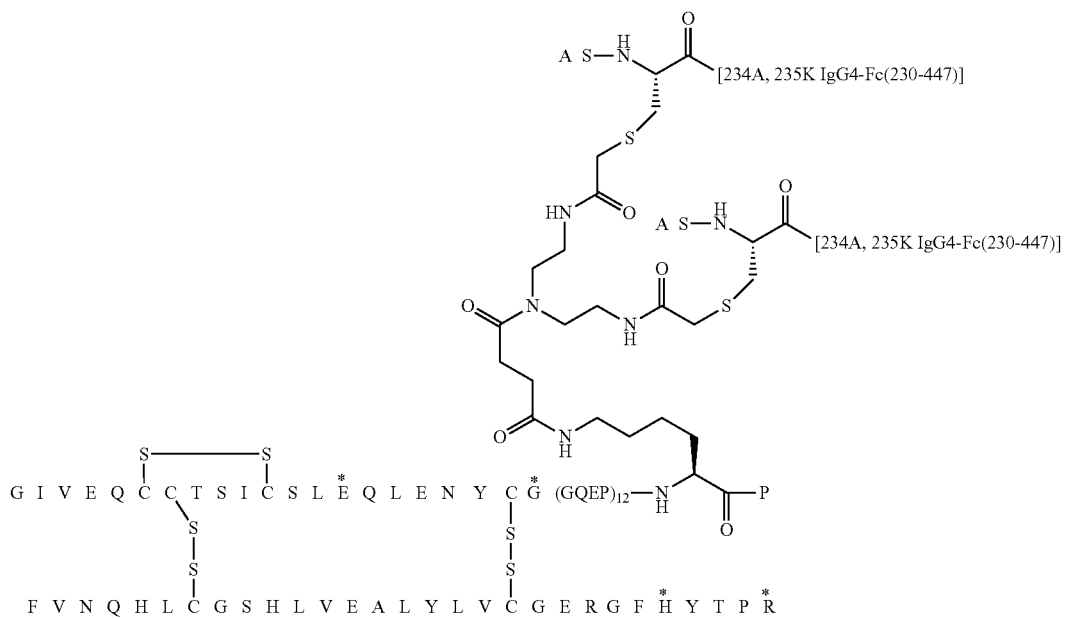

The title compound was synthesised from A14E, A21G, A22(GQEP)₁₂, A70K(N(eps)4-[bis[2-[(2-iodoacetyl)amino] ethyl]amino]-4-oxo-butanoyl), A71P, B25H, B29R, desB30 human insulin prepared as described in Example 4.7, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 60682.1; Found mass: 60681.6.

Example 5.9

Preparation of the A14E, A21G, A22(GQAPGQEP)₆, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl Conjugate

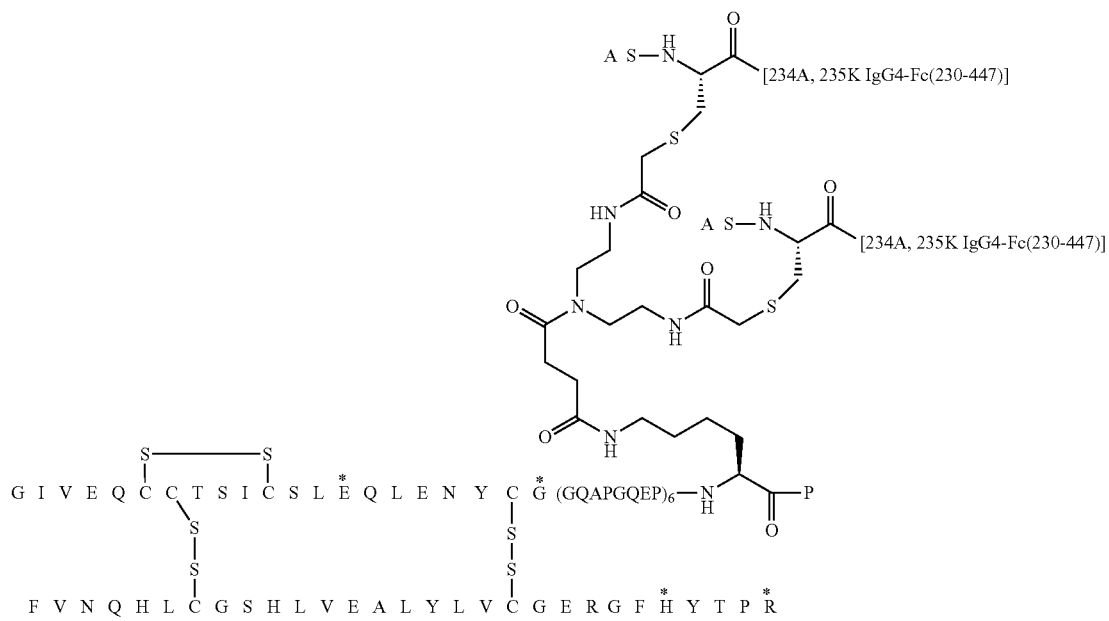

The title compound was synthesised from A14E, A21G, A22(GQAPGQEP)₆, A70K(N(eps)4-[bis[2-[(2-iodoacetyl)amino]ethyl]amino]-4-oxo-butanoyl), A71P, B25H, B29R, desB30 human insulin prepared as described in Example 4.8, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 60334.0; Found mass: 60336.5.

Example 5.10

Preparation of the A14E, A21G, A22(GQEP)₃, A34G, A35O, A36E, A37K^, A38P, B25H, B29R, desB30 human insulin/(227A, 234A, 235K hIgG4-Fc(228-447))4-[bis[2-[(2-acetyl)amino]ethyl]amino]-4-oxo-butanoyl Conjugate

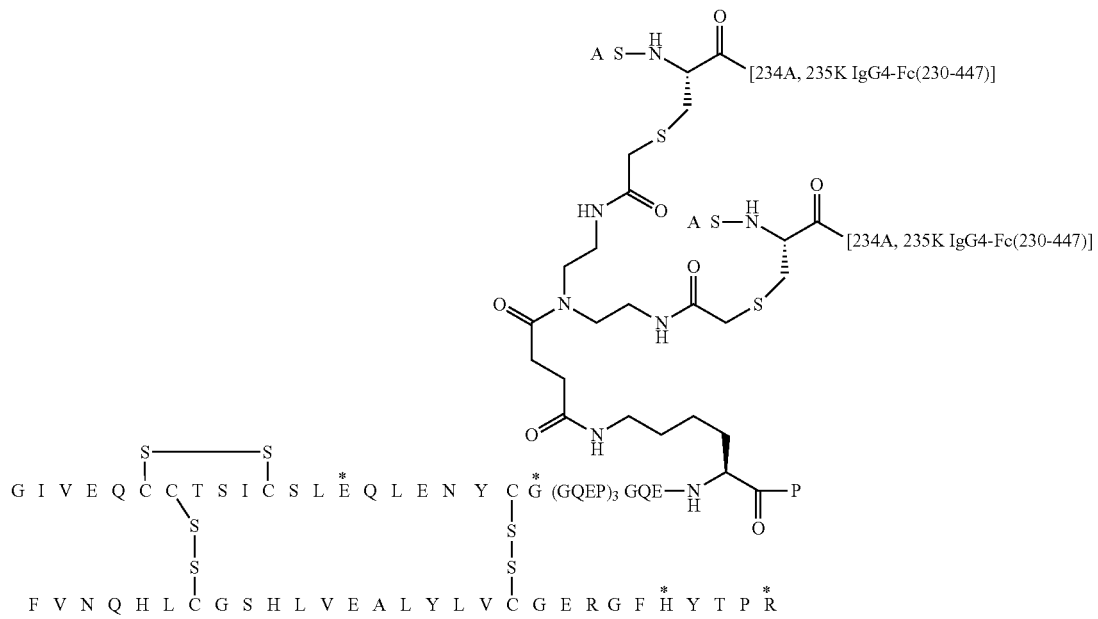

The title compound was synthesised from A14E, A21G, A22(GQEP)₃, A34G, A35Q, A36E, A37K(N(eps)4-[bis[2-[(2-iodoacetyl)amino]ethyl]amino]-4-oxo-butanoyl), A38P, B25H, B29R, desB30 human insulin prepared as described in Example 4.9, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 57293.7; Found mass: 57295.8.

Example 5.11

Preparation of the A14E, B(-78K^), B(-77P), B(-1)(GQEP)$_{19}$, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

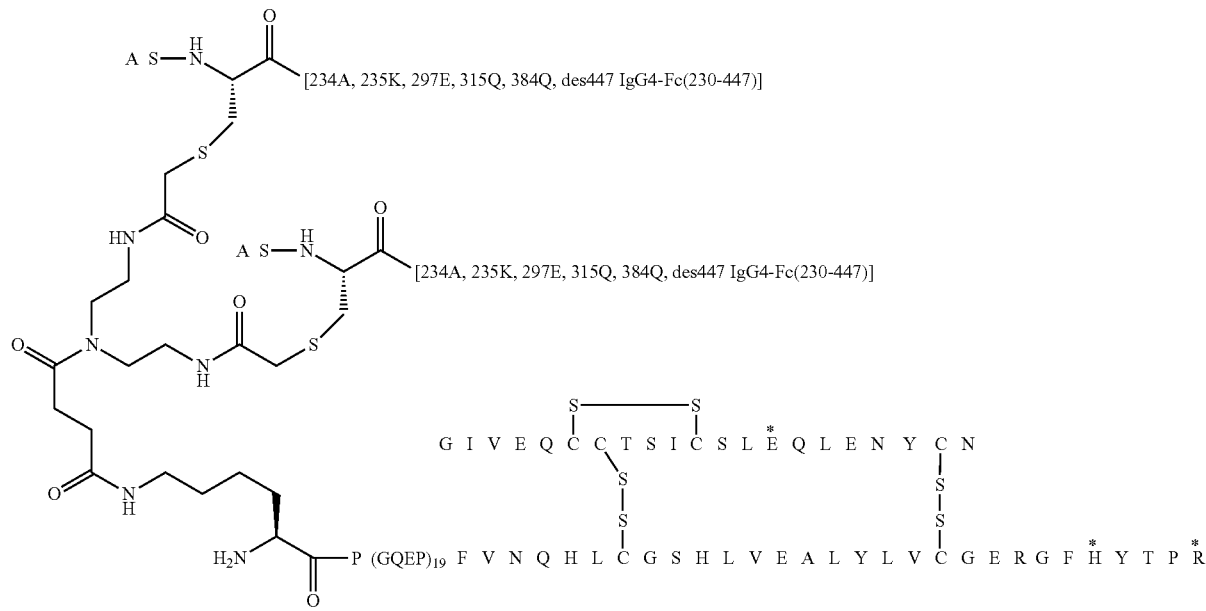

The title compound was synthesised from A14E, B(-78K(N(eps)4-[bis[2-[(2-iodoacetyl)amino]ethyl]amino]-4-oxo-butanoyl)), B(-77P), B(-1)(GQEP)$_{19}$, B25H, B29R, desB30 human insulin prepared as described in Example 4.3, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 63448.9; Found mass: 63451.6.

Example 5.12

Preparation of the (A14E, A21G, A22(GQEP)$_{19}$, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

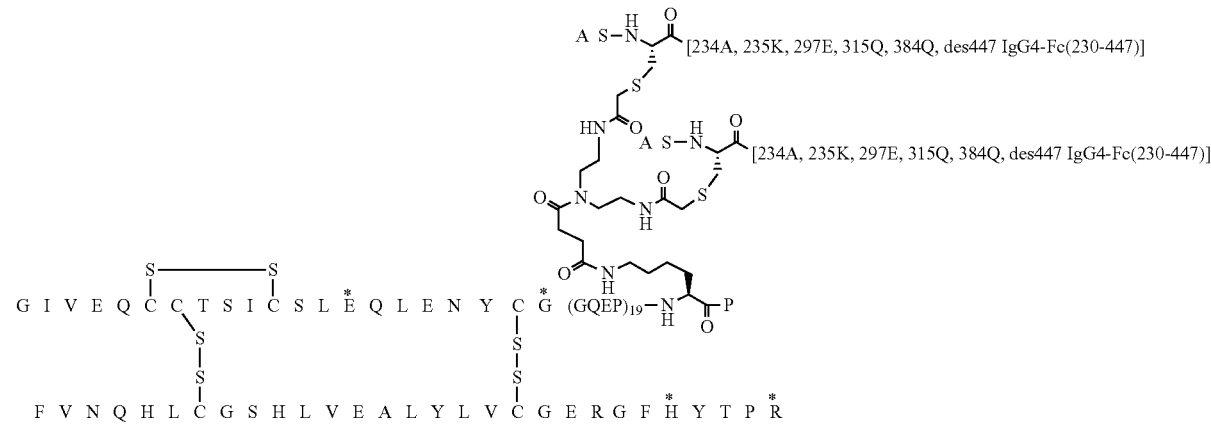

The title compound was synthesised from A14E, A21G, A22(GQEP)$_{19}$, A98K(N(eps)4-[bis[2-[(2-iodoacetyl)amino]ethyl]amino]-4-oxo-butanoyl), A99P, B25H, B29R, desB30 human insulin prepared as described in Example 4.1, and 227A, 234A, 235K, 297E, 315Q, 384Q, des447 hIgG4-Fc (228-447) (Fc15) prepared as described in Example 2, following the general insulin Fc conjugation Procedure 1 described in Example 5.1.

LCMS Method 3: Calc. mass: 63391.8; Found mass: 63394.4.

Example 5.13

Preparation of the A14E, A21G, A22 (GQAPGQAPGQEP)$_6$-GQAP, A98K^, A99P, B3Q, B25H, B29R, desB30 human insulin/(227A, 234A, 235K, 297E, 315Q, 3840, des447 hIgG4-Fc(228-447))4-[bis[2-[(2-acetyl)amino]ethyl]amino]-4-oxo-butanoyl Conjugate

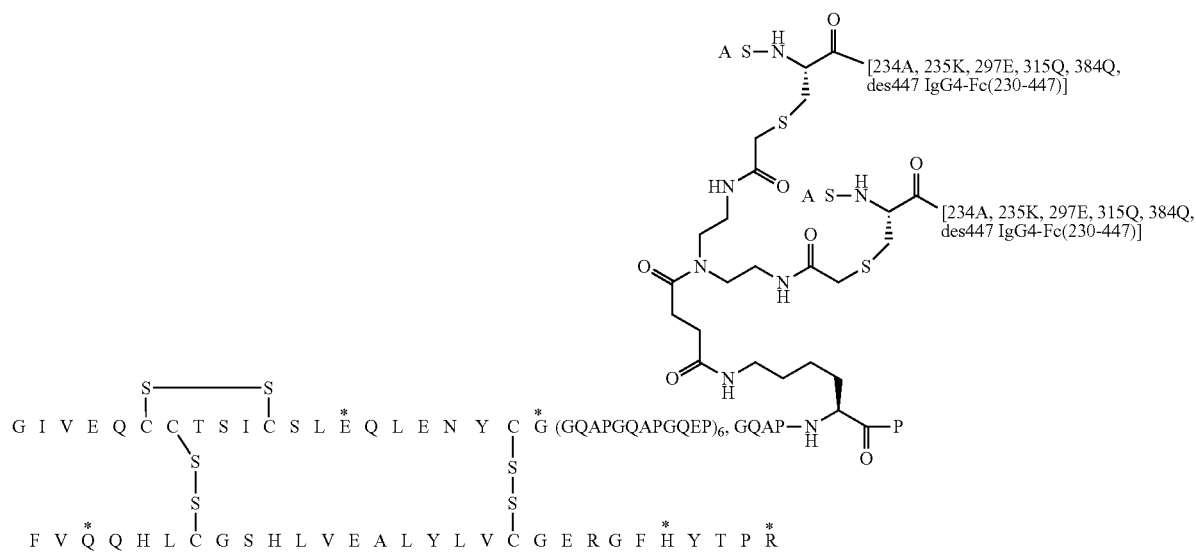

The title compound was synthesised from of A14E, A21G, A22(GQAPGQAPGQEP)$_6$-GQAP, A98K(N(eps)4-[bis[2-[(2-iodoacetyl)amino]ethyl]amino]-4-oxo-butanoyl), A99P, B3Q, B25H, B29R, desB30 human insulin prepared as described in Example 4.4, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass 62651.4; Found mass: 62653.0.

Example 5.14

Preparation of the A14E, A21G, A22(GQAPGQEP)₆, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

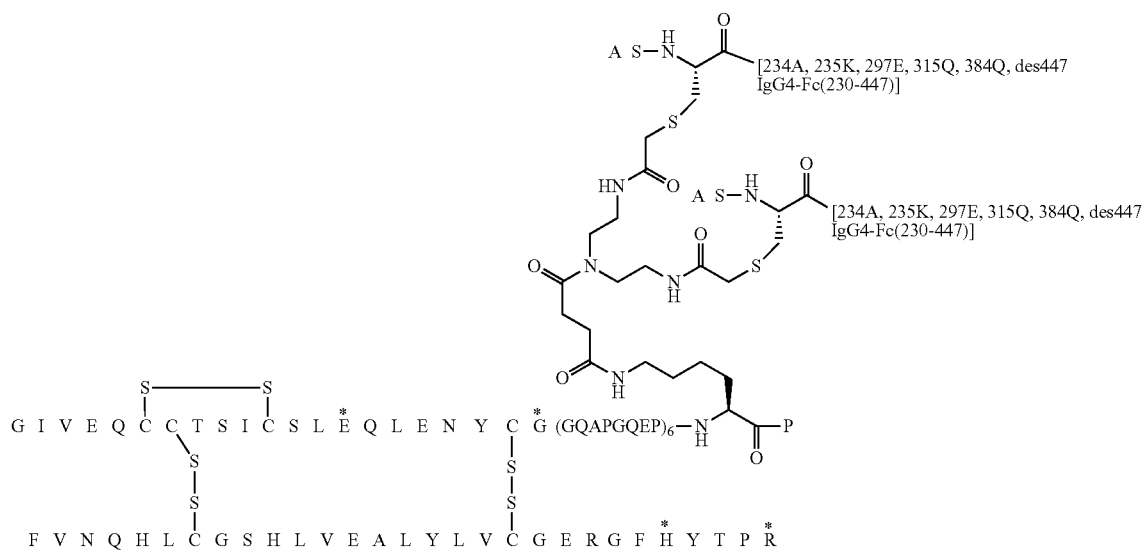

The title compound was synthesised from A14E, A21G, A22(GQAPGQEP)₆, A70K(N(eps)4-[bis[2-[(2-iodoacetyl)amino]ethyl]amino]-4-oxo-butanoyl), A71P, B25H, B29R, desB30 human insulin prepared as described in Example 4.8, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 60164.0; Found mass: 60165.6.

Example 5.15

Preparation of the (A14E, A21G, A22(GQAP)₁₉, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

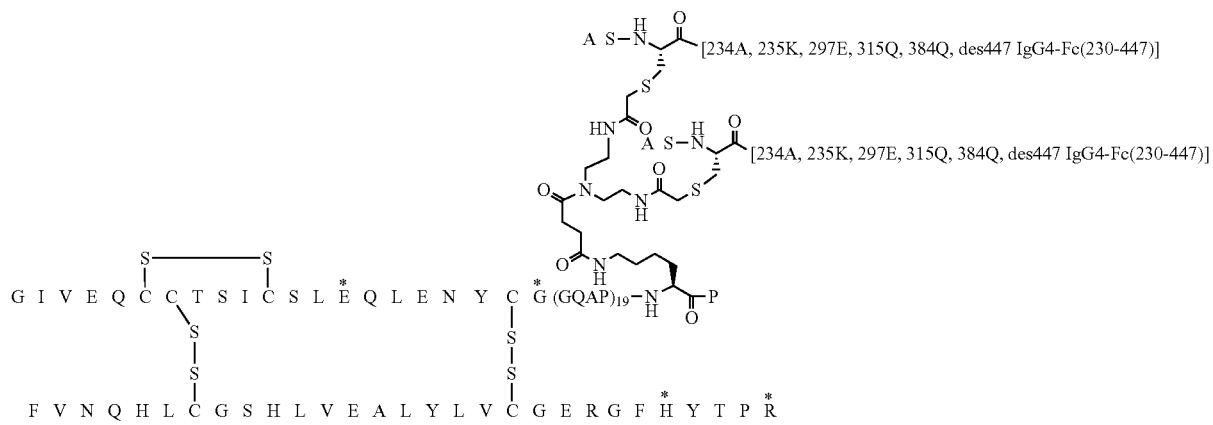

The title compound was synthesised from A14E, A21G, A22(GQAP)$_{19}$, A98K(N(eps)4-[bis[2-[(2-iodoacetyl)amino]ethyl]amino]-4-oxo-butanoyl), A99P, B25H, B29R, desB30 human insulin prepared as described in Example 4.10, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 62289.2; Found mass: 62292.0.

Example 5.16

Preparation of the (A14E, A21G, A22(GQAP)$_{19}$, A98K^, A99P, B25H, B29R, desB30 human insulin)/(227A, 234A, 235K, 297E, 315Q, 384Q, des447 hIgG4-Fc(228-447))6-[bis[2-[(2-acetyl)amino]ethyl]amino]-6-oxo-hexanoyl conjugate

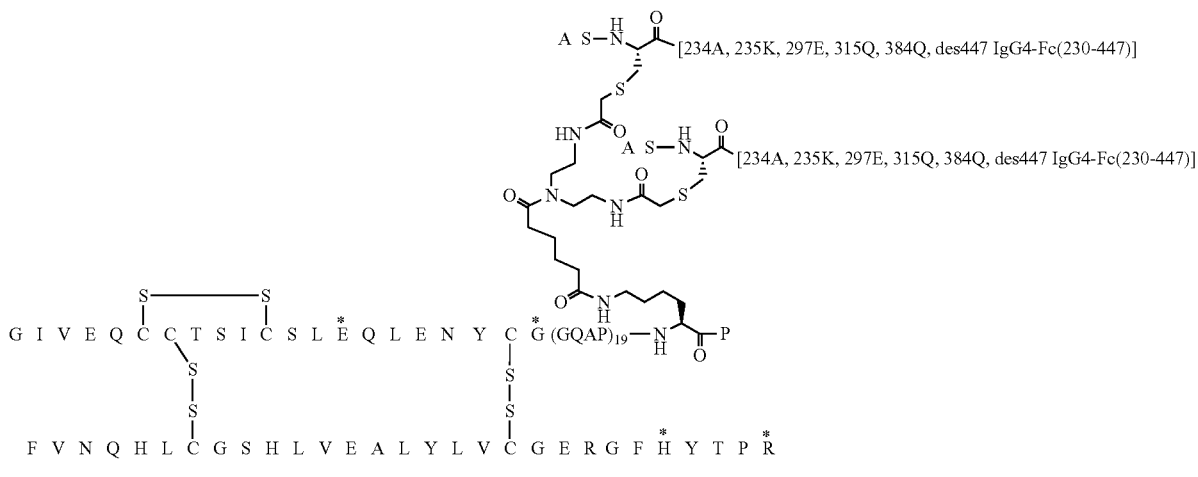

The title compound was synthesised from A14E, A21G, A22(GQAP)$_{19}$, A98K(N(eps)6-[bis[2-[(2-iodoacetyl)amino]ethyl]amino]-6-oxo-hexanoyl), A99P, B25H, B29R, desB30 human insulin prepared as described in Example 4.11, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 62317.3; Found mass: 62323.8.

Example 5.17

Preparation of the A14E, A21G, A22(GQEP)$_{12}$, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

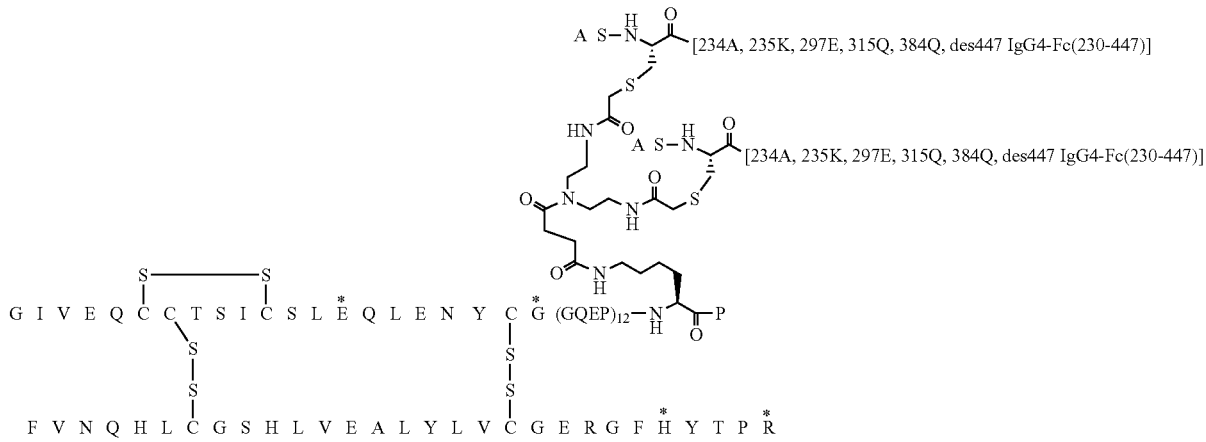

The title compound was synthesised from A14E, A21G, A22(GQEP)$_{12}$, A70K(N(eps)4-[bis[2-[(2-iodoacetyl)amino]ethyl]amino]-4-oxo-butanoyl), A71P, B25H, B29R, desB30 human insulin prepared as described in Example 4.7, and 227A, 234A, 235K, 297E, 315Q, 384Q, des447 hIgG4-Fc (228-447) (Fc15) prepared as described in Example 2, following the general insulin Fc conjugation Procedure 2 described in Example 5.2.

LCMS Method 3: Calc. mass: 60511.9; Found mass: 60517.7.

Example 5.184

Preparation of the A14E, B(-78K^), B(-77P), B(-1)(GQAP)$_{19}$, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

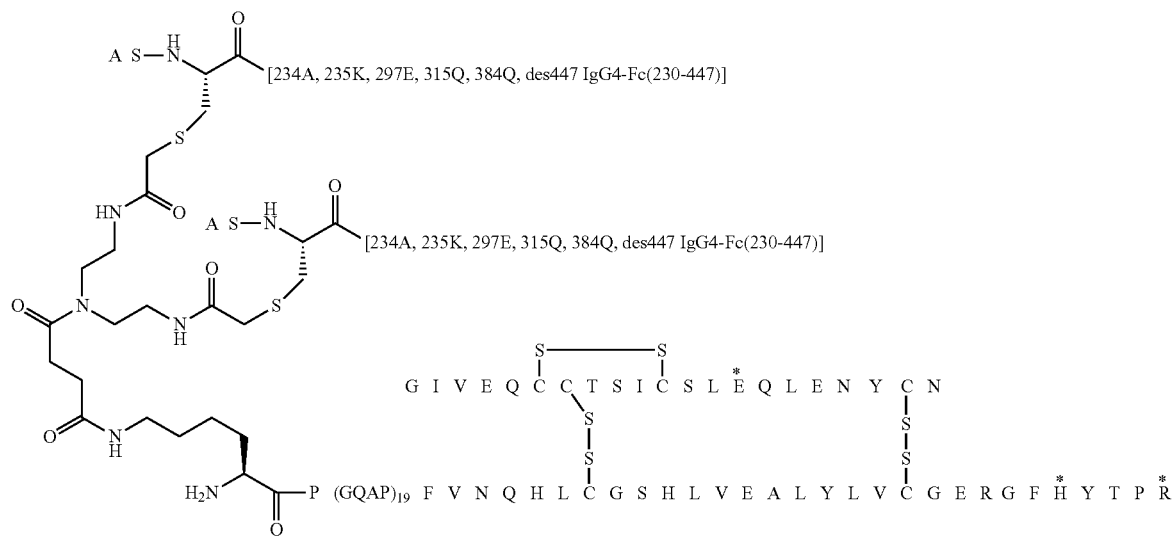

The title compound was synthesised from A14E, B(-78K(N(eps)4-[bis[2-[(2-iodoacetyl)amino]ethyl]amino]-4-oxo-butanoyl)), B(-77P), B(-1)(GQAP)$_{19}$, B25H, B29R, desB30 human insulin prepared as described in Example 4.12, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 62346.3; Found mass: 62348.

Example 5.19

Preparation of the A14E, A21G, A22 (GQAPGQAPGQEP)$_6$-GQAP, A98K^, A99P, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

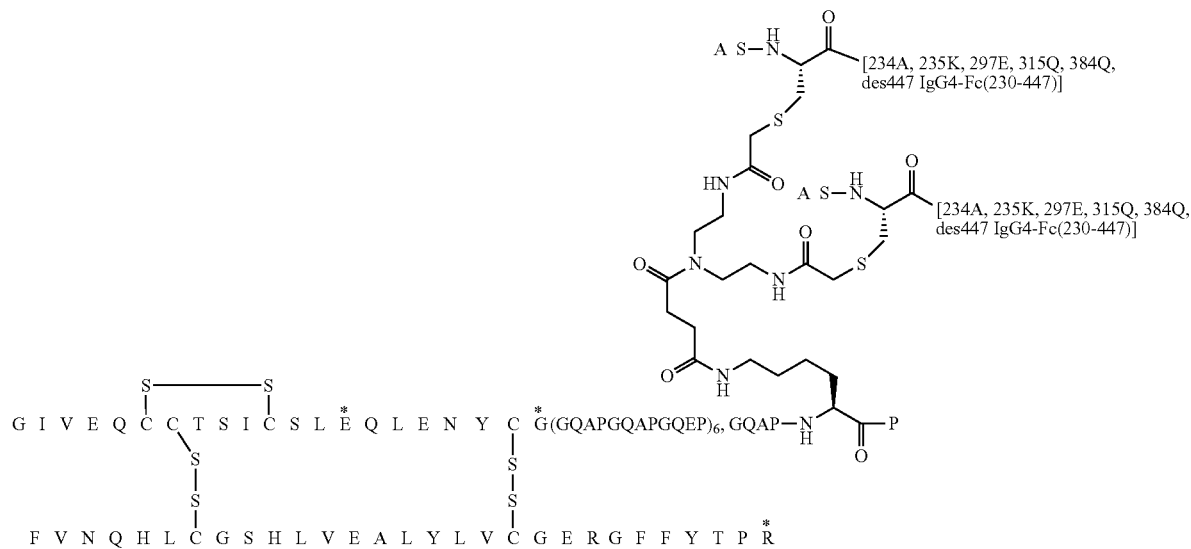

The title compound was synthesised from of A14E, A21G, A22(GQAPGQAPGQEP)$_6$-GQAP, A98K(N(eps)4-[bis[2-[(2-iodoacetyl)amino]ethyl]amino]-4-oxo-butanoyl), A99P, B29R, desB30 human insulin prepared as described in Example 4.13, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass 62647.4; Found mass: 62649.7.

Example 5.20

Preparation of the A14E, A21G, A22 (GQAPGQAPGQAPGQEP)$_6$-GQAP, A122K^, A123P, B25H, B29R, desB30 human insulin/(227A, 234A, 235K, 297E, 315Q, 384Q, des447 hIgG4-Fc (228-447))4-[bis[2-[(2-acetyl)amino]ethyl]amino]-4-oxo-butanoyl Conjugate

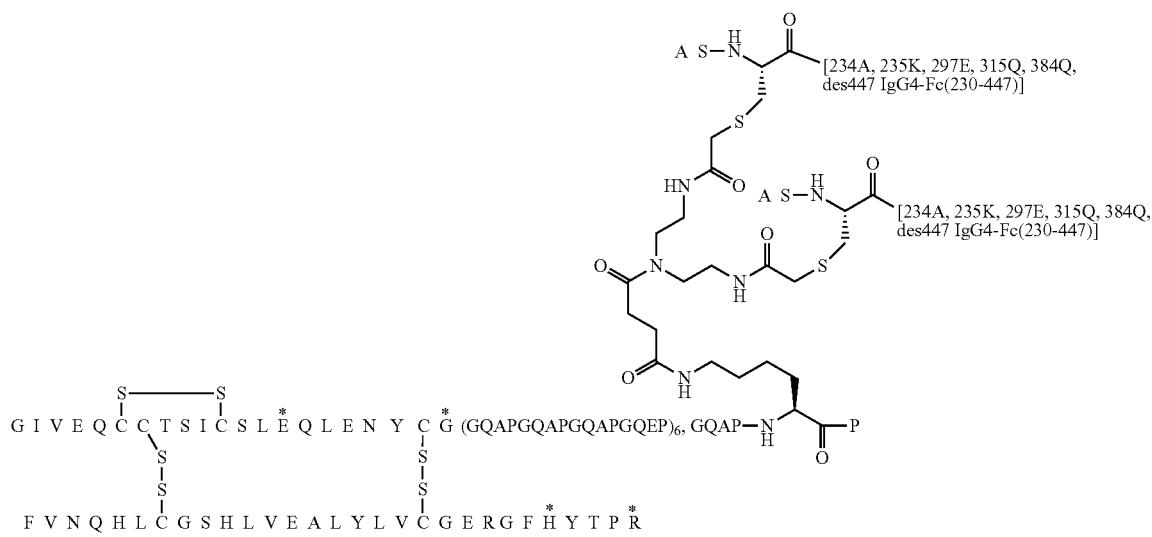

The title compound was synthesised from of A14E, A21G, A22(GQAPGQAPGQAPGQEP)$_6$-GQAP, A122K(N(eps)4-[bis[2-[(2-iodoacetyl)amino]ethyl]amino]-4-oxo-butanoyl), A123P, B25H, B29R, desB30 human insulin prepared as described in Example 4.14, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass 64757.7; Found mass: 64757.5.

Example 5.21

Preparation of the A14E, A21Q, A22(G)$_{18}$, A40K^, B25H, B29R, desB30 human insulin/(227A, 234A, 235K hIgG4-Fc(228-447))4-[bis[2-[(2-acetyl)amino]ethyl]amino]-4-oxo-butanoyl Conjugate

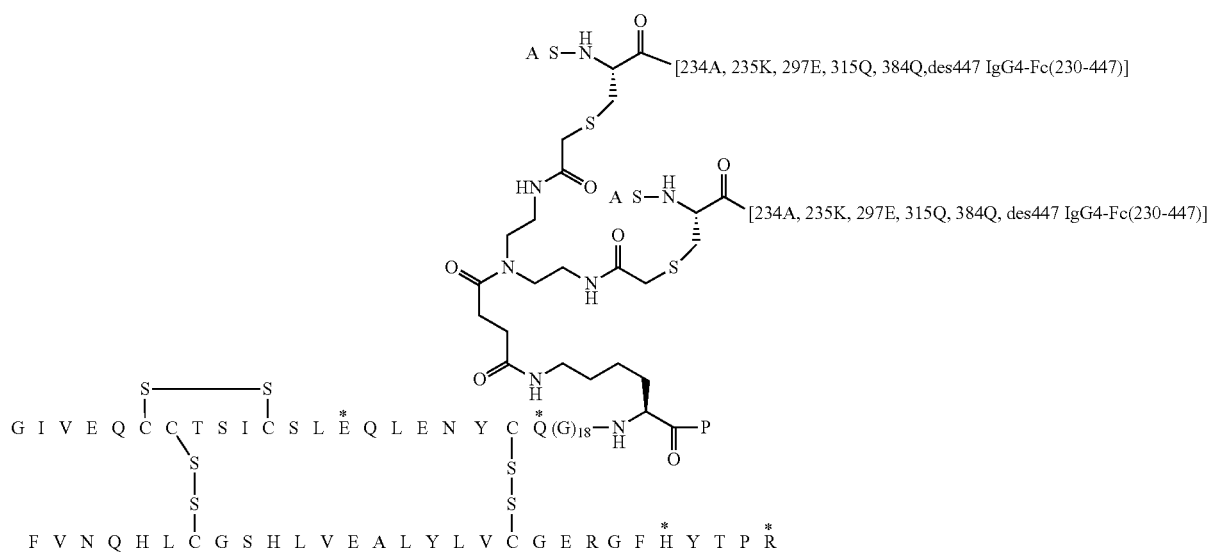

The title compound was synthesised from A14E, A21Q, A22(G)$_{18}$, A40K(N(eps)4-[bis[2-[(2-iodoacetyl)amino]ethyl]amino]-4-oxo-butanoyl), B25H, B29R, desB30 human insulin prepared as described in Example 4.15, and 227A, 234A, 235K hIgG4-Fc(228-447) (Fc9) prepared as described in Example 2, following the general insulin Fc conjugation Procedure 1 described in Example 5.1.

LCMS Method 3: Calc. mass: 56746.1; Found mass: 56750.1.

Example 5.22

Preparation of the (A14E, A21G, A22(GQAP)$_{24}$, A118G, A119Q, A120A, A121K^, A122P, B25H, B29R, desB30 human insulin)/(227A, 234A, 235K, 297E, 315Q, 3840, des447 hIgG4-Fc(228-447))3,5-bis[(2-acetyl)amino]benzoyl Conjugate

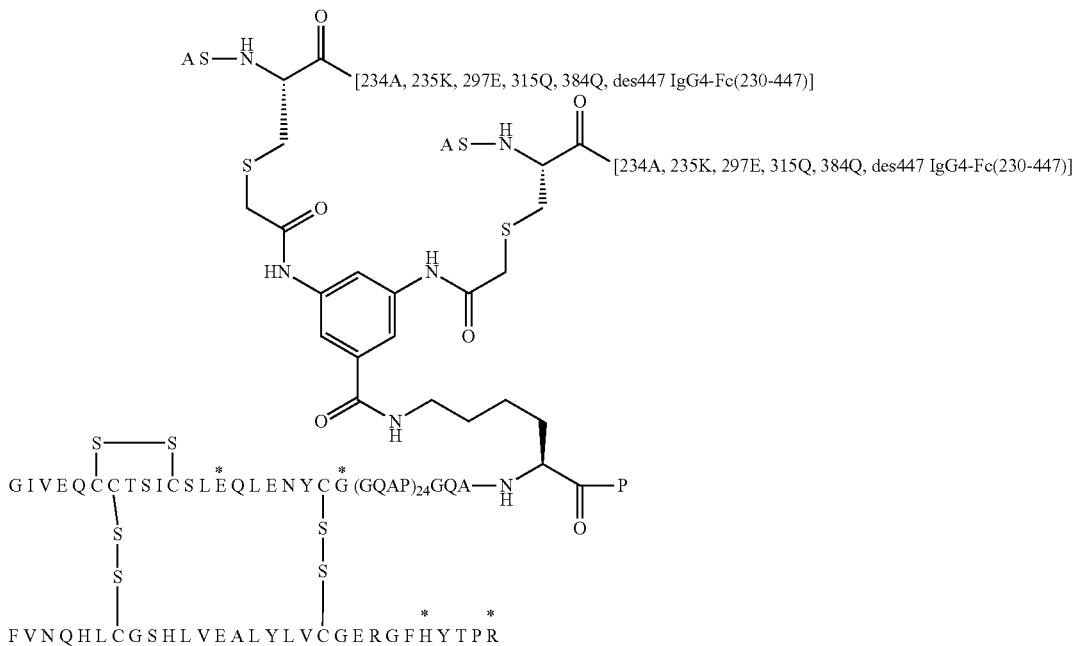

The title compound was synthesised from A14E, A21G, A22(GQAP)$_{24}$, A118G, A119Q, A120A, A121K(N(eps) 3,5-bis[(2-bromoacetyl)amino]benzoyl), A122P, B25H, B29R, desB30 human insulin prepared as described in Example 4.16, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 10: Calc. mass: 64261; Found mass: 64263.

Example 5.23

Preparation of the (A14E, A21G, A22(GQAP)$_{24}$, A118G, A119Q, A120A, A121K^, A122P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

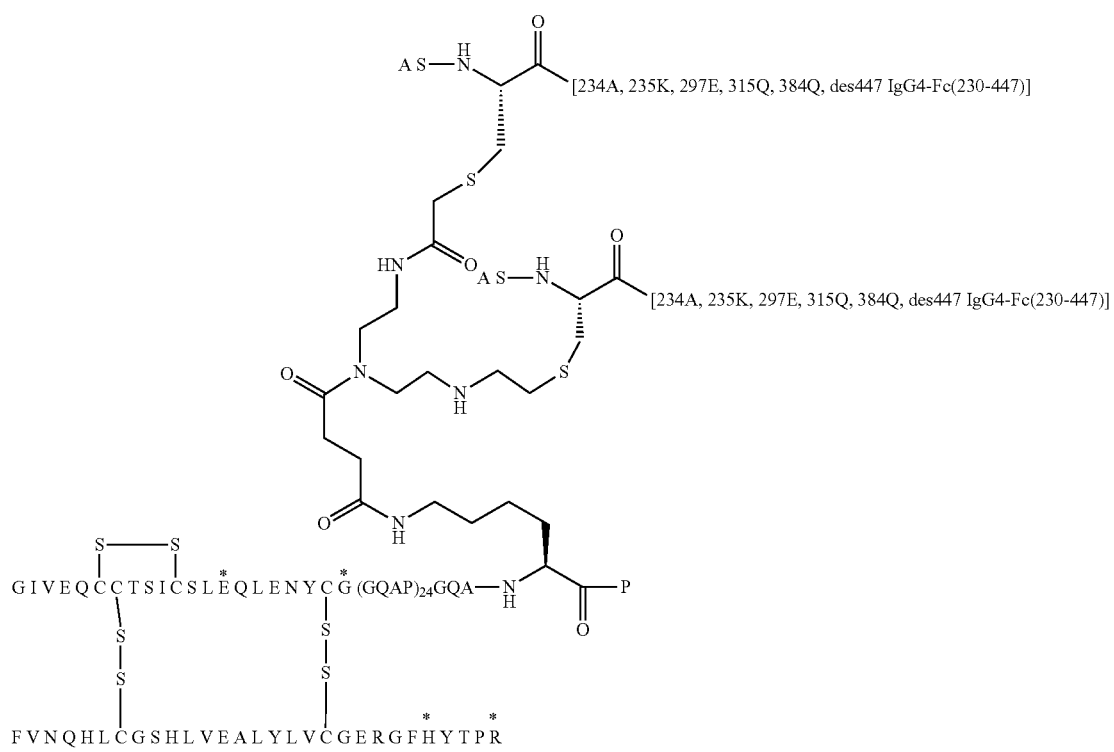

The title compound was synthesised from A14E, A21G, A22(GQAP)$_{24}$, A118G, A119Q, A120A, A121K(N(eps) 4-[bis[2-[(2-iodoacetyl)amino]ethyl]amino]-4-oxo-butanoyl), A122P, B25H, B29R, desB30 human insulin prepared as described in Example 4.17, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 10: Calc. mass: 64312; Found mass: 64322.

Example 5.24

Preparation of the A14E, A21G, A22 (GQAPGQAPGQEP)₆-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]carbamoylamino]butanoyl Conjugate

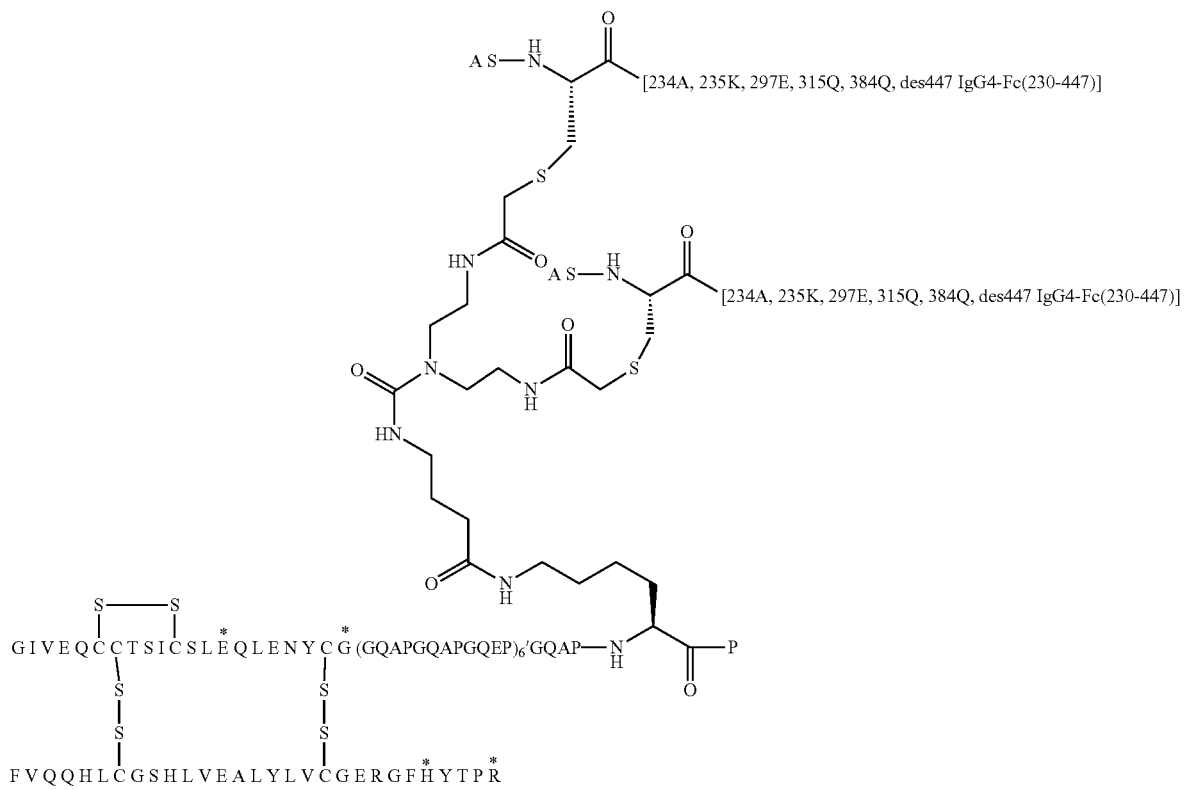

The title compound was synthesised from of A14E, A21G, A22(GQAPGQAPGQEP)₆-GQAP, A98K(N(eps)4-[bis[2-[(2-iodoacetyl)amino]ethyl]carbamoylamino]butanoyl), A99P, B3Q, B25H, B29R, desB30 human insulin prepared as described in Example 4.18, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass 62680.4; Found mass: 62682.8.

Example 5.25

Preparation of the (A14A, A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

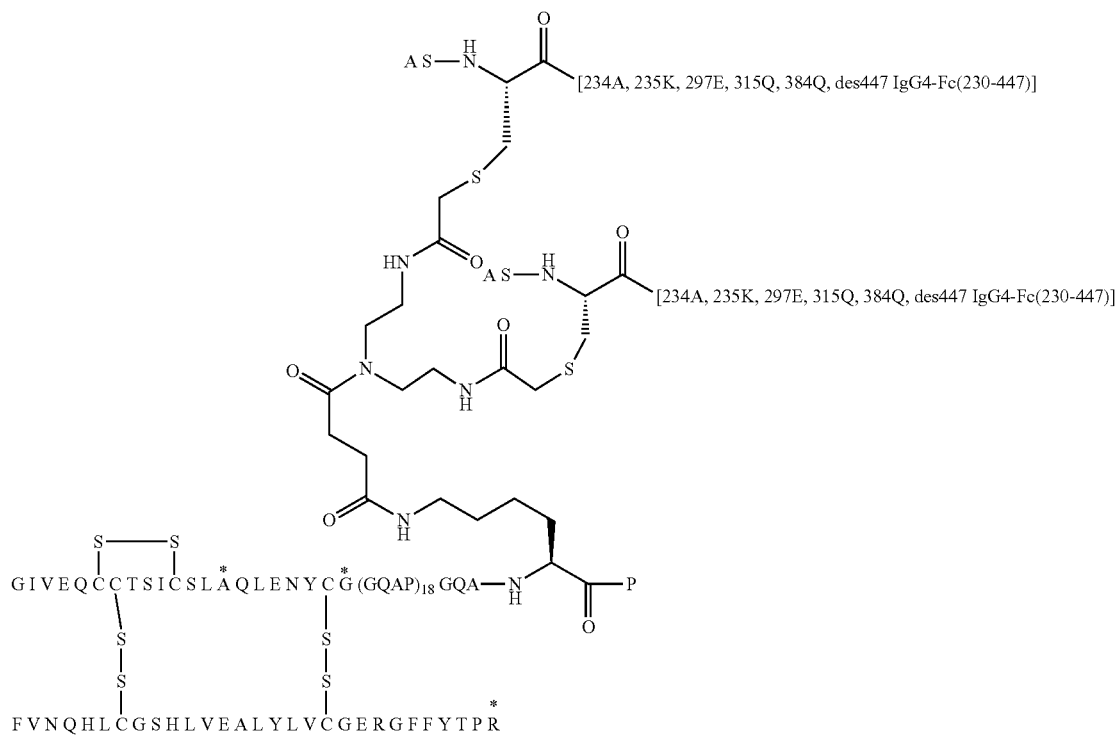

The title compound was synthesised from A14A, A21G, A22(GQAP)$_{18}$, A94G, A95Q, A96A, A97K(N(eps)4-[bis[2-[(2-iodoacetyl)amino]ethyl]amino]-4-oxo-butanoyl), A98P, B29R, desB30 human insulin prepared as described in Example 4.19, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 3: Calc. mass: 62144.1; Found mass: 62143.9.

Example 5.26

Preparation of the (A14E, A21G, A22(GQAP)$_{18}$, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

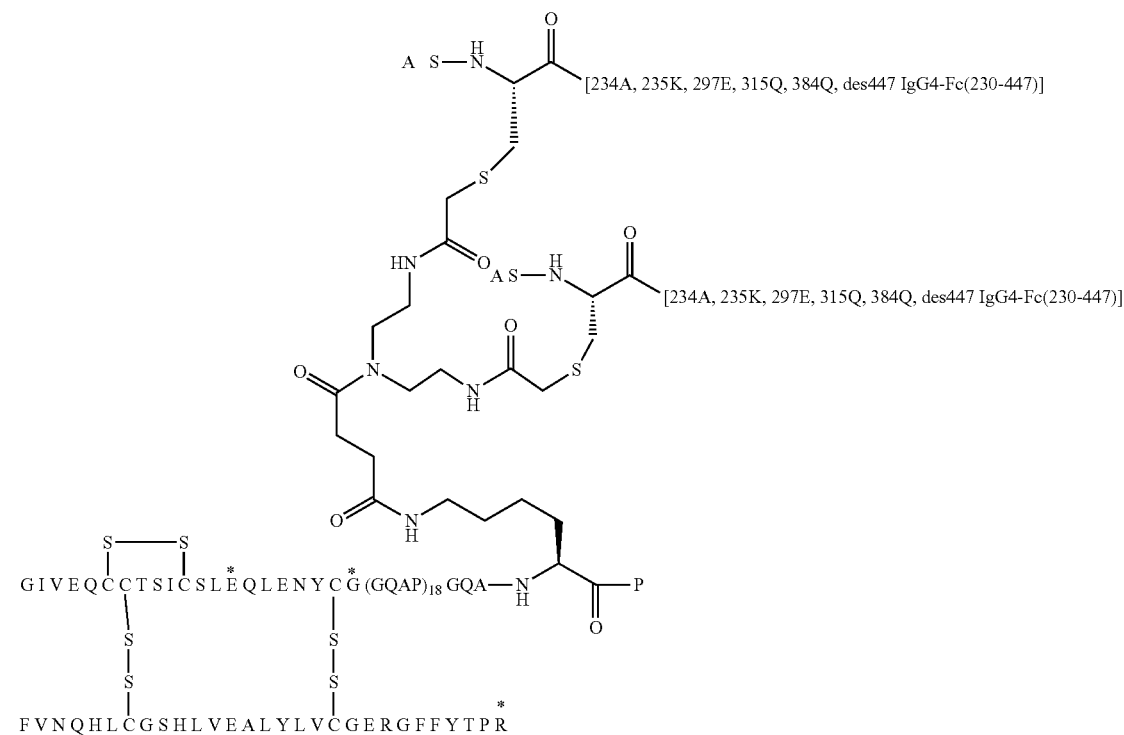

The title compound was synthesised from A14E, A21G, A22(GQAP)$_{18}$, A94G, A95Q, A96A, A97K(N(eps)4-[bis[2-[(2-iodoacetyl)amino]ethyl]amino]-4-oxo-butanoyl), A98P, B29R, desB30 human insulin prepared as described in Example 4.20, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 10: Calc. mass: 62202; Found mass: 62205.

Example 5.27

Preparation of the (A1(N(alpha)acetyl), A14E, A21G, A22(GQAP)$_{19}$, A98K^, A99P, B1(N(alpha)acetyl), B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

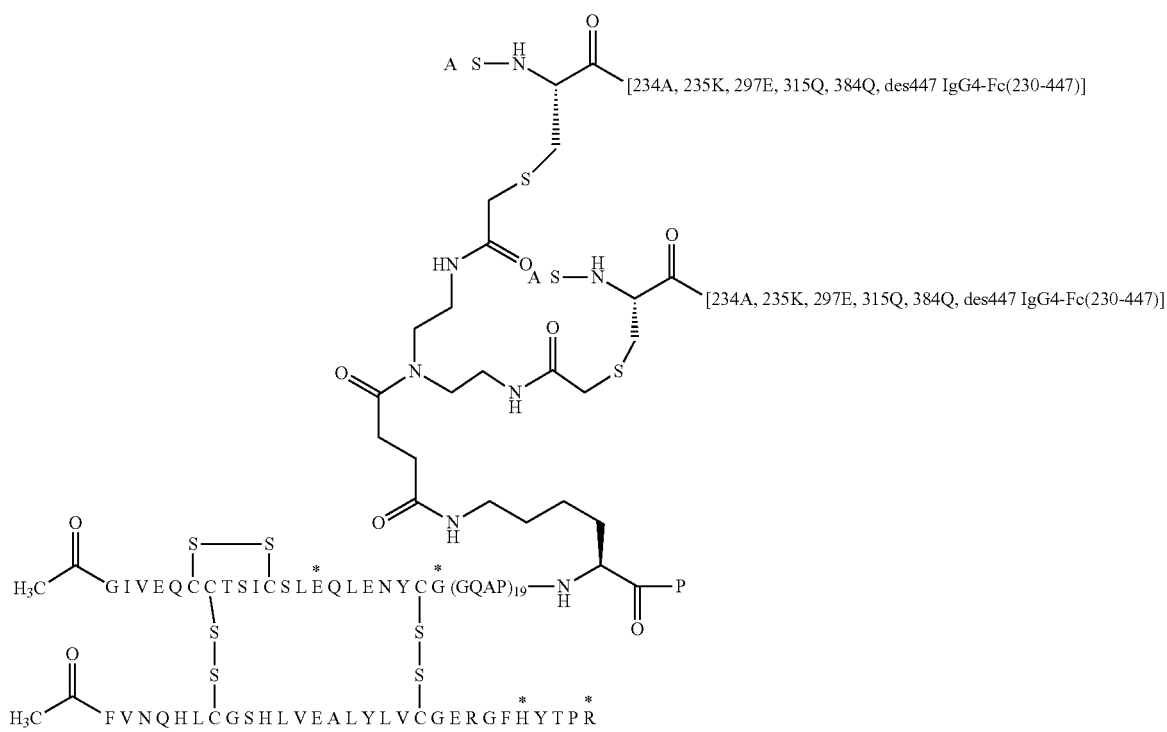

The title compound was synthesised from A1(N(alpha)acetyl), A14E, A21G, A22(GQAP)$_{19}$, A98K(N(eps)4-[bis[2-[(2-iodoacetyl)amino]ethyl]amino]-4-oxo-butanoyl), A99P, B1(N(alpha)acetyl), B25H, B29R, desB30 human insulin prepared as described in Example 4.21, and 227A, 234A, 235K, 297E, 315Q, 384Q, des447 hIgG4-Fc(228-447) (Fc15) prepared as described in Example 2, following the general insulin Fc conjugation Procedure 1 described in Example 5.1.

LCMS Method 10: Calc. mass: 62373.3; Found mass: 623376.5.

Example 5.28

Preparation of the (A21G, A22(GQAP)₁₈, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

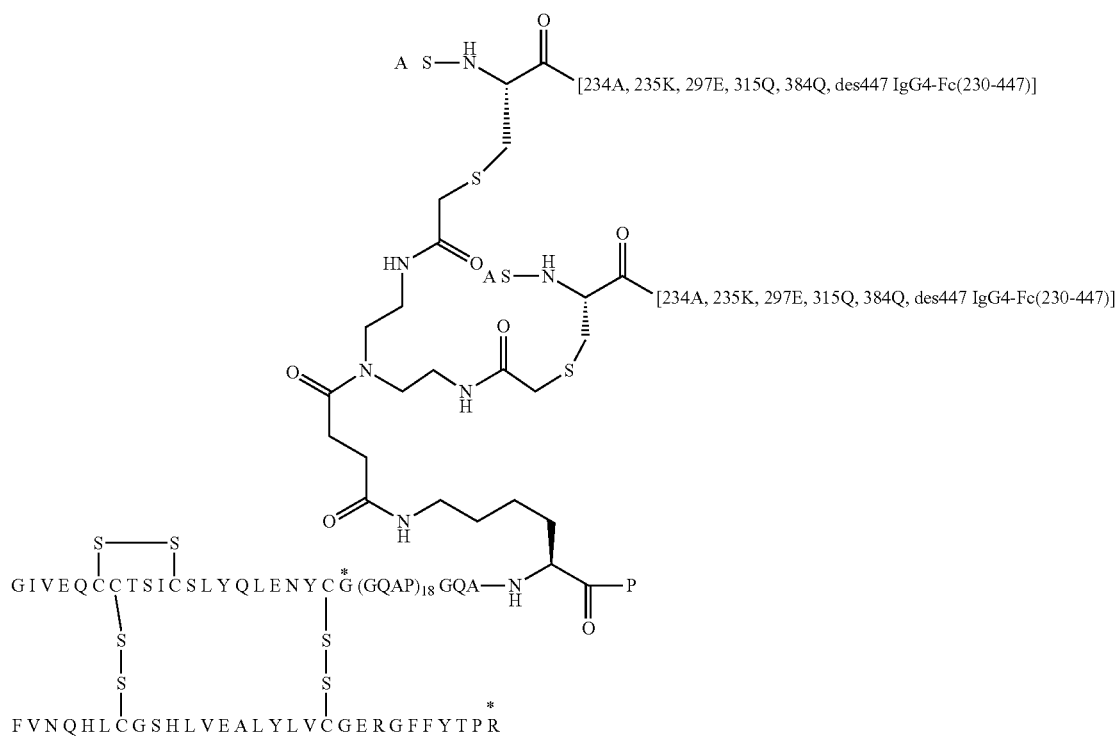

The title compound was synthesised from A21G, A22 (GQAP)₁₈, A94G, A95Q, A96A, A97K(N(eps)4-[bis[2-[(2-iodoacetyl)amino]ethyl]amino]-4-oxo-butanoyl), A98P, B29R, desB30 human insulin prepared as described in Example 4.22, and 227A, 234A, 235K, 297E, 315Q, 384Q, des447 hIgG4-Fc(228-447) (Fc15) prepared as described in Example 2, following the general insulin Fc conjugation Procedure 2 described in Example 5.2.

LCMS Method 3: Calc. mass: 62236.2; Found mass: 62338.6.

Example 5.29

Preparation of the (A14E, A21G, A22(GQAP)$_{24}$, A118G, A119Q, A120A, A121K^, A122P, B29R, desB30 human insulin)/(227A, 234A, 235K, 297E, 315Q, 384Q, des447 hIgG4-Fc(228-447))3,5-bis[(2-acetyl)amino]benzoyl Conjugate

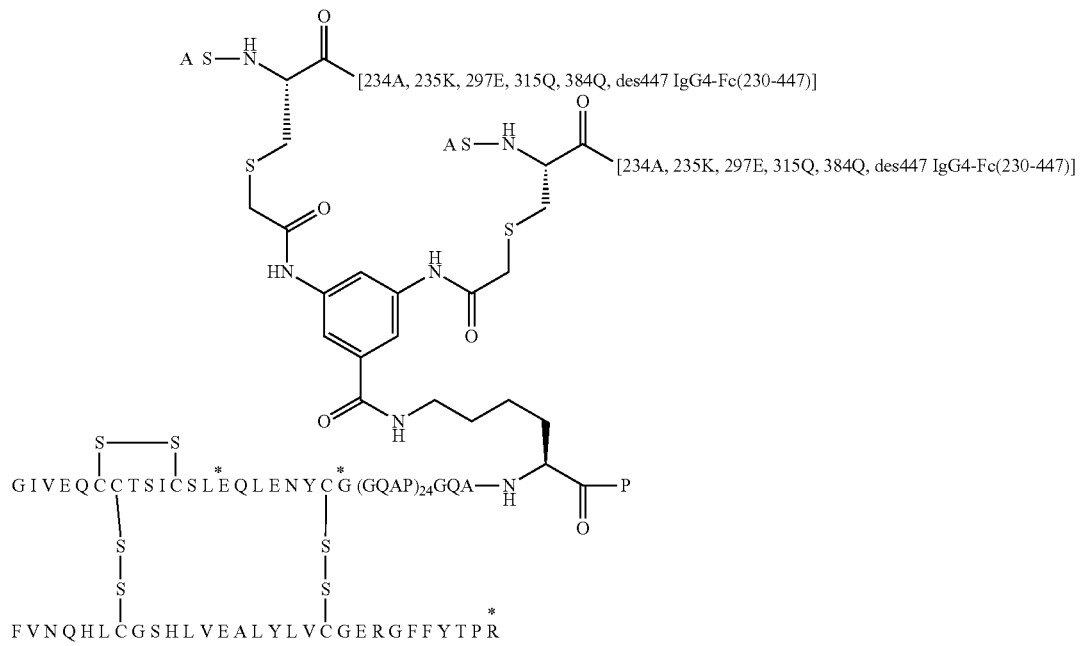

The title compound was synthesised from A14E, A21G, A22(GQAP)$_{24}$, A118G, A119Q, A120A, A121K(N(eps)$_{3,5}$-bis[(2-bromoacetyl)amino]benzoyl), A122P, B29R, desB30 human insulin prepared as described in Example 4.23, and 227A, 234A, 235K, 297E, 315Q, 384Q, des447 hIgG4-Fc (228-447) (Fc15) prepared as described in Example 2, following the general insulin Fc conjugation Procedure 2 described in Example 5.2.

LCMS Method 3: Calc. mass: 64271.3; Found mass: 64273.7.

Example 5.30

Preparation of the A14E, A21G, A22(GQAP)$_{18}$, A94G, A95Q, A96A, A97K^, A98P, B16E, B25H, B29R, desB30 human insulin)/(227A, 234A, 235K, 297E, 315Q, 384Q, des447 hIgG4-Fc(228-447))3,5-bis[(2-acetyl)amino]benzoyl Conjugate

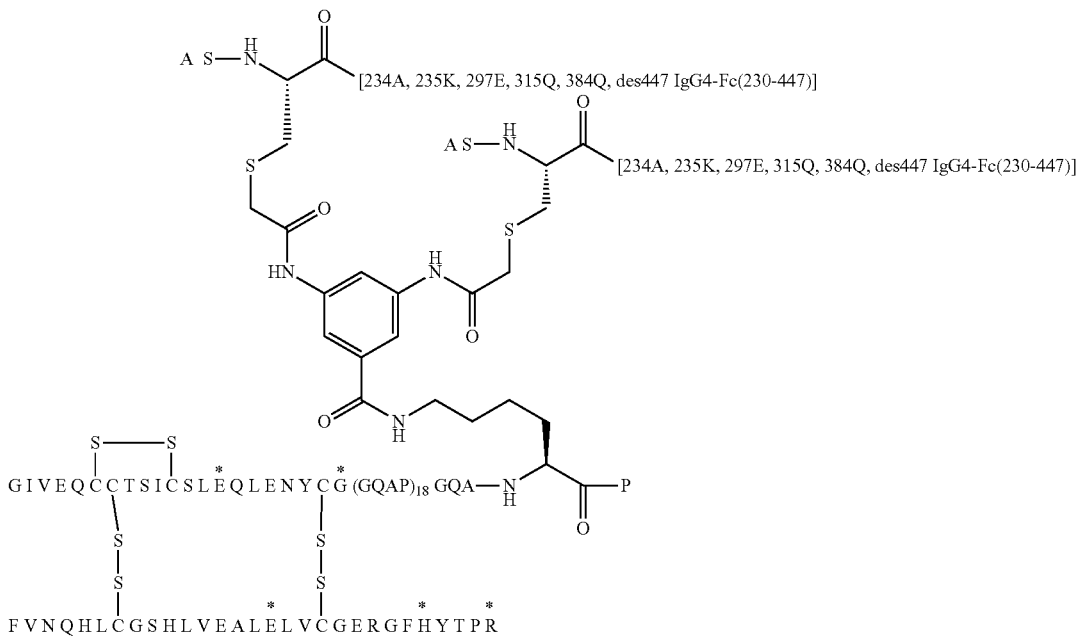

The title compound was synthesised from A14E, A21G, A22(GQAP)$_{18}$, A94G, A95Q, A96A, A97K(N(eps) 3,5-bis[(2-bromoacetyl)amino]benzoyl), A98P, B16E, B25H, B29R, desB30 human insulin prepared as described in Example 4.24, and 227A, 234A, 235K, 297E, 315Q, 384Q, des447 hIgG4-Fc(228-447) (Fc15) prepared as described in Example 2, following the general insulin Fc conjugation Procedure 2 described in Example 5.2.

LCMS Method 3: Calc. mass: 62107; Found mass: 62109.

Example 5.31

Preparation of the (A14E, A21G, A22(GQAP)$_{18}$, A94G, A95Q, A96A, A97K^, A98P, B16E, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl Conjugate

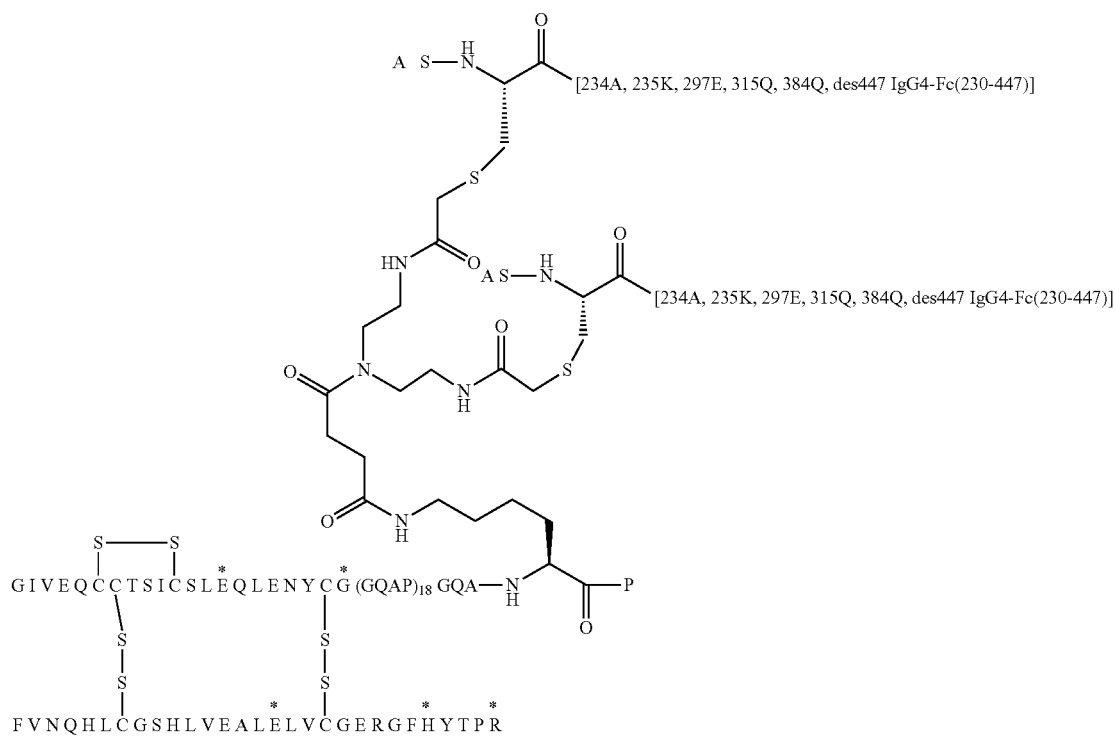

The title compound was synthesised from A14E, A21G, A22(GQAP)$_{18}$, A94G, A95Q, A96A, A97K(N(eps)4-[bis[2-[(2-iodoacetyl)amino]ethyl]amino]-4-oxo-butanoyl), A98P, B16E, B25H, B29R, desB30 human insulin prepared as described in Example 4.25, and 227A, 234A, 235K, 297E, 315Q, 384Q, des447 hIgG4-Fc(228-447) (Fc15) prepared as described in Example 2, following the general insulin Fc conjugation Procedure 2 described in Example 5.2.

LCMS Method 7: Calc. mass: 62158.1; Found mass: 62160.7.

Example 5.32

Preparation of the A14E, A21G, A22(GQEP)$_6$, A46K^, A47P, B25H, B29R, desB30 human insulin/ (227A, 234A, 235K, 297E, 315Q, 384Q, des447 hIgG4-Fc(228-447))4-[bis[2-[(2-acetyl)amino]ethyl]amino]-4-oxo-butanoyl Conjugate

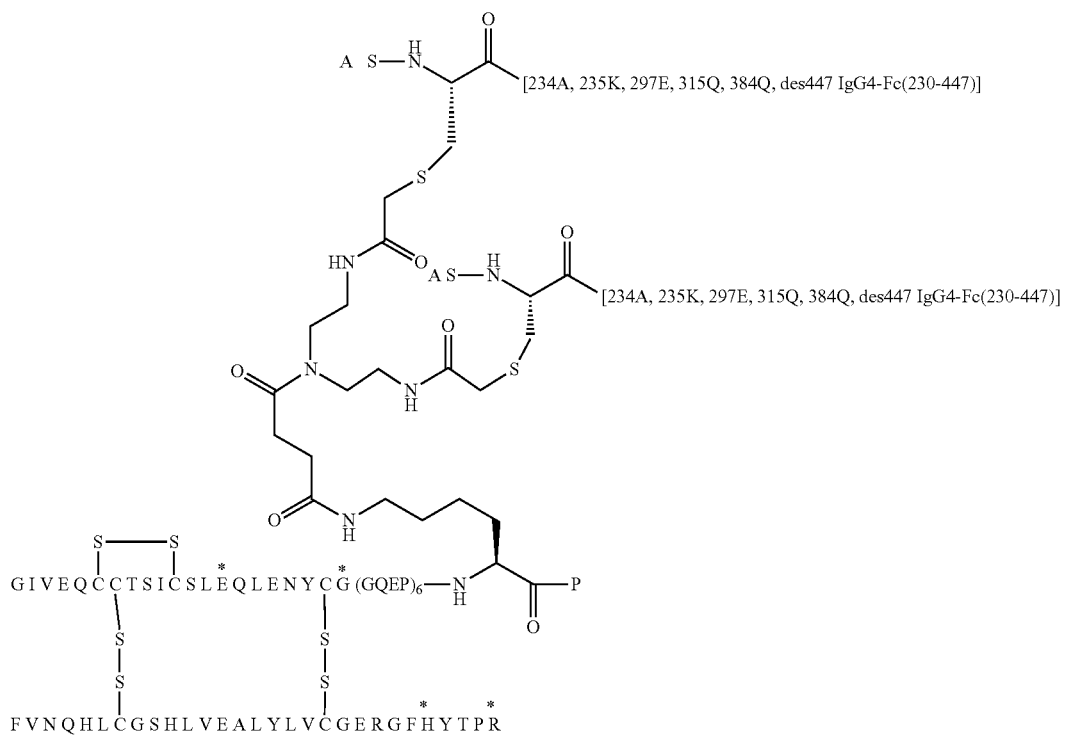

The title compound was synthesised from A14E, A21G, A22(GQEP)$_6$, A46K(N(eps)4-[bis[2-[(2-iodoacetyl)amino]ethyl]amino]-4-oxo-butanoyl), A47P, B25H, B29R, desB30 human insulin prepared as described in Example 4.6, and 227A, 234A, 235K, 297E, 315Q, 384Q, des447 hIgG4-Fc (228-447) (Fc15) prepared as described in Example 2, following the general insulin Fc conjugation Procedure 2 described in Example 5.2.

LCMS Method 3: Calc. mass: 58213.7; Found mass: 58213.2.

Example 5.33

Preparation of the (A14E, A21G, A22(GQEP)$_{19}$, 98K^, A99P, B25H, B29R, desB30 human insulin)/(226A, 227G, 228P, 234A, 235K, des447 hIgG4-Fc (228-447))3,5-bis[(2-acetyl)amino]benzoyl Conjugate

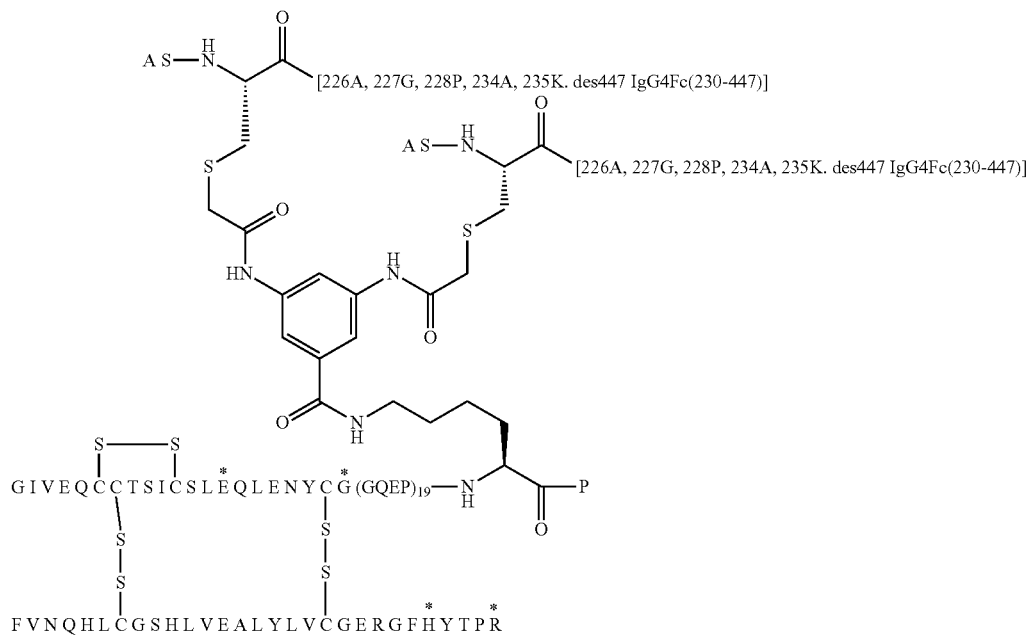

The title compound was synthesised from A14E, A21G, A22(GQEP)$_{19}$, A98K(N(eps) 3,5-bis[(2-bromoacetyl) amino]benzoyl), A99P, B25H, B29R, desB30 human insulin prepared as described in Example 4.26, and 226A, 227G, 228P, 234A, 235K, des447 IgG4-Fc(228-447) (Fc17) prepared as described in Example 2, following the general insulin Fc conjugation Procedure 2 described in Example 5.2.

LCMS Method 3: Calc. mass: 63388.8; Found mass: 63391.1.

Example 6: Insulin Receptor Affinity

The insulin receptor affinities of the conjugates were measured as described in (Vienberg S. G. et al: Receptor-isoform-selective insulin analogues give tissue-preferential effects; Biochemical Journal 2011 440 (3) p. 301-308), see results in Table 3. The affinities are reported relative to affinity of human insulin for insulin receptor A (100%).

TABLE 3

| In vitro data | |
|---|---|
| Compound of Example No. | Insulin receptor affinity [IC50 relative to HI (%)] Mean Value |
| 5.1 | 5.07 |
| 5.2 | 6.10 |
| 5.3 | 2.57 |
| 5.4 | 2.14 |
| 5.5 | 3.34 |
| 5.6 | 5.07 |
| 5.7 | 2.43 |
| 5.8 | 10.58 |
| 5.9 | 2.96 |
| 5.10 | 2.47 |
| 5.11 | 1.72 |
| 5.12 | 1.85 |
| 5.13 | 5.55 |
| 5.14 | 5.37 |
| 5.15 | 3.68 |
| 5.16 | 3.86 |
| 5.17 | 3.98 |
| 5.18 | 2.78 |
| 5.19 | 4.00 |
| 5.20 | 5.49 |
| 5.21 | 2.10 |
| 5.22 | 3.56 |
| 5.23 | 4.70 |
| 5.24 | 4.60 |
| 5.25 | 4.49 |
| 5.26 | 3.95 |
| 5.27 | 1.07 |
| 5.29 | 3.06 |
| 5.31 | 0.47 |
| 5.32 | 2.16 |
| 5.33 | 3.85 |

The data show that all of the tested compounds of the invention bind to the insulin receptor in the range 0.5 to 10% relative to human insulin. These affinities are considered adequate to facilitate blood glucose lowering following in vivo administration. Furthermore, as can be seen from example 9, the compounds of the invention are also agonists of the insulin receptor. From example 8 it can be seen that the compounds of the invention all potently can lower blood glucose after subcutaneous administration to rats.

Example 7: PK Studies

Insulin-Fc conjugates were tested in vivo by intravenous and subcutaneous administration to SD rats. Blood samples were collected and the insulin-Fc concentrations were measured by immuno-assay. The resulting mean residence time and half-life values from intravenous and subcutaneous dosing are shown in Table 4.

TABLE 4

Rat iv/sc PK data

| Compound of Example No. | PK rat iv [$T\frac{1}{2}$ (h)] Mean Value | PK rat sc [$T\frac{1}{2}$ (h)] Mean Value |
| --- | --- | --- |
| 5.1 | 32.6 | 39.1 |
| 5.2 | 42.8 | 44.0 |
| 5.3 | 35.6 | 33.1 |
| 5.4 | 26.4 | 32.2 |
| 5.5 | 44.7 | 35.7 |
| 5.6 | 31.1 | 30.1 |
| 5.7 | 36.5 | 32.3 |
| 5.8 | 36.3 | 36.6 |
| 5.9 | 36.3 | 31.7 |
| 5.11 | 30.7 | 33.1 |
| 5.12 | 23.3 | 25.1 |
| 5.13 | 53.3 | 43.4 |
| 5.14 | 46.6 | 54.0 |
| 5.15 | 58.4 | 67.6 |
| 5.16 | 25.7 | 36.2 |
| 5.17 | 46.2 | 40.3 |
| 5.18 | 24.9 | 28.0 |
| 5.19 | 30.8 | 55.0 |
| 5.21 | 43.2 | 38.8 |
| 5.23 | 57.1 | 73.2 |
| 5.24 | 50.6 | 51.9 |
| 5.25 | 47.7 | 44.5 |
| 5.26 | 49.8 | 53.5 |
| 5.27 | 40.7 | 50.4 |

It is concluded that the insulin-Fc conjugates of the invention all display very long PK profiles when administered to rats.

Example 8: PD Studies

The pharmacodynamic effect of the Insulin Fc conjugates of the examples were investigated in normal male Sprague-Dawley rats weighing approx. 350 g at study start.

Animals had free access to food and water during the experiment period. They were dosed subcutaneously in the neck region with a dose of 30 nmol/kg (unless otherwise stated in the figures below). Blood samples for blood glucose and plasma insulin analysis were collected from the tongue veins up to 10 days post dosing. Blood glucose was measured using Biosen S Line (EKF).

Figure 2:
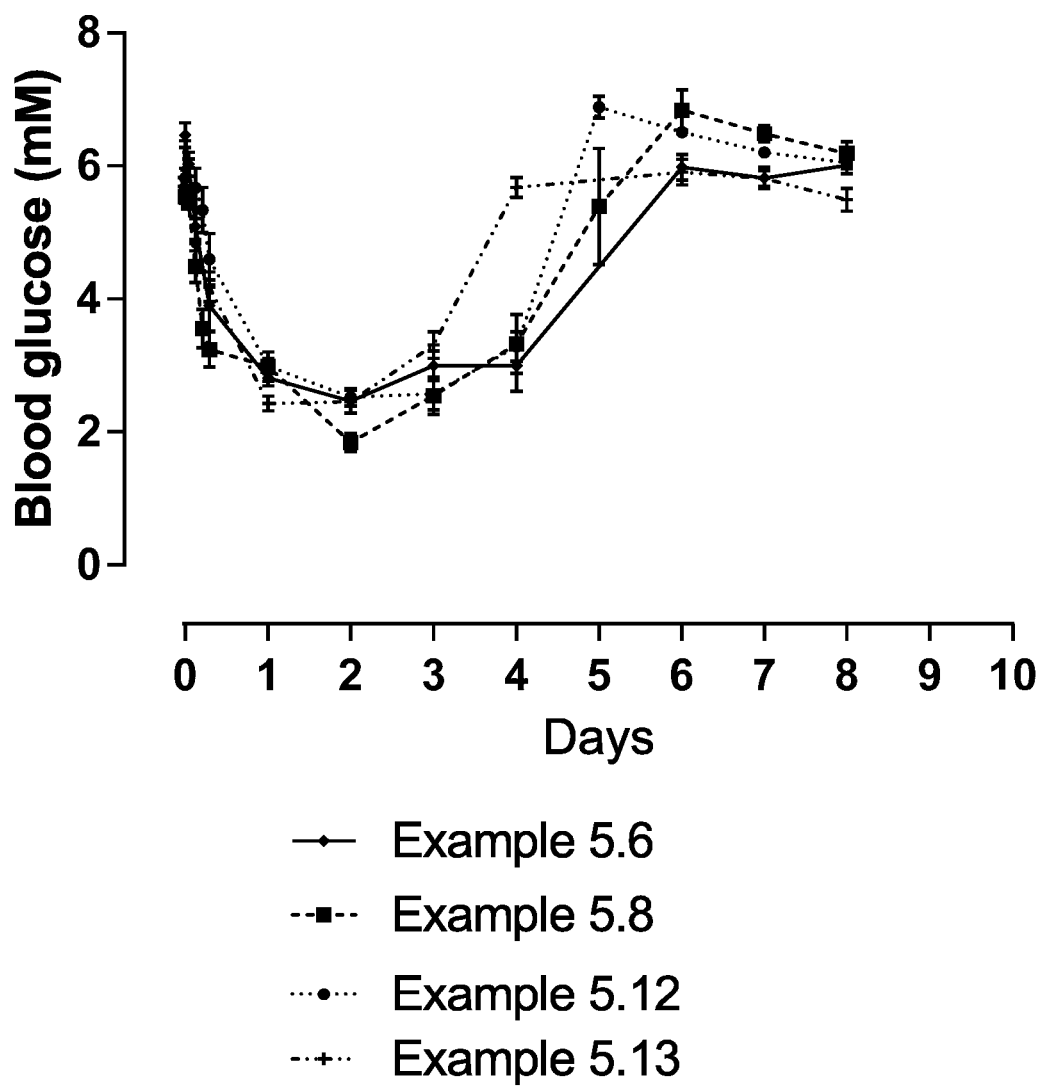
FIG. 2 shows the blood glucose lowering effect of the compounds of Examples 5.6, 5.8, 5.12, and 5.13. The compounds were administered (sc) to fed Sprague-Dawley rats in a dose of 30 nmol/kg.
Figure 3:
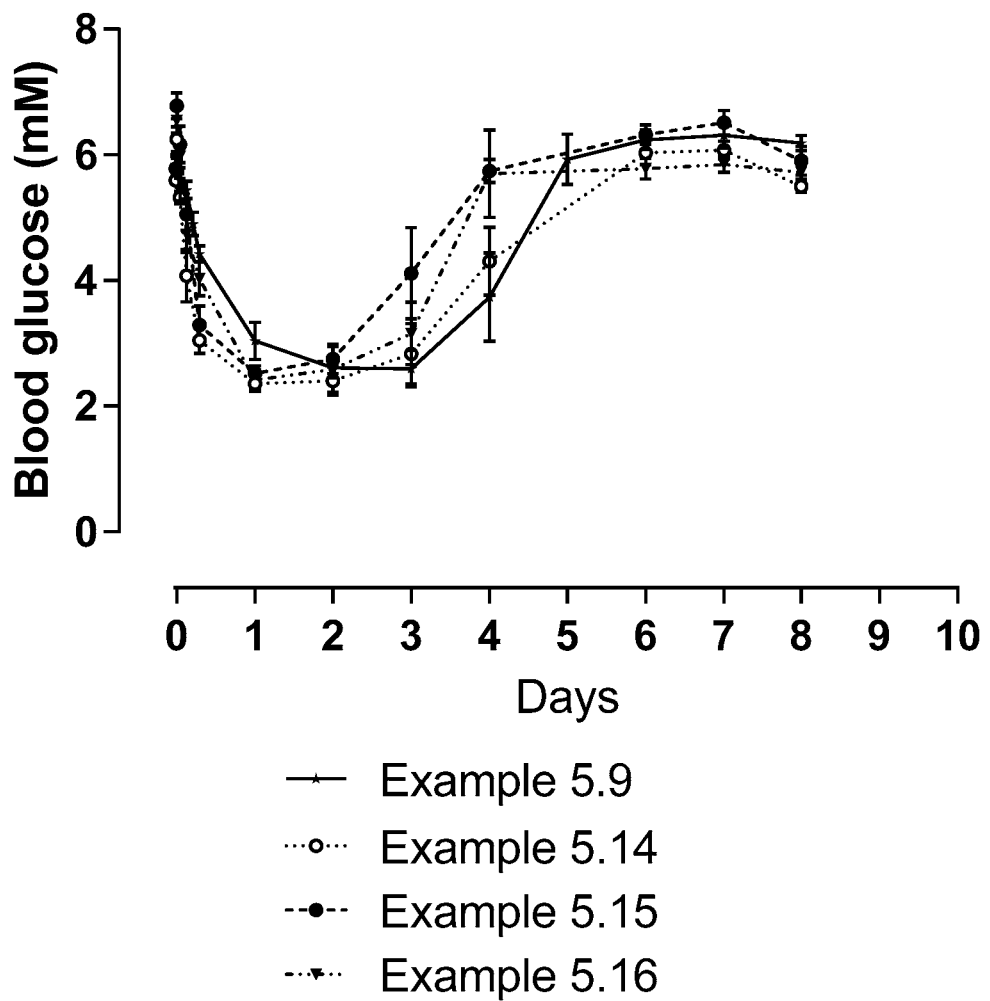
FIG. 3 shows the blood glucose lowering effect of the compounds of Examples 5.9, 5.14, 5.15, and 5.16. The compounds were administered (sc) to fed Sprague-Dawley rats in a dose of 30 nmol/kg.
Figure 4:
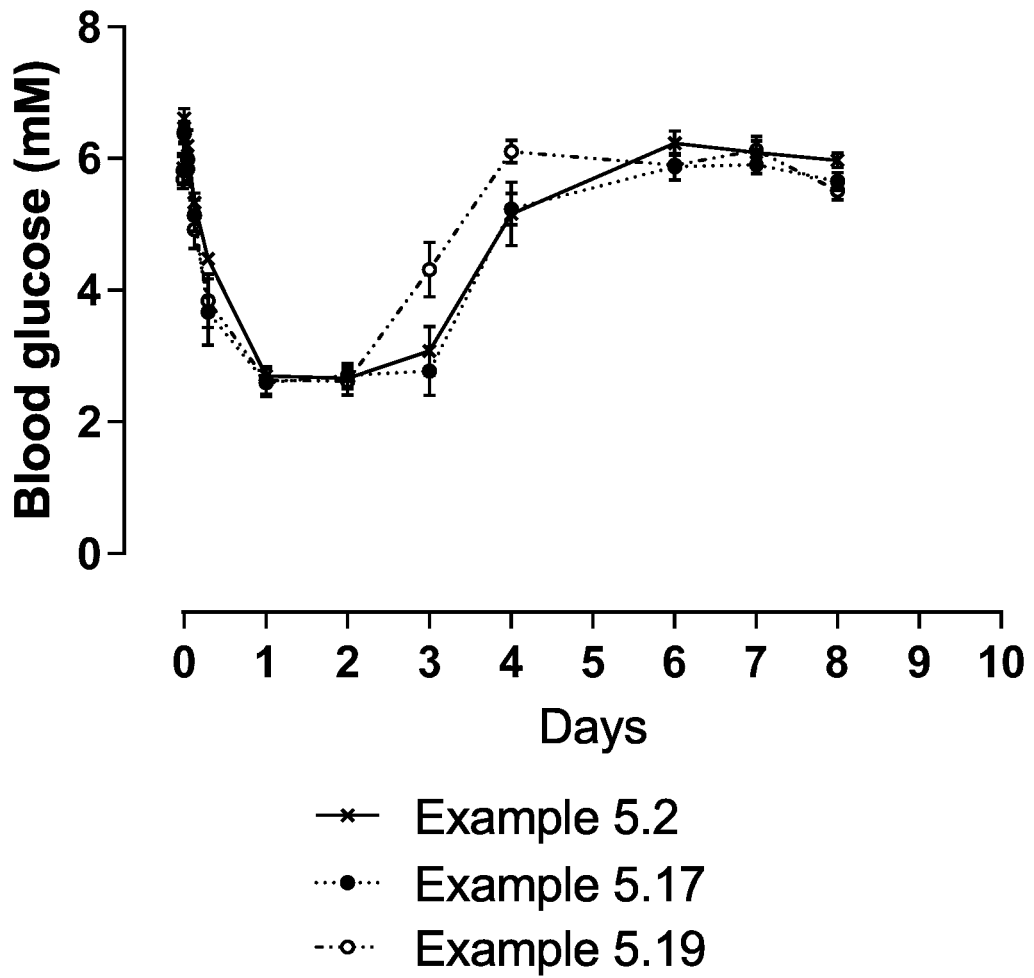
FIG. 4 shows the blood glucose lowering effect of the compounds of Examples 5.2, 5.17, and 5.19. The compounds were administered (sc) to fed Sprague-Dawley rats in a dose of 30 nmol/kg.
Figure 5:
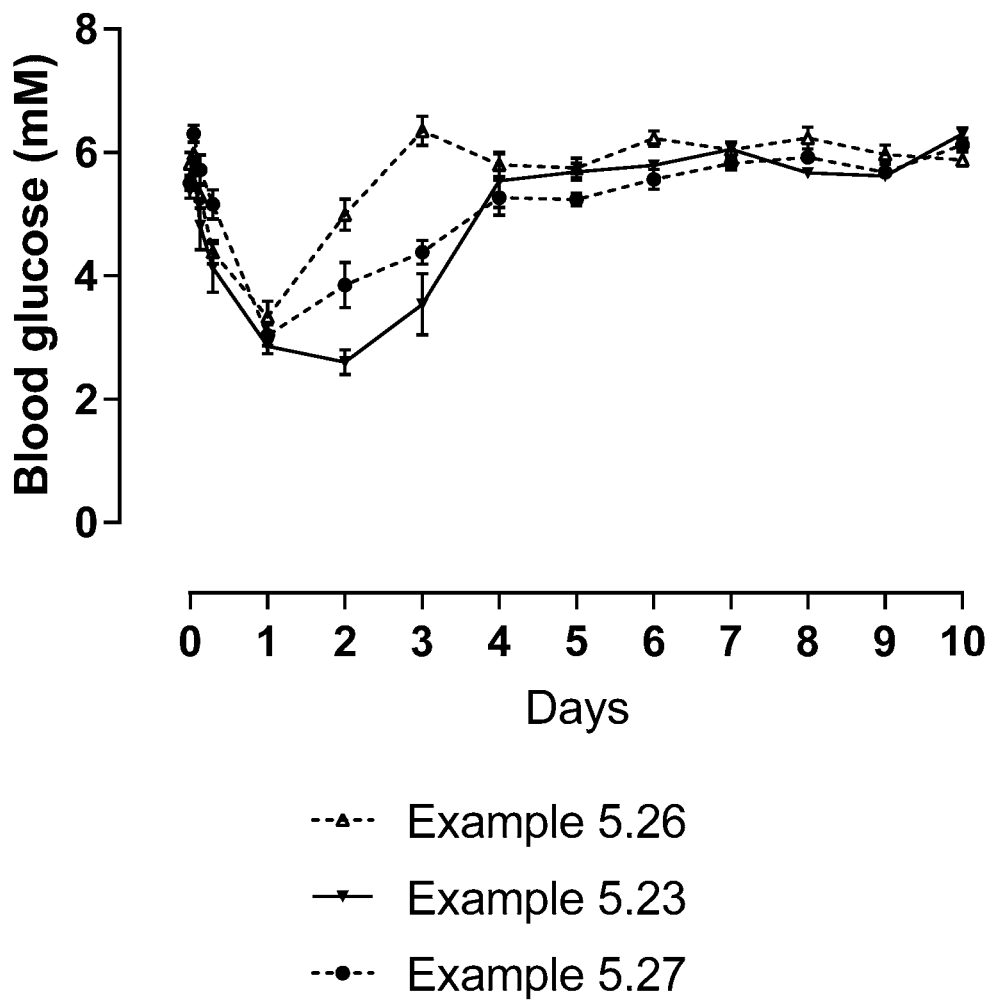
FIG. 5 shows the blood glucose lowering effect of the compounds of Examples 5.26, 5.23, and 5.27. The compounds were administered (sc) to fed Sprague-Dawley rats in a dose of 30 nmol/kg.
Figure 6:
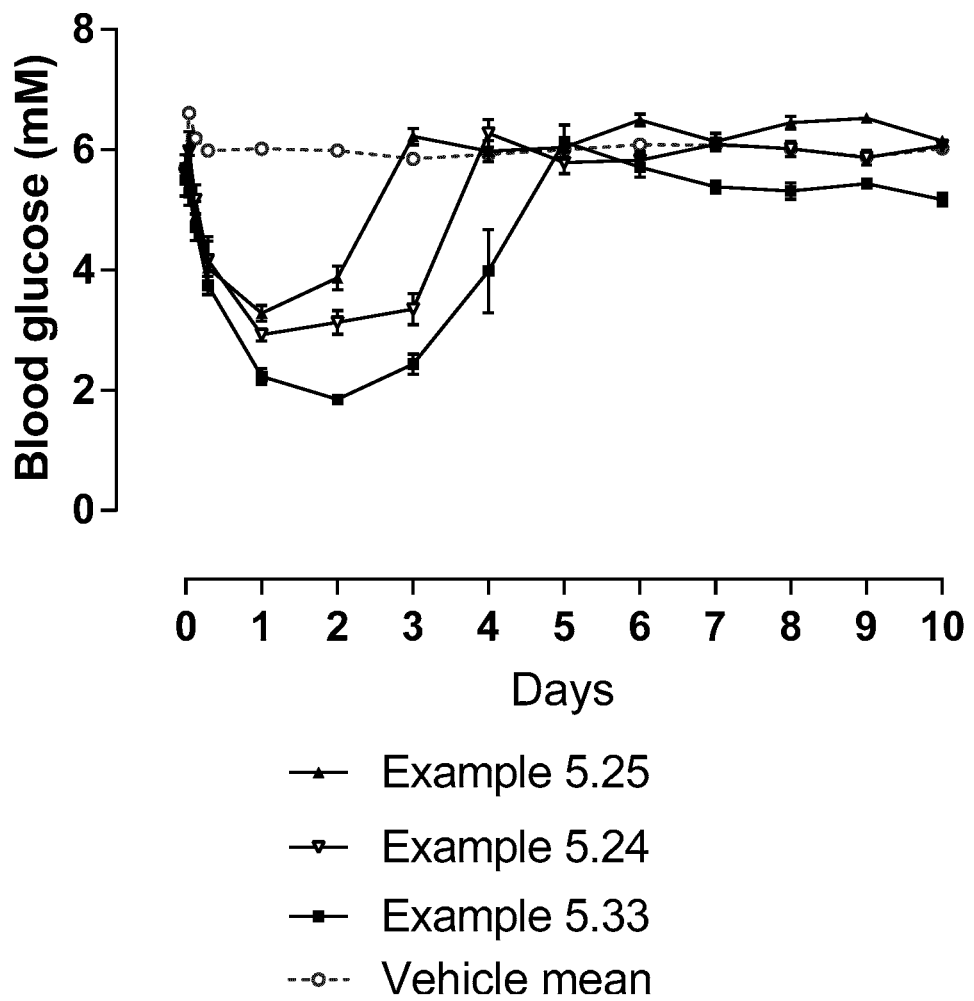
FIG. 6 shows the blood glucose lowering effect of the compounds of Examples 5.24, 5.25, 5.33 and of vehicle. The compounds were administered (sc) to fed Sprague-Dawley rats in a dose of 30 nmol/kg.
Figure 7:
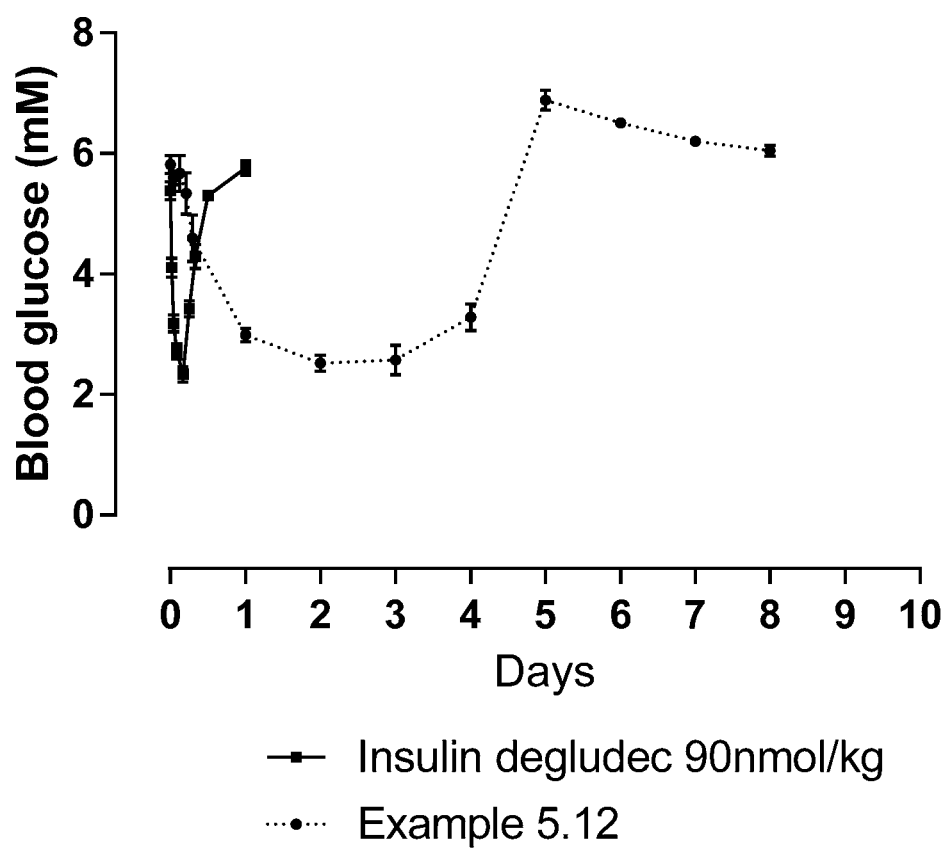
FIG. 7 shows the blood glucose lowering effect of the compound of Example 5.12 and insulin decludec. The compound was administered (sc to fed Sprague-Dawley rats in a dose of 30 nmol/kg (unless otherwise indicated).

Blood glucose profiles are shown in FIG. 1-7.

In addition to the figures, the blood glucose profiles are also shown in tables 5a-g below.

TABLE 5a

Average blood glucose profiles (from FIG. 1), dose 30 nmol/kg unless otherwise stated, following subcutaneous dosing of compounds of the invention to rats.

| Time (days) | Ex 5.21 (mM, dose: 300 nmol/kg) | Ex 5.5 (mM) | Ex 5.1 (mM) | Ex 5.7 (mM) |
| --- | --- | --- | --- | --- |
| 0 | 5.254 | 5.266 | 6.68 | 5.918 |
| 0.006944 | 5.972 | | | |
| 0.041667 | 4.224 | 5.276 | 5.888 | 5.682 |
| 0.125 | 3.238 | 4.894 | 4.988 | 4.502 |
| 0.208333 | 2.842 | 4.422 | | 3.974 |
| 0.291667 | 3.212 | 4.358 | 3.752 | 3.428 |
| 0.3336 | 3.494 | | | |
| 1 | 2.58 | 3.106 | 2.524 | 2.758 |
| 2 | 2.118 | 2.33 | 2.036 | 2.15 |
| 3 | 2.074 | 2.786 | 2.964 | 2.3 |
| 4 | 2.37 | 4.764 | 3.244 | 2.81 |
| 5 | 2.478 | 5.842 | | 4.404 |
| 6 | 4.534 | 6.016 | 6.508 | 6.702 |
| 7 | 5.588 | 5.76 | 6.18 | 6.518 |
| 8 | 6.552 | 5.794 | 5.996 | 6.33 |
| 9 | 5.644 | | | |
| 10 | 5.788 | | | |

TABLE 5b

Average blood glucose profiles (from FIG. 2), dose 30 nmol/kg unless otherwise stated, following subcutaneous dosing of compounds of the invention to rats.

| Time (days) | Ex 5.6 (mM) | Ex 5.8 (mM) | Ex 5.12 (mM) | Ex 5.13 (mM) |
| --- | --- | --- | --- | --- |
| 0 | 6.46 | 5.538 | 5.816 | 6.384 |
| 0.041667 | 6.024 | 5.44 | 5.598 | 5.976 |
| 0.125 | 5.092 | 4.488 | 5.674 | 4.892 |
| 0.208333 | | 3.55 | 5.338 | |
| 0.291667 | 3.90 | 3.238 | 4.598 | 4.184 |
| 1 | 2.808 | 2.978 | 2.986 | 2.428 |
| 2 | 2.464 | 1.844 | 2.524 | 2.452 |
| 3 | 2.996 | 2.545 | 2.576 | 3.308 |
| 4 | 2.996 | 3.325 | 3.284 | 5.676 |
| 5 | | 5.39 | 6.884 | |
| 6 | 5.98 | 6.8425 | 6.506 | 5.908 |
| 7 | 5.82 | 6.4875 | 6.202 | 5.812 |
| 8 | 6.012 | 6.1875 | 6.046 | 5.492 |

TABLE 5c

Average blood glucose profiles (from FIG. 3), dose 30 nmol/kg unless otherwise stated, following subcutaneous dosing of compounds of the invention to rats.

| Time (days) | Ex 5.9 (mM) | Ex 5.14 (mM) | Ex 5.15 (mM) | Ex 5.16 (mM) |
| --- | --- | --- | --- | --- |
| 0 | 5.812 | 6.248 | 6.748 | 6.544 |
| 0.041667 | 5.448 | 5.32 | 6.168 | 5.972 |
| 0.125 | 5.438 | 4.08 | 5.052 | 4.74 |
| 0.208333 | 4.902 | | | |
| 0.291667 | 4.426 | 3.048 | 3.292 | 4.028 |
| 1 | 3.044 | 2.356 | 2.524 | 2.42 |
| 2 | 2.614 | 2.4 | 2.752 | 2.592 |
| 3 | 2.594 | 2.832 | 4.116 | 3.156 |
| 4 | 3.734 | 4.304 | 5.744 | 5.7 |
| 5 | 5.932 | | | |
| 6 | 6.244 | 6.032 | 6.32 | 5.784 |
| 7 | 6.312 | 6.076 | 6.516 | 5.848 |
| 8 | 6.186 | 5.5 | 5.904 | 5.72 |

TABLE 5d

Average blood glucose profiles (from FIG. 4), dose 30 nmol/kg unless otherwise stated, following subcutaneous dosing of compounds of the invention to rats.

| Time (days) | Ex 5.2 (mM) | Ex 5.17 (mM) | Ex 5.19 (mM) |
|---|---|---|---|
| 0 | 6.608 | 6.372 | 6.4 |
| 0.041667 | 6.196 | 5.84 | 5.988 |
| 0.125 | 5.328 | 5.14 | 4.92 |
| 0.291667 | 4.48 | 3.672 | 3.84 |
| 1 | 2.7 | 2.6 | 2.632 |
| 2 | 2.66 | 2.704 | 2.62 |
| 3 | 3.08 | 2.772 | 4.312 |
| 4 | 5.156 | 5.232 | 6.104 |
| 6 | 6.232 | 5.88 | 5.9 |
| 7 | 6.092 | 5.908 | 6.128 |
| 8 | 5.972 | 5.656 | 5.512 |

TABLE 5e

Average blood glucose profiles (from FIG. 5), dose 30 nmol/kg unless otherwise stated, following subcutaneous dosing of compounds of the invention to rats.

| Time (days) | Ex 5.26 (mM) | Ex 5.23 (mM) | Ex 5.27 (mM) |
|---|---|---|---|
| 0 | 5.82 | 5.384 | 5.504 |
| 0.041667 | 5.984 | 5.768 | 6.308 |
| 0.125 | 5.3 | 4.808 | 5.72 |
| 0.291667 | 4.384 | 4.136 | 5.164 |
| 1 | 3.332 | 2.86 | 3.036 |
| 2 | 4.992 | 2.6 | 3.852 |
| 3 | 6.352 | 3.536 | 4.384 |
| 4 | 5.804 | 5.544 | 5.272 |
| 5 | 5.752 | 5.684 | 5.236 |
| 6 | 6.232 | 5.796 | 5.564 |
| 7 | 6.048 | 6.056 | 5.824 |
| 8 | 6.236 | 5.672 | 5.924 |
| 9 | 5.972 | 5.62 | 5.68 |
| 10 | 5.88 | 6.308 | 6.12 |

TABLE 5f

Average blood glucose profiles (from FIG. 6), dose 30 nmol/kg unless otherwise stated, following subcutaneous dosing of compounds of the invention to rats.

| Time (days) | Ex 5.25 (mM) | Ex 5.24 (mM) | Ex 5.33 (mM) | Vehicle |
|---|---|---|---|---|
| 0 | 5.724 | 5.604 | 5.496 | 5.404 |
| 0.041667 | 6.104 | 5.98 | 5.284 | 6.232 |
| 0.125 | 4.9 | 5.172 | 4.716 | 5.784 |
| 0.291667 | 4.032 | 4.164 | 3.744 | 5.86 |
| 1 | 3.28 | 2.924 | 3.744 | 5.668 |
| 2 | 3.864 | 3.128 | 2.232 | 6.128 |
| 3 | 6.224 | 3.352 | 1.844 | 5.912 |
| 4 | 5.976 | 6.272 | 2.432 | 5.436 |
| 5 | 6.036 | 5.788 | 3.98 | 5.544 |
| 6 | 6.496 | 5.824 | 6.132 | 5.892 |
| 7 | 6.14 | 6.092 | 5.712 | 5.852 |
| 8 | 6.452 | 6.016 | 5.38 | 5.992 |
| 9 | 6.528 | 5.872 | 5.316 | 5.828 |
| 10 | 6.144 | 6.072 | 5.44 | 5.796 |

TABLE 5g

Average blood glucose profiles (from FIG. 7), dose 30 nmol/kg unless otherwise stated, following subcutaneous dosing of compounds of the invention to rats.

| Time (days) | Ex 5.12 (mM) | Insulin degludec (mM, dose: 90 nmol/kg) |
|---|---|---|
| 0 | 5.516 | 5.382 |
| 0.020833 |  | 4.104 |
| 0.041667 | 6.16 | 3.182 |
| 0.083333 |  | 2.718 |
| 0.125 | 4.608 |  |
| 0.166667 |  | 2.336 |
| 0.25 |  | 3.424 |
| 0.291667 | 3.988 |  |
| 0.3336 |  | 4.292 |
| 0.5 |  | 5.302 |
| 1 | 2.88 | 5.758 |
| 2 | 2.348 |  |
| 3 | 2.972 |  |
| 4 | 6.028 |  |
| 5 | 6.06 |  |
| 6 | 5.74 |  |
| 7 | 5.716 |  |
| 8 | 5.568 |  |
| 9 | 5.204 |  |
| 10 | 5.556 |  |

It can be concluded from the data obtained and shown in FIG. 1 to FIG. 7, and in tables 5a-g, that all the compounds of the invention very potently were able to lower blood glucose over long time (3-5 days) in rats. For comparison, insulin degludec, marketed as Tresiba® as an ultra-long-acting insulin, at a 3-fold higher dose was only able to lower blood glucose for less than half a day.

Example 9: Insulin-Stimulated Lipogenesis

Insulin-stimulated lipogenesis was measured in isolated rat adipocytes in presence of 1% HSA as described in Moody A J, Stan M A, Stan M, Gliemann J. A Simple Free Fat Cell Bioassay for Insulin. Hormone And Metabolic Research. 1974; 6(1):12-6, see results in Table 6. The activities are reported relative to the activity of human insulin (100%).

TABLE 6

Lipogenesis data

| Compound of Example No. | Lipogenesis in rat adipocytes [Potency (%)] Mean Value |
|---|---|
| 5.21 | 0.95 |
| 5.3 | 0.55 |
| 5.4 | 0.36 |
| 5.5 | 2.21 |
| 5.1 | 6.69 |
| 5.7 | 1.88 |
| 5.8 | 5.31 |
| 5.11 | 0.39 |
| 5.12 | 2.35 |
| 5.9 | 3.02 |
| 5.13 | 3.07 |
| 5.2 | 3.57 |
| 5.17 | 4.39 |
| 5.14 | 4.86 |
| 5.18 | 0.87 |
| 5.15 | 3.68 |
| 5.16 | 4.34 |
| 5.24 | 3.83 |
| 5.20 | 5.41 |
| 5.19 | 3.02 |
| 5.26 | 3.23 |

TABLE 6-continued

Lipogenesis data

| Compound of Example No. | Lipogenesis in rat adipocytes [Potency (%)] Mean Value |
|---|---|
| 5.25 | 2.08 |
| 5.23 | 5.36 |
| 5.22 | 4.64 |
| 5.29 | 2.64 |
| 5.31 | 0.60 |
| 5.33 | 5.44 |
| 5.32 | 3.72 |

It is concluded that the lipogenesis activity data are in the same range as the corresponding insulin receptor affinity data, and, consequently, that the insulin-Fc conjugates of the invention all possess insulin agonist activities.

The invention claimed is:

1. An oligomer extended insulin-Fc conjugate represented by Formula I':

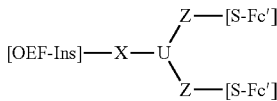

wherein

Ins represents an analogue of human insulin, wherein said insulin analogue is a two-chain insulin molecule comprising an A- and a B-chain;

OEF indicates a polar recombinant extension fused to the insulin A-chain C-terminus, or fused to the insulin B-chain N-terminus, wherein the extension comprises a combination of (i) and (ii):
(i) one or more of the following amino acid residues: Ala (A), Asp (D), Glu (E), Gly (G), Pro (P), Gln (Q), Ser (S), and Thr (T); and
(ii) a lysine (K) residue, to render an [OEF-Ins] construct;

the [OEF-Ins] construct is connected to the trivalent linking group X-U(-Z)$_2$ via the epsilon amino group of a lysine (K) residue;

X represents a covalent bond, or a divalent linking group, connecting [OEF-Ins] and U;

U represents a central trivalent linking unit, connecting the two Z-[S-Fc'] groups to X; or, in case X represents a covalent bond, U is connecting the two Z-[S-Fc'] groups to the epsilon amino group of a lysine residue in the [OEF-Ins] construct;

Z is absent or represents a divalent linking group connecting the central linking unit (U) to a thiol moiety (S) of a monomer Fc polypeptide (Fc'), or a fragment thereof; or, in case Z is absent, U is connected directly to [S-Fc']; and

[S-Fc'] represents an Fc' component, wherein the Fc' component is a monomer Fc polypeptide or a fragment thereof, with the S representing a sulphur atom originating from a cysteine (C) residue comprised within the Fc' component.

2. The oligomer extended insulin-Fc conjugate of claim 1, wherein X represents
a covalent bond;
a divalent linker of the structure —C(O)—(CH$_2$)$_1$—C(O)—, wherein l represents an integer in the range of from 1 to 20; or
a divalent linker of the structure —C(O)—(CH$_2$)$_o$—NH—C(O)—, wherein o represents an integer in the range of from 1 to 20.

3. The oligomer extended insulin-Fc conjugate according to claim 1, wherein the central trivalent linking unit (U) and divalent linking group (Z) are represented by Formula IV'

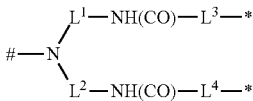

wherein,
N is a nitrogen atom and represents the central linking unit (U) according to Formula I';

L$_1$-NH(CO)-L$_3$ and L$_2$-NH(CO)-L$_4$, respectively, represents the divalent linking group (Z) according to Formula I';
* indicates the point of attachment to a sulphur atom originating from a disulphide bridge of Fc (i.e. the [S-Fc'] moiety according to Formula I');
# indicates the point of attachment to X; and
L$^1$ and L$^2$, independently of each other, represent —(CH$_2$)$_{m1}$—; wherein
m1 represents an integer in the range of from 1 to 6; and
L$^3$ and L$^4$, independently of each other, represent —(CH$_2$)$_{n1}$—;
wherein n1 represents an integer in the range of from 1 to 6.

4. The oligomer extended insulin-Fc conjugate according to claim 1, wherein X represents a covalent bond and wherein U—(—Z)$_2$ represents a 3,5-disubstituted benzoyl moiety as illustrated by Formula VII:

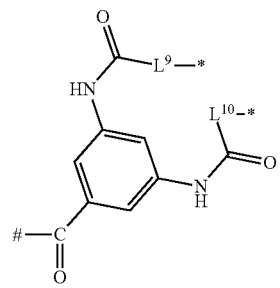

wherein
indicates the point of attachment to the sulphur atom of Formula I';
# indicates the point of attachment to the epsilon amino group in a lysine residue in the [OEF-Ins] construct; and
L$^9$ and L$^{10}$, independently of each other, represents —(CH$_2$)$_{n3}$—; wherein
n3 represents an integer in the range of from 1 to 6.

5. The oligomer extended insulin-Fc conjugate of claim 1, wherein
Ins represents an analogue of human insulin containing one or more of the following substitutions: A 14A or A 14E, A21G or A21Q, B3Q, B16E or B16H, B25H, B29R, and desB30.

6. The oligomer extended insulin-Fc conjugate of claim 1, wherein
OEF represents a polar recombinant OEF extension fused to the insulin A-chain C-terminus, or fused to the insulin B-chain N-terminus, which extension includes one or more of the following amino acid residues: Ala (A), Glu (E), Gly (G), Pro (P), and Gln (Q), in a combination with a lysine (K) residue, to render an [OEF-Ins] construct with a total number of amino acid residues of the OEF in the range of 15 to 110.

7. The oligomer extended insulin-Fc conjugate of claim 1, wherein Fc' represents a monomer of an IgG1 Fc polypeptide, of an IgG2 Fc polypeptide, of an IgG4 Fc polypeptide, or a fragment thereof.

8. The oligomer extended insulin-Fc conjugate of claim 1, selected from the group consisting of
(A14E, A21G, A22(GQEP)$_{19}$, A98KK^, A99P, B25H, B29R, desB30 human insulin)/(227A, 234A, 235K hIgG4-Fc(228-447))4-[bis[2-[(2-acetyl)amino]ethyl]amino]-4-oxo-butanoyl conjugate;

A14E, A21G, A22(GQEP)₁₉, A98KK^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(-78K^), B(-77P), B(-1)(GQAPGQAPGQEP)₆-GQAP, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, B(-78K^), B(-77P), B(-1)(GQEP)₁₉, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98KK^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)₁₉, A98K^, A99P, B3Q, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)₆, A46K^, A47P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)₁₂, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQAPGQEP)₆, A70K^, A71P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, A21G, A22(GQEP)₃, A34G, A35Q, A36E, A37K^, A38P, B25H, B29R, desB30 human insulin/(227A, 234A, 235K hIgG4-Fc(228-447))4-[bis[2-[(2-acetyl)amino]ethyl]amino]-4-oxo-butanoyl conjugate;

A14E, B(-78K^), B(-77P), B(-1)(GQEP)₁₉, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQEP)₁₉, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQEP)₆, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQEP)₁₉, A98K^, A99P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)₁₉, A98K^, A99P, B25H, B29R, desB30 human insulin)/(227A, 234A, 235K, 297E, 315Q, 384Q, des447 hIgG4-Fc(228-447))6-[bis[2-[(2-acetyl)amino]ethyl]amino]-6-oxo-hexanoyl conjugate;

A14E, A21G, A22(GQEP)₁₂, A70K^, A71P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, B(-78K^), B(-77P), B(-1)(GQAP)₁₉, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98K^, A99P, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQAPGQEP)₆-GQAP, A122K^, A123P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21Q, A22(G)₁₈, A40K^, B25H, B29R, desB30 human insulin/(227A, 234A, 235K hIgG4-Fc(228-447))4-[bis[2-[(2-acetyl)amino]ethyl]amino]-4-oxo-butanoyl conjugate;

(A14E, A21G, A22(GQAP)₂₄, A118G, A119Q, A120A, A121K^, A122P, B25H, B29R, desB30 human insulin)/(227A, 234A, 235K, 297E, 315Q, 384Q, des447 hIgG4-Fc(228-447))3,5-bis[(2-acetyl)amino]benzoyl conjugate;

(A14E, A21G, A22(GQAP)₂₄, A118G, A119Q, A120A, A121K^, A122P, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQAPGQAPGQEP)₆-GQAP, A98K^, A99P, B3Q, B25H, B29R, desB30 human insulin/(227A, 234A, 235K, 297E, 315Q, 384Q, des447 hIgG4-Fc(228-447))4-[bis[2-[(2-acetyl)amino]ethyl]carbamoylamino]butanoyl conjugate;

(A14A, A21G, A22(GQAP)₁₈, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)₁₈, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A1(N(alpha)acetyl), A14E, A21G, A22(GQAP)₁₉, A98K^, A99P, B1(N(alpha)acetyl), B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A21G, A22(GQAP)₁₈, A94G, A95Q, A96A, A97K^, A98P, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

(A14E, A21G, A22(GQAP)₂₄, A118G, A119Q, A120A, A121K^, A122P, B29R, desB30 human insulin)/(227A, 234A, 235K, 297E, 315Q, 384Q, des447 hIgG4-Fc(228-447))3,5-bis[(2-acetyl)amino]benzoyl conjugate;

A14E, A21G, A22(GQAP)₁₈, A94G, A95Q, A96A, A97K^, A98P, B16E, B25H, B29R, desB30 human insulin)/(227A, 234A, 235K, 297E, 315Q, 384Q, des447 hIgG4-Fc(228-447))3,5-bis[(2-acetyl)amino]benzoyl conjugate;

(A14E, A21G, A22(GQAP)$_{18}$, A94G, A95Q, A96A, A97K^, A98P, B16E, B25H, B29R, desB30 human insulin)/(227A, 234A, 235K, 297E, 315Q, 384Q, des447 hIgG4-Fc(228-447))4-[bis[2-[(2-acetyl)amino]ethyl]amino]-4-oxo-butanoyl conjugate;

A14E, A21G, A22(GQEP)$_6$, A46K^, A47P, B25H, B29R, desB30 human insulin/(227A, 234A, 235K, 297E, 315Q, 384Q, des447 hIgG4-Fc(228-447))4-[bis[2-[(2-acetyl)amino]ethyl]amino]-4-oxo-butanoyl conjugate; and (A14E, A21G, A22(GQEP)$_{19}$, 98K^, A99P, B25H, B29R, desB30 human insulin)/(226A, 227G, 228P, 234A, 235K, des447 hIgG4-Fc(228-447))3,5-bis[(2-acetyl)amino]benzoyl conjugate.

9. A pharmaceutical composition comprising the insulin-Fc conjugate of claim 1 and one or more pharmaceutically acceptable carriers or diluents.

10. A method of treatment or alleviation of a metabolic disease or disorder or condition of a living animal body, including a human, the method comprising administering to such a living animal body in need thereof a therapeutically effective amount of the oligomer extended insulin-Fc conjugate of claim 1.

11. The method of claim 10, wherein the metabolic disease or disorder is Type 1 diabetes or Type 2 diabetes.

12. The oligomer extended insulin-Fc conjugate of claim 1, wherein the Fc' component is aglycosylated.

13. The oligomer extended insulin-Fc conjugate of claim 1, wherein the Fc' component is a fragment of a hIgG4 derived Fc sequence, starting at position 228 and ending at position 447, which sequence contains one or more extensions and/or substitutions selected from the group of 226A or 226G, 227A or 227G, 228P, 234A, 235A or 235K, N297E or N297Q, 315Q, 384Q, and des447.

14. The oligomer extended insulin-Fc conjugate of claim 13, wherein the Fc' component is 226A, 227G, 228P, 234A, 235K, des447 hIgG4-Fc(228-447).

15. The oligomer extended insulin-Fc conjugate of claim 1, wherein OEF indicates a polar recombinant extension fused to the insulin A-chain C-terminus.

16. The oligomer extended insulin-Fc conjugate of claim 1, wherein OEF indicates a polar recombinant extension fused to the insulin B-chain N-terminus.

17. The oligomer extended insulin-Fc conjugate of claim 1, wherein X represents a covalent bond.

18. The oligomer extended insulin-Fc conjugate of claim 1, wherein the [OEF-Ins] construct is connected to the trivalent linking group X-U(-Z)$_2$ via the epsilon amino group of the K residue of the extension.

19. A method of lowering blood glucose in a subject in need thereof, the method comprising administering to the subject a therapeutically effective amount of the oligomer extended insulin-Fc conjugate of claim 1.

* * * * *

SEQUENCE LISTING

```
<160> NUMBER OF SEQ ID NOS: 76

<210> SEQ ID NO 1
<211> LENGTH: 220
<212> TYPE: PRT
<213> ORGANISM: Homo sapiens
<220> FEATURE:
<221> NAME/KEY: PEPTIDE
<222> LOCATION: (1)..(220)
<223> OTHER INFORMATION: Human IgG1-Fc(228-447)

<400> SEQUENCE: 1

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Glu Glu Met Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 2
<211> LENGTH: 227
<212> TYPE: PRT
<213> ORGANISM: Homo sapiens
```

```
<220> FEATURE:
<221> NAME/KEY: PEPTIDE
<222> LOCATION: (1)..(227)
<223> OTHER INFORMATION: Human IgG2-Fc(220-446)

<400> SEQUENCE: 2

Arg Lys Cys Cys Val Glu Cys Pro Pro Cys Pro Ala Pro Pro Val Ala
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Phe
65                  70                  75                  80

Arg Val Val Ser Val Leu Thr Val Val His Gln Asp Trp Leu Asn Gly
                85                  90                  95

Lys Glu Tyr Lys Cys Lys Val Ser Asn Lys Gly Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ser Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 220
<212> TYPE: PRT
<213> ORGANISM: Homo sapiens
<220> FEATURE:
<221> NAME/KEY: PEPTIDE
<222> LOCATION: (1)..(220)
<223> OTHER INFORMATION: Human IgG4-Fc(228-447)

<400> SEQUENCE: 3

Ser Cys Pro Ala Pro Glu Phe Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser Gln Glu Asp Pro Glu Val Gln Phe
        35                  40                  45

Asn Trp Tyr Val Asp Gly Val Glu Val His Asn Ala Lys Thr Lys Pro
    50                  55                  60

Arg Glu Glu Gln Phe Asn Ser Thr Tyr Arg Val Val Ser Val Leu Thr
65                  70                  75                  80
```

-continued

```
Val Leu His Gln Asp Trp Leu Asn Gly Lys Glu Tyr Lys Cys Lys Val
                85                  90                  95

Ser Asn Lys Gly Leu Pro Ser Ser Ile Glu Lys Thr Ile Ser Lys Ala
            100                 105                 110

Lys Gly Gln Pro Arg Glu Pro Gln Val Tyr Thr Leu Pro Pro Ser Gln
        115                 120                 125

Glu Glu Met Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Glu
            180                 185                 190

Gly Asn Val Phe Ser Cys Ser Val Met His Glu Ala Leu His Asn His
        195                 200                 205

Tyr Thr Gln Lys Ser Leu Ser Leu Ser Leu Gly Lys
    210                 215                 220

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Human IgG1 hinge

<400> SEQUENCE: 4

Pro Lys Ser Cys Asp Lys Thr His Thr Cys Pro Pro Cys Pro
1               5                   10

<210> SEQ ID NO 5
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Human IgG2 hinge

<400> SEQUENCE: 5

Arg Lys Cys Cys Val Glu Cys Pro Pro Cys Pro
1               5                   10

<210> SEQ ID NO 6
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Human IgG4 hinge

<400> SEQUENCE: 6

Glu Ser Lys Tyr Gly Pro Pro Cys Pro Ser Cys Pro
1               5                   10

<210> SEQ ID NO 7
<211> LENGTH: 99
<212> TYPE: PRT
<213> ORGANISM: Artificial Sequence
<220> FEATURE:
<223> OTHER INFORMATION: A-chain of OEF-Ins-1, and OEF-Ins-5.
```

<400> SEQUENCE: 7

Gly Ile Val Glu Gln Cys Cys Thr Ser Ile Cys Ser Leu Glu Gln Leu
1               5                   10                  15

Glu Asn Tyr Cys Gly Gly Gln Glu Pro Gly Gln Glu Pro Gly Gln Glu
            20                  25                  30

Pro Gly Gln Glu Pro Gly Gln Glu Pro Gly Gln Glu Pro Gly Gln Glu
        35                  40                  45

Pro Gly Gln Glu Pro Gly Gln Glu Pro Gly Gln Glu Pro Gly Gln Glu
    50                  55                  60

Pro Gly Gln Glu Pro Gly Gln Glu Pro Gly Gln Glu Pro Gly Gln Glu
65                  70                  75                  80

Pro Gly Gln Glu Pro Gly Gln Glu Pro Gly Gln Glu Pro Gly Gln Glu
                85                  90                  95

Pro Lys Pro

<210> SEQ ID NO 8
<211> LENGTH: 21
<212> TYPE: PRT
<213> ORGANISM: Artificial Sequence
<220> FEATURE:
<223> OTHER INFORMATION: A-chain of OEF-Ins-2, OEF-Ins-4, OEF-Ins-10,
      OEF-Ins-11, and OEF-Ins-12.

<400> SEQUENCE: 8

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 9
<211> LENGTH: 99
<212> TYPE: PRT
<213> ORGANISM: Artificial Sequence
<220> FEATURE:
<223> OTHER INFORMATION: A-chain of OEF-Ins-3, and OEF-Ins-14.

<400> SEQUENCE: 9

Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Ala Pro Gly Gln Glu
            20                  25                  30

Pro Gly Gln Ala Pro Gly Gln Ala Pro Gly Gln Glu Pro Gly Gln Ala
        35                  40                  45

Pro Gly Gln Ala Pro Gly Gln Glu Pro Gly Gln Ala Pro Gly Gln Ala
    50                  55                  60

Pro Gly Gln Glu Pro Gly Gln Ala Pro Gly Gln Ala Pro Gly Gln Glu
65                  70                  75                  80

Pro Gly Gln Ala Pro Gly Gln Ala Pro Gly Gln Glu Pro Gly Gln Ala
                85                  90                  95

Pro Lys Pro

<210> SEQ ID NO 10
<211> LENGTH: 47
<212> TYPE: PRT
<213> ORGANISM: Artificial Sequence
<220> FEATURE:
<223> OTHER INFORMATION: A-chain of OEF-Ins-7.

<400> SEQUENCE: 10

-continued

Gly Ile Val Glu Gln Cys Cys Thr Ser Ile Cys Ser Leu Glu Gln Leu
1               5                   10                  15

Glu Asn Tyr Cys Gly Gly Gln Glu Pro Gly Gln Glu Pro Gly Gln Glu
            20                  25                  30

Pro Gly Gln Glu Pro Gly Gln Glu Pro Gly Gln Glu Pro Lys Pro
        35                  40                  45

<210> SEQ ID NO 11
<211> LENGTH: 71
<212> TYPE: PRT
<213> ORGANISM: Artificial Sequence
<220> FEATURE:
<223> OTHER INFORMATION: A-chain of OEF-Ins-6.

<400> SEQUENCE: 11

Gly Ile Val Glu Gln Cys Cys Thr Ser Ile Cys Ser Leu Glu Gln Leu
1               5                   10                  15

Glu Asn Tyr Cys Gly Gly Gln Glu Pro Gly Gln Glu Pro Gly Gln Glu
            20                  25                  30

Pro Gly Gln Glu Pro Gly Gln Glu Pro Gly Gln Glu Pro Gly Gln Glu
        35                  40                  45

Pro Gly Gln Glu Pro Gly Gln Glu Pro Gly Gln Glu Pro Gly Gln Glu
    50                  55                  60

Pro Gly Gln Glu Pro Lys Pro
65                  70

<210> SEQ ID NO 12
<211> LENGTH: 71
<212> TYPE: PRT
<213> ORGANISM: Artificial Sequence
<220> FEATURE:
<223> OTHER INFORMATION: A-chain of OEF-Ins-9.

<400> SEQUENCE: 12

Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Glu Pro Gly Gln Ala
            20                  25                  30

Pro Gly Gln Glu Pro Gly Gln Ala Pro Gly Gln Glu Pro Gly Gln Ala
        35                  40                  45

Pro Gly Gln Glu Pro Gly Gln Ala Pro Gly Gln Glu Pro Gly Gln Ala
    50                  55                  60

Pro Gly Gln Glu Pro Lys Pro
65                  70

<210> SEQ ID NO 13
<211> LENGTH: 38
<212> TYPE: PRT
<213> ORGANISM: Artificial Sequence
<220> FEATURE:
<223> OTHER INFORMATION: A-chain of OEF-Ins-8.

<400> SEQUENCE: 13

Gly Ile Val Glu Gln Cys Cys Thr Ser Ile Cys Ser Leu Glu Gln Leu
1               5                   10                  15

Glu Asn Tyr Cys Gly Gly Gln Glu Pro Gly Gln Glu Pro Gly Gln Glu
            20                  25                  30

Pro Gly Gln Glu Lys Pro
        35

<210> SEQ ID NO 14
<211> LENGTH: 99
<212> TYPE: PRT
<213> ORGANISM: Artificial Sequence
<220> FEATURE:
<223> OTHER INFORMATION: A-chain of OEF-Ins-13.

<400> SEQUENCE: 14

```
Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
                85                  90                  95

Pro Lys Pro
```

<210> SEQ ID NO 15
<211> LENGTH: 123
<212> TYPE: PRT
<213> ORGANISM: Artificial Sequence
<220> FEATURE:
<223> OTHER INFORMATION: A-chain of OEF-Ins-15.

<400> SEQUENCE: 15

```
Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Ala Pro Gly Gln Ala
            20                  25                  30

Pro Gly Gln Glu Pro Gly Gln Ala Pro Gly Gln Ala Pro Gly Gln Ala
        35                  40                  45

Pro Gly Gln Glu Pro Gly Gln Ala Pro Gly Gln Ala Pro Gly Gln Ala
    50                  55                  60

Pro Gly Gln Glu Pro Gly Gln Ala Pro Gly Gln Ala Pro Gly Gln Ala
65                  70                  75                  80

Pro Gly Gln Glu Pro Gly Gln Ala Pro Gly Gln Ala Pro Gly Gln Ala
                85                  90                  95

Pro Gly Gln Glu Pro Gly Gln Ala Pro Gly Gln Ala Pro Gly Gln Ala
                100                 105                 110

Pro Gly Gln Glu Pro Gly Gln Ala Pro Lys Pro
        115                 120
```

<210> SEQ ID NO 16
<211> LENGTH: 122
<212> TYPE: PRT
<213> ORGANISM: Artificial Sequence
<220> FEATURE:
<223> OTHER INFORMATION: A-chain of OEF-Ins-20, and OEF-Ins-21.

<400> SEQUENCE: 16

```
Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Ala Pro Gly Gln Ala
            20                  25                  30
```

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
            85                  90                  95

Pro Gly Gln Ala Pro Gly Gln Ala Pro Gly Gln Ala Pro Gly Gln Ala
                100                 105                 110

Pro Gly Gln Ala Pro Gly Gln Ala Lys Pro
        115                 120

<210> SEQ ID NO 17
<211> LENGTH: 98
<212> TYPE: PRT
<213> ORGANISM: Artificial Sequence
<220> FEATURE:
<223> OTHER INFORMATION: A-chain of OEF-Ins-16.

<400> SEQUENCE: 17

Gly Ile Val Glu Gln Cys Cys Thr Ser Ile Cys Ser Leu Ala Gln Leu
1               5                   10                  15

Glu Asn Tyr Cys Gly Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
            85                  90                  95

Lys Pro

<210> SEQ ID NO 18
<211> LENGTH: 98
<212> TYPE: PRT
<213> ORGANISM: Artificial Sequence
<220> FEATURE:
<223> OTHER INFORMATION: A-chain of OEF-Ins-17, OEF-Ins-18, and
      OEF-Ins-23.

<400> SEQUENCE: 18

Gly Ile Val Glu Gln Cys Cys Thr Ser Ile Cys Ser Leu Glu Gln Leu
1               5                   10                  15

Glu Asn Tyr Cys Gly Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
            85                  90                  95

Lys Pro

<210> SEQ ID NO 19
<211> LENGTH: 40
<212> TYPE: PRT
<213> ORGANISM: Artificial Sequence
<220> FEATURE:
<223> OTHER INFORMATION: A-chain of OEF-Ins-19.

<400> SEQUENCE: 19

Gly Ile Val Glu Gln Cys Cys Thr Ser Ile Cys Ser Leu Glu Gln Leu
1               5                   10                  15

Glu Asn Tyr Cys Gln Gly Gly Gly Gly Gly Gly Gly Gly Gly
            20                  25                  30

Gly Gly Gly Gly Gly Gly Gly Lys
        35                  40

<210> SEQ ID NO 20
<211> LENGTH: 98
<212> TYPE: PRT
<213> ORGANISM: Artificial Sequence
<220> FEATURE:
<223> OTHER INFORMATION: A-chain of OEF-Ins-22.

<400> SEQUENCE: 20

Gly Ile Val Glu Gln Cys Cys Thr Ser Ile Cys Ser Leu Tyr Gln Leu
1               5                   10                  15

Glu Asn Tyr Cys Gly Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
                85                  90                  95

Lys Pro

<210> SEQ ID NO 21
<211> LENGTH: 29
<212> TYPE: PRT
<213> ORGANISM: Artificial Sequence
<220> FEATURE:
<223> OTHER INFORMATION: B-chain of OEF-Ins-1, OEF-Ins-6, OEF-Ins-7,
      OEF-Ins-8, OEF-Ins-9, OEF-Ins-13, OEF-Ins-15, OEF-Ins-18,
      OEF-Ins-19, and OEF-Ins-20.

<400> SEQUENCE: 21

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Arg
            20                  25

<210> SEQ ID NO 22
<211> LENGTH: 107
<212> TYPE: PRT
<213> ORGANISM: Artificial Sequence
<220> FEATURE:
<223> OTHER INFORMATION: B-chain of OEF-Ins-4.

<400> SEQUENCE: 22

Lys Pro Gly Gln Glu Pro Gly Gln Glu Pro Gly Gln Glu Pro Gly Gln

```
                1               5                  10                  15
Glu Pro Gly Gln Glu Pro Gly Gln Glu Pro Gly Gln Glu Pro Gly Gln
                        20                  25                  30

Glu Pro Gly Gln Glu Pro Gly Gln Glu Pro Gly Gln Glu Pro Gly Gln
            35                  40                  45

Glu Pro Gly Gln Glu Pro Gly Gln Glu Pro Gly Gln Glu Pro Gly Gln
        50                  55                  60

Glu Pro Gly Gln Glu Pro Gly Gln Glu Pro Gly Gln Glu Pro Phe Val
65                  70                  75                  80

Asn Gln His Leu Cys Gly Ser His Leu Val Glu Ala Leu Tyr Leu Val
                85                  90                  95

Cys Gly Glu Arg Gly Phe His Tyr Thr Pro Arg
            100                 105

<210> SEQ ID NO 23
<211> LENGTH: 29
<212> TYPE: PRT
<213> ORGANISM: Artificial Sequence
<220> FEATURE:
<223> OTHER INFORMATION: B-chain of OEF-Ins-3, and OEF-Ins-5.

<400> SEQUENCE: 23

Phe Val Gln Gln His Leu Cys Gly Ser His Leu Val Glu Ala Leu Tyr
1               5                   10                  15

Leu Val Cys Gly Glu Arg Gly Phe His Tyr Thr Pro Arg
            20                  25

<210> SEQ ID NO 24
<211> LENGTH: 107
<212> TYPE: PRT
<213> ORGANISM: Artificial Sequence
<220> FEATURE:
<223> OTHER INFORMATION: B-chain of OEF-Ins-2.

<400> SEQUENCE: 24

Lys Pro Gly Gln Ala Pro Gly Gln Ala Pro Gly Gln Glu Pro Gly Gln
1               5                   10                  15

Ala Pro Gly Gln Ala Pro Gly Gln Glu Pro Gly Gln Ala Pro Gly Gln
            20                  25                  30

Ala Pro Gly Gln Glu Pro Gly Gln Ala Pro Gly Gln Ala Pro Gly Gln
        35                  40                  45

Glu Pro Gly Gln Ala Pro Gly Gln Ala Pro Gly Gln Glu Pro Gly Gln
    50                  55                  60

Ala Pro Gly Gln Ala Pro Gly Gln Glu Pro Gly Gln Ala Pro Phe Val
65                  70                  75                  80

Gln Gln His Leu Cys Gly Ser His Leu Val Glu Ala Leu Tyr Leu Val
                85                  90                  95

Cys Gly Glu Arg Gly Phe His Tyr Thr Pro Arg
            100                 105

<210> SEQ ID NO 25
<211> LENGTH: 78
<212> TYPE: PRT
<213> ORGANISM: Artificial Sequence
<220> FEATURE:
<223> OTHER INFORMATION: B-chain of OEF-Ins-12.

<400> SEQUENCE: 25

Lys Pro Gly Gln Ala Pro Gly Gln Ala Pro Gly Gln Ala Pro Gly Gln
1               5                   10                  15
```

```
Ala Pro Gly Gln Ala Pro Gly Gln Ala Pro Gly Gln Ala Pro Gly Gln
            20                  25                  30

Ala Pro Gly Gln Ala Pro Gly Gln Ala Pro Gly Gln Ala Pro Gly Gln
        35                  40                  45

Ala Pro Gly Gln Ala Pro Gly Gln Ala Pro Gly Gln Ala Pro Gly Gln
    50                  55                  60

Ala Pro Gly Gln Ala Pro Gly Gln Ala Pro Gly Gln Ala Pro
65                  70                  75

<210> SEQ ID NO 26
<211> LENGTH: 29
<212> TYPE: PRT
<213> ORGANISM: Artificial Sequence
<220> FEATURE:
<223> OTHER INFORMATION: B-chain of OEF-Ins-14, OEF-Ins-16, OEF-Ins-17,
      OEF-Ins-21, and OEF-Ins-22.

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg
            20                  25

<210> SEQ ID NO 27
<211> LENGTH: 55
<212> TYPE: PRT
<213> ORGANISM: Artificial Sequence
<220> FEATURE:
<223> OTHER INFORMATION: B-chain of OEF-Ins-10.

<400> SEQUENCE: 27

Lys Pro Gly Gln Glu Pro Gly Gln Glu Pro Gly Gln Glu Pro Gly Gln
1               5                   10                  15

Glu Pro Gly Gln Glu Pro Gly Gln Glu Pro Phe Val Asn Gln His Leu
            20                  25                  30

Cys Gly Ser His Leu Val Glu Ala Leu Tyr Leu Val Cys Gly Glu Arg
        35                  40                  45

Gly Phe His Tyr Thr Pro Arg
    50                  55

<210> SEQ ID NO 28
<211> LENGTH: 47
<212> TYPE: PRT
<213> ORGANISM: Artificial Sequence
<220> FEATURE:
<223> OTHER INFORMATION: B-chain of OEF-Ins-11.

<400> SEQUENCE: 28

Lys Pro Gly Gln Glu Pro Gly Gln Glu Pro Gly Gln Glu Pro Gly Gln
1               5                   10                  15

Glu Pro Phe Val Asn Gln His Leu Cys Gly Ser His Leu Val Glu Ala
            20                  25                  30

Leu Tyr Leu Val Cys Gly Glu Arg Gly Phe His Tyr Thr Pro Arg
        35                  40                  45

<210> SEQ ID NO 29
<211> LENGTH: 29
<212> TYPE: PRT
<213> ORGANISM: Artificial Sequence
<220> FEATURE:
<223> OTHER INFORMATION: B-chain of OEF-Ins-23.
```

```
<400> SEQUENCE: 29

Phe Val Asn Gln His Leu Cys Gly Ser His Leu Val Glu Ala Leu Glu
1               5                   10                  15

Leu Val Cys Gly Glu Arg Gly Phe His Tyr Thr Pro Arg
            20                  25

<210> SEQ ID NO 30
<211> LENGTH: 221
<212> TYPE: PRT
<213> ORGANISM: Artificial Sequence
<220> FEATURE:
<223> OTHER INFORMATION: Fc fragment of Fc9.

<400> SEQUENCE: 30

Ala Ser Cys Pro Ala Pro Glu Ala Lys Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 31
<211> LENGTH: 221
<212> TYPE: PRT
<213> ORGANISM: Artificial Sequence
<220> FEATURE:
<223> OTHER INFORMATION: Fc fragment of Fc1.

<400> SEQUENCE: 31

Ala Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45
```

```
Phe Asn Trp Tyr Val Asp Gly Val Glu Val His Asn Ala Lys Thr Lys
 50                  55                  60
Pro Arg Glu Glu Gln Phe Asn Ser Thr Tyr Arg Val Val Ser Val Leu
 65                  70                  75                  80
Thr Val Leu His Gln Asp Trp Leu Asn Gly Lys Glu Tyr Lys Cys Lys
                 85                  90                  95
Val Ser Asn Lys Gly Leu Pro Ser Ser Ile Glu Lys Thr Ile Ser Lys
                100                 105                 110
Ala Lys Gly Gln Pro Arg Glu Pro Gln Val Tyr Thr Leu Pro Pro Ser
            115                 120                 125
Gln Glu Glu Met Thr Lys Asn Gln Val Ser Leu Thr Cys Leu Val Lys
130                 135                 140
Gly Phe Tyr Pro Ser Asp Ile Ala Val Glu Trp Glu Ser Asn Gly Gln
145                 150                 155                 160
Pro Glu Asn Asn Tyr Lys Thr Thr Pro Pro Val Leu Asp Ser Asp Gly
                165                 170                 175
Ser Phe Phe Leu Tyr Ser Arg Leu Thr Val Asp Lys Ser Arg Trp Gln
                180                 185                 190
Glu Gly Asn Val Phe Ser Cys Ser Val Met His Glu Ala Leu His Asn
            195                 200                 205
His Tyr Thr Gln Lys Ser Leu Ser Leu Ser Leu Gly Lys
210                 215                 220

<210> SEQ ID NO 32
<211> LENGTH: 220
<212> TYPE: PRT
<213> ORGANISM: Artificial Sequence
<220> FEATURE:
<223> OTHER INFORMATION: Fc fragment of Fc15.

<400> SEQUENCE: 32

Ala Ser Cys Pro Ala Pro Glu Ala Lys Gly Gly Pro Ser Val Phe Leu
 1               5                  10                  15
Phe Pro Pro Lys Pro Lys Asp Thr Leu Met Ile Ser Arg Thr Pro Glu
                 20                  25                  30
Val Thr Cys Val Val Val Asp Val Ser Gln Glu Asp Pro Glu Val Gln
             35                  40                  45
Phe Asn Trp Tyr Val Asp Gly Val Glu Val His Asn Ala Lys Thr Lys
 50                  55                  60
Pro Arg Glu Glu Gln Phe Glu Ser Thr Tyr Arg Val Val Ser Val Leu
 65                  70                  75                  80
Thr Val Leu His Gln Asp Trp Leu Gln Gly Lys Glu Tyr Lys Cys Lys
                 85                  90                  95
Val Ser Asn Lys Gly Leu Pro Ser Ser Ile Glu Lys Thr Ile Ser Lys
                100                 105                 110
Ala Lys Gly Gln Pro Arg Glu Pro Gln Val Tyr Thr Leu Pro Pro Ser
            115                 120                 125
Gln Glu Glu Met Thr Lys Asn Gln Val Ser Leu Thr Cys Leu Val Lys
130                 135                 140
Gly Phe Tyr Pro Ser Asp Ile Ala Val Glu Trp Glu Ser Gln Gly Gln
145                 150                 155                 160
Pro Glu Asn Asn Tyr Lys Thr Thr Pro Pro Val Leu Asp Ser Asp Gly
                165                 170                 175
Ser Phe Phe Leu Tyr Ser Arg Leu Thr Val Asp Lys Ser Arg Trp Gln
                180                 185                 190
```

Glu Gly Asn Val Phe Ser Cys Ser Val Met His Glu Ala Leu His Asn
            195                 200                 205

His Tyr Thr Gln Lys Ser Leu Ser Leu Ser Leu Gly
    210                 215                 220

<210> SEQ ID NO 33
<211> LENGTH: 221
<212> TYPE: PRT
<213> ORGANISM: Artificial Sequence
<220> FEATURE:
<223> OTHER INFORMATION: Fc fragment of Fc2.

<400> SEQUENCE: 33

Ala Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Gln Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Gln Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 34
<211> LENGTH: 222
<212> TYPE: PRT
<213> ORGANISM: Artificial Sequence
<220> FEATURE:
<223> OTHER INFORMATION: Fc fragment of Fc3.

<400> SEQUENCE: 34

Gly Ala Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

```
Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 35
<211> LENGTH: 221
<212> TYPE: PRT
<213> ORGANISM: Artificial Sequence
<220> FEATURE:
<223> OTHER INFORMATION: Fc fragment of Fc4.

<400> SEQUENCE: 35

Ala Ser Cys Pro Ala Pro Glu Leu Lys Gly Gly Pro Ser Val Phe Leu
  1               5                  10                  15

Phe Pro Pro Lys Pro Lys Asp Thr Leu Met Ile Ser Arg Thr Pro Glu
                 20                  25                  30

Val Thr Cys Val Val Val Asp Val Ser His Glu Asp Pro Glu Val Lys
             35                  40                  45

Phe Asn Trp Tyr Val Asp Gly Val Glu Val His Asn Ala Lys Thr Lys
         50                  55                  60

Pro Arg Glu Glu Gln Tyr Asn Ser Thr Tyr Arg Val Val Ser Val Leu
 65                  70                  75                  80

Thr Val Leu His Gln Asp Trp Leu Gln Gly Lys Glu Tyr Lys Cys Lys
                 85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Gln Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205
```

His Tyr Thr Gln Lys Ser Leu Ser Leu Ser Pro Gly Lys
    210                 215                 220

<210> SEQ ID NO 36
<211> LENGTH: 221
<212> TYPE: PRT
<213> ORGANISM: Artificial Sequence
<220> FEATURE:
<223> OTHER INFORMATION: Fc fragment of Fc5.

<400> SEQUENCE: 36

Ala Ser Cys Pro Ala Pro Glu Phe Lys Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Gln Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Gln Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 37
<211> LENGTH: 221
<212> TYPE: PRT
<213> ORGANISM: Artificial Sequence
<220> FEATURE:
<223> OTHER INFORMATION: Fc fragment of Fc6.

<400> SEQUENCE: 37

Ala Ser Cys Pro Ala Pro Glu Ala Ala Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu

```
                65                  70                  75                  80
Thr Val Leu His Gln Asp Trp Leu Asn Gly Lys Glu Tyr Lys Cys Lys
                    85                  90                  95

Val Ser Asn Lys Gly Leu Pro Ser Ser Ile Glu Lys Thr Ile Ser Lys
                    100                 105                 110

Ala Lys Gly Gln Pro Arg Glu Pro Gln Val Tyr Thr Leu Pro Pro Ser
                    115                 120                 125

Gln Glu Glu Met Thr Lys Asn Gln Val Ser Leu Thr Cys Leu Val Lys
                    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Val Leu Asp Ser Asp Gly
                    165                 170                 175

Ser Phe Phe Leu Tyr Ser Arg Leu Thr Val Asp Lys Ser Arg Trp Gln
                    180                 185                 190

Glu Gly Asn Val Phe Ser Cys Ser Val Met His Glu Ala Leu His Asn
                    195                 200                 205

His Tyr Thr Gln Lys Ser Leu Ser Leu Ser Leu Gly Lys
                    210                 215                 220
```

<210> SEQ ID NO 38
<211> LENGTH: 222
<212> TYPE: PRT
<213> ORGANISM: Artificial Sequence
<220> FEATURE:
<223> OTHER INFORMATION: Fc fragment of Fc7.

<400> SEQUENCE: 38

```
Ala Ser Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                    20                  25                  30

Glu Val Thr Cys Val Val Val Asp Val Ser His Glu Asp Pro Glu Val
                    35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                    85                  90                  95

Lys Val Ser Asn Lys Ala Leu Pro Ala Pro Ile Glu Lys Thr Ile Ser
                    100                 105                 110

Lys Ala Lys Gly Gln Pro Arg Glu Pro Gln Val Tyr Thr Leu Pro Pro
                    115                 120                 125

Ser Arg Glu Glu Met Thr Lys Asn Gln Val Ser Leu Thr Cys Leu Val
                    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                    165                 170                 175

Gly Ser Phe Phe Leu Tyr Ser Lys Leu Thr Val Asp Lys Ser Arg Trp
                    180                 185                 190

Gln Gln Gly Asn Val Phe Ser Cys Ser Val Met His Glu Ala Leu His
                    195                 200                 205

Asn His Tyr Thr Gln Lys Ser Leu Ser Leu Ser Pro Gly Lys
```

<210> SEQ ID NO 39
<211> LENGTH: 221
<212> TYPE: PRT
<213> ORGANISM: Artificial Sequence
<220> FEATURE:
<223> OTHER INFORMATION: Fc fragment of Fc8.

<400> SEQUENCE: 39

```
Ala Ser Cys Pro Ala Pro Glu Phe Lys Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

<210> SEQ ID NO 40
<211> LENGTH: 222
<212> TYPE: PRT
<213> ORGANISM: Artificial Sequence
<220> FEATURE:
<223> OTHER INFORMATION: Fc fragment of Fc10.

<400> SEQUENCE: 40

```
Ala Ser Pro Cys Pro Ala Pro Glu Leu Lys Gly Ala Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80
```

Leu Thr Val Leu His Gln Asp Trp Leu Asn Gly Lys Glu Tyr Lys Cys
            85                  90                  95

Lys Val Ser Asn Lys Ala Leu Pro Ser Ser Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
            130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
            210                 215                 220

<210> SEQ ID NO 41
<211> LENGTH: 222
<212> TYPE: PRT
<213> ORGANISM: Artificial Sequence
<220> FEATURE:
<223> OTHER INFORMATION: Fc fragment of Fc11.

<400> SEQUENCE: 41

Ala Ser Pro Cys Pro Ala Pro Glu Ala Lys Gly Ala Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Ala Leu Pro Ser Ser Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
            130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
            210                 215                 220

-continued

```
<210> SEQ ID NO 42
<211> LENGTH: 222
<212> TYPE: PRT
<213> ORGANISM: Artificial Sequence
<220> FEATURE:
<223> OTHER INFORMATION: Fc fragment of Fc12.

<400> SEQUENCE: 42

Ala Ser Pro Cys Pro Ala Pro Glu Ala Lys Gly Ala Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Gln Gly Lys Glu Tyr Lys Cys
                85                  90                  95

Lys Val Ser Asn Lys Ala Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Gln Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 43
<211> LENGTH: 222
<212> TYPE: PRT
<213> ORGANISM: Artificial Sequence
<220> FEATURE:
<223> OTHER INFORMATION: Fc fragment of Fc13.

<400> SEQUENCE: 43

Ala Ser Pro Cys Pro Ala Pro Glu Ala Glu Gly Ala Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95
```

Lys Val Ser Asn Lys Ala Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 44
<211> LENGTH: 221
<212> TYPE: PRT
<213> ORGANISM: Artificial Sequence
<220> FEATURE:
<223> OTHER INFORMATION: Fc fragment of Fc14.

<400> SEQUENCE: 44

Ala Ser Cys Pro Ala Pro Glu Ala Lys Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Gln Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220

<210> SEQ ID NO 45

```
<211> LENGTH: 220
<212> TYPE: PRT
<213> ORGANISM: Artificial Sequence
<220> FEATURE:
<223> OTHER INFORMATION: Fc fragment of Fc16.

<400> SEQUENCE: 45

Ala Ser Cys Pro Ala Pro Glu Ala Lys Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Glu Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly
    210                 215                 220

<210> SEQ ID NO 46
<211> LENGTH: 442
<212> TYPE: PRT
<213> ORGANISM: Artificial Sequence
<220> FEATURE:
<223> OTHER INFORMATION: Fc fragment of Fc17.

<400> SEQUENCE: 46

Ala Gly Pro Cys Pro Ala Pro Glu Ala Lys Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
```

```
            100                 105                 110
Lys Ala Lys Gly Gln Pro Arg Glu Pro Gln Val Tyr Thr Leu Pro Pro
            115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Ala Gly Pro
    210                 215                 220

Cys Pro Ala Pro Glu Ala Lys Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 47
<211> LENGTH: 21
<212> TYPE: PRT
<213> ORGANISM: Artificial Sequence
<220> FEATURE:
<223> OTHER INFORMATION: A-chain of A14E, A21G human insulin

<400> SEQUENCE: 47

Gly Ile Val Glu Gln Cys Cys Thr Ser Ile Cys Ser Leu Glu Gln Leu
1               5                   10                  15

Glu Asn Tyr Cys Gly
```

20

<210> SEQ ID NO 48
<211> LENGTH: 29
<212> TYPE: PRT
<213> ORGANISM: Artificial Sequence
<220> FEATURE:
<223> OTHER INFORMATION: B-chain of B3Q, B29R, desB30 human insulin

<400> SEQUENCE: 48

Phe Val Gln Gln His Leu Cys Gly Ser His Leu Val Glu Ala Leu Tyr
1               5                   10                  15

Leu Val Cys Gly Glu Arg Gly Phe Phe Tyr Thr Pro Arg
            20                  25

<210> SEQ ID NO 49
<211> LENGTH: 21
<212> TYPE: PRT
<213> ORGANISM: Artificial Sequence
<220> FEATURE:
<223> OTHER INFORMATION: A-chain of A14E, A21Q human insulin

<400> SEQUENCE: 49

Gly Ile Val Glu Gln Cys Cys Thr Ser Ile Cys Ser Leu Glu Gln Leu
1               5                   10                  15

Glu Asn Tyr Cys Gln
            20

<210> SEQ ID NO 50
<211> LENGTH: 21
<212> TYPE: PRT
<213> ORGANISM: Artificial Sequence
<220> FEATURE:
<223> OTHER INFORMATION: A-chain of human insulin

<400> SEQUENCE: 50

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 51
<211> LENGTH: 29
<212> TYPE: PRT
<213> ORGANISM: Artificial Sequence
<220> FEATURE:
<223> OTHER INFORMATION: B-chain of B16H, B25H, B29R, desB30 human
      insulin

<400> SEQUENCE: 51

Phe Val Asn Gln His Leu Cys Gly Ser His Leu Val Glu Ala Leu His
1               5                   10                  15

Leu Val Cys Gly Glu Arg Gly Phe His Tyr Thr Pro Arg
            20                  25

<210> SEQ ID NO 52
<211> LENGTH: 21
<212> TYPE: PRT
<213> ORGANISM: Artificial Sequence
<220> FEATURE:
<223> OTHER INFORMATION: A-chain of A14A, A21G human insulin

<400> SEQUENCE: 52

Gly Ile Val Glu Gln Cys Cys Thr Ser Ile Cys Ser Leu Ala Gln Leu
1               5                   10                  15

```
Glu Asn Tyr Cys Gly
            20

<210> SEQ ID NO 53
<211> LENGTH: 20
<212> TYPE: PRT
<213> ORGANISM: Artificial Sequence
<220> FEATURE:
<223> OTHER INFORMATION: A-chain OEF

<400> SEQUENCE: 53

Gln Gly Gly Gly Gly Gly Gly Gly Gly Gly Gly Gly Gly Gly Gly Gly
1               5                   10                  15

Gly Gly Gly Lys
            20

<210> SEQ ID NO 54
<211> LENGTH: 78
<212> TYPE: PRT
<213> ORGANISM: Artificial Sequence
<220> FEATURE:
<223> OTHER INFORMATION: A-chain OEF

<400> SEQUENCE: 54

Gly Gly Gln Ala Pro Gly Gln Ala Pro Gly Gln Ala Pro Gly Gln Ala
1               5                   10                  15

Pro Gly Gln Ala Pro Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Lys Pro
65                  70                  75

<210> SEQ ID NO 55
<211> LENGTH: 79
<212> TYPE: PRT
<213> ORGANISM: Artificial Sequence
<220> FEATURE:
<223> OTHER INFORMATION: A-chain OEF

<400> SEQUENCE: 55

Gly Gly Gln Ala Pro Gly Gln Ala Pro Gly Gln Ala Pro Gly Gln Ala
1               5                   10                  15

Pro Gly Gln Ala Pro Gly Gln Ala Pro Gly Gln Ala Pro Gly Gln Ala
            20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Lys Pro
65                  70                  75

<210> SEQ ID NO 56
<211> LENGTH: 51
<212> TYPE: PRT
<213> ORGANISM: Artificial Sequence
<220> FEATURE:
<223> OTHER INFORMATION: A-chain OEF

<400> SEQUENCE: 56
```

```
Gly Gly Gln Ala Pro Gly Gln Glu Pro Gly Gln Ala Pro Gly Gln Glu
1               5                   10                  15

Pro Gly Gln Ala Pro Gly Gln Glu Pro Gly Gln Ala Pro Gly Gln Glu
                20                  25                  30

Pro Gly Gln Ala Pro Gly Gln Glu Pro Gly Gln Ala Pro Gly Gln Glu
                35                  40                  45

Pro Lys Pro
    50

<210> SEQ ID NO 57
<211> LENGTH: 79
<212> TYPE: PRT
<213> ORGANISM: Artificial Sequence
<220> FEATURE:
<223> OTHER INFORMATION: A-chain OEF

<400> SEQUENCE: 57

Gly Gly Gln Ala Pro Gly Gln Ala Pro Gly Gln Glu Pro Gly Gln Ala
1               5                   10                  15

Pro Gly Gln Ala Pro Gly Gln Glu Pro Gly Gln Ala Pro Gly Gln Ala
                20                  25                  30

Pro Gly Gln Glu Pro Gly Gln Ala Pro Gly Gln Ala Pro Gly Gln Glu
                35                  40                  45

Pro Gly Gln Ala Pro Gly Gln Ala Pro Gly Gln Glu Pro Gly Gln Ala
                50                  55                  60

Pro Gly Gln Ala Pro Gly Gln Glu Pro Gly Gln Ala Pro Lys Pro
65                  70                  75

<210> SEQ ID NO 58
<211> LENGTH: 103
<212> TYPE: PRT
<213> ORGANISM: Artificial Sequence
<220> FEATURE:
<223> OTHER INFORMATION: A-chain OEF

<400> SEQUENCE: 58

Gly Gly Gln Ala Pro Gly Gln Ala Pro Gly Gln Ala Pro Gly Gln Glu
1               5                   10                  15

Pro Gly Gln Ala Pro Gly Gln Ala Pro Gly Gln Ala Pro Gly Gln Glu
                20                  25                  30

Pro Gly Gln Ala Pro Gly Gln Ala Pro Gly Gln Ala Pro Gly Gln Glu
                35                  40                  45

Pro Gly Gln Ala Pro Gly Gln Ala Pro Gly Gln Ala Pro Gly Gln Glu
                50                  55                  60

Pro Gly Gln Ala Pro Gly Gln Ala Pro Gly Gln Ala Pro Gly Gln Glu
65                  70                  75                  80

Pro Gly Gln Ala Pro Gly Gln Ala Pro Gly Gln Ala Pro Gly Gln Glu
                85                  90                  95

Pro Gly Gln Ala Pro Lys Pro
                100

<210> SEQ ID NO 59
<211> LENGTH: 102
<212> TYPE: PRT
<213> ORGANISM: Artificial Sequence
<220> FEATURE:
<223> OTHER INFORMATION: A-chain OEF

<400> SEQUENCE: 59
```

Gly Gly Gln Ala Pro Gly Gln Ala Pro Gly Gln Ala Pro Gly Gln Ala
1               5                   10                  15

Pro Gly Gln Ala Pro Gly Gln Ala Pro Gly Gln Ala Pro Gly Gln Ala
                20                  25                  30

Pro Gly Gln Ala Pro Gly Gln Ala Pro Gly Gln Ala Pro Gly Gln Ala
        35                  40                  45

Pro Gly Gln Ala Pro Gly Gln Ala Pro Gly Gln Ala Pro Gly Gln Ala
    50                  55                  60

Pro Gly Gln Ala Pro Gly Gln Ala Pro Gly Gln Ala Pro Gly Gln Ala
65                  70                  75                  80

Pro Gly Gln Ala Pro Gly Gln Ala Pro Gly Gln Ala Pro Gly Gln Ala
            85                  90                  95

Pro Gly Gln Ala Lys Pro
            100

<210> SEQ ID NO 60
<211> LENGTH: 18
<212> TYPE: PRT
<213> ORGANISM: Artificial Sequence
<220> FEATURE:
<223> OTHER INFORMATION: A-chain OEF

<400> SEQUENCE: 60

Gly Gly Gln Glu Pro Gly Gln Glu Pro Gly Gln Glu Pro Gly Gln Glu
1               5                   10                  15

Lys Pro

<210> SEQ ID NO 61
<211> LENGTH: 27
<212> TYPE: PRT
<213> ORGANISM: Artificial Sequence
<220> FEATURE:
<223> OTHER INFORMATION: A-chain OEF

<400> SEQUENCE: 61

Gly Gly Gln Glu Pro Gly Gln Glu Pro Gly Gln Glu Pro Gly Gln Glu
1               5                   10                  15

Pro Gly Gln Glu Pro Gly Gln Glu Pro Lys Pro
            20                  25

<210> SEQ ID NO 62
<211> LENGTH: 51
<212> TYPE: PRT
<213> ORGANISM: Artificial Sequence
<220> FEATURE:
<223> OTHER INFORMATION: A-chain OEF

<400> SEQUENCE: 62

Gly Gly Gln Glu Pro Gly Gln Glu Pro Gly Gln Glu Pro Gly Gln Glu
1               5                   10                  15

Pro Gly Gln Glu Pro Gly Gln Glu Pro Gly Gln Glu Pro Gly Gln Glu
                20                  25                  30

Pro Gly Gln Glu Pro Gly Gln Glu Pro Gly Gln Glu Pro Gly Gln Glu
        35                  40                  45

Pro Lys Pro
    50

<210> SEQ ID NO 63
<211> LENGTH: 79
<212> TYPE: PRT
<213> ORGANISM: Artificial Sequence

```
<220> FEATURE:
<223> OTHER INFORMATION: A-chain OEF

<400> SEQUENCE: 63

Gly Gly Gln Glu Pro Gly Gln Glu Pro Gly Gln Glu Pro Gly Gln Glu
1               5                   10                  15

Pro Gly Gln Glu Pro Gly Gln Glu Pro Gly Gln Glu Pro Gly Gln Glu
                20                  25                  30

Pro Gly Gln Glu Pro Gly Gln Glu Pro Gly Gln Glu Pro Gly Gln Glu
            35                  40                  45

Pro Gly Gln Glu Pro Gly Gln Glu Pro Gly Gln Glu Pro Gly Gln Glu
        50                  55                  60

Pro Gly Gln Glu Pro Gly Gln Glu Pro Gly Gln Glu Pro Lys Pro
65                  70                  75

<210> SEQ ID NO 64
<211> LENGTH: 78
<212> TYPE: PRT
<213> ORGANISM: Artificial Sequence
<220> FEATURE:
<223> OTHER INFORMATION: B-chain OEF

<400> SEQUENCE: 64

Lys Pro Gly Gln Ala Pro Gly Gln Ala Pro Gly Gln Glu Pro Gly Gln
1               5                   10                  15

Ala Pro Gly Gln Ala Pro Gly Gln Glu Pro Gly Gln Ala Pro Gly Gln
                20                  25                  30

Ala Pro Gly Gln Glu Pro Gly Gln Ala Pro Gly Gln Ala Pro Gly Gln
            35                  40                  45

Glu Pro Gly Gln Ala Pro Gly Gln Ala Pro Gly Gln Glu Pro Gly Gln
        50                  55                  60

Ala Pro Gly Gln Ala Pro Gly Gln Glu Pro Gly Gln Ala Pro
65                  70                  75

<210> SEQ ID NO 65
<211> LENGTH: 78
<212> TYPE: PRT
<213> ORGANISM: Artificial Sequence
<220> FEATURE:
<223> OTHER INFORMATION: B-chain OEF

<400> SEQUENCE: 65

Lys Pro Gly Gln Glu Pro Gly Gln Glu Pro Gly Gln Glu Pro Gly Gln
1               5                   10                  15

Glu Pro Gly Gln Glu Pro Gly Gln Glu Pro Gly Gln Glu Pro Gly Gln
                20                  25                  30

Glu Pro Gly Gln Glu Pro Gly Gln Glu Pro Gly Gln Glu Pro Gly Gln
            35                  40                  45

Glu Pro Gly Gln Glu Pro Gly Gln Glu Pro Gly Gln Glu Pro Gly Gln
        50                  55                  60

Glu Pro Gly Gln Glu Pro Gly Gln Glu Pro Gly Gln Glu Pro
65                  70                  75

<210> SEQ ID NO 66
<211> LENGTH: 78
<212> TYPE: PRT
<213> ORGANISM: Artificial Sequence
<220> FEATURE:
<223> OTHER INFORMATION: B-chain OEF

<400> SEQUENCE: 66
```

```
Lys Pro Gly Gln Ala Pro Gly Gln Ala Pro Gly Gln Ala Pro Gly Gln
1               5                   10                  15

Ala Pro Gly Gln Ala Pro Gly Gln Ala Pro Gly Gln Ala Pro Gly Gln
            20                  25                  30

Ala Pro Gly Gln Ala Pro Gly Gln Ala Pro Gly Gln Ala Pro Gly Gln
        35                  40                  45

Ala Pro Gly Gln Ala Pro Gly Gln Ala Pro Gly Gln Ala Pro Gly Gln
    50                  55                  60

Ala Pro Gly Gln Ala Pro Gly Gln Ala Pro Gly Gln Ala Pro
65                  70                  75

<210> SEQ ID NO 67
<211> LENGTH: 26
<212> TYPE: PRT
<213> ORGANISM: Artificial Sequence
<220> FEATURE:
<223> OTHER INFORMATION: B-chain OEF

<400> SEQUENCE: 67

Lys Pro Gly Gln Ala Pro Gly Gln Ala Pro Gly Gln Ala Pro Gly Gln
1               5                   10                  15

Ala Pro Gly Gln Ala Pro Gly Gln Ala Pro
            20                  25

<210> SEQ ID NO 68
<211> LENGTH: 5
<212> TYPE: PRT
<213> ORGANISM: Artificial Sequence
<220> FEATURE:
<223> OTHER INFORMATION: IgG1/IgG4 hinge sequence

<400> SEQUENCE: 68

Ala Gly Pro Cys Pro
1               5

<210> SEQ ID NO 69
<211> LENGTH: 4
<212> TYPE: PRT
<213> ORGANISM: Artificial Sequence
<220> FEATURE:
<223> OTHER INFORMATION: IgG1 hinge

<400> SEQUENCE: 69

Ala Ser Pro Cys
1

<210> SEQ ID NO 70
<211> LENGTH: 4
<212> TYPE: PRT
<213> ORGANISM: Artificial Sequence
<220> FEATURE:
<223> OTHER INFORMATION: IgG1 hinge

<400> SEQUENCE: 70

Pro Pro Cys Pro
1

<210> SEQ ID NO 71
<211> LENGTH: 5
<212> TYPE: PRT
<213> ORGANISM: Artificial Sequence
<220> FEATURE:
<223> OTHER INFORMATION: IgG1 hinge
```

```
<400> SEQUENCE: 71

Ala Ser Pro Cys Pro
1               5

<210> SEQ ID NO 72
<211> LENGTH: 4
<212> TYPE: PRT
<213> ORGANISM: Artificial Sequence
<220> FEATURE:
<223> OTHER INFORMATION: IgG1/IgG4 hinge

<400> SEQUENCE: 72

Ala Ser Cys Pro
1

<210> SEQ ID NO 73
<211> LENGTH: 5
<212> TYPE: PRT
<213> ORGANISM: Artificial Sequence
<220> FEATURE:
<223> OTHER INFORMATION: IgG4 hinge

<400> SEQUENCE: 73

Ala Gly Ser Cys Pro
1               5

<210> SEQ ID NO 74
<211> LENGTH: 4
<212> TYPE: PRT
<213> ORGANISM: Artificial Sequence
<220> FEATURE:
<223> OTHER INFORMATION: IgG4 hinge

<400> SEQUENCE: 74

Pro Ser Cys Pro
1

<210> SEQ ID NO 75
<211> LENGTH: 5
<212> TYPE: PRT
<213> ORGANISM: Artificial Sequence
<220> FEATURE:
<223> OTHER INFORMATION: IgG4 hinge

<400> SEQUENCE: 75

Gly Ala Ser Cys Pro
1               5

<210> SEQ ID NO 76
<211> LENGTH: 21
<212> TYPE: PRT
<213> ORGANISM: Artificial Sequence
<220> FEATURE:
<223> OTHER INFORMATION: A-chain of A21G human insulin

<400> SEQUENCE: 76

Gly Ile Val Glu Gln Cys Cys Thr Ser Ile Cys Ser Leu Tyr Gln Leu
1               5                   10                  15

Glu Asn Tyr Cys Gly
            20
```